(12) United States Patent
Brower-Toland et al.

(10) Patent No.: US 11,555,201 B2
(45) Date of Patent: Jan. 17, 2023

(54) COMPOSITIONS AND METHODS FOR ALTERING FLOWERING AND PLANT ARCHITECTURE TO IMPROVE YIELD POTENTIAL

(71) Applicant: MONSANTO TECHNOLOGY LLC, St. Louis, MO (US)

(72) Inventors: Brent Brower-Toland, St. Louis, MO (US); Shunhong Dai, Creve Coeur, MO (US); Karen Gabbert, St. Louis, MO (US); Alexander Goldshmidt, Davis, CA (US); Miya Howell, Ballwin, MO (US); Brad McDill, Carlsbad, CA (US); Dan Ovadya, Davis, CA (US); Beth Savidge, Davis, CA (US); Vijay Sharma, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 189 days.

(21) Appl. No.: 15/787,359

(22) Filed: Oct. 18, 2017

(65) Prior Publication Data

US 2018/0105819 A1 Apr. 19, 2018

Related U.S. Application Data

(60) Provisional application No. 62/410,355, filed on Oct. 19, 2016, provisional application No. 62/411,408, filed on Oct. 21, 2016.

(51) Int. Cl.
*C12N 15/82* (2006.01)
*C07K 14/415* (2006.01)

(52) U.S. Cl.
CPC .......... *C12N 15/827* (2013.01); *C07K 14/415* (2013.01); *C12N 15/8218* (2013.01); *C12N 15/8261* (2013.01); *Y02A 40/146* (2018.01)

(58) Field of Classification Search
CPC .......................... C12N 15/8218; C12N 15/827
See application file for complete search history.

(56) References Cited

U.S. PATENT DOCUMENTS

| | | |
|---|---|---|
| 5,322,938 A | 6/1994 | McPherson et al. |
| 5,352,605 A | 10/1994 | Fraley et al. |
| 5,850,019 A | 12/1998 | Maiti et al. |
| 5,880,330 A | 3/1999 | Weigel et al. |
| 6,225,530 B1 | 5/2001 | Weigel et al. |
| 6,372,211 B1 | 4/2002 | Isaac et al. |
| 6,420,547 B1 | 7/2002 | Maiti et al. |
| 7,393,948 B1 | 7/2008 | Sekar et al. |
| 7,872,170 B2 | 1/2011 | Hassan et al. |
| 8,552,037 B2 | 10/2013 | Uchikawa et al. |
| 8,809,628 B2 | 8/2014 | Wu et al. |
| 8,935,880 B2 | 1/2015 | Ovadya et al. |
| 10,294,486 B2 * | 5/2019 | Brower-Toland ........................... C12N 15/8261 |

| | | |
|---|---|---|
| 2004/0031072 A1 | 2/2004 | La Rosa et al. |
| 2004/0053411 A1 | 3/2004 | Cullen et al. |
| 2004/0268441 A1 | 12/2004 | Vance et al. |
| 2005/0037988 A1 | 2/2005 | Zamore et al. |
| 2005/0144669 A1 | 6/2005 | Reinhart et al. |
| 2005/0223428 A1 | 10/2005 | Torii et al. |
| 2009/0070898 A1 | 3/2009 | Allen et al. |
| 2010/0017904 A1 | 1/2010 | Abad et al. |
| 2010/0192249 A1 | 7/2010 | Creelman et al. |
| 2010/0333232 A9 | 12/2010 | Amasino et al. |
| 2011/0035839 A1 | 2/2011 | Lutfiyya et al. |
| 2011/0061125 A1 | 3/2011 | Saijo et al. |
| 2011/0296555 A1 | 12/2011 | Ivashuta et al. |
| 2014/0020128 A1 | 1/2014 | Laskar et al. |
| 2014/0259905 A1 | 9/2014 | Ovadya et al. |
| 2015/0247154 A1 | 9/2015 | Ivashuta et al. |
| 2015/0307890 A1 | 10/2015 | Wu et al. |
| 2016/0017347 A1 | 1/2016 | Allen et al. |

(Continued)

FOREIGN PATENT DOCUMENTS

| | | |
|---|---|---|
| CN | 1302328 A | 7/2001 |
| CN | 101519441 A | 9/2009 |
| CN | 102146124 A | 8/2011 |

(Continued)

OTHER PUBLICATIONS

McConnell et al, (2001, "Role of PHABULOSA and PHAVOLUTA in Determining Radial Patterning in Shoots", Nature 411 (6838): 709-713).*
Bowie et al, (1990, "Deciphering the Message in Protein Sequences: Tolerance to Amino Acid Substitutions", Science 247:1306-1310).*
Benfey et al (1990, "The Cauliflower Mosaic Virus 35S Promoter: Combinatorial Regulation of Transcription In Plants", Science 250: 959-966).*

(Continued)

*Primary Examiner* — Cynthia E Collins
(74) *Attorney, Agent, or Firm* — Morrison & Foerster LLP

(57) ABSTRACT

The present invention provides recombinant DNA constructs, vectors and molecules useful for attenuating and/or refining the expression of a florigenic FT gene or transgene using targeting sequences of small RNA molecules. Transgenic plants, plant cells and tissues, and plant parts comprising the recombinant constructs, vectors, and molecules are also provided. Transgenic plants comprising a florigenic FT transgene may produce more bolls, siliques, fruits, nuts, or pods per node on the transgenic plant via suppression, relative to a control or wild type plant. Methods are further provided for introducing the recombinant DNA constructs, vectors, and molecules into a plant, and planting transgenic plants in the field including at higher densities. Transgenic plants of the present invention may provide greater yield potential than wild type or control plants.

23 Claims, 20 Drawing Sheets

Specification includes a Sequence Listing.

(56) References Cited

U.S. PATENT DOCUMENTS

2016/0304891 A1   10/2016   Brower-Toland et al.

FOREIGN PATENT DOCUMENTS

| CN | 102149821 | A  | 8/2011  |
|----|-----------|----|---------|
| CN | 102994516 | B  | 4/2014  |
| EA | 023910    | B1 | 7/2016  |
| JP | 2008054512| A  | 3/2008  |
| JP | 2011067192| A  | 4/2011  |
| KR | 101315345 | B1 | 10/2013 |
| RU | 2456278   | C2 | 7/2012  |
| WO | WO 2013/192081 | A1 | 12/2013 |
| WO | WO 2016/172051 | A2 | 10/2016 |

OTHER PUBLICATIONS

Benfey et al (1989, "The CaMV 35S Enhancer Contains At Least Two Domains Which Can Confer Different Developmental and Tissue-Specific Patterns", EMBO J, 8(8):2195-2202).*
Emery et al (2003, "Radial Patterning of *Arabidopsis* Shoots by Class III HD-ZIP and KANADI Genes", Current Biology 13:1768-1774).*
Jones (2002, "Revealing Micro-RNAs and Plants", Trends in Plant Science 7 (11): 473-475).*
Abe et al., "FD, a bZIP Protein Mediating Signals from the Floral Pathway Integrator FT at the Shoot Apex," *Science* 309:1052-1055 (2005).
Allen et al., "microRNA-Directed Phasing during Trans-Acting siRNA Biogenesis in Plants," *Cell*, 121:207-221 (2005).
Amasino et al., "The Timing of Flowering," *Plant Physiology*, 154:516-520 (2010).
Banfield et al., "The Structure of *Antirrhinum* Centroradialis Protein (CEN) Suggests a Role as a Kinase Regulator," *J. Mol. Biol.*, 297(5):1159-1170 (2000).
Blackman et al., "The Role of Recently Derived FT Paralogs in Sunflower Domestication," *Current Biology*, 20:629-635 (2010).
Chen et al., "ERECTA family genes regulate development of cotyledons during embryogenesis," *FEBS Letters*, 588:3912-3917 (2014).
Chenna et al., "Multiple sequence alignment with the Clustal series of programs," *Nucleic Acids Research*, 31(13):3497-3500 (2003).
Corbesier et al., "FT Protein Movement Contributes to Long-Distance Signaling in Floral Induction of *Arabidopsis*," *Science*, 316:1030-1033 (2007).
Fernandez et al., "Flexible Tools for Gene Expression and Silencing in Tomato," *Plant Physiology*, 151:1729-1740 (2009).
Finn et al., "Pfam: the protein families database," *Nucleic Acids Research (Database Issue)*, 42:D222-D230 (2014).
Fleury et al., "The *Arabidopsis thaliana* Homolog of Yeast BRE1 Has a Function in Cell Cycle Regulation during Early Leaf and Root Growth," *The Plant Cell*, 19:417-432 (2007).
Harig et al., "Proteins from the Flowering Locus T-like subclade of the PEBP family act antagonistically to regulate floral initiation in tobacco," *The Plant Journal*, 72:908-921 (2012).
He et al., "BAK1 Directly Regulates Brassinosteroid Perception and BRI1 Activation," *JIPB*, 55(12):1264-1270 (2013).
Ho et al., "Structural Features Determining Flower-Promoting Activity of *Arabidopsis* Flowering Locus T," *The Plant Cell*, 26:552-564 (2014).
Holtorf et al., "Comparison of different constitutive and inducible promoters for the overexpression of transgenes in *Arabidopsis thaliana*," *Plant Molecular Biology*, 29(4):637-646 (1995).
Hsu et al., "Poplar FT2 Shortens the Juvenile Phase and Promotes Seasonal Flowering," *The Plant Cell*, 18:1846-1861 (2006).
International Search Report and Written Opinion dated Mar. 5, 2018 in International Application No. PCT/US17/57202.
Jaeger et al., "FT Protein Acts as a Long-Range Signal in *Arabidopsis*," *Current Biology*, 17:1050-1054 (2007).

Jaeger, et al., "Interlocking Feedback Loops Govern the Dynamic Behavior of the Floral Transition in *Arabidopsis*," *The Plant Cell*, 25:820-833 (2013).
Jiang et al., "Ligand Perception, Activation, and Early Signaling of Plant Steroid Receptor Brassinosteroid Insensitive 1," *JIPB*, 55(12):1198-1211 (2013).
Kojima et al., "Hd3a, a Rice Ortholog of the *Arabidopsis* FT Gene, Promotes Transition to Flowering Downstream of Hd1 under Short-Day Conditions," *Plant Cell Physiology*, 43(10):1096-1105 (2002).
Kong et al., "Two Coordinately Regulated Homologs of Flowering Locus T Are involved in the Control of Photoperiodic Flowering in Soybean," *Plant Physiology*, 154:1220-1231 (2010).
Larkin et al., "Clustal W and Clustal X version 2.0," *Bioinformatics*, 23(21):2947-2948 (2007).
Li et al., "Receptor-Like Kinases: Key Regulators of Plant Development and Defense," *JIPB*, 55(12):1184-1187 (2013).
Lifschitz et al., "The tomato FT ortholog triggers systemic signals that regulate growth and flowering and substitute for diverse environmental stimuli," *PNAS*, 103(16):6398-6403 (2006).
Lin et al., "Big Roles of Small Kinases: The Complex Functions of Receptor-Like Cytoplasmic Kinases in Plant Immunity and Development," *JIPB*, 55(12):1188-1197 (2013).
Mantegazza et al., "Analysis of the *Arabidopsis* REM gene family predicts functions during flower development," *Annals of Botany*, 114(7):1507-1515 (2014).
McGarry et al., "Manipulating plant architecture with members of the CETS gene family," *Plant Science*, 188/189:71-81 (2012).
Molinero-Rosales et al., "Single Flower Truss regulates the transition and maintenance of flowering in tomato," *Planta*, 218:427-434 (2004).
Niederhuth et al., "Letting Go Is Never Easy: Abscission and Receptor-Like Protein Kinases," *JIPB*, 55(12):1251-1263 (2013).
Parizotto et al., "In vivo investigation of the transcription, processing, endonucleolytic activity, and functional relevance of the spatial distribution of a plant miRNA," *Genes Dev.*, 18:2237-2242 (2004).
Pastore et al., "Late Meristem Identity2 acts together with LEAFY to activate APETALA1," *Development*, 138:3189-3198 (2011).
Patel et al., "BAR expressolog identification: expression profile similarity ranking of homologous genes in plant species," *The Plant Journal*, 71:1038-1050 (2012).
Shpak et al., "Stomatal Patterning and Differentiation by Synergistic Interactions of Receptor Kinases," *Science*, 309:290-293 (2005).
Shpak, E.D., "Diverse Roles of ERECTA Family Genes in Plant Development," *JIPB* 55(12):1238-1250 (2013).
Taoka et al., "14-3-3 proteins act as intracellular receptors for rice Hd3a florigen," *Nature*, 476:332-335 (2011).
Thompson et al., "CLUSTAL W: improving the sensitivity of progressive multiple sequence alignment through sequence weighting, position-specific gap penalties and weight matrix choice," *Nucleic Acids Research*, 22:4673-4680 (1994).
Toufighi et al., "The Botany Array Resource: e-Northerns, Expression Angling, and promoter analyses," *The Plant Journal*, 43:153-163 (2005).
Tränkner et al., "Over-expression of an FT-homologous gene of apple induces early flowering in annual and perennial plants," *Planta*, 232:1309-1324 (2010).
Turck et al., "Regulation and Identitiy of Florigen: Flowering Locus T Moves Center Stage," *Annu. Rev. Plant Biol.*, 59:573-594 (2008).
Vaucheret, H., "MicroRNA-Dependent Trans-Acting siRNA Production," *Science Signaling STKE*, 2005(300):pe43 (2005).
Wickland et al., "The Flowering Locus T/Terminal Flower 1 Gene Family: Functional Evolution and Molecular Mechanisms," *Molecular Plant*, 8:983-997 (2015).
Wierzba et al., "Notes from the Underground: Receptor-Like Kinases in *Arabidopsis* Root Development," *JIPB*, 55(12):1224-1237 (2013).
Wu et al., "Receptor-Like Kinases in Plant Innate Immunity," *JIPB*, 55(12):1271-1286 (2013).
Xiang et al., "Functional analysis of Flowering Locus T Orthologs from Spring Orchid (*Cymbidium goeringii* Rchb. f.) that regulates the vegetative to reproductive transition," *Plant Physiology and Biochemistry*, 58:98-105 (2012).

(56) References Cited

OTHER PUBLICATIONS

Yokoyama et al., "The *Arabidopsis* ERECTA gene is expressed in the shoot apical meristem and organ primordia," *The Plant Journal*, 15(3):301-310 (1998).
Yoshikawa et al., "A pathway for the biogenesis of trans-acting siRNAs in *Arabidopsis*," *Genes Dev.*, 19:2164-2175 (2005).
Zhai et al., "GmFT4, a Homolog of Flowering Locus T, Is Positively Regulated by E1 and Functions as a Flowering Repressor in Soybean," *PLoS ONE*, 9(2):e89030 (2014).
Zhang et al., "Structure-function Aspects of Extracellular Leucine-rich Repeat-containing Cell Surface Receptors in Plants," *JIPB*, 55(12):1212-1223 (2013).
Bartel, "MicroRNAs: Genomics, Biogenesis, Mechanism, and Function," *Cell*, 116:281-297 (2004).
Boutros et al., "Genome-Wide RNAi Analysis of Growth and Viability in *Drosophila* Cells," *Science*, 303:832-835 (2004).
Byrne, "Shoot Meristem Function and Leaf Polarity: The Role of Class III HD-ZIP Genes," *PLOS Genetics*, 2(6)e89:0785-0790 (2006).
Chen et al., "Functional analysis of regulatory elements in a plant embryo-specific gene," *Proc. Natl. Acad. Sci. USA*, 83:8560-8564 (1986).
Dietzl et al., "A genome-wide transgenic RNAi library for conditional gene inactivation in *Drosophila*," *Nature*, 448:151-157 (2007).
Gase et al., "Efficient screening of transgenic plant lines for ecological research," *Molecular Ecology Resources*, 11:890-902 (2011).
Goehring et al., "Screening and large-scale expression of membrane proteins in mammalian cells for structural studies," *Nat. Protoc.*, 9(11):2574-2585 (2014).
Greene et al., "Spectrum of Chemically Induced Mutations From a Large-Scale Reverse-Genetic Screen in *Arabidopsis*," *Genetics*, 164:731-740 (2003).
Guo et al., "Protein tolerance to random amino acid change," *PNAS*, 101(25):9205-9210 (2004).
Hormoz, "Amino acid composition of proteins reduces deleterious impact of mutations," Scientific Reports, 3:1-10 (2013).
Lee et al., "A systematic RNAi screen identifies a critical role for mitochondria in C. elegans longevity," *Nature Genetics*, 33:40-48 (2003).
Mallory et al., "MicroRNA control of PHABULOSA in leaf development: importance of pairing to the microRNA 5' region," *The EMBO Journal*, 23(16):3356-3364 (2004).
Montes et al., "Sample sequencing of vascular plants demonstrates widespread conservation and divergence of microRNAs," *Nature Communications*, 5(3722)1-15 (2014).
Rhoades et al., "Prediction of Plant MicroRNA Targets," *Cell*, 110:513-520 (2002).
Schwab et al., "Specific Effects of MicroRNAs on the Plant Transcriptome," *Developmental Cell*, 8:517-527 (2005).
Wilke et al., "Predicting the Tolerance of Proteins to Random Amino Acid Substitution," *Biophysical Journal*, 89:3714-3720 (2005).
Zhang, "miRU: an automated plant miRNA target prediction server," *Nucleic Acids Research*, 33:W701-W704 (2005).
Singh et al., "Primer Premier: Program for Design of Degenerate Primers from a Protein Sequence," *BioTechniques*, 24:318-319 (1998).
Danilevskaya et al., "A Genomic and Expression Compendium of the Expanded PEBP Gene Family from Maize" *Plant Physiology*, 146:250-264 (2008).
Efroni et al., "A Protracted and Dynamic Maturation Schedule Underlies *Arabidopsis* Leaf Development," *The Plant Cell*, 20:2293-2306 (2008).
International Search Report dated Oct. 14, 2016, in International Application No. PCT/US2016/028130.
Li et al., "Molecular characterization and functional analysis of a Flowering locus T homolog gene from a Phalaenopsis orchid," *Genetics and Molecular Research*, 13(3):5982-5994 (2014).

Lifschitz et al., "The tomato FT ortholog triggers systemic signals that regulate growth and flowering and substitute for diverse environmental stimuli," *Proceedings of the National Academy of Sciences*, 103:6398-6403 (2006).
Liu et al., "The Soybean Stem Growth Habit Gene Dt1 is an Ortholog of *Arabidopsis* Terminal Flower1," *Plant Physiology*, 153:198-210 (2010).
McGarry et al., "Geminivirus-Mediated Delivery of Florigen Promotes Determinate Growth in Aerial Organs and Uncouples Flowering from Photoperiod in Cotton," *PLOS One*, 7(5):e36746 (2012).
McGarry et al., "Virus-Induced Flowering: An Application of Reproductive Biology to Benefit Plant Research and Breeding," *Plant Physiology*, 173:47-55 (2017).
Mouradov et al., "Control of Flowering Time: Interacting Pathways as a Basis for Diversity," *The Plant Cell*, S111-S130 (2002).
Nan et al., "GmFT2a and GmFT5a Redundantly and Differentially Regulate Flowering through Interaction with and Upregulation of the bZIP Transcription Factor GmFDL19 in Soybean," *PLoS ONE*, 9(5):e97669 (2014).
Notaguchi et al., "Long-Distance, Graft-Transmissible Action of *Arabidopsis* Flowering Locus T Protein to Promote Flowering," *Plant Cell Physiology*, 49(11): 1645-1658 (2008).
Partial European Search Report dated Sep. 3, 2018, in European Application No. 16783657.6.
Ratcliffe et al., "A common mechanism controls the life cycle and architecture of plants," *Development*, 125:1609-1615 (1998).
Shani et al., "Stage-Specific Regulation of *Solanum lycopersicum* Leaf Maturation by Class 1 Knotted1-Like Homeobox Proteins," *The Plant Cell*, 21:3078-3092 (2009).
Shannon et al., "A Mutation in *Arabidopsis* TFL1 Gene Affects Inflorescence Meristem Development," *The Plant Cell*, 3:877-892 (1991).
Sun et al., "GmFT2a, a Soybean Homolog of Flowering Locus T, Is Involved in Flowering Transition and Maintenance," *PLoS ONE*, 6(12):e29238 (2011).
Caldwell et al., "A structured mutant population for forward and reverse genetics in Barley (*Hordeum vulgare* L.)," *Plant Journal*, 40:143-150 (2004).
Fahlgren et al., "P-SAMS: a web site for plant artificial microRNA and synthetic trans-acting small interfering RNA design," *Bioinformatics*, 32:157-158 (2016).
Guo et al., "RNA Silencing in Plants: Mechanisms, Technologies and Applications in Horticultural Crops," *Current Genomics*, 17:476-489 (2016).
Herrerra-Carrillo and Berkhout, "Dicer-independent processing of small RNA duplexes: mechanistic insights and applications," *Nucleic Acids Research*, 45:10369-10379 (Oct. 13, 2017).
Hilson et al., "Versatile Gene-Specific Sequence Tags for *Arabidopsis* Functional Genomics: Transcript Profiling and Reverse Genetics Applications," *Genome Research*, 14:2176-2189 (2004).
Huijser and Schmid, "The control of developmental phase transitions in plants," *Development*, 138:4117-4129 (2011).
Sessions et al., "A High-Throughput *Arabidopsis* Reverse Genetics Screen," *Plant Cell*, 14:2985-2994 (2002).
Wang and Malcolm, "Two-Stage PCR Protocol Allowing Introduction of Multiple Mutations, Deletions and Insertions Using QuickChangeTM Site-Directed Mutagenesis," *Biotechniques*, 26:680-682 (1999).
Yeoh, C. C. et al. (2011). "Developing a Method for Customized Induction of Flowering," BMC Biotechnol. 11 (36):1-11.
GenBank Accession No. AB550122, last updated Mar. 10, 2010, located at https://www.ncbi.nlm.nih.gov/nuccore/AB550122.1/, last visited on Jun. 24, 2022, two pages.
Mathieu, J. et al. (Jun. 19, 2007). "Export of FT Protein from Phloem Companion Cells Is Sufficient for Floral Induction in *Arabidopsis*," Current Biology 17:1055-1060.
McGarry, R. C. et al. (Apr. 2013). "Phloem-mobile Signals Affecting Flowers: Applications for Crop Breeding," Trends Plant Sci. 18(4): 198-206.

(56) References Cited

OTHER PUBLICATIONS

Tsuji, H. et al. (Mar. 21, 2013). "Structure and Function of Flowering Hormone 'Florigen'," located at http://leading.lifesciencedb.jp/2-e004, last visited on Nov. 4, 2021, 12 pages.

* cited by examiner

| | SEQUENCE | 1 | 2 | 3 | 4 | 5 | 6 | 7 | 8 | 9 | 10 |
|---|---|---|---|---|---|---|---|---|---|---|---|
| 1 | Gm.FT2a | - | 90.6 (481) | 69.5 (369) | 71 (377) | 66.7 (354) | 60.6 (322) | 68.7 (365) | 64.2 (341) | 73.4 (390) | 66.5 (353) |
| 2 | Gm.FT2b | 90.6 (481) | - | 67.6 (359) | 69.9 (371) | 64.2 (341) | 58.4 (310) | 65.9 (350) | 62 (329) | 70.4 (374) | 65.9 (350) |
| 3 | Nt.FT | 70.3 (369) | 68.4 (359) | - | 76.6 (402) | 67.4 (354) | 58.5 (307) | 67 (352) | 62.9 (330) | 73.7 (387) | 67.8 (356) |
| 4 | Le.FT | 70.6 (377) | 69.5 (371) | 75.3 (402) | - | 67.4 (360) | 60.1 (321) | 67.4 (360) | 64.6 (345) | 73 (390) | 66.9 (357) |
| 5 | Gm.FT5A | 68.2 (354) | 65.7 (341) | 68.2 (354) | 69.4 (360) | - | 61.1 (317) | 65.9 (342) | 62.6 (325) | 70.7 (367) | 65.7 (341) |
| 6 | Zm.ZCN8 | 61 (322) | 58.7 (310) | 58.1 (307) | 60.8 (321) | 60 (317) | - | 57 (301) | 59.3 (313) | 61.4 (324) | 56.3 (297) |
| 7 | At.FT | 69.1 (365) | 66.3 (350) | 66.7 (352) | 68.2 (360) | 64.8 (342) | 57 (301) | - | 65.9 (348) | 72.5 (383) | 82.2 (434) |
| 8 | Os.HD3A | 63.1 (341) | 60.9 (329) | 61.1 (330) | 63.9 (345) | 60.2 (325) | 58 (313) | 64.4 (348) | - | 71.1 (384) | 63.9 (345) |
| 9 | Pt.FT | 74.3 (390) | 71.2 (374) | 73.7 (387) | 74.3 (390) | 69.9 (367) | 61.7 (324) | 73 (383) | 73.1 (384) | - | 71.8 (377) |
| 10 | At.TSF | 66.9 (353) | 66.3 (350) | 67.4 (356) | 67.6 (357) | 64.6 (341) | 56.3 (297) | 82.2 (434) | 65.3 (345) | 71.4 (377) | - |

FIG. 1A

| SEQUENCE | | 1 | 2 | 3 | 4 | 5 | 6 | 7 | 8 | 9 | 10 |
|---|---|---|---|---|---|---|---|---|---|---|---|
| 1 | Gm.FT2a | - | 90.9 (160) | 74.4 (131) | 79.5 (140) | 65.6 (116) | 60.2 (106) | 72.2 (127) | 76.7 (135) | 80.7 (142) | 71.6 (126) |
| 2 | Gm.FT2b | 90.9 (160) | - | 72.2 (127) | 75.6 (133) | 61.9 (109) | 57.4 (101) | 71.6 (126) | 71.6 (126) | 76.1 (134) | 71 (125) |
| 3 | Nt.FT | 75.3 (131) | 73 (127) | - | 77.6 (135) | 65.5 (114) | 59.2 (103) | 74.1 (129) | 71.8 (125) | 77.6 (135) | 72.4 (126) |
| 4 | Le.FT | 79.1 (140) | 75.1 (133) | 76.3 (135) | - | 66.1 (117) | 59.3 (105) | 75.7 (134) | 79.1 (140) | 84.7 (150) | 75.1 (133) |
| 5 | Gm.FT5a | 67.4 (116) | 63.4 (109) | 66.3 (114) | 68 (117) | - | 58.7 (101) | 65.1 (112) | 65.1 (112) | 69.2 (119) | 67.4 (116) |
| 6 | Zm.ZCN8 | 60.6 (106) | 57.7 (101) | 58.9 (103) | 60 (105) | 57.7 (101) | - | 56.6 (99) | 58.3 (102) | 62.3 (109) | 56.6 (99) |
| 7 | At.FT | 72.6 (127) | 72 (126) | 73.7 (129) | 76.6 (134) | 64 (112) | 56.6 (99) | - | 71.4 (125) | 77.7 (136) | 81.7 (143) |
| 8 | Os.HD3A | 75.4 (135) | 70.4 (126) | 69.8 (125) | 78.2 (140) | 62.6 (112) | 57 (102) | 69.8 (125) | - | 79.3 (142) | 69.8 (125) |
| 9 | Pt.FT | 81.6 (142) | 77 (134) | 77.6 (135) | 86.2 (150) | 68.4 (119) | 62.6 (109) | 78.2 (136) | 81.6 (142) | - | 75.9 (132) |
| 10 | At.TSF | 72 (126) | 71.4 (125) | 72 (126) | 76 (133) | 66.3 (116) | 56.6 (99) | 81.7 (143) | 71.4 (125) | 75.4 (132) | - |

*FIG. 1B*

CLUSTAL 2.0.9 MULTIPLE SEQUENCE ALIGNMENT

```
Gm.FT2a    MPS---GSRDPLVVGGVIGDVLDPFEYSIPMRVTYNNRDVSNGCEEKPSQVVNQPRVNIGG
Gm.FT2b    MPR---GSRDPLVVGRVIGDVLDPEECSIPMRVTYNNKDVSNGCEEKPSQVVNQPRINIGG
Le.FT      MP----RERDPLVVGRVVGDVLDPFTRTIGLRVIYRDREVNNGCELRPSQVINQPRVEVGG
Pt.FT      MS----RDRDPLSVGRVIGDVLDPFTKSISLRVTYSSREVNNGCELKPSQVANQPRVDIGG
Os.HD3a    MAGSGRDRDPLVGRVVGDVLDAFVRSTNLKVTYGSKTVSNGCELKPSMVTHQPRVEVGG
At.FT      MS---INIRDPLIVSRVVGDVLDPFNRSITLKVTYGQREVTNGLDLRPSQVQNKPRVEIGG
At.TSF     MS---LSRRDPLVVGSVVGDVLDPFTRLVSLKVTYGHREVTNGLDLRPSQVLNKPIVEIGG
Nt.FT      ------MPRIDPLIVGRVVGDVLDPFTRSVDLRVVYNNREVNNACGLKPSQIVTQPRVQIGG
Gm.FT5a    ------MARENPLIVIGGVIGDVLNPFTSSVSLTVSINNRAISNGLELRPSQVNRPRVTVGG
Zm.ZCN8    ------MSATDHLVMARVIQDVLDPFTPTIPLRITYNNRLLLPSAELKPSAVVSKPRVDIGG
                      *  :  ****:.*

Gm.FT2a    DDLRNFYTLIAVDPDAPSPSDPNLREYLHWLVTDIPATTGASFGHEVVTYESPRPMMGIH
Gm.FT2b    DDFRNFYTLIAVDPDAPSPSDPNLREYLHWLVTDIPATTGPTFGHEVVTYENPRPMMGIH
Le.FT      DDLRTFFTLVMVDPDAPSPSDPNLREYLHWLVTDIPATTGSSFGQEIVSYESPRPSMGIH
Pt.FT      EDLRTFYTLVMVDPDAPSPSDPSLREYLHWLVTDIPATTGASFGHETVCYESPRPTMGIH
Os.HD3a    NDMRTFYTLVMVDPDAPSPSDPNLREYLHWLVTDIPGTTAASFGQEVMCYESPRPTMGIH
At.FT      EDLRNFYTLVMVDPDVPSPSNPHLREYLHWLVTDIPGTTFGNEIVCYENPSPTAGIH
At.TSF     DDFRNFYTLVMVDPDVPSPSNPNFEVLHWLVTDIPATTGPTFGHEVVTYENPRPMMGIH
Nt.FT      DDLRNFYTLVMVDPDAPSPSNPHQREYLHWLVTDIPATTGNAFGNEVVCYESPRPPSGIH
Gm.FT5a    EDLRTFYTLVMVDADAPSPSNPVLREYLHWMVTDIPATTDTSFGNEVICYENPQPSLGIH
Zm.ZCN8    SDMRAFYTLVLIDPDAPSPSHPSLREYLHMVTDIPETTSVNFGQELIFYERPDPRSGIH
            .:* *:**:: :.** *****.* :* :***::*** .**:* *  * *    * ***
```

FIG. 1C

```
Gm.FT2a   RLVFVLFRQLGRETVYAPGWRQNFNTKEFAELYNLGLPVAAVYFNIQRESGSGGRRLY--    176
Gm.FT2b   RIVFVLFRQQGRETVYAPGWRQNFITREFAELYNLGLPVAAVYFNIQRESGCGGRRLC--    176
Le.FT     REVFVLFRQLGRQTVYAPGWRQNFNTRDFAELYNLGLPVAAVYFNCQRESGSGGRRSAD    177
Pt.FT     REVFVLFRQLGRQTVYAPGWRQNFNTRDFAEVYNLGSPVAAVYFNCQRESGSGGRRR--    174
Os.HD3a   RLVFVLFRQLGRQTVYAPGWRQNFNTKDFAELYNLGSPVAAVYFNCQREAGSGGRRVYP-    179
At.FT     RVVFILFRQLGRQTVYAPGWRQNFNTREFAETYNLGLPVAAVYFNCQRESGCGGRRL---    175
At.TSF    RIVLVLFRQLGRQTVYAPGWRQQFNTREFAEIYNLGLPVAASYFNCQRENGCGGRRT---    175
Nt.FT     REVFVLFRQLGRETVYAPGWRQNFSTRDFAEVYNLGLPVSAVYFNCHRESGTGGRRAY--    174
Gm.FT5a   RIVFVLFQQLGRDTVITPEMRHNENSRNFAEINNL-APVAAAYANCQRERGCGGRRY---    172
Zm.ZCN8   RLVFVLFRQLGRGTVFAPEMRHNFNCRSFARQYHLSIATAT-HFNCQREGGSGGRRFEE    175
          *.*.::***:* ** ***.:   .*: . ..*:      .   ::: .  * ****
```

FIG. 1C  
CONTINUED pAt.Erecta::Gm.FT2a    pAt.Erecta::Gm.FT2a /
                       pAP1::miRNA-FT2a::T-Apx pAt.Erecta::Gm.FT2a        pAt.Erecta::Gm.FT2a
                            + miR172 target site

COMPOSITIONS AND METHODS FOR ALTERING FLOWERING AND PLANT ARCHITECTURE TO IMPROVE YIELD POTENTIAL

CROSS-REFERENCE TO RELATED APPLICATIONS

This application claims the benefit of priority of U.S. Provisional Application No. 62/410,355, filed Oct. 19, 2016 and U.S. Provisional Application No. 62/411,408, filed Oct. 21, 2016, both of which are incorporated by reference in their entireties herein.

FIELD OF THE INVENTION

The present invention relates to compositions and methods for modulating floral development and vegetative growth by genetic modification of crop plants to increase yield.

INCORPORATION OF SEQUENCE LISTING

A sequence listing contained in the file named P34461US02_SEQ.txt which is 177,799 bytes (measured in MS-Windows®) and created on Oct. 18, 2017, comprises 110 nucleotide sequences, is filed electronically herewith and incorporated by reference in its entirety.

BACKGROUND

The transition from vegetative growth to flowering is a crucial process during plant development that is necessary for the production of grain yield in crop plants. There are several major pathways controlling flowering time in land plants that respond to environmental or developmental cues, including photoperiodism (i.e., day length), vernalization (i.e., response to winter cold), and plant hormones (e.g., gibberellins or GA), in addition to the autonomous (environmentally independent) pathways. Molecular networks controlling flowering time in plants involve the vernalization and photoperiod pathways. Under inductive photoperiodic conditions, CONSTANS (CO) activity in source leaves increases expression of FLOWERING LOCUS T (FT), which translocates to the meristem to trigger expression of downstream floral activating genes, including LEAFY (LFY), APETALA1 (AP1) and SUPPRESSOR OF OVEREXPRESSION OF CO 1 (SOC1). Other genes, such as FLOWERING LOCUS C (FLC) and TERMINAL FLOWER 1 (TFL1), act to inhibit the expression or activity of these genes.

Except for day length neutral plants, most flowering plants respond to daily photoperiodic cycles and are classified as either short day (SD) or long day (LD) plants based on the photoperiod conditions required to induce flowering. The photoperiod refers to the relative length or duration of light and dark periods within a 24-hour cycle. In general, long day plants tend to flower when the day length exceeds a photoperiod threshold (e.g., as the days are getting longer in the spring), whereas short day plants tend to flower when the day length falls below a photoperiod threshold (e.g., as the days are getting shorter after the summer solstice). In other words, SD plants flower as the days are getting shorter, while LD plants flower as the days are getting longer. Soybean is an example of a short day (SD) plant in which flowering is induced when plants are exposed to shorter daylight conditions.

Plant growers are always looking for new methods to manipulate the yield of a plant, especially to enhance the seed yield of agronomically important crops. Thus, there is a continuing need in the art for improved compositions and methods for increasing yields of various crop plants. It is presently proposed that improved crop yields may be achieved by enhancing agronomic traits related to flowering and reproductive development.

SUMMARY

According to an aspect, the present disclosure provides a recombinant DNA construct comprising a first expression cassette and a second expression cassette, wherein the first expression cassette comprises a polynucleotide sequence encoding a florigenic FT protein operably linked to a first plant expressible promoter, and the second expression cassette comprises a transcribable DNA sequence encoding a RNA molecule comprising a targeting sequence that is at least 80% complementary to at least 15 consecutive nucleotides of the polynucleotide sequence of the first expression cassette, and wherein the transcribable DNA sequence is operably linked to a second plant expressible promoter.

According to an aspect, the present disclosure provides a recombinant DNA construct comprising a polynucleotide sequence encoding a florigenic FT protein operably linked to a plant expressible promoter, wherein the polynucleotide sequence comprises a sequence that encodes a target site or sensor in a mRNA transcript encoded by the polynucleotide sequence, and wherein the target site of the mRNA transcript is at least 80% complementary to an endogenous RNA molecule, such as an endogenous miRNA or siRNA molecule.

According to an aspect, the present disclosure provides a recombinant DNA construct comprising a transcribable DNA sequence encoding a RNA molecule comprising a targeting sequence that is at least 80% complementary to at least 15 consecutive nucleotides of a polynucleotide sequence encoding a florigenic FT protein, wherein the transcribable DNA sequence is operably linked to plant expressible promoter.

According to an aspect, the present disclosure provides transgenic plants, plant cells, plant tissues, and plant parts comprising an insertion of a recombinant DNA construct of the present disclosure into the genome of such plants, plant cells, plant tissues, and plant parts.

According to an aspect, the present disclosure provides methods for producing a transgenic plant comprising (a) transforming at least one cell of an explant with a recombinant DNA construct of the instant disclosure; and (b) regenerating or developing the transgenic plant from the transformed explant. The methods may further comprise (c) selecting a transgenic plant having one or more of the following traits or phenotypes: earlier flowering, longer reproductive or flowering duration, increased number of flowers per node, increased number of floral racemes per node, increased number of pods, bolls, siliques, fruits, or nuts per node, and increased number of seeds per node, as compared to a control plant not having the recombinant DNA construct.

According to an aspect, the instant disclosure provides methods of planting a transgenic crop plant, comprising planting the transgenic crop plant at a higher density in the field, where the transgenic crop plant comprises an insertion of a recombinant DNA construct of the instant disclosure.

According to an aspect, the present disclosure provides a transgenic plant comprising a polynucleotide sequence encoding a polynucleotide sequence encoding a florigenic FT protein operably linked to a first plant expressible promoter, and the second expression cassette comprises a transcribable DNA sequence encoding a RNA molecule comprising a targeting sequence that is at least 80% complementary to at least 15 consecutive nucleotides of the polynucleotide sequence of the first expression cassette, and wherein the transcribable DNA sequence is operably linked to a second plant expressible promoter. According to an aspect, the present disclosure provides a transgenic plant comprising a transcribable DNA sequence encoding a RNA molecule comprising a targeting sequence that is at least 80% complementary to at least 15 consecutive nucleotides of a polynucleotide sequence encoding a florigenic FT protein, wherein the transcribable DNA sequence is operably linked to plant expressible promoter.

According to an aspect, the present disclosure provides a transgenic plant may have more seeds, pods, bolls, siliques, fruits, nuts or tubers per node on average than a non-transgenic control plant, such as an average of at least 1%, at least 2%, at least 5%, at least 10%, at least 15%, at least 20%, at least 25%, at least 30%, at least 35%, at least 40%, at least 45%, at least 50%, at least 60%, at least 70%, at least 75%, at least 80%, at least 90%, at least 100%, at least 125%, at least 150%, at least 175%, at least 200%, at least 250%, at least 300%, at least 350%, or at least 400% more seeds, pods, bolls, siliques, fruits, nuts or tubers per node than a non-transgenic control plant. According to an aspect, a transgenic plant may have an average of at least 2, at least 3, at least 4, at least 5, at least 6, at least 7, at least 8, at least 9, or at least 10 more seeds, pods, bolls, siliques, fruits, nuts or tubers per node than a non-transgenic control plant. According to an aspect, a transgenic plant may have an average of 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, or 4 to 5 more seeds, pods, bolls, siliques, fruits, nuts or tubers per node than a non-transgenic control plant. According to an aspect, a transgenic plant may have an average of at least 1, at least 2, at least 3, at least 4, at least 5, at least 6, at least 7, at least 8, at least 9, or at least 10 more seeds, pods, bolls, siliques, fruits, nuts or tubers per node as compared to a wild type or non-transgenic control plant. According to an aspect, a transgenic plant may flower at least 1, at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, or at least 45 days earlier than a non-transgenic control plant.

According to an aspect, the present disclosure provides a transgenic plant is provided comprising a polynucleotide sequence encoding a florigenic FT protein operably linked to a vegetative stage promoter, wherein expression of the florigenic FT protein is suppressed in a late vegetative and/or reproductive tissue.

According to an aspect, the present disclosure provides a recombinant DNA construct is provided comprising a polynucleotide sequence encoding a florigenic FT protein and operably linked to a vegetative stage promoter, and at least one sequence encoding an RNA targeting sequence that is complementary to at least a portion of the polynucleotide sequence.

According to an aspect, the present disclosure provides a transgenic plant is provided comprising a recombinant polynucleotide sequence encoding a florigenic FT protein operably linked to a vegetative stage promoter, wherein expression of the polynucleotide sequence is spatially and temporally restricted by a small RNA molecule.

According to an aspect, the present disclosure provides a recombinant DNA construct is provided comprising an expression cassette, wherein the expression cassette comprises a polynucleotide sequence encoding a florigenic FT protein operably linked to a promoter, wherein the promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to a polynucleotide sequence selected from the group consisting of SEQ ID NOs: 39, 40, 41, 42, 43, 44, 45, 46, 47, 48, 49, 50, 51, 52, 53 or 54, or a functional portion thereof.

BRIEF DESCRIPTION OF THE DRAWINGS

FIG. 1A provides a matrix table showing a comparison of nucleotide sequences for each combination of the various FT genes including their percent identity.

FIG. 1B provides a matrix table showing a comparison of protein sequences for each combination of the various FT proteins including their percent identity.

FIG. 1C provides a CLUSTAL 2.0.9 multiple sequence alignment of various FT proteins identified as Gm.FT2a with SEQ ID NO: 2, Gm.FT2b with SEQ ID NO: 6, Le.FT with SEQ ID NO: 12, Pt.FT with SEQ ID NO: 20, Os.HD3a with SEQ ID NO: 18, At.FT with SEQ ID NO: 14, At. TSF with SEQ ID NO: 16, Nt.FT with SEQ ID NO: 10, Gm.FT5a with SEQ ID NO: 4 and Zm.ZCN8 with SEQ ID NO: 8.

FIGS. 3A to 3O are a set of black and white images of stained tissues, and the images in FIGS. 4A to 4O correspond to FIGS. 3A to 3O but are filtered for blue GUS staining. FIGS. 3A to 3C and 4A to 4C show expression in a 3-day-old germinating seedling; FIGS. 3M to 3O and 4M to 4O show expression in the 30 d old mature and immature leaves of the reproductive shoot. Bars are 100 μm.

FIGS. 5A to 5F are a set of black and white images of stained tissues, and the images in FIGS. 6A to 6F correspond to FIGS. 5A to 5F but are filtered for blue GUS staining. FIGS. 5A and 6A show expression in the inflorescence stems or pedicels (arrows), and FIGS. 5B and 6B show expression in the floral peduncle (arrows). Expression is also shown in the vasculature and parenchyma cells (FIGS. 5C and 6C), in stamen filaments (FIGS. 5D and 6D; arrow), and un-pollinated ovules (FIGS. 5E, 5F, 6E and 6F; arrows). Bars are 1 mm.

FIG. 9A depicts a null segregant showing normal axillary buds, whereas FIG. 9B and FIG. 9C (corresponding to plants homozygous or hemizygous for the Gm.FT2a transgene, respectively) each show early flowering and increased pods per node relative to the null segregant.

DETAILED DESCRIPTION

Figure 2:
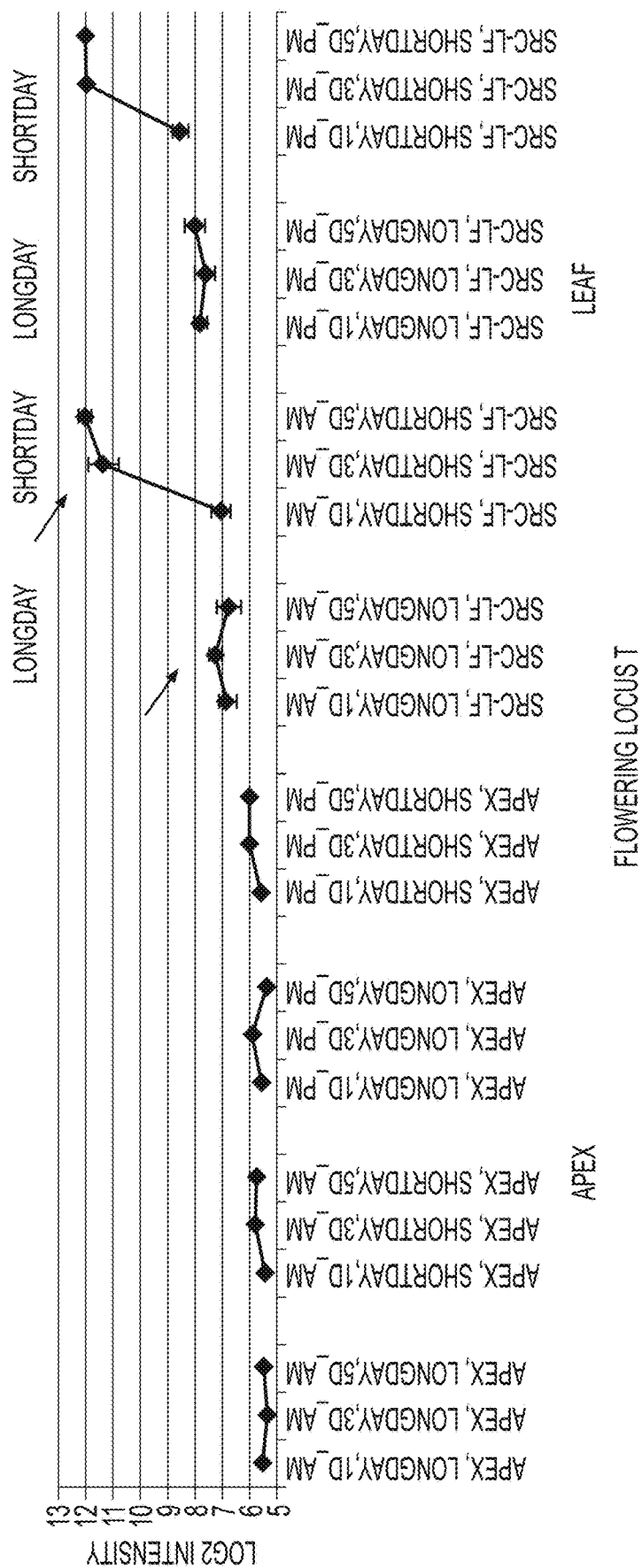
FIG. 2 shows the total FT transcript levels in soybean leaf and apex tissues collected at 1, 3 and 5 days after either a short day or long day light treatment.
Figure 3A:
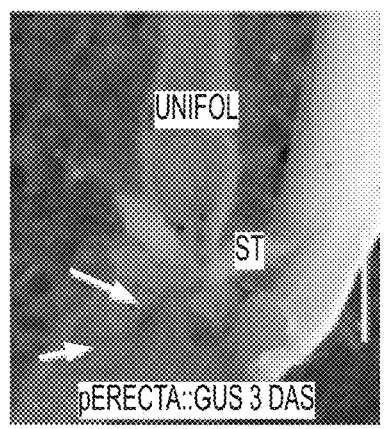
FIGS. 3A to 3O and FIGS. 4A to 4O show the expression pattern of the pAt.Erecta promoter by monitoring GUS activity during early soybean development.
Figure 3B:
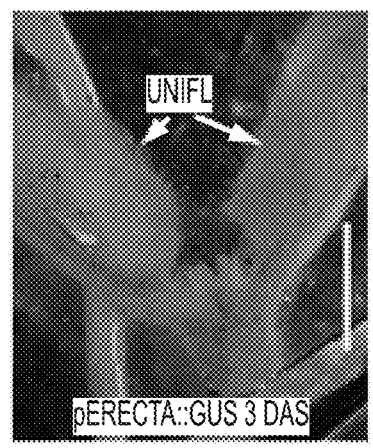
Figure 3C:
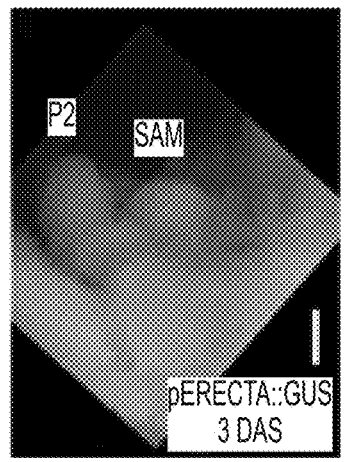
Figure 3D:
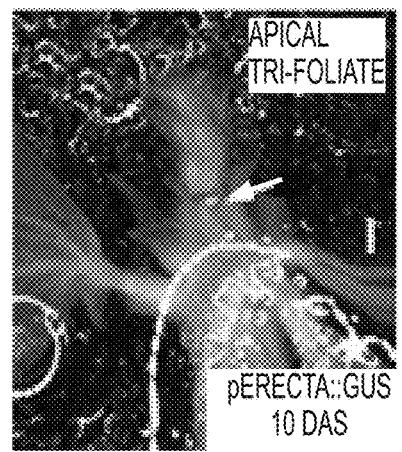
FIGS. 3D to 3I and 4D to 4I show expression in a 10-day-old vegetative shoot (grown in 14 hour light/10 hour dark photoperiod)
Figure 3E:
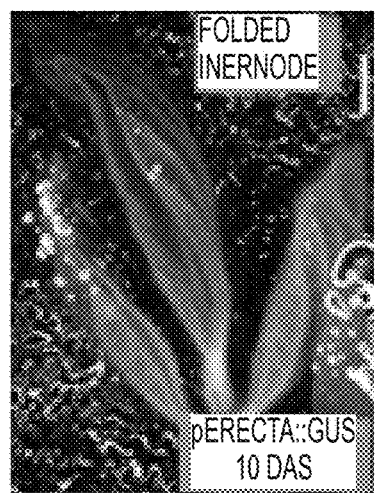
Figure 3F:
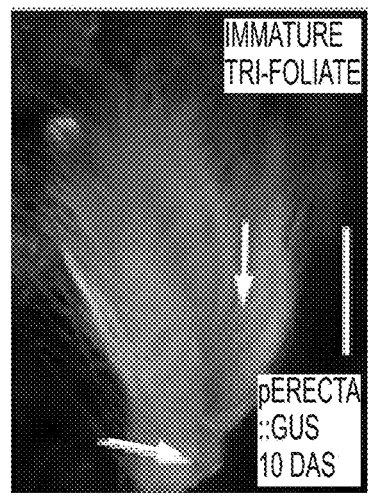
Figure 3G:
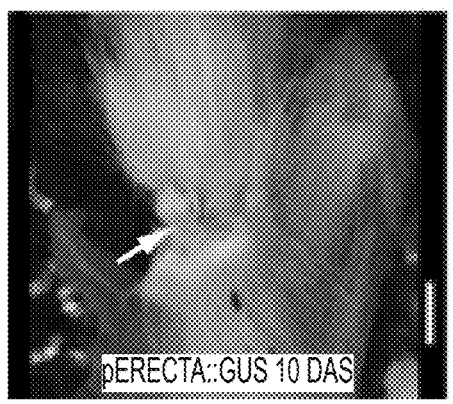
Figure 3H:
Figure 3I:
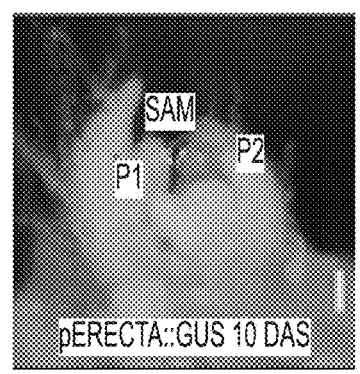
Figure 3J:
FIGS. 3J to 3L and 4J to 4L show expression in a 16-day-old reproductive shoot.
Figure 3K:
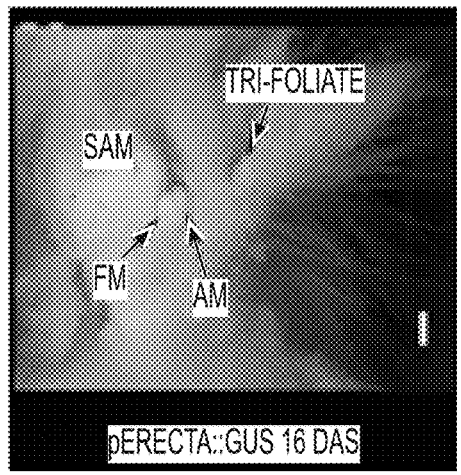
Figure 3L:
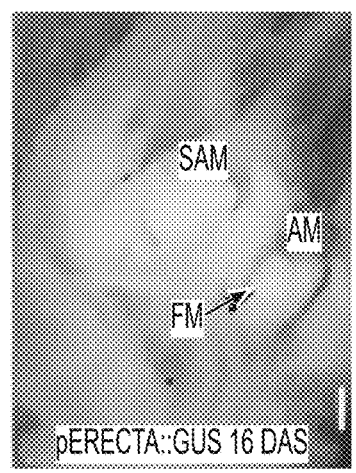
Figure 3M:
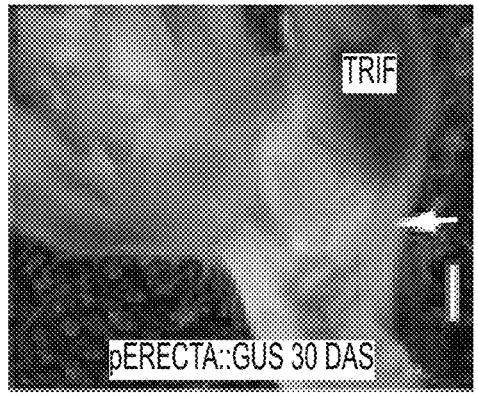
Figure 3N:
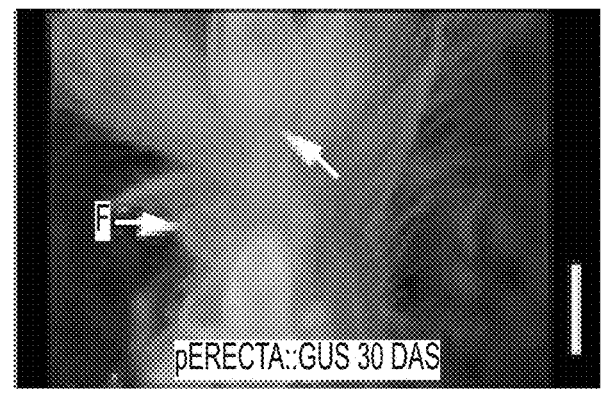
Figure 3O:

The goal of improving yield is common to all crops across agriculture. The present invention includes methods and compositions for improving yield in flowering (angiosperm) or seed-bearing plants by modification of traits associated with flowering time, reproductive development, and vegetative growth to improve one or more flowering and/or yield-related traits or phenotypes, such as the number of flowers, seeds and/or pods per plant, and/or the number of flowers, seeds and/or pods per node (and/or per main stem) of the plant. Without being bound by any theory, compositions and methods of the present invention may operate to improve yield of a plant by increasing the number of floral meristems, increasing synchronization of lateral meristem release, and/or extending the time period for pod or seed development in the plant (e.g., reproductive duration).

Previously, it was discovered that growing short day plants, such as soybean, under long day conditions (e.g., about 14-16 hours of light per day) and then briefly subjecting those plants to short day growing conditions (e.g., about 9-11 hours of light per day for about 3-21 days) before returning the plants to long day (non-inductive) growing conditions, produced plants having increased numbers of pods/seeds per plant (and pods/seeds per node and/or per branch). See, e.g., U.S. Pat. No. 8,935,880 and U.S. Patent Application Publication No. 2014/0259905, the entire contents and disclosures of which are incorporated herein by reference. The artificial early "short day" inductive light treatments during vegetative stages of development revealed not only that flowering time could be altered in a way that alters one or more yield-related traits or phenotypes (e.g., by causing an increased number of pods or seeds per node on a plant), but also that the effect of these treatments was dosage-dependent with the number of flowers, seeds and/or pods per plant (and/or per node of the plant) depending on (i) the duration of the short day exposure (i.e., floral induction signal dosage) and (ii) the length of the post-short day photoperiods under long day conditions (i.e., the dosage or length of the vegetative growth inducing signal after the short day induction signal). Soybean plants experiencing a lower or less prolonged early short day induction (eSDI) treatment (prior to returning to long day growing conditions) had more flowers, pods and seeds per plant with more normal plant height and maturity, whereas soybean plants exposed to a greater or more prolonged eSDI treatment produced shorter, earlier-terminating plants with fewer pods and seeds per plant (albeit perhaps with an increased number of pods and/or seeds per node).

This short day induction phenotype in soybean was used to identify genes having altered expression in these plants through transcriptional profiling. These studies identified several genes with altered expression in these treated soybean plants including an endogenous FT gene, Gm.FT2a, having increased expression in response to the short day induction treatment. Thus, it is proposed that transgenic FT expression may be used in place of short day induction to increase seed yield, alter reproductive traits or phenotypes in plants, or both. Ectopic expression of a Gm.FT2a transgene or other FT sequence, or a functional fragment, homolog or ortholog thereof, in a flowering or seed-bearing plant may be used to increase seed yield and/or alter one or more reproductive phenotypes or traits, which may involve an increase in the number of pods/seeds per plant (and/or the number of pods/seeds per node or main stem of the plant). As explained further below and depending on the particular plant species, these yield-related or reproductive phenotypes or traits may also apply to other botanical structures analogous to pods of leguminous plants, such as bolls, siliques, fruits, nuts, tubers, etc. Thus, a plant ectopically expressing a FT sequence may instead have an increased number of bolls, siliques, fruits, nuts, tubers, etc., per node(s), main stem, and/or branch(es) of the plant, and/or an increased number of bolls, siliques, fruits, nuts, tubers, etc., per plant.

Flowering Locus T (FT) genes play a key role in higher plants and function to integrate floral pathways. FT proteins have been shown to function as a mobile signal or florigen transported from leaves to the shoot apical apex where it triggers initiation of reproductive development in diverse species. See, e.g., Jaeger, K. E. et al., "Interlocking feedback loops govern the dynamic behavior of the floral transition in *Arabidopsis*," *The Plant Cell*, 25:820-833 (2013); Corbesier, L et al., "FT protein movement contributes to long distance signaling in floral induction of *Arabidopsis*," *Science* 316: 1030-1033 (2007); Jaeger, K E et al., "FT protein acts as a long range signal in *Arabidopsis*," *Curr Biol* 17: 1050-1054 (2007); and Amasino, R. M. et al., "The Timing of Flowering," *Plant Physiology*, 154(2):516-520 (2010), the entire contents and disclosures of which are incorporated herein by reference. In *Arabidopsis*, FT protein binds to 14-3-3 and Flowering Locus D (FD) proteins in the meristem to form a flowering complex triggering activation of key floral meristem identity genes, such as APETATAL1 (AP1) and SOC1 at the shoot apex. See, e.g., Taoka, K. et al., "14-3-3 protein act as intracellular receptors for rice Hd3a florigen." *Nature* 476:332-335 (2011). The TERMINAL FLOWER 1 (TFL1) gene is a key repressor of FT targets that maintains the center of the shoot apical meristem (SAM) in a vegetative state. TFL1 acts by repressing the LEAFY (LFY) and AP1 genes. Thus, the relative concentrations of FT and TFL1 in the target tissues act competitively to control the timing of the reproductive transition of meristems from a vegetative state that may terminate further vegetative growth. See, e.g., Abe, M et al., *Science* 309: 1052-1055 (2005); and McGarry, R C et al., *Plant Science* 188/189: 71-81 (2012).

FT genes have been identified from many diverse species, and ectopic FT expression has been reported to induce early flowering. See, e.g., Kong, F. et al., "Two Coordinately Regulated Homologs of Flowering Locus T Are Involved in the Control of Photoperiodic Flowering in Soybean," *Plant*

*Physiology* 154: 1220-1231 (2010); Turck, F. et al., "Regulation and identity of florigen: Flowering Locus T moves center stage," *Ann Rev Plant Biol* 59: 573-594 (2008); Blackman, B K et al., "The role of recently derived FT paralogs in sunflower domestication," *Curr Biol* 20: 629-635 (2010); Lifschitz, E. et al., "The tomato FT orthologs triggers systemic signals that regulate growth and flowering and substitute for diverse environmental stimuli," PNAS 103: 6398-6403 (2006); Trankner, C. et al., "Over-expression of an FT-homologous gene of apple induces early flowering in annual and perennial plants," *Planta* 232: 1309-1324 (2010); and Xiang, L. et al., "Functional analysis of Flowering Locus T orthologs from spring orchid (*Cymbidium goeringii* Rchb. f.) that regulates the vegetative to reproductive transition," *Plant Cell & Biochem* 58: 98-105 (2012), the entire contents and disclosures of which are incorporated herein by reference. However, prior studies with expression of FT transgenes used constitutive or tissue specific promoters that produced either very severe phenotypes, non-cell autonomous (systemic) phenotypes, or autonomous leaf specific phenotypes with plants or seedlings flowering earlier than controls and terminating at early stages of development. Given these findings, ectopic FT expression was generally not seen as a viable approach to increasing yield in plants by inducing flowers or altering flowering time.

Without being bound by theory, an early florigenic signal (e.g., short days for soybean and other SD plants) may trigger an early vegetative to reproductive transition in plants but may also cause termination of a subset of its primary meristems. However, by returning those plants to non-inductive growth conditions (e.g., long days for SD plants) after the initial SD signal, the remaining meristematic reserves of the plant may be preserved to allow for continued vegetative growth of the plant. Thus, a greater number of productive flowers, pods and/or seeds per node (and/or per plant) may develop during the extended reproductive phase. With early floral induction, a greater overlap may also be created between reproductive development and vegetative growth of the plant, which may further promote or coincide with an extended reproductive and/or flowering duration. As used herein, "reproductive duration" refers to the length of time from the initiation of flowering until the end of seed/pod development and/or filling, whereas "flowering duration" or "duration of flowering" refers the length of time from the appearance of the first open flower until the last open flower closes. By returning to non-inductive growth conditions after early floral induction, more abundant resources may be available and directed toward the production of an increased number of earlier synchronized and successful (i.e., non-aborting) flowers, pods and/or seeds per plant, unlike normal floral development in short day plants, which may later coincide with declining plant resources due to termination of meristematic growth and maturation of the plant.

As mentioned above, however, a floral induction signal (e.g., early short day conditions) may also cause early termination of the plant in addition to early flowering. Therefore, it is proposed that an optimal dosage and timing of the floral induction signal may be needed to maximize yield by balancing (i) the early vegetative to reproductive transition and/or synchronization of flowering with the early floral induction signal (leading to potential yield gains at each node of the plant) against (ii) earlier growth termination (leading to smaller plants with fewer internodes, less branching, and fewer nodes and/or flowers per plant). Lower dosages of a floral induction signal may be sufficient to induce flowering while lessening or minimizing earlier termination of the plant, such that larger plants are produced with increased numbers of flowers, pods and/or seeds per node (and/or per plant). On the other hand, higher dosages of a floral induction signal may cause early termination of the plant (in addition to early flowering) to produce smaller plants with relatively fewer numbers of flowers, pods and/or seeds per plant due to the smaller plant size with fewer internodes and/or branches per plant, despite having perhaps a greater number of flowers, pods and/or seeds per node (and/or per plant) relative to wild-type or control plants under normal growth conditions. As stated above, these effects of ectopic FT expression may also include an increased number of bolls, siliques, fruits, nuts, tubers, etc., per node (and/or per plant), depending on the particular plant species.

The "short day" light induction phenotype mentioned above in soybean was used to screen for genes having altered expression in those plants through transcriptional profiling, which led to the identification of an endogenous FT gene, Gm.FT2a, having increased expression in response to the short day induction treatment. Accordingly, it is proposed that expression of a florigenic FT transgene, such as Gm.FT2a, may be used as a floral induction signal to cause early flowering and increased flowers, pods and/or seeds per node (and/or per plant) relative to a wild type or control plant not having the FT transgene. According to embodiments of the present invention, appropriate control of the timing, location and dosage of florigenic FT expression during vegetative stages of development can be used to induce flowering and produce plants having increased flowers, pods and/or seeds per node relative to a wild type or control plant not having the FT transgene. Instead of the eSDI light treatment, FT may be expressed at a low level in the vegetative meristem to provide the early floral induction signal. Accordingly, a promoter from the Erecta gene (pErecta or pEr) having lower meristematic expression during vegetative stages of development was selected for initial testing with a Gm.FT2a transgene. However, given that prior studies showed that constitutive FT expression produced plants having a severe, early termination phenotype, and further that the site of action for FT produced peripherally and translocated from the leaves is in the meristem, it was possible that direct meristematic expression of FT could produce even more potent and severe phenotypes (and/or non-viable plants) relative to constitutive FT expression.

The effects of Gm.FT2a overexpression with the pErecta promoter were immediately seen in $R_0$ transformed soybean plants, which had early flowering, reduced seed yield (e.g., only about 8 seeds/plant), and very early termination, suggesting that the balance between floral induction and floral repression/vegetative growth was strongly in favor of flowering and early termination. However, enough R1 seed was salvaged from these plants to allow for additional experiments to be performed. It was proposed that growing the $R_1$ soybean seed under long day (floral repressive) photoperiod conditions in the greenhouse might delay the early flowering and termination phenotypes observed in the $R_0$ plants. Given the theorized dosage response, it was further proposed that segregating FT2a homozygous, hemizygous and null soybean plants could be tested together in the greenhouse to evaluate the dosage response resulting from FT overexpression. In these experiments (as described further below), it was observed that segregating plants did have different phenotypes: null plants were similar to wild-type plants in terms of plant architecture and pods per node (and per plant), while homozygous plants terminated early with a severe dwarf phenotype (although possibly with an increased number of pods per node). However, hemizygous plants were larger and more similar to null or wild-type plants but exhibited the increased flowering phenotype with an increased number of pods per node (and/or per plant). These findings show that vegetative stage and/or meristematic expression of a florigenic FT transgene may be used to produce a high yielding plant (similar to the eSDI treatment), and that the effect of FT expression may be dosage-dependent since soybean plants hemizygous for the FT2a transgene under the control of a weak meristematic promoter displayed the high yield phenotype of increased pods per node without the more severe early termination and short plant height phenotypes observed with homozygous FT2a plants when grown under long day (vegetative) conditions.

Accordingly, vegetative stage expression of an FT transgene at the appropriate dosage level may be used to induce early flowering and produce plants having increased flowers, pods bolls, siliques, fruits, nuts, tubers, and/or seeds per node relative to a wild type or control plant not having the FT transgene. The appropriate dosage level of FT may be achieved based on the promoter selected to drive expression of the FT transgene. A weaker or lower expression level of the FT transgene in the vegetative meristem may be used to provide the early floral induction signal while maintaining or prolonging duration of reproductive and/or floral development and not causing termination of plant development to occur too early. Again, the promoter from the Erecta gene (pErecta or pEr) having low meristematic expression during vegetative stages of development was selected for initial testing with a Gm.FT2a transgene in soybean plants. As described further below, other promoters with similar patterns and levels of expression in the vegetative meristem had similar effects in soybean plants, such as early flowering and/or increased pods per node. Separately or in addition to promoter selection to affect the expression level of the transgene, different FT transgenes from soybean or other species may be used, which may reduce the "dosage" of the early FT signal being delivered to the vegetative meristem depending on the level of activity of the transgenic FT protein in a plant cell. Indeed, several FT transgenes from soybean and other plant species were tested and shown to have variable effects on flowering and other reproductive traits when transgenically expressed in soybean plants.

Without being bound by theory, it is further proposed that increased numbers of pods per node in transgenic FT plants may result at least in part from an increase in the number of inflorescence and floral meristems induced from vegetative shoot apical and axillary meristems at each of the affected node(s), which may give rise to a greater number of flowers and/or released floral racemes at those node(s). Such an increase in the number of floral meristems induced at each node of the plant in response to FT overexpression may operate through one or more mechanisms or pathways, which may be independent of flowering time and/or reproductive duration. However, meristematic changes may be microscopic at first, and thus not observed to cause "early flowering" at such stage by simple visual inspection even though reproductive changes to the meristem may have already begun to occur. Early vegetative FT expression may cause more reproductive meristems to form and develop earlier than normal at one or more node(s) of the transgenic plant. These reproductive meristems may then allow or cause a greater number of floral racemes to form and elongate with flowers at each node. Without being bound by theory, it is further theorized that later expression of FT during reproductive stages may function to repress further floral development at each node. Thus, later developing flowers within the respective raceme may become terminated, and thus more of the plant's resources may be directed to the earlier developing flowers and reproductive structures within the raceme to more effectively produce full-sized pods. The early floral induction signal may also cause a greater proportion of the existing meristem potential to become reproductive and undergo floral development. Accordingly, increased synchronization of floral development may occur with a greater number of mature pods being formed per node of the plant.

As mentioned above, however, the floral induction signal also causes earlier termination of plant development in addition to early flowering. Although soybean plants expressing various FT transgene(s) with a vegetative stage meristem promoter, such as the pErecta promoter, have increased pods per node on the main stem of the plant, many of these transgenic FT plants still exhibit reduced plant height and/or branching, leading to fewer nodes per plant, main stem and/or branch(es). Thus, while the level of FT expression in the plant may be controlled by selection of a particular vegetative stage promoter to mitigate developmental off types and enhance yield by delaying early termination, transgenic FT-expressing soybean plants may still have a reduced number of flowering nodes per plant, which may decrease the overall yield of the plant, despite the increased number of pods per existing node on the main stem.

It is therefore presently proposed that despite the increased pods per node observed in soybean plants with vegetative stage FT expression, the level of FT transgene expression may need to be further attenuated, controlled or limited to mitigate these early termination phenotypes, and thus achieve a more optimal yield. If the increased number of pods (or other botanical structures, such as bolls, siliques, fruits, nuts, tubers, etc.) per node of the plant can be maintained while increasing the number of nodes per plant, such as by avoiding or delaying early termination, then the overall yield of the plant may be further optimized or improved.

According to embodiments of the present invention, it is presently proposed that plant yield may be increased or enhanced by attenuating or modifying the level and/or timing of FT transgene expression through suppression. As described further below, the amount and/or spatiotemporal pattern of transgenic FT may be reduced and/or refined via naturally occurring and/or artificially created RNA molecules that target the transgenic FT for suppression. It is theorized that while transgenic FT expression in axillary and apical meristems may initiate their transition into floral meristems, continued FT expression, such as during reproductive stages of development, may cause early termination of meristems and a stunting of overall plant height and branching. Although a vegetative stage promoter to express the FT transgene may be selected and used to lessen the early termination phenotype and maintain or prolong vegetative growth and reproductive duration of the plant, additional suppression of the FT transgene may further mitigate the early termination phenotype and improve or enhance the growth, development and reproductive duration of the plant. Indeed, the present inventors have observed that suppression of the FT transgene in soybean can result in a more normal plant height and branching with a greater number of nodes per plant, relative to transgenic FT expression alone (i.e., without suppression). These soybean plants with the combined expression/suppression of the FT transgene still maintain a higher number of pods per node while further mitigating the earlier termination phenotype with transgenic FT expression alone.

Suppression of an FT transgene may be achieved in different ways. According to a first approach, the FT transgene of a first expression cassette may be suppressed by a second expression cassette encoding a RNA molecule that targets the FT transgene for suppression. The RNA molecule may be encoded by a transcribable DNA sequence operably linked to a plant expressible promoter, wherein the transcribable DNA sequence comprises a targeting sequence that corresponds to at least a portion of the FT transgene, and/or to a sequence complementary thereto. According to a second approach, an FT transgene may encode a target site for an endogenous RNA molecule, wherein the target site is complementary to the endogenous RNA molecule, such that the endogenous RNA molecule targets the FT transgene for suppression. The endogenous RNA molecule may be naturally occurring in the plant cell in which the FT transgene is expressed. According to this approach, a second expression cassette may not be needed for suppression. Both of these suppression approaches may also be used together. For example, an FT transgene may be present in a first expression cassette and used in combination with a second expression cassette comprising a transcribable DNA sequence encoding a RNA molecule comprising a targeting sequence that corresponds to at least a portion of the FT transgene (and/or a sequence complementary thereto) (i.e., a first target site), such that the RNA molecule targets the FT transgene for suppression, and wherein the FT transgene further comprises a second target site for an endogenous RNA molecule that also targets the FT transgene for suppression. The first and second target sites may be the same or different in sequence and may be present at the same or different location(s) within the FT transcript. As used herein, a first polynucleotide sequence or molecule "corresponds" to a second polynucleotide sequence or molecule if the first sequence or molecule is similar, identical and/or complementary to the second sequence or molecule, such as greater than 30%, greater than 40%, greater than 50%, greater than 60%, greater than 70%, greater than 80%, greater than 90%, greater than 95% or 100% identical and/or complementary.

According to an aspect of the present invention, a recombinant DNA molecule, vector or construct is provided comprising at least two expression cassettes including a first expression cassette and a second expression cassette, wherein the first expression cassette comprises a polynucleotide sequence encoding a FT protein (i.e., an FT transgene) operably linked to a first plant expressible promoter, and wherein the second expression cassette comprises a transcribable DNA sequence operably linked to a second plant expressible promoter, wherein the transcribable DNA sequence comprises a sequence that corresponds to at least a portion of the FT transgene. The transcribable DNA sequence may encode a RNA molecule comprising a targeting sequence that is complementary to at least a portion of the pre-mRNA or mature mRNA encoded by the polynucleotide sequence encoding the FT protein (i.e., the FT transgene) of the first expression cassette, such that the RNA molecule functions to suppress the FT transgene. The "targeting sequence" of the RNA molecule encoded by the transcribable DNA sequence may comprise all or a portion of the RNA molecule and is encoded by the sequence of the transcribable DNA sequence that corresponds to at least a portion of the FT transgene and/or to a sequence complementary thereto. Thus, a transcribable DNA sequence may encode a RNA molecule that comprises a targeting sequence that is complementary to at least a portion of an mRNA transcript of a FT transgene. Depending on the particular FT transgene and/or targeting sequence of the RNA molecule encoded by the transcribable DNA sequence, an endogenous FT gene may also be suppressed by the second expression cassette in addition to the FT transgene, or an endogenous FT gene may be suppressed by the second expression cassette instead of the FT transgene. Many of the FT gene and protein sequences may be identical or similar to one or more native or endogenous FT gene(s) in a plant being transformed, and thus can serve as a basis for designing RNA molecules and targeting sequences for suppression of those native and endogenous gene(s). Whether a transcribable DNA sequences encodes a RNA molecule that targets and suppresses an FT transgene, an endogenous FT gene, or both, the total expression level and activity of FT genes and transgenes may be controlled, limited or reduced in one or more tissues of a transgenic plant. In one aspect, a nucleic acid molecule comprising a targeting sequence is capable of hybridizing to a complementary nucleic acid sequence (e.g., a target site) to form a double-stranded nucleic acid (e.g., dsRNA). In one aspect, hybridization of a targeting sequence of a first nucleic acid molecule (e.g., a suppression RNA molecule) to a target site sequence of a second nucleic acid molecule (e.g., an mRNA transcript of an FT transgene) can lead to the suppression of the second nucleic acid molecule. For example, if the polynucleotide sequence of the FT transgene is native to the plant in which it is expressed (or closely related), then the RNA molecule may further target the corresponding native FT gene for suppression, especially if the RNA molecule targets a coding (exon) sequence of the FT transgene. In such cases, the combined suppression of the native and transgenic FT genes via the RNA molecule encoded by the transcribable DNA sequence may further reduce the dosage of FT protein in relevant tissues of the plant. However, even with transgenic expression of a native FT gene, the non-protein coding sequences, such as the 5' UTR, 3' UTR, leader, and/or intron sequence(s), can be varied without affecting the sequence of the encoded FT protein. As used herein, a "polynucleotide coding sequence" or "polynucleotide sequence" of a transgene may comprise not only the protein coding (or exon) sequence(s) but also any other transcribable sequences associated with the coding sequence of the transgene that might form part of the encoded pre-mRNA or mature mRNA sequence, such as a 5' UTR, 3' UTR, leader, and/or intron sequence(s). Thus, as used herein, a "polynucleotide coding sequence" of an FT transgene and a "polynucleotide sequence" encoding an FT protein may be used interchangeably.

According to embodiments of the present invention, the first expression cassette and the second expression cassette may be present in the same recombinant DNA molecule, vector or construct, or the first expression cassette and the second expression cassette may be present in separate recombinant DNA molecules, vectors and/or constructs. Thus, according to some embodiments, two recombinant DNA molecules, vectors or constructs may be provided comprising a first recombinant DNA molecule, vector or construct and a second recombinant DNA molecule, vector or construct, wherein the first recombinant DNA molecule, vector or construct comprises a first expression cassette comprising a polynucleotide sequence encoding a FT protein (i.e., a FT transgene) operably linked to a first plant expressible promoter, and wherein the second recombinant DNA molecule, vector or construct comprises a second expression cassette comprising a transcribable DNA sequence operably linked to a second plant expressible promoter, wherein the transcribable DNA sequence corresponds to at least a portion of the FT transgene, and/or to a sequence complementary thereto. The transcribable DNA sequence may encode a RNA molecule comprising a targeting sequence that is complementary to at least a portion of the pre-mRNA or mature mRNA encoded by the FT transgene of the first expression cassette, such that the RNA molecule functions to suppress the FT transgene.

A recombinant DNA molecule, vector or construct comprising an FT transgene as provided herein may be used in plant transformation to generate a transgenic plant comprising the FT transgene. According to some embodiments, the FT transgene may be present in a first expression cassette and used in combination with a second expression cassette comprising a transcribable DNA sequence encoding a RNA molecule comprising a targeting sequence that corresponds to at least a portion of the FT transgene and/or a sequence complementary thereto, wherein both the first and second expression cassettes are transformed into a plant as the same or separate transformation event(s). According to some embodiments, an FT transgene transformed into a plant may comprise a target site for an endogenous RNA molecule that may target and trigger suppression of the FT transgene.

The polynucleotide coding sequence of an FT transgene may include Gm.FT2a (SEQ ID NO: 1), or any polynucleotide sequence encoding the Gm.FT2a protein (SEQ ID NO: 2). The polynucleotide coding sequence of an FT transgene may also correspond to other FT genes in soybean or other plants. For example, other polynucleotide coding sequences from soybean that may be used as an FT transgene according to present embodiments include: Gm.FT5a (SEQ ID NO: 3) or a polynucleotide sequence encoding a Gm.FT5a protein (SEQ ID NO: 4), or Gm.FT2b (SEQ ID NO: 5) or a polynucleotide sequence encoding a Gm.FT2b protein (SEQ ID NO: 6). In addition, examples of polynucleotide coding sequences from other plant species that may be used include: Zm.ZCN8 (SEQ ID NO: 7) from maize or a polynucleotide sequence encoding Zm.ZCN8 protein (SEQ ID NO: 8), Nt.FT-like or Nt.FT4 (SEQ ID NO: 9) from tobacco or a polynucleotide sequence encoding Nt.FT-like or Nt.FT4 protein (SEQ ID NO: 10), Le.FT or SFT (SEQ ID NO: 11) from tomato or a polynucleotide sequence encoding Le.FT or SFT protein (SEQ ID NO: 12), At.FT (SEQ ID NO: 13) from *Arabidopsis* or a polynucleotide sequence encoding At.FT protein (SEQ ID NO: 14), At.TSF (SEQ ID NO: 15) from *Arabidopsis* or a polynucleotide sequence encoding At.TSF protein (SEQ ID NO: 16), Os.HD3a (SEQ ID NO: 17) from rice or a polynucleotide sequence encoding Os.HD3a protein (SEQ ID NO: 18), or Pt.FT (SEQ ID NO: 19) from *Populus trichocarpa* or a polynucleotide sequence encoding Pt.FT protein (SEQ ID NO: 20). Additional examples of polynucleotide coding sequences for FT transgenes and proteins that may also be used include the following: Gm.FT5b (SEQ ID NO: 21) from soybean, or any polynucleotide sequence encoding the Gm.FT5b protein (SEQ ID NO: 22); Gh.FT1 (SEQ ID NO: 23) from cotton, or any polynucleotide sequence encoding the Gh.FT1 protein (SEQ ID NO: 24); Bn.FTA2a (SEQ ID NO: 25) from canola, or any polynucleotide sequence encoding the Bn.FTA2a protein (SEQ ID NO: 26); Ta.FT3B1 (SEQ ID NO: 27) from wheat, or any polynucleotide sequence encoding the Ta.FT3B1 protein (SEQ ID NO: 28); or Ps.FTa1 (SEQ ID NO: 29) from pea, or any polynucleotide sequence encoding the Ps.FTa1 protein (SEQ ID NO: 30). Polynucleotide coding sequences for FT transgenes encoding additional FT proteins from other species having known amino acid sequences may also be used according to embodiments of the present invention, which may, for example, include the following: Md.FT1 and Md.FT2 from apple (*Malus domestica*); Hv.FT2 and Hv.FT3 from barley (*Hordeum vulgare*); Cs.FTL3 from *Chrysanthemum*; Ls.FT from lettuce (*Lactuca sativa*); Pn.FT1 and Pn.FT2 from Lombardy poplar (*Populus nigra*); Pa.FT from London plane tree (*Platanus acerifolia*); Dl.FT1 from Longan (*Dimocarpus longan*); Ps.FTa1, Ps.FTa2, Ps.FTb1, Ps.FTb2, and Ps.FTc from pea (*Pisum sativum*); Ac.FT from pineapple (*Ananas comosus*); Cm-FTL1 and Cm-FTL2 from pumpkin (*Cucurbita maxima*); Ro.FT from rose; Cg.FT from spring orchid (*Cymbidium*); Fv.FT1 from strawberry (*Fragaria vesca*); Bv.FT2 from sugar beet (*Beta Vulgaris*); Ha.FT4 from sunflower (*Helianthus annuus*); and Ta.FT or TaFT1 from wheat (*Triticum aestivum*), and sequences that are at least 60% identical, at least 65% identical, at least 70% identical, at least 75% identical, at least 80% identical, at least 85% identical, or at least 90%, at least 91%, at least 92%, at least 93%, at least 94%, at least 95%, at least 96%, at least 97%, at least 98%, or at least 99% identical to one or more of such known polynucleotide and/or protein sequences. See, e.g., Wickland, D P et al., "*The Flowering Locus T/Terminal Flower* 1 Gene Family: Functional Evolution and Molecular Mechanisms", *Molecular Plant* 8: 983-997 (2015), the content and disclosure of which is incorporated herein by reference.

Unless otherwise stated, nucleic acid or polynucleotide sequences described herein are provided (left-to-right) in the 5' to 3' direction, and amino acid or protein sequences are provided (left-to-right) in the N-terminus to C-terminus direction. Additional known or later discovered FT genes and proteins from these or other species may also be used according to embodiments of the present invention. These FT genes may be known or inferred from their nucleotide and/or protein sequences, which may be determined by visual inspection or by use of a computer-based searching and identification tool or software (and database) based on a comparison algorithm with known FT sequences, structural domains, etc., and according to any known sequence alignment technique, such as BLAST, FASTA, etc.

According to embodiments of the present invention, an FT transgene of a recombinant DNA molecule, vector or construct may comprise a polynucleotide sequence that (when optimally aligned) is at least 60% identical, at least 65% identical, at least 70% identical, at least 75% identical, at least 80% identical, at least 85% identical, or at least 90%, at least 91%, at least 92%, at least 93%, at least 94%, at least 95%, at least 96%, at least 97%, at least 98%, at least 99%, or 100% identical to one or more of the polynucleotide FT coding sequences listed above (e.g., SEQ ID NOS: 1, 3, 5, 7, 9, 11, 13, 15, 17, 19, 21, 23, 25, 27, or 29), or to any other known florigenic FT coding sequence. Sequence identity percentages among polynucleotide sequences of the above listed full length coding sequences of FT genes are presented in FIG. 1A. Each cell in the table in FIG. 1A shows the percentage identity for the FT gene in the corresponding row (query sequence) as compared to the FT gene in the corresponding column (subject sequence) divided by the total length of the query sequence, and the number in parenthesis is the total number of identical bases between the query and subject sequences. As shown in this figure, the percentage identities among polynucleotide sequences for these sampled FT genes range from about 60% to about 90% identity. Thus, a polynucleotide sequence that is within one or more of these sequence identity ranges or has a higher sequence identity may be used according to embodiments of the present invention to induce flowering, increase yield, and/or alter one or more reproductive traits of a plant. Similar polynucleotide coding sequences for FT may be designed or chosen based on known FT protein sequences, conserved amino acid residues and domains, the degeneracy of the genetic code, and any known codon optimizations for the particular plant species to be transformed.

According to embodiments of the present invention, an FT transgene may comprise a polynucleotide sequence encoding an amino acid or protein sequence that (when optimally aligned) is at least 60% identical, at least 65% identical, at least 70% identical, at least 75% identical, at least 80% identical, at least 85% identical, or at least 90%, at least 91%, at least 92%, at least 93%, at least 94%, at least 95%, at least 96%, at least 97%, at least 98%, at least 99%, or 100% identical to any one or more of the FT protein or amino acid sequences listed above (e.g., SEQ ID NOS: 2, 4, 6, 8, 10, 12, 14, 16, 18, 20, 22, 24, 26, 28, or 30) or any other known florigenic FT protein sequence, or a functional fragment thereof. Such a "functional fragment" is defined as a protein having a polypeptide sequence that is identical or highly similar to a full-length FT protein but lacking one or more amino acid residues, portions, protein domains, etc., of the full-length FT protein, as long as the fragment remains active in causing one or more of the phenotypic effects or changes similar to the full-length protein when transgenically expressed in a plant. Sequence identity percentages among the above listed full length FT proteins are presented in FIG. 1B. The percentages are calculated as described above in reference to FIG. 1A based on the number of identical amino acid residues (in parenthesis) between the query and subject FT protein sequences. Multiple sequence alignment of these FT proteins is also shown in FIG. 1C. As can be seen from these figures, the percentage identity among protein sequences for these FT genes ranges from about 60% to about 90% identity. Thus, a polynucleotide sequence encoding an amino acid or protein sequence that is within one or more of these sequence identity ranges or has a higher sequence identity may be used according to embodiments of the present invention to induce flowering, increase seed yield, and/or alter one or more reproductive traits of a plant. These FT protein sequences encoded by a polynucleotide sequence of the present invention may be designed or chosen based on known FT protein sequences and their conserved amino acid residues and domains.

As described below, an FT transgene comprising any one of the above coding sequences may further include one or more expression and/or regulatory element(s), such as enhancer(s), promoter(s), leader(s), intron(s), etc., and an FT transgene may comprise a genomic sequence encoding an FT protein or amino acid sequence, or a fragment or portion thereof.

As used herein, the term "sequence identity" or "percent identity" refers to the extent to which two optimally aligned DNA or protein sequences are identical. Various pair-wise or multiple sequence alignment algorithms and programs are known in the art, such as ClustalW, etc., that may be used to compare the sequence identity or similarity between two or more sequences, such as between two or more FT genes or protein sequences, or an FT gene (nucleotide) or protein sequence and another nucleotide or protein sequence. For example, the percentage identity of one sequence (query) to another sequence (subject) may be calculated as described above in reference to FIGS. 1A and 1B (i.e., with the sequences optimally aligned, divide the number of identical bases or residues by the total number of bases or residues for the query sequence, and multiply by 100%). Although other alignment and comparison methods are known in the art, the alignment and percent identity between two sequences (including the percent identity ranges described above) may be as determined by the ClustalW algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); and Larkin M A et al., "Clustal W and Clustal X version 2.0," *Bioinformatics* 23: 2947-48 (2007), the entire contents and disclosures of which are incorporated herein by reference. For purposes of the present invention, when two sequences are optimally aligned (with allowance for gaps in their alignment), the "percent identity" for the query sequence is calculated as described above in reference to FIGS. 1A and 1B—i.e., Percent Identity=(Number of Identical Positions between query and subject sequences/Total Number of Positions in the Query Sequence)×100%, with each sequence consisting of a series of positions (nucleotide bases or amino acid residues). The two optimally aligned sequences may also be described as being a certain percent identical. A percent identity may optionally be described instead in reference to a defined window of comparison (e.g., an alignment window) between the two sequences, in which case the number of identical positions within the window of comparison is divided by the nucleotide length of the window of comparison, and multiplied by 100%. An alignment window may be defined as the region of identity, similarity or overlap between the two sequences.

A recombinant polynucleotide or protein molecule, construct or vector may be isolated. As used herein, the term "isolated" refers to at least partially separating a molecule from other molecules typically associated with it in its natural state. In one embodiment, the term "isolated" refers to a DNA molecule that is separated from the nucleic acids that normally flank the DNA molecule in its natural state. For example, a DNA molecule encoding a protein that is naturally present in a bacterium would be an isolated DNA molecule if it was not within the DNA of the bacterium from which the DNA molecule encoding the protein is naturally found. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

An FT protein sequence encoded by a polynucleotide sequence or transgene of the present invention may also be designed or chosen to have one or more amino acid substitution(s) known to be chemically and/or structurally conservative (e.g., replacing one amino acid with another having similar chemical or physical properties, such as hydrophobicity, polarity, charge, steric effect, acid/base chemistry, similar side chain group, such as hydroxyl, sulfhydryl, amino, etc.) to avoid or minimize structural changes to the protein that might affect its function. For example, valine is often a conservative substitute for alanine, and threonine may be a conservative substitute for serine. Additional examples of conservative amino acid substitutions in proteins include: valine/leucine, valine/isoleucine, phenylalanine/tyrosine, lysine/arginine, aspartic acid/glutamic acid, and asparagine/glutamine. An FT protein sequence encoded by a polynucleotide sequence or transgene of the present invention may also include proteins that differ in one or more amino acids from those of a known FT protein or similar sequence as a result of deletion(s) and/or insertion(s) involving one or more amino acids.

Various FT genes and proteins from different plant species may be identified and considered FT homologs or orthologs for use in the present invention if they have a similar nucleic acid and/or protein sequence and share conserved amino acids and/or structural domain(s) with at least one known FT gene or protein. As used herein, the term "homolog" in reference to a FT gene or protein is intended to collectively include any homologs, analogs, orthologs, paralogs, etc., of the FT gene or protein, and the term "homologous" in reference to polynucleotide or protein sequences is intended to mean similar or identical sequences including synthetic, artificial or engineered polynucleotide or protein sequences. Such a FT homolog may also be defined as having the same or similar biological function as known FT genes (e.g., acting to similarly influence flowering and/or other reproductive or yield-related traits or phenotypes when ectopically expressed in a plant).

Sequence analysis and alignment of FT protein sequences from different plant species further reveals a number of conserved amino acid residues and at least one conserved structural domain. By subjecting the various aligned FT protein sequences (see, e.g., FIGS. 1B and 1C) to a protein domain identification tool using a Pfam database (e.g., Pfam version 26.0, released November 2011, or later version), these FT proteins have been found to contain and share at least a portion of a putative phosphatidyl ethanolamine-binding protein (PEBP) domain (Pfam domain name: PBP_N; Accession number: PF01161). See, e.g., Banfield, M J et al., "The structure of *Antirrhinum* centroradialis protein (CEN) suggests a role as a kinase inhibitor," *Journal of Mol Biol.,* 297(5): 1159-1170 (2000), the entire contents and disclosure of which are incorporated herein by reference. This PEBP domain was found to correspond, for example, to amino acids 28 through 162 of the full length Gm.FT2a protein (See Table 5 below). Thus, FT proteins encompassed by embodiments of the present invention may include those identified or characterized as having or containing at least a PEBP domain (Accession number: PF01161) according to Pfam analysis. Accordingly, the present invention may further include a polynucleotide sequence(s) encoding an FT protein having at least a PEBP domain. As known in the art, the "Pfam" database is a large collection of multiple sequence alignments and hidden Markov models covering many common protein families and containing information about various protein families and their domain structure(s). By identifying a putative Pfam structural domain(s) for a given protein sequence, the classification and function of the protein may be inferred or determined. See, e.g., Finn, R D et al., "The Pfam protein families database," *Nucleic Acids Research (Database Issue),* 42:D222-D230 (2014), the entire contents and disclosure of which are incorporated herein by reference.

Embodiments of the present invention may further include polynucleotide sequence(s) encoding inductive or florigenic FT proteins. An FT protein encoded by a polynucleotide sequence may be "inductive" or "florigenic" if the FT protein, when ectopically expressed in a plant, is able to cause earlier flowering and/or an increased prolificacy in the number of flowers, pods, bolls, siliques, fruits, nuts, tubers, and/or seeds per one or more node(s) of the plant. Without being bound by theory, such increased prolificacy in the number of flowers, pods, bolls, siliques, fruits, nuts, tubers, and/or seeds per node(s) of the plant may result from an increase in the number of meristems at those node(s) that undergo a vegetative to reproductive transition and produce flowers. Such an increased prolificacy at each node due to ectopic expression of a "florigenic" FT may be due to increased synchronization of the release and floral development of early racemes and lateral meristems at each node. Although a "florigenic" FT protein may function to induce earlier flowering when ectopically expressed in a plant, a transgenically expressed "florigenic" FT protein may increase the number of flowers, pods, bolls, siliques, fruits, nuts, tubers, and/or seeds per node(s) of a plant through one or more pathways or mechanisms that are independent of, or in addition to, any florigenic effects related to flowering time and/or reproductive duration.

Florigenic FT-like genes from various plant species are generally well conserved. However, many proteins in the PEBP family have amino acid sequences that are substantially similar to florigenic FT proteins but do not behave as florigens. For example, Terminal Flower (TFL) genes from various plant species have similar protein sequences to florigenic FT genes but actually delay flowering. Recent work has identified specific amino acid residues that are generally not shared between florigenic FT proteins and other PEBP proteins, such as TFLs, and substitutions at many of these positions have been shown to convert florigenic FT proteins into floral repressor proteins. See, e.g., Ho and Weigel, *Plant Cell* 26: 552-564 (2014); Danilevskaya et al., *Plant Physiology* 146(1): 250-264 (2008); Harig et al., *Plant Journal* 72: 908-921 (2012); Hsu et al., *Plant Cell* 18: 1846-1861 (2006); Kojima et al., *Plant Cell Physiology* 43(10): 1096-1105 (2002); Kong et al., *Plant Physiology* 154: 1220-1231 (2010); Molinero-Rosales et al., *Planta* 218: 427-434 (2004); Zhai et al., *PLoS ONE,* 9(2): e89030 (2014), and Wickland D P et al. (2015), supra, the entire contents and disclosures of which are incorporated herein by reference. Thus, these amino acid residues can serve as signatures to further define and distinguish florigenic FT proteins of the present invention.

According to embodiments of the present invention, an "inductive" or "florigenic" FT protein may be further defined or characterized as comprising one or more of the following amino acid residue(s) (amino acid positions refer to corresponding or optimally aligned positions of the full-length *Arabidopsis* FT protein, SEQ ID NO: 14): a proline at amino acid position 21 (P21); an arginine or lysine at amino acid position 44 (R44 or K44); a glycine at amino acid position 57 (G57); a glutamic acid or an aspartic acid at amino acid position 59 (E59 or D59); a tyrosine at amino acid position 85 (Y85); a leucine at amino acid position 128 (L128); a glycine at amino acid position 129 (G129); a threonine at amino acid position 132 (T132); an alanine at amino acid position 135 (A135); a tryptophan at amino acid position 138 (W138); a glutamic acid or an aspartic acid at amino acid position 146 (E146 or D146); and/or a cysteine at amino acid position 164 (C164). Corresponding amino acid positions of other FT proteins can be determined by alignment with the *Arabidopsis* FT sequence (see, e.g., FIG. 1C). One skilled in the art would be able to identify corresponding amino acid positions of other FT proteins based on their sequence alignment. Several of these key residues fall within an external loop domain of FT-like proteins, defined as amino acids 128 through 145 of the *Arabidopsis* full-length FT sequence (SEQ ID NO: 14) and corresponding sequences of other FT proteins (see, e.g., FIG. 1C). Thus, polynucleotides of the present invention may encode florigenic FT proteins having one or more of these conserved amino acid residues.

Florigenic FT proteins of the present invention may also have one or more other amino acids at one or more of the above identified residue positions. For example, in reference to the above amino acid positions of the *Arabidopsis* FT (At.FT) protein sequence (SEQ ID NO: 14), a florigenic FT protein may alternatively have one or more of the following amino acids: an alanine (in place of proline) at the position corresponding to position 21 of the At.FT protein sequence (P21A), or possibly other small, nonpolar residues, such as glycine or valine, at this position; a histidine (in place of lysine or arginine) at the amino acid position corresponding to position 44 of the At.FT protein sequence, or possibly other polar amino acids at this position; an alanine or cysteine (in place of glycine) at the amino acid position corresponding to position 57 of the At.FT protein sequence, or possibly other small, nonpolar residues, such proline or valine, at this position; an asparagine or serine (in place of glutamic acid or aspartic acid) at the amino acid position corresponding to position 59 of the At.FT protein sequence, or possibly other small, polar residues, such as glutamine, cysteine, or threonine, at this position; a variety of polar and nonpolar uncharged residues (other than tyrosine) at the amino acid position corresponding to position 85 of the At.FT protein sequence; a nonpolar or hydrophobic uncharged residue (other than leucine), such as isoleucine, valine, or methionine, at the amino acid position corresponding to position 128 of the At.FT protein sequence; a variety of smaller nonpolar and uncharged residues (other than glycine), such as alanine, valine, leucine, isoleucine, methionine, etc., at the amino acid position corresponding to position 129 of the At.FT protein sequence, although some polar and charged residues may be tolerated at this position; a polar uncharged residue (other than threonine) at the amino acid position corresponding to position 132 of the At.FT protein sequence; a variety of amino acids other than proline, such as threonine, at the amino acid position corresponding to position 135 of the At.FT protein sequence; a variety of other bulky nonpolar or hydrophobic amino acids (in place of tryptophan), such as methionine or phenylalanine, at the amino acid position corresponding to position 138 of the At.FT protein sequence; a variety of other polar or non-positively charged amino acids, such as asparagine or serine, at the amino acid position corresponding to position 146 of the At.FT protein sequence; and/or a variety of other polar or nonpolar amino acids (in place of cysteine, such as isoleucine, at the amino acid position corresponding to position 164 of the At.FT protein sequence. One skilled in the art would be able to identify corresponding amino acid positions and substitutions of FT proteins based on their sequence alignment to the *Arabidopsis* FT protein sequence. In addition, other chemically conservative amino acid substitutions are also contemplated within the scope of florigenic FT proteins based on the knowledge of one skilled in the art of protein biochemistry. Accordingly, polynucleotides of the present invention may further encode florigenic FT proteins having one or more conservative amino acid substitutions. Indeed, florigenic FT proteins encoded by polynucleotides of the present invention include native sequences and artificial sequences containing one or more conservative amino acid substitutions, as well as functional fragments thereof.

Florigenic FT proteins of the present invention may also be defined as excluding (i.e., not having) one or more amino acid substitutions that may be characteristic of, or associated with, TFL or other non-florigenic or anti-florigenic proteins. For example, in reference to the amino acid positions of the *Arabidopsis* FT protein sequence (SEQ ID NO: 14), a florigenic FT protein may exclude one or more of the following amino acids (i.e., at corresponding or optimally aligned positions of the florigenic FT protein): a phenylalanine or serine at the position corresponding to position 21 of the At.FT protein sequence (e.g., in place of proline or alanine); a phenylalanine at the position corresponding to position 44 of the At.FT protein sequence (e.g., in place of arginine or lysine); a histidine, glutamic acid, or aspartic acid at the position corresponding to position 57 of the At.FT protein sequence (e.g., in place of glycine); a glycine or alanine at the position corresponding to position 59 of the At.FT protein sequence (e.g., in place of glutamic acid or aspartic acid); a histidine at the position corresponding to position 85 of the At.FT protein sequence (e.g., in place of tyrosine); a lysine, arginine, alanine, or methionine at the position corresponding to position 109 of the At.FT protein sequence; a lysine or arginine at the position corresponding to position 128 of the At.FT protein sequence (e.g., in place of leucine); a glutamine or asparagine at the position corresponding to position 129 of the At.FT protein sequence (e.g., in place of glycine); a valine or cysteine at the position corresponding to position 132 of the At.FT protein sequence (e.g., in place of threonine); a lysine, arginine, or alanine at the position corresponding to position 134 of the At.FT protein sequence (e.g., in place of tyrosine); a proline at the position corresponding to position 135 of the At.FT protein sequence (e.g., in place of alanine or threonine); a serine, aspartic acid, glutamic acid, alanine, lysine, or arginine at the position corresponding to position 138 of the At.FT protein sequence (e.g., in place of tryptophan or methionine); a lysine or arginine at the position corresponding to position 140 of the At.FT protein sequence; a lysine or arginine at the position corresponding to position 146 of the At.FT protein sequence (e.g., in place of acidic or uncharged polar residues); a lysine or arginine at the position corresponding to position 152 of the At.FT protein sequence; and/or an alanine at the position corresponding to position 164 of the At.FT protein sequence (e.g., in place of cysteine or isoleucine). One skilled in the art would be able to identify corresponding amino acid positions and substitutions of other FT proteins based on their sequence alignment. Accordingly, embodiments of the present invention may exclude polynucleotides that encode FT-like proteins having one or more of the above amino acid substitutions associated with TFL or other anti-florigens. However, an FT protein may tolerate one or some of these amino acid substitutions while still maintaining florigenic activity.

A florigenic FT protein of the present invention may also be defined as being similar to a known FT protein in addition to having one or more of the above signature or conserved amino acid residues. For example, a florigenic protein may be defined as having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or least 99% identity to a sequence selected from the group consisting of SEQ ID NOs: 2, 4, 6, 8, 10, 12, 14, 16, 18, 20, 22, 24, 26, 28, and 30, or a functional fragment thereof, in addition to one or more of the following signature residues: a tyrosine or other uncharged polar or nonpolar residue (e.g., alanine, tryptophan, methionine, leucine, threonine, cysteine, serine, or asparagine) at the amino acid position corresponding to position 85 of the At.FT protein sequence; a leucine or other nonpolar or hydrophobic residue (e.g., isoleucine, valine, or methionine) at the amino acid position corresponding to position 128 of the At.FT protein sequence; and/or a tryptophan or other large nonpolar or hydrophobic residue (e.g., methionine or phenylalanine) at the amino acid position corresponding to position 138 of the At.FT protein sequence. Such a florigenic FT protein may be further defined as having additional signature amino acid residue(s), such as one or more of the following: a glycine or other small nonpolar and uncharged residue (e.g., alanine, valine, leucine, isoleucine, or methionine) at the amino acid position corresponding to position 129 of the At.FT protein sequence; and/or a threonine at the amino acid position corresponding to position 132 of the At.FT protein sequence.

A florigenic FT protein of the present invention may also be defined as having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or least 99% identity to a sequence selected from the group consisting of SEQ ID NOs: 2, 4, 6, 8, 10, 12, 14, 16, 18, 20, 22, 24, 26, 28, and 30, or a functional fragment thereof, but not having (i.e., excluding) one or more non-florigenic or anti-florigenic residues, such as one or more of the following: a histidine at the amino acid position corresponding to position 85 of the At.FT protein sequence; a lysine or arginine at the amino acid position corresponding to position 128 of the At.FT protein sequence; and/or a serine, aspartic acid, glutamic acid, lysine or arginine at the amino acid position corresponding to position 138 of the At.FT protein sequence. Such a florigenic FT protein may be further defined as not having (i.e., excluding) one or more additional residues, such as one or more of the following: a glutamine or asparagine at the amino acid position corresponding to position 129 of the At.FT protein sequence; and/or a valine or cysteine at the amino acid position corresponding to position 132 of the At.FT protein sequence.

According to embodiments of the present invention, a recombinant DNA molecule, vector or construct is provided comprising a polynucleotide sequence encoding a FT protein that is operably linked to one or more promoter(s) and/or other regulatory element(s) that are operable in a plant cell to control or bias the timing and/or location of FT expression when transformed into a plant. According to some embodiments, the FT transgene may be present in a first expression cassette and used with a second expression cassette comprising a transcribable DNA sequence that corresponds to at least a portion of the FT transgene, and/or to a sequence complementary thereto, and encodes a RNA molecule that targets the FT transgene for suppression. According to some embodiments, the FT transgene may comprise a target site for an endogenous RNA molecule that may target and trigger suppression of the FT transgene.

As commonly understood in the art, the term "promoter" may generally refer to a DNA sequence that contains an RNA polymerase binding site, transcription start site, and/or TATA box and causes, initiates, directs, assists and/or promotes the transcription and expression of an associated transcribable polynucleotide sequence and/or gene (or transgene). A promoter may be synthetically produced, engineered, varied and/or derived from a known or naturally occurring promoter sequence or other promoter sequence (e.g., as provided herein). A promoter may also include a chimeric promoter comprising a combination of two or more heterologous sequences. A promoter of the present invention may thus include variants of promoter sequences that are similar in composition, but not identical to, other promoter sequence(s) known or provided herein. As used herein, the term "operably linked" refers to a functional linkage between a promoter or other regulatory element and an associated transcribable polynucleotide sequence or coding sequence of a gene (or transgene), such that the promoter, etc., operates to initiate, assist, affect, cause, direct, and/or promote the transcription and expression of the associated coding or transcribable polynucleotide sequence, at least in particular tissue(s), developmental stage(s), and/or under certain condition(s). A "plant expressible promoter" refers to a promoter that may be used to express in a plant, plant cell and/or plant tissue an associated coding sequence, transgene or transcribable polynucleotide sequence that is operably linked to the promoter.

A promoter may be classified according to a variety of criteria relating to the pattern of expression of a coding sequence or gene (including a transgene) operably linked to the promoter, such as constitutive, developmental, tissue-specific, inducible, etc. Promoters that initiate transcription in all or most tissues of the plant are referred to as "constitutive" promoters. Promoters that initiate transcription during certain periods or stages of development are referred to as "developmental" promoters. Promoters whose expression is enhanced in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. A promoter that expresses in a certain cell type of the plant is referred to as a "cell type specific" promoter. An "inducible" promoter is a promoter that initiates transcription in response to an environmental stimulus such as cold, drought, heat or light, or other stimuli, such as wounding or chemical application. A promoter may also be classified in terms of its origin, such as being heterologous, homologous, chimeric, synthetic, etc. The term "heterologous" in reference to a promoter or other regulatory sequence in relation to an associated polynucleotide sequence (e.g., a transcribable DNA sequence, coding sequence, gene or transgene) is a promoter or regulatory sequence that is not operably linked to such associated polynucleotide sequence in nature—e.g., the promoter or regulatory sequence has a different origin relative to its associated polynucleotide sequence, and/or not naturally occurring in a plant species to be transformed with the promoter or regulatory sequence. The term "heterologous" more broadly includes a combination of two or more DNA molecules or sequences when such a combination is not normally found in nature. As used herein, the phrase "not normally found in nature" means not found in nature without human introduction. For example, two or more DNA molecules or sequences would be heterologous with respect to each other if they are normally found in different genomes or at different loci in the same genome, or if they are not identically combined in nature. According to many embodiments, a plant expressible promoter operably linked to a polynucleotide sequence encoding an FT protein is heterologous with respect to the polynucleotide sequence encoding the FT protein.

According to embodiments of the present invention, a recombinant DNA molecule, vector or construct is provided comprising a florigenic FT transgene or coding sequence operably linked to a promoter that functions in a plant, which may be introduced or transformed into a plant to cause the plant to have an altered flowering, reproductive and/or yield-related trait or phenotype. Embodiments of the present invention provide a recombinant DNA molecule comprising an FT transgene or coding sequence operably linked to a "vegetative stage" promoter to cause, when introduced or transformed into a plant, expression of the FT transgene earlier in the development of the plant (i.e., during the vegetative growth phase of the plant) to produce an increased level of FT in target tissues than would otherwise occur in a wild type plant at the same stage of development. Timing FT transgene expression during the vegetative stage(s) of development may be important for affecting one or more reproductive, flowering and/or yield-related traits or phenotypes by providing a timely inductive signal for the production of an increased number of floral meristems and successful flowers at one or more node(s) of the plant. Vegetative stage expression may be necessary to trigger early flowering and allow for improved reproductive, flowering and/or yield-related traits or phenotypes, such as increased flowers, pods, etc., per node of the plant. Without being bound by any theory, vegetative stage expression of an FT transgene in a plant may operate to synchronize and/or increase early flowering at one or more node(s) to produce more flowers per node of the plant. The promoters described below as a part of the present invention provide options for timing FT expression.

As used herein, a "vegetative stage" promoter includes any promoter that initiates, causes, drives, etc., transcription or expression of its associated gene, transgene or transcribable DNA sequence during one or more vegetative stage(s) of plant development, such as during one or more of Ve, Vc, V1, V2, V3, V4, etc., and/or any or all later vegetative stages of development (e.g., up to $V_n$ stage). In other words, the term "vegetative stage" is in reference to the vegetative developmental stage(s) of the plant as a whole. Such a "vegetative stage" promoter may be further defined as initiating, causing, driving, etc., transcription or expression of its associated gene/transgene or transcribable DNA sequence in one or more vegetative tissue(s) of a plant, such as one or more vegetative meristem tissue(s). Such a "vegetative stage" promoter may be further defined as a "vegetative stage preferred" promoter that initiates, causes, drives, etc., transcription or expression of its associated gene, transgene or transcribable DNA sequence at least preferentially or mostly, if not exclusively, during one or more vegetative stage(s) of plant development (as opposed to reproductive stages). However, a "vegetative stage" and a "vegetative stage preferred" promoter may each also permit, allow, cause, drive, etc., transcription or expression of its associated gene, transgene or transcribable DNA sequence during reproductive phase(s) or stage(s) of development in one or more cells or tissues of the plant, such as in one or more floral or reproductive tissue(s). In fact, a "vegetative stage" promoter may even initiate, cause, drive, etc., transcription or expression of its associated gene, transgene or transcribable DNA sequence in one or more reproductive or floral tissues at a greater level or extent than in vegetative tissue(s), provided that the "vegetative stage" promoter also initiates, causes, drives, etc., transcription or expression of its associated gene, transgene or transcribable DNA sequence during one or more vegetative stage(s) of plant development.

The features and characteristics associated with vegetative stages of development for a given plant species are known in the art. For dicot plants, vegetative morphological features and characteristics of the plant during vegetative stages of development may include cotyledon form, vegetative meristems (apical, lateral/axillary, and root), leaf arrangement, leaf shape, leaf margin, leaf venation, petioles, stipules, ochrea, hypocotyl, and roots. According to embodiments of the present invention, a "vegetative stage" promoter may also be further defined by the particular vegetative stage during which observable or pronounced transcription or expression of its associated gene (or transgene) is first caused, initiated, etc. For example, a vegetative stage promoter may be a Vc stage promoter, a V1 stage promoter, a V2 stage promoter, a V3 stage promoter, etc. As such, a "Vc stage" promoter is defined as a vegetative stage promoter that first initiates or causes transcription of its associated gene, transgene or transcribable DNA sequence during the Vc stage of plant development, a "V1 stage" promoter is defined as a vegetative stage promoter that first initiates or causes transcription of its associated gene, transgene or transcribable DNA sequence during the V1 stage of plant development, a "V2 stage" promoter is defined as a vegetative stage promoter that first initiates or causes transcription of its associated gene, transgene or transcribable DNA sequence during the V2 stage of plant development, and so on, although expression of the associated gene, transgene or transcribable DNA sequence may be present continuously or discontinuously in one or more tissues during later vegetative (and or reproductive) stage(s) of development. One skilled in the art would be able to determine the timing of expression of a given gene, transgene or transcribable DNA sequence during plant development using various molecular assays and techniques known in the art.

According to embodiments of the present invention, a "vegetative stage" promoter may include a constitutive, tissue-preferred, or tissue-specific promoter. For example, a vegetative stage promoter may drive expression of its associated FT gene/transgene or transcribable DNA sequence in one or more plant tissue(s), such as in one or more of the root(s), stem(s), leaf/leaves, meristem(s), etc., during a vegetative stage(s) of plant development. However, such a vegetative stage promoter may preferably drive expression of its associated FT transgene or coding sequence or transcribable DNA sequence in one or more meristem(s) of the plant. According to many embodiments, a "vegetative stage" promoter may be a "meristem-specific" or "meristem-preferred" promoter to cause expression of the FT transgene or coding sequence or transcribable DNA sequence in meristematic tissue. FT proteins are known to operate in the meristems of a plant to help trigger the transition from vegetative to reproductive growth after translocation of the FT protein from the leaves. In contrast, embodiments of the present invention provide for expression of an FT transgene directly in the meristem of a plant to induce flowering and cause the plant to adopt an altered reproductive and/or yield-related trait or phenotype. Thus, according to embodiments of the present invention, a recombinant DNA molecule, construct or vector is provided comprising an FT transgene or coding sequence operably linked to a "meristem-specific" or "meristem-preferred" promoter that drives expression of the FT transgene at least preferentially in one or more meristematic tissues of a plant when transformed into the plant. As used herein, "meristem-preferred promoter" refers to promoters that preferentially cause expression of an associated gene, transgene or transcribable DNA sequence in at least one meristematic tissue of a plant relative to other plant tissues, such as in one or more apical and/or axillary meristems, whereas a "meristem-specific promoter" refers to promoters that cause expression of an associated gene, transgene or transcribable DNA sequence exclusively (or almost exclusively) in at least one meristematic tissue of a plant.

According to embodiments of the present invention, a recombinant DNA molecule is provided comprising an FT coding sequence operably linked to a vegetative stage promoter, which may also be a meristem-preferred and/or meristem-specific promoter. For example, the promoter may include the pAt.Erecta promoter from *Arabidopsis* (SEQ ID NO: 31), or a functional fragment or portion thereof. Two examples of a truncated portion of the pAt.Erecta promoter according to embodiments of the present invention are provided as SEQ ID NO: 32 and SEQ ID NO: 48. See, e.g., Yokoyama, R. et al., "The *Arabidopsis* ERECTA gene is expressed in the shoot apical meristem and organ primordia," *The Plant Journal* 15(3): 301-310 (1998). pAt.Erecta is an example of a vegetative stage promoter that is also meristem-preferred. Other vegetative stage, meristem-preferred or meristem-specific promoters have been identified based on their characterized expression profile (see, e.g., Examples 4 and 7 below) that may also be used to drive FT expression according to embodiments of the present invention. For example, promoters from the following soybean receptor like kinase (RLK) genes were identified that could be used as vegetative stage, meristem-preferred promoters: Glyma10g38730 (SEQ ID NO: 33), Glyma09g27950 (SEQ ID NO: 34), Glyma06g05900 (SEQ ID NO: 35), and Glyma17g34380 (SEQ ID NO: 36), and any functional portion thereof. Vegetative stage, meristem-preferred promoters according to embodiments of the present invention may also include receptor like kinase (RLK) gene promoters from potato: PGSC0003DMP400032802 (SEQ ID NO: 37) and PGSC0003DMP400054040 (SEQ ID NO: 38), and any functional portion thereof. Given the characterization provided herein of the pAt.Erecta promoter driving FT expression and the similar expression profiles identified for other RLK, Erecta or Erecta-like (Erl) genes, vegetative-stage, meristem-preferred or meristem-specific promoters of the present invention may further comprise any known or later identified promoter sequences of RLK, Erecta and Erecta-like genes from other dicotyledonous species having vegetative-stage pattern of expression in the meristems of plants.

Additional examples of vegetative stage, meristem-preferred or meristem-specific promoters may include those from the following *Arabidopsis* genes: Pinhead (At.PNH) (SEQ ID NO: 39), *Angustifolia* 3 or At.AN3 (SEQ ID NO: 40), At.MYB17 (At.LMI2 or Late Meristem Identity 2; At3g61250) (SEQ ID NO: 41), Kinesin-like gene (At5g55520) (SEQ ID NO: 42), AP2/B3-like genes, including At.REM17 (SEQ ID NO: 43) or At.REM19, and Erecta-like 1 and 2 genes, At.Erl1 (SEQ ID NO: 44) and At.Erl2 (SEQ ID NO: 45), and any functional portion thereof. Another example is an At.AP1 promoter (pAt.AP1 or pAP1) from *Arabidopsis* (SEQ ID NO: 49), or a functional portion thereof. However, the pAt.AP1 promoter may be considered more of a late vegetative and reproductive stage promoter. Given the later pattern of vegetative and reproductive stage expression, the pAt.AP1 and related promoters may be useful for driving expression of an FT transgene and/or FT suppression element. Further examples identified from similar genes and/or genes having a similar expression pattern as the pAt.AP1 promoter in their native plant species may include a promoter from one of the following genes: AT1G26310.1 (SEQ ID NO: 50), AT3G30260.1 (SEQ ID NO: 51), or AT5G60910.1 (SEQ ID NO: 52) from *Arabidopsis*; Glyma01g08150 (SEQ ID NO: 53), Glyma02g13420 (SEQ ID NO: 54), Glyma08g36380 (SEQ ID NO: 55), or Glyma16g13070 (SEQ ID NO: 56) from soybean; Solyc02g065730 (SEQ ID NO: 57), Solyc02g089210 (SEQ ID NO: 58), Solyc03g114830 (SEQ ID NO: 59), or Solyc06g069430 (SEQ ID NO: 60) from tomato; or GRMZM2G148693 (SEQ ID NO: 61), GRMZM2G553379 (SEQ ID NO: 62), GRMZM2G072582 (SEQ ID NO: 63), or GRMZM2G147716 (SEQ ID NO: 64) from corn, or any functional portion thereof.

A vegetative stage promoter, which may also be a meristem-preferred or meristem-specific promoter, may include both early and late vegetative stage promoters depending on their pattern of expression during vegetative stages of development. An "early vegetative stage" promoter first initiates or causes observable or detectable transcription or expression of its associated gene/transgene or transcribable DNA sequence during one or more earlier vegetative stages (i.e., Ve through V5 stages), whereas a "late vegetative stage" first initiates or causes observable or detectable transcription or expression of its associated gene/transgene or transcribable DNA sequence during one or more later vegetative stages (i.e., V6 stage and later). An early or late vegetative stage promoter may also be an early or late vegetative stage preferred promoter. An "early vegetative stage preferred" promoter initiates, causes, drives, etc., transcription or expression of its associated gene/transgene or transcribable DNA sequence more predominantly or to a greater extent during one or more earlier vegetative stages (i.e., Ve through V5 stages) as compared to later vegetative stages. Likewise, a "late vegetative stage preferred" promoter initiates, causes, drives, etc., transcription or expression of its associated gene/transgene or transcribable DNA sequence more predominantly or to a greater extent during one or more later vegetative stages (i.e., V6 stage and later) as compared to earlier vegetative stages. Accordingly, an early vegetative stage promoter may also be a late vegetative stage preferred promoter if the promoter first initiates or causes observable or detectable transcription or expression of its associated gene/transgene or transcribable DNA sequence during earlier vegetative stages, but also initiates, causes, drives, etc., transcription or expression of its associated gene/transgene or transcribable DNA sequence more predominantly or to a greater extent during later vegetative stages. The vegetative stage promoter examples listed above may include early and late vegetative stage promoters, which may also be early vegetative stage preferred or late vegetative stage preferred.

The polynucleotide sequence of a vegetative stage promoter (or a functional fragment or portion thereof) may also have a relaxed sequence identity relative to any of the foregoing vegetative stage promoters while still maintaining a similar or identical pattern of expression of an associated transcribable DNA sequence, gene or transgene operably linked to the promoter. For example, a vegetative stage promoter may comprise a polynucleotide sequence that is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to a polynucleotide sequence selected from the above SEQ ID NOs: 31, 32, 33, 34, 35, 36, 37, 38, 39, 40, 41, 42, 43, 44, 45, 48, 49, 50, 51, 52, 53, 54, 55, 56, 57, 58, 59, 60, 61, 62, 63, or 64, or a functional portion thereof. A "functional portion" of a known or provided promoter sequence is defined as one or more continuous or discontinuous portion(s) of the known or provided promoter sequence that may functionally drive, cause, promote, etc., expression of its associated gene, transgene or transcribable DNA sequence in a manner that is identical or similar to the known or provided promoter sequence. Based on the present disclosure, one skilled in the art would be able to determine if a promoter comprising one or more portion(s) of a known or provided promoter sequence, and/or having a shorter sequence and/or a sequence with a more relaxed sequence identity relative to a known or provided promoter sequence, causes a similar pattern of expression and/or similar phenotypes or effects when its associated reporter gene or FT transgene is expressed in a plant as compared to the known or provided promoter sequence.

According to some embodiments, a "reproductive stage" promoter (defined below) may be operably linked and used to express an FT transgene or coding sequence, as long as the reproductive stage promoter provides (i.e., initiates, causes, drives, etc.) at least some level of FT transgene expression during a vegetative stage(s) of plant development to provide an early floral induction signal. Examples of reproductive stage promoters are provided below. Whether a given promoter should be categorized as an early or late vegetative stage promoter and/or a reproductive stage promoter depends on the particular plant species in which the promoter is used. A promoter having a defined pattern of expression in one plant species, such as its native plant species, may have a different, altered or shifted pattern of expression when expressed in a different plant species (e.g., heterologously in a different plant species), although it is anticipated that the pattern of expression with a given promoter would most often be similar (if not identical or nearly identical) between different plant species. For example, a reproductive stage promoter in one plant species may function as an earlier vegetative stage promoter when used to express a transgene or transcribable DNA sequence in another plant species. Thus, a reproductive stage promoter may be used heterologously in some cases to express an FT transgene and induce early flowering. For example, the pAt.AP1 promoter (SEQ ID NO: 49) has a more reproductive stage preferred pattern of expression in its native *Arabidopsis* plant species, but may drive an earlier pattern of vegetative stage expression in the meristem when used heterologously in soybean plants, in addition to driving reproductive stage expression.

As stated above, a recombinant DNA molecule, construct or vector of the present invention may comprise an expression cassette comprising a polynucleotide sequence encoding an FT protein (i.e., a FT transgene) that is operably linked to a vegetative stage promoter, which may also be a meristem-preferred or meristem-specific promoter. The polynucleotide coding sequence of the FT transgene or expression cassette may also be operably linked to one or more additional regulatory element(s), such as an enhancer(s), leader, transcription start site (TSS), linker, 5' and 3' untranslated region(s), intron(s), polyadenylation signal, termination region or sequence, etc., that are suitable or necessary for regulating or allowing expression of the FT transgene or cassette to effectively produce an FT protein in a plant cell. Such additional regulatory element(s) may be optional and used to enhance or optimize expression of the transgene. For purposes of the present invention, an "enhancer" may be distinguished from a "promoter" in that an enhancer typically lacks a transcription start site, TATA box, or equivalent sequence and is thus insufficient alone to drive transcription. As used herein, a "leader" may be defined generally as the DNA sequence of the untranslated 5' region (5' UTR) of a gene (or transgene) between the transcription start site (TSS) and the protein coding sequence start site.

As used herein in reference to a polynucleotide, a "construct" is a polynucleotide segment or sequence comprising one or more sequence elements, such as a coding sequence or a transcribable DNA sequence and one or more expression or regulatory elements, such as a promoter, enhancer, etc. An "expression cassette" is a type of construct comprising a coding sequence or a transcribable DNA sequence that can express the coding sequence or transcribable DNA sequence in a suitable host cell, such as a plant or bacterial cell, and one or more promoter and/or regulatory elements operably linked to the coding sequence or transcribable DNA sequence. A "vector" is a polynucleotide or DNA molecule that may comprise one or more constructs and/or expression cassettes and that is suitable for stability, storage or another use or purpose, such as delivery to, transformation of, and/or maintenance in, a plant or host cell. A "vector" may include a plasmid or circular DNA molecule, a linear DNA molecule, a transformation vector suitable for plant transformation, etc. A DNA molecule or vector may comprise one or more construct(s), expression cassette(s), selectable marker(s), replication and/or maintenance element(s), etc.

According to embodiments of the present invention, the term "recombinant" in reference to a polynucleotide (DNA or RNA) molecule, protein, construct, vector, etc., refers to a polynucleotide or protein molecule or sequence that is not normally found in nature and/or is present in a context in which it is not normally found in nature, including a polynucleotide (DNA or RNA) molecule, protein, construct, etc., comprising a combination of two or more polynucleotide or protein sequences that would not naturally occur contiguously or in close proximity together without human intervention, and/or a DNA molecule, construct, etc., comprising at least two DNA sequences that are heterologous with respect to each other. A recombinant DNA molecule, construct, etc., may comprise DNA sequence(s) that is/are separated from other polynucleotide sequence(s) that exist in proximity to such DNA sequence(s) in nature, and/or a DNA sequence that is adjacent to (or contiguous with) other polynucleotide sequence(s) that are not naturally in proximity with each other. A recombinant DNA molecule, construct, etc., may also refer to a DNA molecule or sequence that has been genetically engineered and constructed outside of a cell. For example, a recombinant DNA molecule may comprise any suitable plasmid, vector, etc., and may include a linear or circular DNA molecule. Such plasmids, vectors, etc., may contain various maintenance elements including a prokaryotic origin of replication and selectable marker, as well as a FT expressing transgene or expression cassette perhaps in addition to a plant selectable marker gene, etc.

According to embodiments of the present invention, a second expression cassette is provided comprising a transcribable polynucleotide or DNA sequence operably linked to a plant expressible promoter, wherein the transcribable DNA sequence comprises a sequence that corresponds to at least a portion of an FT transgene and/or a sequence complementary thereto, and targets the FT transgene for suppression. The transcribable DNA sequence may encode a RNA molecule comprising a targeting sequence that is complementary to at least a portion of the pre-mRNA or mature mRNA encoded by a polynucleotide sequence encoding an FT protein (i.e., an FT transgene), such that the RNA molecule suppresses the FT transgene. Accordingly, a recombinant DNA molecule, construct or vector is provided for transformation into a plant comprising the second expression cassette. Such a recombinant DNA molecule, construct or vector may further comprise a first expression cassette comprising a polynucleotide coding sequence encoding a FT protein (i.e., a FT transgene) operably linked to a first plant expressible promoter, and wherein the second expression cassette comprises the transcribable DNA sequence operably linked to a second plant expressible promoter. Alternatively, two recombinant DNA molecules, constructs or vectors may be provided for plant transformation comprising a first recombinant DNA molecule, construct or vector and a second recombinant DNA molecule, construct or vector, wherein the first recombinant DNA molecule, construct or vector comprises the first expression cassette comprising an FT transgene, and the second recombinant DNA molecule, construct or vector comprises the second expression cassette comprising a transcribable DNA sequence that includes a sequence that corresponds to at least a portion of the FT transgene and/or a sequence complementary thereto. According to some embodiments, a plant expressible promoter operably linked to a transcribable DNA sequence that encodes a RNA molecule for suppression of an FT gene or transgene is heterologous with respect to the transcribable DNA sequence.

Any method known in the art for suppression of a target gene may be used to suppress the FT transgene according to embodiments of the present invention including expression of antisense RNAs, double stranded RNAs (dsRNAs) or inverted repeat RNA sequences, or via co-suppression or RNA intereference (RNAi) through expression of small interfering RNAs (siRNAs), short hairpin RNAs (shRNAs), trans-acting siRNAs (ta-siRNAs), or micro RNAs (miRNAs). See, e.g., U.S. Patent Application Publication Nos. 2009/0070898, 2011/0296555, and 2011/0035839, the contents and disclosures of which are incorporated herein by reference. Accordingly, the RNA molecule encoded by a transcribable DNA sequence may be an antisense RNA, double stranded RNA (dsRNA) or inverted repeat RNA, a small interfering RNA (siRNA), a short hairpin RNA (shRNA), a trans-acting siRNA (ta-siRNA), or a micro RNA (miRNA), and including precursor RNAs, such as a precursor siRNA or miRNA, that may be processed or cleaved into a mature RNA molecule, such as a mature siRNA or miRNA. The term "suppression" as used herein, refers to a lowering, reduction or elimination of the expression level of the mRNA and/or protein encoded by the targeted gene and/or transgene in a plant, plant cell or plant tissue, which may be limited to a particular tissue and/or stage of plant development depending on the promoter used to express the RNA molecule.

According to embodiments of the present invention, a recombinant DNA molecule, construct or vector is provided comprising a transcribable DNA sequence and/or suppression element(s) encoding a RNA molecule or sequence that targets an FT transgene for suppression, wherein the transcribable DNA sequence is operably linked to a plant-expressible promoter. Since the RNA molecule is for suppression, the RNA molecule encoded by a transcribable DNA sequence may be a non-coding RNA molecule. For purposes of the present invention, a "non-coding RNA molecule" is a RNA molecule that does not encode a protein. According to some embodiments, a recombinant DNA molecule, construct or vector may comprise a first expression cassette comprising an FT transgene and a second expression cassette comprising a transcribable DNA sequence encoding a RNA molecule that targets the FT transgene for suppression. Alternatively, a first expression cassette comprising an FT transgene and a second expression cassette comprising a transcribable DNA sequence for suppression of the FT transgene may be present in two different recombinant DNA molecules, constructs or vectors.

The transcribable DNA sequence may comprise a suppression element that is at least 15 nucleotides in length, such as from about 15 nucleotides in length to about 27 nucleotides in length, or 15, 16, 17, 18, 19, 20, 21, 22, 23, 24, 25, 26, or 27 nucleotides in length, wherein the suppression element corresponds to at least a portion of the target FT transgene to be suppressed, and/or to a DNA sequence complementary thereto. In many embodiments, the transcribable DNA sequence or suppression element may be at least 17, at least 19, at least 20, at least 21, at least 22, or at least 23 nucleotides (or more) in length (e.g., at least 25, at least 30, at least 50, at least 100, at least 200, at least 300, at least 500, at least 1000, at least 1500, at least 2000, at least 3000, at least 4000, or at least 5000 nucleotides in length). Depending on the length and sequence of a transcribable DNA sequence or suppression element, one or more sequence mismatches or non-complementary bases may be tolerated without a loss of suppression. Indeed, even shorter RNAi suppression elements ranging from about 15 nucleotides to about 27 nucleotides in length may have one or more mismatches or non-complementary bases, yet still be effective at suppressing a target FT transgene. Accordingly, a sense or anti-sense suppression element may comprise a sequence that is at least 80%, at least 85%, at least 90%, at least 95%, at least 96%, at least 97%, at least 98%, at least 99%, at least 99.5%, or 100% identical or complementary to a corresponding sequence of at least a segment or portion of the targeted FT transgene, or its complementary sequence, respectively.

A transcribable DNA sequence of the present invention for targeted suppression of a FT transgene may include one or more of the following suppression element(s) and/or targeting sequence(s): (a) a DNA sequence that includes at least one anti-sense DNA sequence that is anti-sense or complementary to at least one segment or portion of the targeted FT transgene; (b) a DNA sequence that includes multiple copies of at least one anti-sense DNA sequence that is anti-sense or complementary to at least one segment or portion of the targeted FT transgene; (c) a DNA sequence that includes at least one sense DNA sequence that comprises at least one segment or portion of the targeted FT transgene; (d) a DNA sequence that includes multiple copies of at least one sense DNA sequence that each comprise at least one segment or portion of the targeted FT transgene; (e) a DNA sequence that includes an inverted repeat of a segment or portion of a targeted FT transgene and/or transcribes into RNA for suppressing the targeted FT transgene by forming double-stranded RNA, wherein the transcribed RNA includes at least one anti-sense DNA sequence that is anti-sense or complementary to at least one segment or portion of the targeted FT transgene and at least one sense DNA sequence that comprises at least one segment or portion of the targeted FT transgene; (f) a DNA sequence that is transcribed into RNA for suppressing the targeted FT transgene by forming a single double-stranded RNA and includes multiple serial anti-sense DNA sequences that are each anti-sense or complementary to at least one segment or portion of the targeted FT transgene and multiple serial sense DNA sequences that each comprise at least one segment or portion of the targeted FT transgene; (g) a DNA sequence that is transcribed into RNA for suppressing the targeted FT transgene by forming multiple double strands of RNA and includes multiple anti-sense DNA sequences that are each anti-sense or complementary to at least one segment or portion of the targeted FT transgene and multiple sense DNA sequences that each comprise at least one segment or portion of the targeted FT transgene, wherein the multiple anti-sense DNA segments and multiple sense DNA segments are arranged in a series of inverted repeats; (h) a DNA sequence that includes nucleotides derived from a miRNA, preferably a plant miRNA; (i) a DNA sequence that includes nucleotides of a siRNA; (j) a DNA sequence that is transcribed into an RNA aptamer capable of binding to a ligand; and (k) a DNA sequence that is transcribed into an RNA aptamer capable of binding to a ligand and DNA that transcribes into a regulatory RNA capable of regulating expression of the targeted FT transgene, wherein the regulation of the targeted FT transgene is dependent on the conformation of the regulatory RNA, and the conformation of the regulatory RNA is allosterically affected by the binding state of the RNA aptamer by the ligand. A transcribable DNA sequence may comprise one or more of the above suppression elements and/or targeting sequence(s), which may correspond to one or more sequences of the FT transgene, and/or its complementary sequence.

Multiple sense and/or anti-sense suppression sequences of a transcribable DNA sequence for more than one FT transgene target sequence may be arranged serially in tandem or arranged in tandem segments or repeats, such as tandem inverted repeats, which may also be interrupted by one or more spacer sequence(s). Furthermore, a sense or anti-sense sequence of a transcribable DNA sequence or suppression element may not be perfectly matched or complementary to the targeted FT transgene sequence, depending on the sequence and length of the transcribable DNA sequence or suppression element. Indeed, even shorter RNAi suppression elements from about 15 nucleotides to about 27 nucleotides in length may have one or more mismatches or non-complementary bases depending on the length of the suppression element or targeting sequence, such as 1, 2, 3, 4, 5, 6, 7, 8, 9 or 10 (or more) mismatches, yet still be effective at suppressing the target FT transgene. Accordingly, a sense or anti-sense suppression element may comprise a sequence that is at least 80%, at least 85%, at least 90%, at least 95%, at least 96%, at least 97%, at least 98%, at least 99%, at least 99.5% or 100% identical or complementary to a corresponding sequence of at least a segment or portion of the targeted FT transgene, or its complementary sequence, respectively.

For anti-sense suppression, a transcribable DNA sequence may comprise a sequence that is anti-sense or complementary to at least a portion or segment of the targeted FT transgene. The transcribable DNA sequence and/or suppression element(s) may comprise multiple anti-sense sequences that are complementary to one or more portions or segments of the targeted FT transgene, or multiple copies of an anti-sense sequence that is complementary to a targeted FT transgene. An anti-sense sequence may be at least 80%, at least 85%, at least 90%, at least 95%, at least 96%, at least 97%, at least 98%, at least 99%, at least 99.5%, or 100% identical to a DNA sequence that is complementary to at least a segment or portion of a targeted FT transgene mRNA. In other words, an anti-sense sequence may be at least 80%, at least 85%, at least 90%, at least 95%, at least 96%, at least 97%, at least 98%, at least 99%, at least 99.5%, or 100% complementary to a targeted FT transgene.

The terms "percent complementarity" or "percent complementary" as used herein in reference to two nucleotide sequences is similar to the concept of percent identity but refers to the percentage of nucleotides of a sequence that optimally base-pair or hybridize to nucleotides a reference sequence when the two sequences are linearly arranged and optimally base paired without secondary folding structures, such as loops, stems or hairpins, but with tolerance for mismatches and gaps in base-pairing between the two sequences. Such a percent complementarity may be between two DNA strands, two RNA strands, or a DNA strand and a RNA strand. The "percent complementarity" may be calculated by (i) optimally base-pairing or hybridizing the two nucleotide sequences in a linear and fully extended arrangement (i.e., without folding or secondary structures) over a window of comparison (e.g., alignment window), (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. For these purposes, an alignment window is defined as the region of complementarity between the two sequences. Optimal base pairing of two sequences may be determined based on the known pairings of nucleotide bases, such as G-C, A-T, and A-U, through hydrogen bonding. If the "percent complementarity" is being calculated in relation to a reference or query sequence without specifying a particular comparison window, then the percent identity is determined by dividing the number of complementary positions between the two linear sequences by the total length of the reference sequence. For purposes of the present invention, when two sequences (query and subject) are optimally base-paired (with allowance for gaps and mismatches or non-base-paired nucleotides), the "percent complementarity" for a query sequence (when a comparison window is not defined) is equal to the number of base-paired positions between the two sequences divided by the total number of positions in the query sequence over its length, which is then multiplied by 100%.

For suppression of an FT transgene using an inverted repeat or a transcribed dsRNA, a transcribable DNA sequence may comprise a sense sequence that comprises a segment or portion of a targeted FT transgene and an anti-sense sequence that is complementary to a segment or portion of the targeted FT transgene, wherein the sense and anti-sense DNA sequences are arranged in tandem. The sense and/or anti-sense sequences, respectively, may each be less than 100% identical or complementary to a segment or portion of the targeted FT transgene as described above. The sense and anti-sense sequences may be separated by a spacer sequence, such that the RNA molecule transcribed from the transcribable DNA sequence forms a stem, loop or stem-loop structure between the sense and anti-sense sequences. The transcribable DNA sequence may instead comprise multiple sense and anti-sense sequences that are arranged in tandem, which may also be separated by one or more spacer sequences. A transcribable DNA sequence comprising multiple sense and anti-sense sequences may be arranged as a series of sense sequences followed by a series of anti-sense sequences, or as a series of tandemly arranged sense and anti-sense sequences.

For suppression of an FT transgene using a microRNA (miRNA), a transcribable DNA sequence may comprise a DNA sequence derived from a miRNA sequence native to a virus or eukaryote, such as an animal or plant, or modified or derived from such a native miRNA sequence. Such native or native-derived miRNA sequences may form a fold back structure and serve as a scaffold for the precursor miRNA, and may correspond to the stem region of a native miRNA precursor sequence, such as from a native (or native-derived) pri-miRNA or pre-miRNA sequence. However, in addition to these native or native-derived miRNA scaffold or preprocessed sequences, engineered miRNAs of the present invention further comprise a sequence corresponding to a segment or portion of the targeted FT transgene. Thus, in addition to the pre-processed or scaffold sequences, the suppression element may be further engineered to comprise a sense and/or anti-sense sequence that corresponds to a segment or portion of a targeted FT transgene, and/or a sequence that is complementary thereto, although one or more sequence mismatches may be tolerated.

Engineered miRNAs are useful for targeted gene suppression with increased specificity. See, e.g., Parizotto et al., *Genes Dev.* 18:2237-2242 (2004), and U.S. Patent Application Publication Nos. 2004/0053411, 2004/0268441, 2005/0144669, and 2005/0037988, the contents and disclosures of which are incorporated herein by reference. miRNAs are non-coding RNAs. When a miRNA precursor molecule is cleaved, a mature miRNA is formed that is typically from about 19 to about 25 nucleotides in length (commonly from about 20 to about 24 nucleotides in length in plants), such as 19, 20, 21, 22, 23, 24, or 25 nucleotides in length, and has a sequence corresponding to the gene targeted for suppression and/or its complement. The mature miRNA hybridizes to target mRNA transcripts and guides the binding of a complex of proteins to the target transcripts, which may function to inhibit translation and/or result in degradation of the transcript, thus negatively regulating or suppressing expression of the targeted gene. miRNA precursors are also useful in plants for directing in-phase production of siRNAs, trans-acting siRNAs (ta-siRNAs), in a process that requires a RNA-dependent RNA polymerase to cause suppression of a target gene. See, e.g., Allen et al., *Cell* 121:207-221 (2005), Vaucheret *Science STKE*, 2005:pe43 (2005), and Yoshikawa et al. *Genes Dev.*, 19:2164-2175 (2005), the contents and disclosures of which are incorporated herein by reference.

According to embodiments of the present invention, a recombinant DNA molecule, construct or vector is provided comprising a transcribable DNA sequence encoding a miRNA or precursor miRNA molecule for targeted suppression of a FT transgene. Such a transcribable DNA sequence may comprise a sequence of at least 19 nucleotides in length that corresponds to a FT transgene and/or a sequence complementary to the FT transgene, although one or more sequence mismatches and/or non-base-paired nucleotides may be tolerated.

An FT transgene may also be suppressed using one or more small interfering RNAs (siRNAs). The siRNA pathway involves the non-phased cleavage of a longer double-stranded RNA intermediate ("RNA duplex") into small interfering RNAs (siRNAs). The size or length of siRNAs typically ranges from about 19 to about 25 nucleotides or base pairs, but common classes of siRNAs include those containing 21 base pairs or 24 base pairs. Thus, a transcribable DNA sequence of the present invention may encode a RNA molecule that is at least about 19 to about 25 nucleotides in length, such as 19, 20, 21, 22, 23, 24, or 25 nucleotides in length. For siRNA suppression, a recombinant DNA molecule, construct or vector is thus provided comprising a transcribable DNA sequence and/or suppression element encoding a siRNA molecule for targeted suppression of a FT transgene.

According to embodiments of the present invention, a recombinant DNA molecule, vector or construct is provided comprising a transcribable DNA sequence encoding a non-coding RNA molecule that binds or hybridizes to a sequence of a target mRNA in a plant cell, such as a coding (exon) and/or untranslated (UTR) sequence of the target mRNA, wherein the target mRNA molecule encodes an FT protein, and wherein the transcribable DNA sequence is operably linked to a plant expressible promoter. In addition to targeting a mature mRNA sequence, a non-coding RNA molecule encoded by a transcribable DNA sequence may target an intron sequence of a FT transgene or transcript. According to other embodiments, a recombinant DNA molecule, vector or construct is provided comprising a transcribable DNA sequence encoding a non-coding RNA (precursor) molecule that is cleaved or processed into a mature non-coding RNA molecule that binds or hybridizes to a target mRNA in a plant cell, wherein the target mRNA molecule encodes an FT protein, and wherein the transcribable DNA sequence is operably linked to a plant expressible promoter, which may be a tissue-specific, tissue-preferred, developmental, and/or other type of promoter.

According to embodiments of the present invention, a recombinant DNA molecule, vector or construct is provided comprising a transcribable DNA sequence encoding a non-coding RNA molecule, wherein the non-coding RNA molecule is at least 80%, at least 85%, at least 90%, at least 95%, at least 96%, at least 97%, at least 98%, at least 99%, at least 99.5%, or 100% complementary to at least a segment or portion of a mRNA molecule (i) expressed from an FT transgene and/or (ii) encoding an FT protein in a plant or plant cell, wherein the transcribable DNA sequence is operably linked to a plant-expressible promoter. A non-coding RNA molecule may target a mature mRNA or pre-mRNA sequence, a 5' or 3' untranslated region (UTR), a coding (exon) sequence and/or an intron or intronic sequence of a FT transgene or transcript. According to some embodiments, the non-coding RNA molecule targets a FT transgene for suppression and is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a polynucleotide (coding) sequence encoding an FT protein (e.g., SEQ ID NO: 1, 3, 5, 7, 9, 11, 13, 15, 17, 19, 21, 23, 25, 27, or 29), or to any other known florigenic FT coding sequence. According to other embodiments, the non-coding RNA molecule is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an FT protein that is at least 80%, at least 85%, at least 90%, at least 95%, at least 96%, at least 97%, at least 98%, at least 99%, at least 99.5%, or 100% identical to SEQ ID NO: 2, 4, 6, 8, 10, 12, 14, 16, 18, 20, 22, 24, 26, 28, or 30, or to any other known florigenic FT protein, or a functional fragment thereof. As used herein, the term "consecutive" in reference to a polynucleotide or protein sequence means without deletions or gaps in the sequence. According to embodiments of the present invention, a non-coding RNA molecule encoded by a transcribable DNA sequence of a recombinant DNA molecule, vector or construct provided herein may be a mature miRNA or siRNA, or a precursor miRNA or siRNA that may be processed or cleaved in a plant cell to form a mature miRNA or siRNA.

According to some embodiments of the present invention, the transcribable DNA sequence may comprise a sequence encoding a targeting sequence of a RNA molecule that is complementary and/or hybridizes to a particular Gm.FT2a gene or transgene mRNA to target the Gm.FT2a gene or transgene for suppression. The transcribable DNA sequence may comprise a sequence (e.g., SEQ ID NO: 65) encoding a targeting sequence (e.g., SEQ ID NO: 66) of an RNA molecule encoded by, and transcribed from, the transcribable DNA sequence. The targeting sequence of the RNA molecule may be any sequence of sufficient length that is complementary to a segment or portion of the mRNA encoded by the FT transgene, and the transcribable DNA sequence may comprise a sequence that encodes, or is transcribed into, the targeting sequence of the RNA molecule. For example, a transcribable DNA sequence encoding a precursor miRNA may comprise SEQ ID NO: 67, which may be processed into a mature miRNA comprising SEQ ID NO: 67 that targets a Gm.FT2a gene or transgene for suppression. The mRNA encoded by the targeted FT gene or transgene may comprise a target site for a RNA molecule encoded by the transcribable DNA sequence. Such a target site in the mRNA of the FT transgene may comprise, for example, SEQ ID NO: 68, which may be encoded by a sequence (e.g., SEQ ID NO: 69) of the FT gene or transgene. Thus, the polynucleotide coding sequence of the FT transgene may comprise a sequence encoding the target site for the RNA molecule.

In addition to a plant expressible promoter, a recombinant DNA molecule, construct, vector or expression cassette comprising a transcribable DNA sequence encoding a non-coding RNA molecule for suppression of an FT transgene may also be operably linked to one or more additional regulatory element(s), such as an enhancer(s), transcription start site (TSS), linker, polyadenylation signal, 5' and/or 3' scaffold or backbone sequences, termination region or sequence, etc., that are suitable, necessary or preferred for regulating or allowing expression of the transcribable DNA sequence in a plant cell or tissue. Such additional regulatory element(s) may be optional and used to enhance or optimize expression of the transcribable DNA sequence.

According to some embodiments, a transcribable DNA sequence may comprise a sequence that corresponds to at least a portion of a non-coding sequence of an FT transgene and/or a sequence complementary thereto, such as a 5' or 3' untranslated region (UTR) or intronic sequence of the FT transgene, which may allow for selective suppression of the FT transgene over an endogenous FT gene. The "non-coding" sequences of an FT transgene (not to be confused with a "non-coding RNA molecule" encoded by a transcribable DNA sequence for suppression of an FT gene or transgene) are the sequences of the FT transgene that are transcribed and form part of the pre-mRNA and/or mature mRNA, but do not encode the transgenic FT protein. Accordingly, the transcribable DNA sequence may encode a RNA molecule comprising a targeting sequence that corresponds to at least a portion of a non-coding sequence of the FT transgene and/or a sequence complementary thereto. Thus, the transcribable DNA sequence may comprise a sequence that corresponds to at least a portion of a pre-mRNA or mature mRNA encoded by the FT transgene. The sequence of the transcribable DNA sequence and encoded targeting sequence of the RNA molecule depend on the particular non-coding sequences of the FT transgene, which may be the same or different or unique relative to endogenous FT gene(s). According to some embodiments, a recombinant DNA molecule, vector or construct is provided comprising an expression cassette that comprises a transcribable DNA sequence having a sequence that corresponds to at least a portion of a non-coding sequence of an FT transgene and/or a sequence complementary thereto. Similarly as described above, two or more expression cassettes may be provided comprising a first expression cassette and a second expression cassette, wherein the first expression cassette comprises a polynucleotide sequence encoding a FT protein (i.e., a FT transgene) operably linked to a first plant expressible promoter, and the second expression cassette comprising a transcribable DNA sequence operably linked to a second plant expressible promoter, wherein the transcribable DNA sequence comprises a sequence that corresponds to at least a portion of a non-coding sequence of the FT transgene and/or a sequence complementary thereto. The first and second expression cassettes may be present in the same DNA molecule, vector or construct, or in separate DNA molecules, vectors or constructs.

A transcribable DNA sequence encoding a RNA molecule that targets an FT transgene for suppression may be operably linked to a plant expressible promoter. The pattern of expression of the RNA molecule may depend on the particular plant expressible promoter. As described above, expression of an FT transgene under the control of a vegetative stage promoter may be used to trigger early flowering and increase the number of flowers, pods, etc., per node of a plant, but may also cause early termination of the plant. It is presently proposed that additional expression of a RNA molecule that targets the FT transgene for suppression may be used to refine and/or attenuate the pattern and level of expression of the FT transgene to further mitigate the early termination phenotypes. This may occur through decreasing the quantity of transcript and protein from the FT transgene (i.e., reducing its level of expression) and/or modifying its pattern of expression (i.e., refinement or restriction of the pattern of transgenic FT expression). Without being bound by theory, a reduced expression of the FT transgene may be sufficient to induce early flowering while mitigating the early termination phenotypes. Likewise, a restricted spatiotemporal pattern of FT expression may reduce FT expression in particular tissues and/or stages of development where transgenic FT may cause earlier termination. Thus, according to embodiments of the present invention, the timings and patterns of expression of the FT transgene and the RNA molecule (targeting the FT transgene for suppression) may be the same, overlapping or more distinct.

According to many embodiments as introduced above, at least two expression cassettes may be provided comprising a first expression cassette and a second expression cassette, wherein the first expression cassette comprises an FT transgene operably linked to a first plant expressible promoter and the second expression cassette comprises a transcribable DNA sequence operably linked to a second plant expressible promoter, wherein the transcribable DNA sequence encodes a RNA molecule that targets the FT transgene for suppression. The two expression cassettes may be present in the same recombinant DNA molecule, construct or vector, or present in separate recombinant DNA molecules, constructs or vectors. As described above, the first plant expressible promoter operably linked to the FT transgene may be a vegetative stage promoter, which may also be a meristem-specific or meristem-preferred promoter. The second plant expressible promoter operably linked to the transcribable DNA sequence may comprise a variety of different promoter types including constitutive, inducible, developmental, tissue-specific, tissue-preferred, vegetative stage, reproductive stage, etc., but the timing and pattern of expression of the RNA molecule should at least partially overlap with the timing and pattern of expression of the FT transgene. According to some embodiments, the second plant expressible promoter may be a constitutive or vegetative stage promoter to reduce the level of expression of the FT transgene. Such a constitutive or vegetative stage promoter may also be a tissue-specific or tissue-preferred promoter and/or may broadly overlap with the timing and pattern of expression of the FT transgene. Indeed, a constitutive or overlapping expression pattern of the transcribable DNA sequence (and RNA suppression molecule) with respect to the FT transgene may be effective at reducing the quantity or dosage of FT expression, especially if suppression of the FT transgene is imperfect or incomplete. In some cases, the FT transgene and suppression construct may even be operably linked to a same or similar promoter. For example, the first plant expressible promoter driving expression of the FT transgene may be an early or late vegetative stage and/or reproductive stage promoter, and the second plant expressible promoter driving expression of the transcribable DNA sequence encoding the RNA molecule for suppression may also be an early or late vegetative stage and/or reproductive stage promoter.

Many examples of constitutive promoters are known in the art, such as a cauliflower mosaic virus (CaMV) 35S and 19S promoter (see, e.g., U.S. Pat. No. 5,352,605), an enhanced CaMV 35S promoter, such as a CaMV 35S promoter with Omega region (see, e.g., Holtorf, S. et al., *Plant Molecular Biology*, 29: 637-646 (1995) or a dual enhanced CaMV promoter (see, e.g., U.S. Pat. No. 5,322,938), a Figwort Mosaic Virus (FMV) 35S promoter (see, e.g., U.S. Pat. No. 6,372,211), a *Mirabilis* Mosaic Virus (MMV) promoter (see, e.g., U.S. Pat. No. 6,420,547), a Peanut Chlorotic Streak Caulimovirus promoter (see, e.g., U.S. Pat. No. 5,850,019), a nopaline or octopine promoter, a ubiquitin promoter, such as a soybean polyubiquitin promoter (see, e.g., U.S. Pat. No. 7,393,948), an *Arabidopsis* S-Adenosylmethionine synthetase promoter (see, e.g., U.S. Pat. No. 8,809,628), etc., or any functional portion of the foregoing promoters, the contents and disclosures of each of the above references are incorporated herein by reference. Alternatively, the second plant expressible promoter may be a vegetative and/or reproductive stage promoter, examples of which are provided herein.

According to other embodiments, the second plant expressible promoter may have a more distinct timing and/or pattern of expression, such as in different plant tissues and/or developmental stages, relative to the FT transgene. Thus, the effective spatiotemporal pattern of expression of the FT transgene may be modified, altered and/or refined depending on the relative expression timings and patterns of the FT transgene and the transcribable DNA sequence encoding the RNA molecule for suppression of the FT transgene (as well as the specific targeting sequence of the RNA molecule). According to many embodiments, however, the transcribable DNA sequence (and RNA molecule) may be expressed at a later developmental stage or tissue relative to the onset of expression of the FT transgene, such that the FT transgene is still able to provide the early floral induction signal before being suppressed by the later expression of the RNA suppression molecule, or stated differently the FT transgene may be suppressed after the early floral induction signal to reduce or mitigate early termination. For example, the first plant expressible promoter driving expression of the FT transgene may be an early vegetative stage promoter, and the second plant expressible promoter driving expression of the transcribable DNA sequence encoding the RNA molecule for suppression may be a late vegetative stage and/or reproductive stage promoter, or the first plant expressible promoter may be a late vegetative stage promoter, and the second plant expressible promoter may be a reproductive stage promoter. More broadly, the second plant expressible promoter may initiate, cause and/or drive expression of its associated transgene or transcribable DNA sequence at a later developmental stage than the first plant expressible promoter, such that the suppression construct is generally expressed after the initial FT floral induction signal during earlier vegetative stage(s) of development. Thus, the second plant expressible promoter may be a later developmental stage promoter than the first plant expressible promoter. For example, the second plant expressible promoter may drive expression at a later developmental stage than the first plant expressible promoter, but in the same tissue type or developmental lineage (e.g., in the meristem) as the first plant expressible promoter. Such a late vegetative stage and/or reproductive stage promoter may also be a tissue-specific or tissue-preferred promoter, such as a meristem-specific or meristem-preferred promoter. Examples of late vegetative stage promoters are provided above.

By expressing the transcribable DNA sequence and RNA molecule for suppression of the FT transgene during one or more later stage(s) of plant development relative to the FT transgene, the effective expression profile of the FT transgene may be modified, altered and/or refined to earlier developmental stages and/or tissues, relative to expression of the FT transgene alone. In some cases, vegetative stage expression of the FT transgene may linger or continue during later vegetative and/or reproductive stages or tissues in the plant. Thus, later expression of the RNA molecule that targets the FT transgene for suppression may reduce the level of FT transgene in those later stage(s) and/or tissue(s) to effectively limit or confine the expression level of the FT transgene to earlier developmental stage(s) and/or tissue(s). As a result, the early floral induction signal may be maintained or preserved, while later FT expression may be attenuated or reduced to avoid or delay early termination of the remaining meristematic reserves of the plant and allow for vegetative growth and development of the plant to continue after flowering.

As used herein, a "reproductive stage" promoter is defined as any promoter that initiates, causes, drives, etc., transcription or expression of its associated gene, transgene, or transcribable DNA sequence during one or more reproductive stage(s) of plant development, such as during one or more of R1, R2, R3, R4, R5, R6, R7, and/or R8 stages of development. Such a "reproductive stage" promoter may be further defined as a "reproductive stage preferred" promoter that initiates, causes, drives, etc., transcription or expression of its associated gene/transgene or transcribable DNA sequence at least preferably or mostly, if not exclusively, during one or more reproductive stage(s) of plant development (as opposed to vegetative stages). However, a "reproductive stage" and a "reproductive stage preferred" promoter may each also initiate, permit, allow, cause, drive, etc., transcription or expression of its associated gene, transgene, or transcribable DNA sequence during vegetative phase(s) or stage(s) of development in one or more cells or tissues of the plant. Thus, a reproductive stage promoter may also be a vegetative stage promoter if expressed during both developmental phases (i.e., during both vegetative and reproductive stages of development). Such a reproductive stage promoter may also be a tissue-specific or tissue-preferred promoter, such as a meristem-specific or meristem-preferred promoter. A "reproductive stage" promoter may be further defined as initiating, causing, driving, etc., transcription or expression of its associated gene/transgene or transcribable DNA sequence in one or more reproductive tissue(s) of a plant. Such a "reproductive stage" promoter may also be defined as a "floral preferred" promoter that initiates, causes, drives, etc., transcription or expression of its associated gene/transgene or transcribable DNA sequence at least preferably or mostly, if not exclusively, in at least one floral or reproductive tissue, such as a floral meristem, or a "floral specific" promoter that initiates, causes, drives, etc., transcription or expression of its associated gene/transgene or transcribable DNA sequence exclusively (or almost exclusively) in at least one floral or reproductive tissue. The features and characteristics of these reproductive stages for a given plant species are known in the art.

Examples of reproductive stage promoters, which may also be early or late vegetative stage promoters depending on their pattern of expression in a given plant species, may include the following promoters from tomato genes: a Sl.Nod promoter (pSl.Nod, pLe.Nod or pNod) (SEQ ID NO: 70), a Sl.MADS5 promoter (pSl.MADS5, pLe.MADS5 or pMADS5) (SEQ ID NO: 71), or a Sl.MADS-RIN promoter (pSl.MADS-RIN, pLe.MADS-RIN or pMADS-RIN) (SEQ ID NO: 72), or any functional portion thereof. Further examples identified as having homology and/or a similar expression pattern as the pSl.MADS5 and/or pSl.MADS-RIN promoter in their native plant species may include a promoter from one of the following genes: AT1G24260.1 (SEQ ID NO: 73), AT2G45650.1 (SEQ ID NO: 74), AT3G02310.1 (SEQ ID NO: 75), or AT5G15800.1 (SEQ ID NO: 76), or AT2G03710.1 (SEQ ID NO: 77) from *Arabidopsis*; Glyma05g28140 (SEQ ID NO: 78), Glyma08g11120 (SEQ ID NO: 79), Glyma11g36890 (SEQ ID NO: 80), Glyma08g27670 (SEQ ID NO: 81), Glyma13g06730 (SEQ ID NO: 82), or Glyma19g04320 (SEQ ID NO: 83) from soybean; Solyc02g089200 (SEQ ID NO: 84), Solyc03g114840 (SEQ ID NO: 85), Solyc12g038510 (SEQ ID NO: 86), Solyc04g005320 (SEQ ID NO: 87) or Solyc05g056620 (SEQ ID NO: 88) from tomato; or GRMZM2G159397 (SEQ ID NO: 89), GRMZM2G003514 (SEQ ID NO: 90), GRMZM2G160565 (SEQ ID NO: 91), GRMZM2G097059 (SEQ ID NO: 92), GRMZM2G099522 (SEQ ID NO: 93) or GRMZM2G071620 (SEQ ID NO: 94) from corn, or any functional portion of any of the foregoing promoters.

According to embodiments of the present invention, a "reproductive stage" promoter may also be further defined by the particular reproductive stage during which observable or pronounced transcription or expression of its associated gene, transgene, or transcribable DNA sequence is first caused, initiated, etc. For example, a reproductive stage promoter may be a R1 stage promoter, a R2 stage promoter, a R3 stage promoter, etc. As such, a "R1 stage" promoter is defined as a reproductive stage promoter that first initiates or causes transcription of its associated gene, transgene, or transcribable DNA sequence during the R1 stage of plant development, a "R2 stage" promoter is defined as a reproductive stage promoter that first initiates or causes transcription of its associated gene, transgene, or transcribable DNA sequence during the R2 stage of plant development, and so on, although expression of the associated gene, transgene, or transcribable DNA sequence may be present continuously or discontinuously in one or more tissues during later reproductive stage(s) of development. The transition from vegetative to reproductive stages (and onset of the R1 stage) is defined according to standard conventions in the art for a given crop plant (i.e., typically as with soybeans the visible appearance of the first open flower on the plant). One skilled in the art would be able to determine the timing of expression of a given gene, transgene, or transcribable DNA sequence during plant development using various molecular assays and techniques known in the art, if such timing of expression is not already known.

According to embodiments of the present invention, a "reproductive stage" promoter may include a constitutive, tissue-preferred, or tissue-specific promoter. For example, a reproductive stage promoter may drive expression of its associated gene, transgene or transcribable DNA sequence in one or more plant tissue(s), such as in one or more of the root(s), stem(s), leaf/leaves, meristem(s), etc., during a reproductive stage(s) of plant development. However, such a reproductive stage promoter may preferably drive expression of its associated gene, transgene or transcribable DNA sequence in one or more meristem(s) of the plant. According to many embodiments, a "reproductive stage" promoter may be a "meristem-specific" or "meristem-preferred" promoter to cause expression of its associated gene, transgene or transcribable DNA sequence in meristematic tissue to at least partially correspond to the pattern of expression of the FT transgene and attenuate and/or refine expression of the FT transgene.

The polynucleotide sequence of these promoters (or a functional portion thereof) may also have a relaxed sequence identity while still maintaining a similar or identical pattern of expression of an associated gene, transgene or transcribable DNA sequence operably linked to the promoter. For example, the late vegetative and/or reproductive stage promoter may comprise a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99% or 100% identical to a polynucleotide sequence selected from the above SEQ ID NOs: 70, 71, 72, 73, 74, 75, 76, 77, 78, 79, 80, 81, 82, 83, 84, 85, 86, 87, 88, 89, 90, 91, 92, 93, or 94, or any functional portion thereof. A "functional portion" of a promoter sequence known or provided herein is defined above.

According to embodiments of the present invention, the RNA molecule encoded by a second expression cassette comprising a transcribable DNA sequence operably linked to a second plant expressible promoter may cause a reduction or elimination in the level of expression of an mRNA transcript and/or protein encoded by an FT transgene in one or more plant tissues via suppression of the FT transgene. With the second expression cassette, the expression level of the transgenic FT transcript and/or protein may be reduced by at least 1%, at least 2%, at least 3%, at least 4%, at least 5%, at least 10%, at least 20%, at least 25%, at least 30%, at least 40%, at least 50%, at least 60%, at least 70%, at least 75%, at least 80%, at least 90%, at least 95%, at least 96%, at least 97%, at least 98%, or at least 99% in one or more plant tissues, such as one or more meristematic tissues, as compared to the mRNA transcript and/or protein level(s) of the FT transgene that would exist in the same plant tissue(s) without the second expression cassette. The mRNA transcript and/or protein level(s) of a FT transgene may be reduced by 1%-100%, 1%-75%, 1%-50%, 1%-25%, 5%-100%, 5%-95%, 5%-90%, 5%-85%, 5%-80%, 5%-75%, 5%-70%, 5%-65%, 5%-60%, 5%-55%, 5%-50%, 5%-45%, 5%-40%, 5%-35%, 5%-30%, 5%-25%, 5%-20%, 5%-15%, 5%-10%, 10%-100%, 10%-90%, 10%-80%, 10%-70%, 10%-60%, 10%-50%, 10%-40%, 10%-30%, 10%-20%, 25%-100%, 25%-75%, 25%-50%, 50%-100%, 50%-75%, or 75%-100% in one or more plant tissues as compared to the mRNA transcript and/or protein level(s) of the FT transgene that would exist in the same plant tissue(s) without the second expression cassette.

According to yet further embodiments, the second expression cassette may instead be designed to encode a RNA molecule that targets an endogenous FT gene for suppression. Selective suppression of the endogenous FT gene may be achieved by targeting its coding sequence if the FT transgene has a different coding sequence than the endogenous gene (i.e., the RNA molecule may comprise a targeting sequence that is complementary to at least a portion of a coding sequence of the endogenous FT gene). Alternatively, even if the coding sequences of the FT transgene and endogenous FT gene are the same or similar, the second expression cassette may be designed to encode a RNA molecule that targets a non-translated or non-coding sequence of a mRNA encoded by the endogenous FT gene, such as within the 5' UTR, 3'UTR, intron, and/or leader sequence(s) of the endogenous FT mRNA transcript, if those sequences are different or lacking in the FT transgene (i.e., the RNA molecule may comprise a targeting sequence that is complementary to at least a portion of a non-translated or non-coding sequence of the endogenous FT gene). According to these embodiments, the transcribable DNA sequence of the second expression cassette may be designed according to the principles provided herein to target a particular coding or non-translated (non-coding) sequence of the mRNA encoded by the endogenous FT gene for suppression, instead of the mRNA sequence encoded by an FT transgene.

According to another broad aspect of the present invention, a recombinant DNA molecule, construct or vector is provided comprising a polynucleotide sequence encoding a FT protein (i.e., a FT transgene) operably linked to a plant expressible promoter, wherein the polynucleotide sequence further comprises a sequence encoding a target site or sensor for an endogenous RNA molecule, such as an endogenous miRNA or siRNA, the target site or sensor being present in the pre-mRNA and/or mature mRNA transcript encoded by the FT transgene, such as within the 5' UTR, 3'UTR, intron, and/or leader sequence(s). As used herein, a "sensor" is a small noncoding RNA target site in a mRNA transcript of an FT transgene that is complementary to an endogemous RNA molecule, such as an endogenous miRNA or siRNA. The endogenous RNA molecule may be naturally occurring in a plant cell or tissue and function to suppress one or more target genes having the target site for the endogenous RNA molecule. It is presently proposed that a FT transgene may be further engineered to have a sequence encoding a mRNA target site or sensor for an endogenous RNA molecule, such that the FT transgene is suppressed by the endogenous RNA molecule. Suppression of the FT transgene may thus be used to mitigate the early termination phenotypes observed with transgenic FT expression alone (i.e., without suppression) similar to suppression via a second expression cassette encoding a RNA suppression molecule. The endogenous RNA molecule may be any known naturally occurring small RNA molecule, such as a miRNA, siRNA, etc., that functions to trigger suppression of one or more target genes in a plant cell. According to many embodiments, the endogenous RNA molecule may be naturally expressed during late vegetative and/or reproductive stages of development (e.g., in one or more late vegetative, reproductive, and/or floral tissue(s)), such that the endogenous RNA molecule causes suppression of the FT transgene after providing the initial floral induction signal. According to many embodiments, the plant expressible promoter, the target site, or both of the FT transgene are heterologous with respect to the polynucleotide coding sequence of the FT transgene.

According to some embodiments, the endogenous RNA molecule may be one or more endogenous miRNA molecules, such as one or more miR156 and/or miR172 RNA molecule(s). The sequence of the endogenous miR156 and/or miR172 molecule(s) will depend on the particular plant species in which the FT transgene will be expressed. An FT transgene may be designed to encode a mRNA target site or sensor for a miR156 or miR172 molecule present in the plant species of interest, which may be selected based on the expression level and timing of the one or more miR156 and miR172 molecule(s). In soybean, there are three miR172 molecules that are expressed at higher levels with timing near the vegetative-to-reproductive transition, miRNA172a (SEQ ID NO: 95), miRNA172c (SEQ ID NO: 96), or miRNA172k (SEQ ID NO: 97), and there are three miR156 molecules that are abundant at the juvenile-to-adult transition, miR156a (SEQ ID NO: 103), miR156c (SEQ ID NO: 104), or miR156q (SEQ ID NO: 105). Thus, a polynucleotide sequence encoding a FT protein may further comprise a sequence encoding one or more target site(s) or sensor(s) for one or more of such endogenous miR156 or miR172 RNA molecule(s). Each of the miR156 or miR172 target site(s) or sensor(s) may be present in the pre-mRNA and/or mature mRNA transcript encoded by the FT transgene, such as within a coding, 5' UTR, 3' UTR, and/or intronic mRNA sequence encoded by the polynucleotide sequence of the FT transgene, although miR156 or miR172 target site(s) or sensor(s) will more commonly be present in a non-coding and/or untranslated sequence. Examples of sequences encoding a target site or sensor for a soybean miR156 molecule include SEQ ID NOs: 106, 108, 109, and 110, which are complementary to one or more miR156 molecules. For example, the sequence provided as SEQ ID NO: 106 encodes SEQ ID NO: 107 as a mRNA target site or sensor for miR156. Examples of sequences encoding a target site or sensor for a soybean miR172 include SEQ ID NOs: 98, 100, and 101, which are complementary to one or more miR172 molecules. For example, the sequence provided as SEQ ID NO: 98 encodes SEQ ID NO: 99 as a mRNA target site or sensor for miR172. However, the sequence of a target site or sensor of a FT transgene may be determined based on the complementary sequence of a known miR156 or miR172 molecule. Indeed, depending on the sequence of the one or more endogenous miR156, miR172 and/or other small RNA molecule(s) naturally present in a given plant species, the transgenic FT expression cassette transformed into such a plant species may be engineered to have a sequence that encodes a target site or sensor for such an endogenous miR156, miR172, or other small RNA molecule. According to some embodiments, a first expression cassette comprising an FT transgene may be engineered to have a sequence encoding a target site or sensor for an endogenous miR156, miR172, or other small RNA molecule, even if a second expression cassette is present in the same recombinant DNA molecule construct or vector, or in the same transgenic plant, that comprises a transcribable DNA sequence encoding a RNA molecule that further targets the same FT transgene for suppression.

According to embodiments of the present invention, the target site for an endogenous RNA molecule will depend on the plant in which the FT transgene will be expressed. miR156 and miR172 sequences (and their target sites or sensors) are known for a variety of dicot species. The target site or sensor of the transgenic FT mRNA that is complementary to an endogenous RNA molecule may be 17, 18, 19, 20, 21, 22, 23, 24, 25, 26 or 27 (or more) nucleotides in length. Typically, a target site or sensor of an FT transgene will be designed to be 100% complementary to an endogenous miR156 or miR172. However, a target site or sensor for an endogenous RNA suppression molecule may not need to be 100% complementary to an endogenous miR156 or miR172 to be effective (i.e., to become hybridized by a miR156 or miR172 and targeted for suppression). For example, less than perfect complementarity may allow for more than one miR156, miR172 and/or other endogenous RNA molecule to hybridize to the target site or sensor. For any given plant species, the target site or sensor encoded by the polynucleotide coding sequence of a FT transgene may vary somewhat and still become bound by, or hybridized with, an endogenous RNA molecule, such as an endogenous miR156 or miR172 RNA molecule, when expressed in a plant cell. Accordingly, the target site of the mRNA transcript encoded by the FT transgene may contain one or more mismatches, such as 1, 2, 3, 4, 5, 6, 7, 8 or more mismatches depending on the alignment length between the endogenous RNA molecule (e.g., miR156, miR172) and the mRNA transcript. Indeed, the target site encoded by a polynucleotide coding sequence of an FT transgene may be at least 80%, at least 85%, at least 90%, at least 91%, at least 92%, at least 93%, at least 94%, at least 95%, at least 96%, at least 97% at least 98%, at least 99%, at least 99.5%, at least 99.9% or 100% complementary to the targeting sequence of an endogenous RNA molecule (e.g., miR156 or miR172), such as the target site or sensor for a miR172 molecule in soybean (SEQ ID NOs: 98, 100 or 101) or the target site or sensor for a miR156 molecule in soybean (SEQ ID NO: 106, 108, 109 or 110).

According to another broad aspect of the present invention, methods are provided for transforming a plant cell, tissue or explant with a recombinant DNA molecule, construct or vector provided herein to produce a transgenic plant. The recombinant DNA molecule, construct or vector may comprise an FT transgene or expression cassette. Depending on the manner of suppression, the FT transgene may further comprise a target site for an endogenous RNA molecule. The recombinant DNA molecule, construct or vector may comprise a second expression cassette comprising a transcribable DNA sequence encoding a RNA molecule that targets the FT transgene for suppression. Alternatively, the FT transgene and the transcribable DNA sequence encoding the RNA molecule may instead be present in two separate DNA molecules, constructs or vectors that may be co-transformed or transformed separately into plants. A recombinant DNA molecule, construct or vector comprising an FT transgene and the transcribable DNA sequence encoding an RNA molecule that targets the FT transgene for suppression may be transformed into a plant. According to other embodiments, a first recombinant DNA molecule, construct or vector comprising an FT transgene and a second recombinant DNA molecule, construct or vector comprising a transcribable DNA sequence encoding an RNA molecule that targets the FT transgene for suppression may each be co-transformed into a plant. According to other embodiments, a plant transformed with a first expression cassette comprising an FT transgene may be transformed with a second expression cassette comprising a transcribable DNA sequence encoding an RNA molecule that targets the FT transgene for suppression, or a plant transformed with a first expression cassette comprising a transcribable DNA sequence encoding an RNA molecule that targets the FT transgene for suppression may be transformed with a second expression cassette comprising an FT transgene. According to yet further embodiments, a first transgenic plant having a first expression cassette comprising (i) an FT transgene or (ii) a transcribable DNA sequence encoding an RNA molecule that targets an FT transgene for suppression may be crossed with a second plant having a second expression cassette comprising (i) a transcribable DNA sequence encoding an RNA molecule that targets the FT transgene for suppression or (ii) an FT transgene, such that one or more progeny plants may be produced comprising both the first and second expression cassettes (i.e., both the FT transgene and transcribable DNA sequence).

Numerous methods are known in the art for transforming chromosomes in a plant cell with a recombinant DNA molecule, construct or vector, which may be used according to methods of the present invention to produce a transgenic plant cell, plant part and plant. Any suitable method or technique for transformation of a plant cell known in the art may be used according to present methods. Effective methods for transformation of plants include bacterially mediated transformation, such as *Agrobacterium*-mediated or *Rhizobium*-mediated transformation, and microprojectile bombardment-mediated transformation. A variety of methods are known in the art for transforming explants with a transformation vector via bacterially mediated transformation or microprojectile bombardment and then subsequently culturing, etc, those explants to regenerate or develop transgenic plants. Other methods for plant transformation, such as microinjection, electroporation, vacuum infiltration, pressure, sonication, silicon carbide fiber agitation, PEG-mediated transformation, etc., are also known in the art. Transgenic plants produced by these transformation methods may be chimeric or non-chimeric for the transformation event depending on the methods and explants used. Suitable methods for plastid transformation with a recombinant DNA molecule or construct are also known in the art.

Methods are further provided for expressing an FT transgene in one or more plant cells or tissues under the control of a vegetative-stage promoter, which may also be a meristem-preferred or meristem-specific promoter. Expression of the FT transgene may be modified, attenuated, and/or refined by the presence of a target site or sensor for an endogenous RNA molecule in the mRNA encoded by the FT transgene, such that the endogenous RNA molecule targets the FT transgene for suppression. In addition to an FT transgene, a RNA molecule that targets the FT transgene for suppression may also be expressed from a transcribable DNA sequence transformed into the plant. Such methods may be used to alter flowering time of a plant and/or the number of productive or successful flowers, fruits, pods, and/or seeds per node of the plant relative to a wild type or control plant not having the FT transgene. Indeed, methods of the present invention may be used to alter reproductive or yield-related phenotype(s) or trait(s) of the transgenic plant.

Transformation of a target plant material or explant may be practiced in tissue culture on nutrient media, for example a mixture of nutrients that allow cells to grow in vitro. Recipient cell targets or explants may include, but are not limited to, meristems, shoot tips, protoplasts, hypocotyls, calli, immature or mature embryos, shoots, buds, nodal sections, leaves, gametic cells such as microspores, pollen, sperm and egg cells, etc., or any suitable portions thereof. It is contemplated that any transformable cell or tissue from which a fertile plant can be regenerated or grown/developed may be used as a target for transformation. Transformed explants, cells or tissues may be subjected to additional culturing steps, such as callus induction, selection, regeneration, etc., as known in the art. Transformed cells, tissues or explants containing a recombinant DNA insertion may be grown, developed or regenerated into transgenic plants in culture, plugs or soil according to methods known in the art. Transgenic plants may be further crossed to themselves or other plants to produce transgenic seeds and progeny. A transgenic plant may also be prepared by crossing a first plant comprising the recombinant DNA sequence or transformation event with a second plant lacking the insertion. For example, a recombinant DNA sequence may be introduced into a first plant line that is amenable to transformation, which may then be crossed with a second plant line to introgress the recombinant DNA sequence into the second plant line. Progeny of these crosses can be further back crossed into the more desirable line multiple times, such as through 6 to 8 generations or back crosses, to produce a progeny plant with substantially the same genotype as the original parental line but for the introduction of the recombinant DNA sequence.

A recombinant DNA construct or expression cassette of the present invention may be included within a DNA transformation vector for use in transformation of a target plant cell, tissue or explant. Such a transformation vector of the present invention may generally comprise sequences or elements necessary or beneficial for effective transformation in addition to the transcribable DNA sequence and/or FT transgene or expression cassette. For *Agrobacterium*-mediated transformation, the transformation vector may comprise an engineered transfer DNA (or T-DNA) segment or region having two border sequences, a left border (LB) and a right border (RB), flanking at least the transcribable DNA sequence and/or FT transgene, such that insertion of the T-DNA into the plant genome will create a transformation event for the transcribable DNA sequence and/or FT transgene. In other words, the transcribable DNA sequence and/or FT transgene would be located between the left and right borders of the T-DNA, perhaps along with an additional transgene(s) or expression cassette(s), such as a plant selectable marker transgene and/or other gene(s) of agronomic interest that may confer a trait or phenotype of agronomic interest to a plant. In addition to protein encoding sequences, a gene of agronomic interest may further comprise a polynucleotide sequence encoding a RNA suppression element. According to some embodiments, the transcribable DNA sequence and/or FT transgene and the plant selectable marker transgene (or other gene of agronomic interest) may be present in separate T-DNA segments on the same or different recombinant DNA molecule(s), such as for co-transformation. A transformation vector or construct may further comprise prokaryotic maintenance elements, which for *Agrobacterium*-mediated transformation may be located in the vector backbone outside of the T-DNA region(s).

According to some embodiments, a first expression cassette comprising an FT transgene and a second expression cassette comprising a transcribable DNA sequence encoding a RNA molecule that targets the FT transgene for suppression may be present in the same T-DNA of a transformation vector (i.e., between the same right and left T-DNA borders); or a first expression cassette comprising an FT transgene may be present in a first T-DNA (comprising a first right border and a first left border), and a second expression cassette comprising a transcribable DNA sequence encoding a RNA molecule that targets the FT transgene for suppression may be present in a second T-DNA (comprising a second right border and a second left border), wherein the first and second T-DNAs are in the same transformation vector; or a first expression cassette comprising an FT transgene may be present in a first T-DNA of a first transformation vector, and a second expression cassette comprising a transcribable DNA sequence encoding a RNA molecule that targets the FT transgene for suppression may be present in a second T-DNA of a second transformation vector. The first and second expression cassettes present in one or two transformation vectors may be co-transformed into a plant cell, or the first and second expression cassettes may be present in two separate transformation vectors and transformed into plant cells separately. A first or second expression cassette may be transformed into one or more plant cells already having a transformation event for the other expression cassette, or the first and second expression cassettes may be transformed into different plant cells that may be developed or regenerated into a first and second transgenic plant. The first or second transgenic plants and/or their progeny may be crossed to each other, such that the first and second expression cassettes are brought together and present in the same plant.

A plant selectable marker transgene in a transformation vector or construct of the present invention may be used to assist in the selection of transformed cells or tissue due to the presence of a selection agent, such as an antibiotic or herbicide, wherein the plant selectable marker transgene provides tolerance or resistance to the selection agent. Thus, the selection agent may bias or favor the survival, development, growth, proliferation, etc., of transformed cells expressing the plant selectable marker gene, such as to increase the proportion of transformed cells or tissues in the $R_0$ plant. Commonly used plant selectable marker genes include, for example, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or EPSPS). Plant screenable marker genes may also be used, which provide an ability to visually screen for transformants, such as luciferase or green fluorescent protein (GFP), or a gene expressing a beta glucuronidase or uidA gene (GUS) for which various chromogenic substrates are known.

According to embodiments of the present invention, methods for transforming a plant cell, tissue or explant with a recombinant DNA molecule or construct may further include site-directed or targeted integration. According to these methods, a portion of a recombinant DNA donor template molecule (i.e., an insertion sequence) may be inserted or integrated at a desired site or locus within a plant genome. The insertion sequence of the donor template may comprise a transgene or construct, such as (i) an FT transgene or construct comprising a polynucleotide sequence encoding a florigenic FT protein operably linked to a vegetative-stage promoter, which may also be a meristem-preferred or meristem-specific promoter, and/or (ii) a transcribable DNA sequence encoding a RNA molecule that targets an FT transgene for suppression and operably linked to a vegetative stage promoter and/or reproductive stage promoter, which may also be a meristem-preferred or meristem-specific promoter. The donor template may also have one or two homology arms flanking the insertion sequence to promote the targeted insertion event through homologous recombination and/or homology-directed repair. Thus, a recombinant DNA molecule of the present invention may further include a donor template for site-directed or targeted integration of a transgene or construct, such as an FT transgene or construct, into the genome of a plant.

Any site or locus within the genome of a plant may potentially be chosen for site-directed integration of a transgene or construct of the present invention. For site-directed integration, a double-strand break or nick may first be made at a selected genomic locus with a site-specific nuclease, such as, for example, a zinc-finger nuclease (ZFN), a meganuclease, a transcription activator-like nuclease (TALEN), an Argonaute (non-limiting examples of Argonaute proteins include *Thermus thermophilus* Argonaute (TtAgo), *Pyrococcus furiosus* Argonaute (PfAgo), Natronobacterium gregoryi Argonaute (NgAgo), an RNA-guided nuclease (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof); a recombinase (without being limiting, for example, a tyrosine recombinase attached to a DNA recognition motif (e.g., Cre recombinase, Flp recombinase, Tnp1 recombinase), a serine recombinase attached to a DNA recognition motif (e.g., PhiC31 integrase, R4 integrase, TP-901 integrase); a transposase (without being limiting, for example, a DNA transposase attached to a DNA binding domain); or any combination thereof. Also provided are guide RNAs (e.g., CRISPR RNAs (crRNAs), trans-activating CRISPR RNAs (tracrRNAs), guide RNAs (gRNAs), single-guide RNAs (sgRNAs)) useful for methods of using RNA-guided nucleases. Any method known in the art for site-directed integration may be used. In the presence of a donor template molecule, the double strand break or nick may then be repaired by homologous recombination between the homology arm(s) of the donor template and the plant genome, or by non-homologous end joining (NHEJ), resulting in site-directed integration of the insertion sequence into a plant genome to create the targeted insertion event at or near the site of the double strand break or nick. Thus, site-specific insertion or integration of a transgene or construct may be achieved.

As used herein, the term "insertion" in reference to plant transformation or site-directed integration refers to an insertion or integration of an exogenous polynucleotide or DNA construct, molecule or sequence, such as a transformation vector or T-DNA sequence or an insertion sequence of a donor template, into the genome of a plant. In this context, the term "exogenous" refers to a polynucleotide or DNA construct, molecule or sequence that is introduced into a plant cell or tissue using any suitable plant transformation or genome editing method or technique known in the art.

According to embodiments of the present invention, a plant that may be transformed with a recombinant DNA molecule or transformation vector comprising an FT transgene and/or a transcribable DNA sequence encoding a RNA molecule that targets an FT transgene for suppression may include a variety of flowering plants or angiosperms, which may be further defined as including various dicotyledonous (dicot) plant species, such as soybean, cotton, alfalfa, canola, sugar beets, alfalfa and other leguminous plants. A dicot plant could be a member of the *Brassica* sp. (e.g., *B. napus, B. rapa, B. juncea*), particularly those *Brassica* species useful as sources of seed oil, alfalfa (*Medicago sativa*), sunflower (*Hehanthus annuus*), safflower (*Carthamus tinctorius*), oil palm (*Elaeis* spp.), sesame (*Sesamum* spp.), coconut (*Cocos* spp.), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), tea (*Camellia* spp.), fruit trees, such as apple (*Malus* spp.), *Prunus* spp., such as plum, apricot, peach, cherry, etc., pear (*Pyrus* spp.), fig (*Ficus casica*), banana (*Musa* spp.), etc., *citrus* trees (*Citrus* spp.), cocoa (*Theobroma cacao*), avocado (*Persea americana*), olive (*Olea europaea*), almond (*Prunus amygdalus*), walnut (*Juglans* spp.), strawberry (*Fragaria* spp.), watermelon (*Citrullus lanatus*), pepper (*Capsicum* spp.), sugar beet (*Beta vulgaris*), grape (*Vitis, Muscadinia*), tomato (*Lycopersicon esculentum, Solanum lycopersicum*), and cucumber (*Cucumis sativis*). Leguminous plants include beans and peas. Beans include, for example, guar, locust bean, fenugreek, soybean, garden beans, cowpea, mungbean, lima bean, fava bean, lentils, and chickpea. Given that the present invention may apply to a broad range of plant species, the present invention further applies to other botanical structures analogous to pods of leguminous plants, such as bolls, siliques, fruits, nuts, tubers, etc.

According to embodiments of the present invention and depending on the particular plant species transformed, a plant ectopically expressing a florigenic FT sequence, which may be modified via suppression as provided herein, may have an altered or greater number of bolls, siliques, fruits, nuts, tubers, etc., per node(s), main stem, and/or branch(es) of the plant, and/or an altered or greater number of bolls, siliques, fruits, nuts, tubers, etc., per plant, relative to a wild type or control plant not having the FT transgene.

According to another broad aspect of the present invention, a transgenic plant(s), plant cell(s), seed(s), and plant part(s) are provided comprising one or more transformation events or insertions into the genome of at least one plant cell thereof, the transformation event or insertion comprising (i) a recombinant DNA sequence, construct or polynucleotide including a Flowering Locus T (FT) transgene, wherein the FT transgene comprises a polynucleotide sequence encoding an FT protein operably linked to a vegetative stage promoter, which may also be a meristem-preferred or meristem-specific promoter, and/or (ii) a transcribable DNA sequence encoding a RNA molecule that targets an FT transgene for suppression operably linked to a vegetative stage and/or reproductive stage promoter, which may also be a meristem-preferred or meristem-specific promoter. As provided herein, the FT transgene may be targeted for suppression by an transgenically expressed and/or endogenous RNA molecule. The RNA molecule may be encoded by a transcribable DNA sequence that is also transformed into the plant, plant part, plant seed or plant cell. The FT protein encoded by the polynucleotide sequence may correspond to a native FT gene in the transgenic plant transformed with the polynucleotide coding sequence, or homologous or otherwise similar to a FT protein native to the transgenic plant (i.e., not native to the transgenic plant but similar to a native or endogenous FT protein), or heterologous to the transgenic plant. Such a transgenic plant may be produced by any suitable transformation method, which may be followed by selection, culturing, regeneration, development, etc., as desired or needed to produce a transgenic $R_0$ plant, which may then be selfed or crossed to other plants to generate R1 seed and subsequent progeny generations and seed through additional crosses, etc. Similarly, embodiments of the present invention further include a plant cell, tissue, explant, etc., comprising one or more transgenic cells having a transformation event or genomic insertion of a recombinant DNA or polynucleotide sequence comprising an FT transgene and/or a transcribable DNA sequence encoding a RNA molecule that targets an FT transgene for suppression.

Transgenic plants, plant cells, seeds, and plant parts of the present invention may be homozygous or hemizygous for a transgenic event or insertion of an FT transgene and/or transcribable DNA sequence into the genome of at least one plant cell thereof, or may contain any number of copies of a transgenic event(s) or insertion(s) comprising an FT transgene and/or transcribable DNA sequence. The dosage or amount of expression of an FT transgene may be altered by its zygosity and/or number of copies, which may affect the degree or extent of phenotypic changes in the transgenic plant, etc. According to some embodiments, a transgenic plant comprising an FT transgene and/or FT suppression element, which may be modified, attenuated and/or refined as provided herein, may be further characterized as having one or more altered flowering or reproductive phenotypes or traits, which may include altered yield-related phenotypes or traits, such as an increase in the number of flowers, pods, etc., and/or seeds per plant (and/or per node of the plant) relative to a wild type or control plant not having the FT transgene (and/or not having a FT suppression element). Such a transgenic plant may be further characterized as having an altered structure, morphology, and/or architecture due to altered plant height, branching patterns, number of floral nodes, etc., relative to a wild type or control plant. Indeed, yield-related phenotypes or traits altered by FT overexpression in a transgenic plant may include: flowering time, reproductive duration, flowering duration, amount or timing of abscission of flowers, pods, siliques, bolls, fruits, nuts, etc., number of flowers per node, number of racemes per node, number of branches per plant, number of nodes per plant, number of nodes on the main stem, number of nodes on branches, number of pods, bolls, siliques, fruits, nuts, etc., per plant, number of pods, bolls, siliques, fruits, nuts, etc., per node, number of pods, bolls, siliques, fruits, nuts, etc., on the main stem, number of pods, seeds, bolls, siliques, fruits, nuts, etc., on branches, seed weight (such as 1000 seed weight), number of seeds per plant, number of seeds on the main stem, number of seeds per node, and/or altered plant architecture, as compared to a wild type or control plant not having the FT transgene (and/or not having a FT suppression element). As used herein, the term "overexpression" in reference to a FT transgene includes ectopic expression of the transgene.

For purposes of the present invention, a "plant" may include an explant, seedling, plantlet or whole plant at any stage of regeneration or development. As used herein, a "transgenic plant" refers to a plant whose genome has been altered by the integration or insertion of a recombinant DNA molecule, construct or sequence. A transgenic plant includes an $R_0$ plant developed or regenerated from an originally transformed plant cell(s) as well as progeny transgenic plants in later generations or crosses from the $R_0$ transgenic plant. As used herein, a "plant part" may refer to any organ or intact tissue of a plant, such as a meristem, shoot organ/structure (e.g., leaf, stem and tuber), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, ground tissue, and the like), or any portion thereof. Plant parts of the present invention may be viable, nonviable, regenerable, and/or non-regenerable. A "propagule" may include any plant part that is capable of growing into an entire plant. For purposes of the present invention, a plant cell transformed with an FT transgene and/or FT suppression element according to embodiments of the present invention may include any plant cell that is competent for transformation as understood in the art based on the method of transformation, such as a meristem cell, an embryonic cell, a callus cell, etc. As used herein, a "transgenic plant cell" simply refers to any plant cell that is transformed with a stably-integrated recombinant DNA molecule or sequence. A transgenic plant cell may include an originally-transformed plant cell, a transgenic plant cell of a regenerated or developed $R_0$ plant, or a transgenic plant cell from any progeny plant or offspring of the transformed $R_0$ plant, including cell(s) of a plant seed or embryo, or a cultured plant or callus cell, etc.

According to many embodiments, a transgenic plant may comprise a polynucleotide sequence encoding a florigenic FT protein operably linked to a vegetative stage promoter. According to some embodiments, expression of a florigenic FT protein in a transgenic plant may be suppressed in a vegetative and/or reproductive stage and/or tissue of a transgenic plant, such as via an endogenous and/or transgenically or ectopically expressed RNA molecule. According to some embodiments, expression of a florigenic FT protein in a transgenic plant may be spatially and/or temporally restricted by a small RNA molecule. According to some embodiments, a transgenic plant may comprise a transcribable DNA sequence encoding a RNA molecule that targets a florigenic FT gene or transgene for suppression.

Embodiments of the present invention may further include methods for making or producing transgenic plants having altered reproductive and/or yield-related traits or phenotypes, such as by transformation, crossing, etc., wherein the method comprises introducing a recombinant DNA molecule, construct or sequence comprising an FT transgene and/or a transcribable DNA sequence encoding a RNA molecule that targets an FT transgene for suppression into a plant cell, and then regenerating or developing the transgenic plant from the transformed plant cell, which may be performed under selection pressure favoring the transgenic event. Such methods may comprise transforming a plant cell with a recombinant DNA molecule or sequence comprising an FT transgene and/or a transcribable DNA sequence, and selecting for a plant having one or more altered phenotypes or traits, such as one or more of the following: flowering time, reproductive duration, flowering duration, amount or timing of abscission of flowers, pods, bolls, siliques, fruits, nuts, etc., number of flowers per node, number of racemes per node, number of branches per plant, number of nodes per plant, number of nodes on the main stem, number of nodes on branches, number of pods, bolls, siliques, fruits, nuts, etc., per plant, number of pods, bolls, siliques, fruits, nuts, etc., per node, number of pods, bolls, siliques, fruits, nuts, etc., on the main stem, number of pods, seeds, bolls, siliques, fruits, nuts, etc., on branches, seed weight (such as 1000 seed weight), number of seeds per plant, number of seeds on the main stem, number of seeds per node, and altered plant architecture, as compared to a wild type or control plant not having the FT transgene (and/or not having an FT suppression element). For example, embodiments of the present invention may comprise methods for producing a transgenic plant having an increased number of flowers, pods, and/or seeds per plant (and/or an increased number of flowers, pods, and/or seeds per node of the plant), wherein the method comprises introducing a recombinant DNA molecule comprising an FT transgene and/or a transcribable DNA sequence into a plant cell, and then regenerating or developing the transgenic plant from the plant cell. The transgenic plant may then be selected based on one or more of the above reproductive and/or yield-related traits or phenotypes. A transgenic plant, plant cell or plant tissue may also be selected based on the presence of an FT transgene and/or FT suppression element using one or more methods or kits known in the art, such as DNA sequencing, hybridization, antibody binding, and/or other molecular techniques.

According to embodiments of the present invention, a transgenic plant may have at least 1%, at least 2%, at least 5%, at least 10%, at least 15%, at least 20%, at least 25%, at least 30%, at least 35%, at least 40%, at least 45%, at least 50%, at least 60%, at least 70%, at least 75%, at least 80%, at least 90%, at least 100%, at least 125%, at least 150%, at least 175%, at least 200%, at least 250%, at least 300%, at least 350%, or at least 400% more flowers, pods, seeds, bolls, siliques, fruits, nuts or tubers than a non-transgenic control plant. According to some embodiments, a transgenic plant may have an average of at least 5%, at least 10%, at least 15%, at least 20%, at least 25%, at least 30%, at least 35%, at least 40%, at least 45%, at least 50%, at least 60%, at least 70%, at least 75%, at least 80%, at least 90%, at least 100%, at least 125%, at least 150%, at least 175%, at least 200%, at least 250%, at least 300%, at least 350%, or at least 400% more flowers, pods, seeds, bolls, siliques, fruits, nuts or tubers per node than a non-transgenic control plant. A transgenic plant may have an average of at least 2, at least 3, at least 4, at least 5, at least 6, at least 7, at least 8, at least 9, or at least 10 pods, bolls, siliques, fruits, nuts or tubers per node. A transgenic plant may have an average of 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, or 4 to 5 pods, bolls, siliques, fruits, nuts or tubers per node. A transgenic plant may have an average of at least 1, at least 2, at least 3, at least 4, at least 5, at least 6, at least 7, at least 8, at least 9, or at least 10 more flowers, pods, seeds, bolls, siliques, fruits, nuts or tubers per node as compared to a non-transgenic control plant. A transgenic plant may be a soybean plant, and the transgenic plant may have more pods and/or seeds per node on average than a non-transgenic control plant. A transgenic plant may flower at least 1, at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, or at least 45 days earlier than a non-transgenic control plant.

According to embodiments of the present invention, a transgenic plant is provided comprising a polynucleotide sequence encoding a florigenic FT protein operably linked to a vegetative stage promoter, wherein expression of the polynucleotide coding sequence is spatially and/or temporally attenuated, restricted, modified, and/or refined by a RNA molecule, which may be a small non-coding RNA molecule. The level of expression or translation of the florigenic FT mRNA and/or protein in the transgenic plant may be suppressed or lowered in one or more meristematic, reproductive and/or floral tissues and/or during one or more reproductive stages. According to some embodiments, the reproductive duration and/or flowering duration of a transgenic plant comprising a FT transgene and/or FT suppression element as provided herein may be at least 1, at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, or at least 45 days longer than the reproductive duration and/or flowering duration of a wild-type or control plant, but may also be no more than (i.e., not greater or more than) 3, 4, 5, 6, 7, 8, 9, 10, 11, 12, 13, 14, 15, 20, 25, 30, 35, 40, 45, 50, 55, or 60 days longer than the reproductive duration and/or flowering duration of a wild-type or control plant. According to some embodiments, the onset of flowering (i.e., the appearance of the first open flower) of a transgenic plant comprising a FT transgene and/or FT suppression element as provided herein may be or occur at least 1, at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, or at least 45 days earlier than a wild-type or control plant, but may also be no more than (i.e., not greater or more than) 3, 4, 5, 6, 7, 8, 9, 10, 11, 12, 13, 14, 15, 20, 25, 30, 35, 40, 45, 50, 55, or 60 days earlier than the onset of flowering of a wild-type or control plant.

According to some embodiments, the number of flowers, seeds, bolls, siliques, fruits, nuts, pods or tubers on a transgenic plant comprising a FT transgene and/or FT suppression element as provided herein may be at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, at least 75%, at least 80%, at least 90%, at least 100%, at least 125%, at least 150%, at least 175%, at least 200%, at least 250%, at least 300%, at least 350%, or at least 400% greater than a wild-type or control plant. According to some embodiments, the number of flowers, seeds, bolls, siliques, fruits, nuts or pods on the main stem of a transgenic plant comprising a FT transgene and/or FT suppression element as provided herein may be at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, at least 75%, at least 80%, at least 90%, at least 100%, at least 125%, at least 150%, at least 175%, or at least 200%, at least 250%, at least 300%, at least 350%, or at least 400% greater than a wild-type or control plant. According to some embodiments, the number of flowers, seeds, bolls, siliques, fruits, nuts or pods per node on the main stem of a transgenic plant comprising a FT transgene and/or FT suppression element as provided herein may be at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, at least 75%, at least 80%, at least 90%, at least 100%, at least 125%, at least 150%, at least 175%, or at least 200%, at least 250%, at least 300%, at least 350%, or at least 400% greater than a wild-type or control plant.

Each of these trait amounts or numbers per plant, main stem or branch, such as the number of flowers, bolls, seeds, siliques, fruits, nuts or pods per plant, main stem or branch may be calculated as an average of two or more plants or determined for one plant, and the amounts or numbers of flowers, bolls, seeds, siliques, fruits, nuts or pods per node may be calculated as an average for one or more plants. Thus, the percentage changes may be calculated between two plants, between a plant and an average of two or more plants, or between two averages (with each average being of two or more plants).

According to some embodiments, the number of flowers, bolls, seeds, siliques, fruits, nuts, pods or tubers per node on a transgenic plant comprising a FT transgene and/or FT suppression element as provided herein may on average be at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, at least 75%, at least 80%, at least 90%, at least 100%, at least 125%, at least 150%, at least 175%, or at least 200%, at least 250%, at least 300%, at least 350%, or at least 400% greater than a wild-type or control plant. According to some embodiments, a transgenic plant comprising a FT transgene and/or FT suppression element as provided herein may have on average at least 2, at least 3, at least 4, at least 5, at least 6, at least 7, at least 8, at least 9, or at least 10 flowers, pods, bolls, seeds, siliques, fruits, nuts, pods or tubers per node. According to some embodiments, a transgenic plant comprising a FT transgene and/or FT suppression element as provided herein may have on average 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 4 to 10, 4 to 9, 4 to 8, 4 to 7, 4 to 6, or 4 to 5 pods, or about 2, about 3, about 4, about 5, about 6, about 7, about 8, about 9, or about 10 flowers, bolls, siliques, fruits, nuts, pods or tubers per node. According to some embodiments, a transgenic plant comprising a FT transgene and/or FT suppression element as provided herein may have on average at least 1, at least 2, at least 3, at least 4, at least 5, at least 6, at least 7, at least 8, at least 9, or at least 10 more flowers, bolls, seeds, siliques, fruits, nuts, pods or tubers per node as compared to a non-transgenic wild-type or control plant.

According to some embodiments, the average number of bolls, siliques, seeds, fruits, nuts, pods or tubers, and/or the average number of flowers, bolls, siliques, seeds, fruits, nuts, pods or tubers per node, on a transgenic plant comprising a FT transgene and/or FT suppression element as provided herein (or on the main stem of such a transgenic plant) may be 1%-400%, 1%-350%, 1%-300%, 1%-250%, 1%-200%, 1%-150%, 1%-100%, 1%-75%, 1%-50%, 1%-25%, 5%-400%, 5%-350%, 5%-300%, 5%-250%, 5%-200%, 5%-150%, 5%-100%, 5%-95%, 5%-90%, 5%-85%, 5%-80%, 5%-75%, 5%-70%, 5%-65%, 5%-60%, 5%-55%, 5%-50%, 5%-45%, 5%-40%, 5%-35%, 5%-30%, 5%-25%, 5%-20%, 5%-15%, 5%-10%, 10%-400%, 10%-350%, 10%-300%, 10%-250%, 10%-200%, 10%-150%, 10%-100%, 10%-90%, 10%-80%, 10%-70%, 10%-60%, 10%-50%, 10%-40%, 10%-30%, 10%-20%, 25%-400%, 25%-350%, 25%-300%, 25%-250%, 25%-200%, 25%-150%, 25%-100%, 25%-75%, 25%-50%, 50%-400%, 50%-350%, 50%-300%, 50%-250%, 50%-200%, 50%-150%, 50%-100%, 50%-75%, 75%-400%, 75%-350%, 75%-300%, 75%-250%, 75%-200%, 75%-150%, 75%-100%, 100%-400%, 100%-350%, 100%-300%, 100%-250%, 100%-200%, or 100%-150% greater than a wild-type or control plant. According to some embodiments, the reproductive duration of a transgenic plant comprising a FT transgene and/or FT suppression element as provided herein may be 1%-400%, 1%-350%, 1%-300%, 1%-250%, 1%-200%, 1%-150%, 1%-100%, 1%-75%, 1%-50%, 1%-25%, 5%-400%, 5%-350%, 5%-300%, 5%-250%, 5%-200%, 5%-150%, 5%-100%, 5%-95%, 5%-90%, 5%-85%, 5%-80%, 5%-75%, 5%-70%, 5%-65%, 5%-60%, 5%-55%, 5%-50%, 5%-45%, 5%-40%, 5%-35%, 5%-30%, 5%-25%, 5%-20%, 5%-15%, 5%-10%, 10%-400%, 10%-350%, 10%-300%, 10%-250%, 10%-200%, 10%-150%, 10%-100%, 10%-90%, 10%-80%, 10%-70%, 10%-60%, 10%-50%, 10%-40%, 10%-30%, 10%-20%, 25%-400%, 25%-350%, 25%-300%, 25%-250%, 25%-200%, 25%-150%, 25%-100%, 25%-75%, 25%-50%, 50%-400%, 50%-350%, 50%-300%, 50%-250%, 50%-200%, 50%-150%, 50%-100%, 50%-75%, 75%-400%, 75%-350%, 75%-300%, 75%-250%, 75%-200%, 75%-150%, 75%-100%, 100%-400%, 100%-350%, 100%-300%, 100%-250%, 100%-200%, or 100%-150% greater in terms of number of days than a wild-type or control plant. According to some embodiments, the onset of flowering of a transgenic plant comprising a FT transgene and/or FT suppression element as provided herein may be 1%-400%, 1%-350%, 1%-300%, 1%-250%, 1%-200%, 1%-150%, 1%-100%, 1%-75%, 1%-50%, 1%-25%, 5%-400%, 5%-350%, 5%-300%, 5%-250%, 5%-200%, 5%-150%, 5%-100%, 5%-95%, 5%-90%, 5%-85%, 5%-80%, 5%-75%, 5%-70%, 5%-65%, 5%-60%, 5%-55%, 5%-50%, 5%-45%, 5%-40%, 5%-35%, 5%-30%, 5%-25%, 5%-20%, 5%-15%, 5%-10%, 10%-400%, 10%-350%, 10%-300%, 10%-250%, 10%-200%, 10%-150%, 10%-100%, 10%-90%, 10%-80%, 10%-70%, 10%-60%, 10%-50%, 10%-40%, 10%-30%, 10%-20%, 25%-400%, 25%-350%, 25%-300%, 25%-250%, 25%-200%, 25%-150%, 25%-100%, 25%-75%, 25%-50%, 50%-400%, 50%-350%, 50%-300%, 50%-250%, 50%-200%, 50%-150%, 50%-100%, 50%-75%, 75%-400%, 75%-350%, 75%-300%, 75%-250%, 75%-200%, 75%-150%, 75%-100%, 100%-400%, 100%-350%, 100%-300%, 100%-250%, 100%-200%, or 100%-150% earlier in terms of number of days than a wild-type or control plant.

According to embodiments of the present invention, transgenic plants provided herein may have a combination of two or more traits or phenotypes described herein, such as two or more of increased pods, bolls, siliques, seeds, fruits, nuts or tubers per node, increased pods, bolls, siliques, seeds, fruits, nuts or tubers on the main stem, increased reproductive duration, earlier onset of flowering, minimal plant height, such as at least 900 or more millimeters (i.e., greater than or equal to 0.9 meters) in the case of soybean, and/or reduced branching, relative to a wild-type or control plant. According to some embodiments, transgenic plants may have an increased number of pods, bolls, siliques, seeds, fruits, or nuts per node on average and an earlier onset of flowering, relative to a wild-type or control plant. Such transgenic plants may further have an increase in the number of pods, bolls, siliques, seeds, fruits, nuts or tubers on the mainstem and/or an increased reproductive duration, relative to a wild-type or control plant.

For example, a transgenic plant provided herein may have at least 1%, at least 2%, at least 5%, at least 10%, at least 15%, at least 20%, at least 25%, at least 30%, at least 35%, at least 40%, at least 45%, at least 50%, at least 60%, at least 70%, at least 75%, at least 80%, at least 90%, at least 100%, at least 125%, at least 150%, at least 175%, at least 200%, at least 250%, at least 300%, at least 350%, or at least 400% more flowers, pods, seeds, bolls, siliques, fruits, nuts or tubers per node, and an onset of flowering that is at least 1, at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, or at least 45 days earlier, relative to a wild-type or control plant. A transgenic plant provided herein may have an average of at least 1, at least 2, at least 3, at least 4, at least 5, at least 6, at least 7, at least 8, at least 9, or at least 10 more flowers, pods, seeds, bolls, siliques, fruits, nuts or tubers per node, and an onset of flowering that is at least 1, at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, or at least 45 days earlier, relative to a wild-type or control plant. Such transgenic plants may further have a reproductive and/or flowering duration that is at least 1, at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, or at least 45 days longer than the reproductive duration and/or flowering duration of a wild-type or control plant, and/or an increased number of flowers, pods, seeds, bolls, siliques, fruits or nuts on the main stem of the transgenic plant that is at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, at least 75%, at least 80%, at least 90%, at least 100%, at least 125%, at least 150%, at least 175%, or at least 200%, at least 250%, at least 300%, at least 350%, or at least 400% greater than a wild-type or control plant.

According to embodiments of the present invention, transgenic plants provided herein may have an altered plant architecture with a minimal plant height and reduced branching, which may be accompanied by a mitigated reduction in the number of nodes per plant. Transgenic plants expressing the FT transgene alone may have a severe dwarf phenotype due to earlier termination that includes short plant height along with reduced branching and nodes per plant. By expressing the FT transgene with a miRNA sensor or second suppression element targeting the FT transgene, these severe early termination phenotypes may be mitigated to produce a more normal plant height while maintaining increased pods per node. According to these embodiments, transgenic plants may have (i) a minimal plant height that is reduced by no more than 5%, 10%, 15%, 20%, 25%, 30%, 35%, or 40% relative to a wild-type or control plant (i.e., the difference in plant heights between the transgenic plant and the wild-type or control plant is no greater than one or more of these percentages), (ii) a total number of branches that is reduced by at least 50%, at least 55%, at least 60%, at least 65%, at least 70%, at least 75%, at least 80%, at least 85%, at least 90%, or at least 95% relative to a wild-type or control plant, and/or (iii) a minimal number of nodes per plant (and/or per main stem) that is reduced by no more than 5%, 10%, 15%, 20%, 25%, 30%, 35%, or 40% relative to a wild-type or control plant (i.e., the difference in number of nodes per plant (and/or per main stem) between the transgenic plant and the wild-type or control plant is no greater than one or more of these percentages). In the case of soybean, a transgenic plant provided herein may have a minimal plant height that is at least 700 millimeters (mm), at least 750 mm, at least 800 mm, at least 850 mm, at least 900 mm, at least 950 mm, at least 1000 mm, at least 1050 mm, at least 1100 mm, at least 1150 mm, at least 1200 mm, at least 1250 mm, at least 1300 mm, at least 1350 mm, or at least 1400 mm; at least 100, at least 125, at least 150, at least 175, at least 200, at least 225, at least 250, at least 275, at least 300, at least 325, at least 350, at least 375, or at least 400 total number of nodes per plant; and/or a total number of branches that is reduced by at least 70%, at least 75%, at least 80%, at least 85%, at least 90%, or at least 95% relative to a wild-type or control plant. All of the foregoing numbers, percentages and differences for a plant further include those values calculated from an average of a plurality of plants of the same type.

According to another broad aspect of the present invention, methods are provided for planting transgenic plants of the present invention at a normal or high density in the field. According to some embodiments, the yield of a crop plant per acre (or per land area) may be increased by planting transgenic plants of the present invention at a higher density in the field. As described herein, transgenic plants of the present invention expressing a florigenic FT protein during vegetative stage(s) of development and/or with suppression of the FT transgene may exhibit increased pods and/or seeds per node (particularly on the main stem), but may also have an altered plant architecture with reduced branching and fewer nodes per branch. Thus, it is proposed that transgenic plants of the present invention may be planted at a higher density to increase yield per acre in the field. For row crops, higher density may be achieved by planting a greater number of seeds/plants per row length and/or by decreasing the spacing between rows. According to some embodiments, a transgenic crop plant of the present invention may be planted at a density in the field (plants per land/field area) that is at least 5%, 10%, 15%, 20%, 25%, 50%, 75%, 100%, 125%, 150%, 175%, 200%, 225%, or 250% higher or greater than a normal planting density for that crop plant according to standard agronomic practices.

For soybean, the typical planting density is in a range from about 100,000 to 150,000 seeds per acre, and the typical row spacing is in a range from about 26 to about 40 inches, such as 30 inch or 36 inch row spacing. Within a given row, about 6-8 soybean seeds may typically be planted per foot. In contrast, high density planting for soybean may include a range of approximately 150,000 to 250,000 seeds per acre, and the row spacing may be within a range from about 10 inches or less to about 25 inches, such as 10 inch, 15 inch or 20 inch row spacing. For high density planting, approximately 9-12 soybean seeds per foot may be planted within each row, perhaps in combination with narrower row spacing. However, high crop density may be achieved by narrow row spacing without an increase in planting density within each row.

For cotton, the typical planting density is in a range from about 28,000 to 45,000 seeds per acre, and the typical row spacing is in a range from about 38 to about 40 inches, such as 38 inch or 40 inch row spacing. Within a given row, about 2-3 cotton seeds may typically be planted per foot. In contrast, high density planting for soybean may include a range of approximately 48,000 to 60,000 seeds per acre, and the row spacing may be within a range from about 30 inches or less to about 36 inches. For high density planting, approximately 3-5 cotton seeds per foot may be planted within each row, perhaps in combination with narrower row spacing. However, high crop density for cotton may be achieved by narrow row spacing without an increase in planting density within each row.

For canola, the typical planting density is in a range from about 360,000 to 550,000 seeds per acre, and the typical row spacing between openers is in a range from about 6 inches to about 16 inches. Within a given row, about 8-12 canola seeds may typically be planted per foot. In contrast, high density planting for soybean may include a range of approximately 450,000 to 680,000 seeds per acre, and the row spacing may be within a range from about 5 inches or less to about 10 inches. For high density planting, approximately 10-16 canola seeds per foot may be planted within each row, perhaps in combination with the narrower row spacing. However, high crop density for canola may be achieved by narrow row spacing without an increase in planting density within each row.

The following are non-limiting exemplary embodiments of the present disclosure:

1. A recombinant DNA construct comprising a first expression cassette and a second expression cassette, wherein the first expression cassette comprises a polynucleotide sequence encoding a florigenic FT protein operably linked to a first plant expressible promoter, and the second expression cassette comprises a transcribable DNA sequence encoding a RNA molecule comprising a targeting sequence that is at least 80% complementary to at least 15 consecutive nucleotides of the polynucleotide sequence of the first expression cassette, and wherein the transcribable DNA sequence is operably linked to a second plant expressible promoter.

2. The recombinant DNA construct of embodiment 1, wherein the targeting sequence of the RNA molecule is from about 15 to about 27 nucleotides in length.

3. The recombinant DNA construct of embodiments 1 or 2, wherein the targeting sequence of the RNA molecule is 15, 16, 17, 18, 19, 20, 21, 22, 23, 24, 25, 26 or 27 nucleotides in length.

4. The recombinant DNA construct of any one of embodiments 1-3, wherein the targeting sequence of the RNA molecule is at least 85%, at least 90%, at least 95%, at least 96%, at least 97%, at least 98%, at least 99%, at least 99.5% or 100% complementary to at least 15 consecutive nucleotides of the polynucleotide sequence of the first expression cassette.

5. The recombinant DNA construct of any one of embodiments 1-4, wherein the targeting sequence of the RNA molecule is at least 80% complementary to at least 15 consecutive nucleotides of a mRNA transcript encoded by the polynucleotide sequence of the first expression cassette.

6. The recombinant DNA construct of any one of embodiments 1-5, wherein the targeting sequence of the RNA molecule is at least 80% complementary to at least 15 consecutive nucleotides of an exonic or coding sequence of the mRNA transcript.

7. The recombinant DNA construct of any one of embodiments 1-5, wherein the targeting sequence of the RNA molecule is at least 80% complementary to at least 15 consecutive nucleotides of a non-coding sequence of the mRNA transcript.

8. The recombinant DNA construct of any one of embodiments 1-7, wherein the RNA molecule encoded by the transcribable DNA sequence is a precursor miRNA or siRNA.

9. The recombinant DNA construct of any one of embodiments 1-8, wherein the transcribable DNA sequence comprises a sequence that is at least 80%, at least 85%, at least 90%, at least 95%, at least 96%, at least 97%, at least 98%, at least 99% or 100% complementary to SEQ ID NO: 68 or 69.

10. The recombinant DNA construct of any one of embodiments 1-9, wherein the transcribable DNA sequence comprises a sequence that is at least at least 80%, at least 85%, at least 90%, at least 95%, at least 96%, at least 97%, at least 98%, at least 99% or 100% identical to SEQ ID NO: 65.

11. The recombinant DNA construct of any one of embodiments 1-10, wherein the polynucleotide sequence of the first expression cassette comprises a sequence that is at least at least 80%, at least 85%, at least 90%, at least 95%, at least 96%, at least 97%, at least 98%, at least 99% or 100% identical to SEQ ID NO: 69.

12. The recombinant DNA construct of any one of embodiments 1-11, wherein the florigenic FT protein comprises an amino acid sequence having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or least 99% identity to a sequence selected from the group consisting of SEQ ID NOs: 2, 4, 6, 8, 10, 12, 14, 16, 18, 20, 22, 24, 26, 28, and 30, or a functional fragment thereof.

13. The recombinant DNA construct of embodiment 12, wherein the florigenic FT protein further comprises one or more of the following amino acids: a tyrosine or other uncharged polar or nonpolar residue at the amino acid position of the florigenic FT protein corresponding to amino acid position 85 of SEQ ID NO: 14; a leucine or other nonpolar residue at the amino acid position of the florigenic FT protein corresponding to amino acid position 128 of SEQ ID NO: 14; and a tryptophan or other large nonpolar residue at the amino acid position of the florigenic FT protein corresponding to amino acid position 138 of SEQ ID NO: 14.

14. The recombinant DNA construct of embodiment 12, wherein the florigenic FT protein does not have one or more of the following amino acids: a histidine at the amino acid position corresponding to a lysine or arginine at the amino acid position corresponding to position 85 of SEQ ID NO: 14; a lysine or arginine at the amino acid position corresponding to position 128 of SEQ ID NO: 14; and a serine, aspartic acid, glutamic acid, lysine or arginine at the amino acid position corresponding to position 138 of SEQ ID NO: 14.

15. The recombinant DNA construct of embodiment 12, wherein the florigenic FT protein comprises an amino acid sequence selected from the group consisting of SEQ ID NOs: 2, 4, 6, 8, 10, 12, 14, 16, 18, 20, 22, 24, 26, 28, and 30, or a functional fragment thereof.

16. The recombinant DNA construct of any one of embodiments 1-15, wherein the polynucleotide sequence is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to a sequence selected from the group consisting of SEQ ID NOs: 1, 3, 5, 7, 9, 11, 13, 15, 17, 19, 21, 23, 25, 27, and 29.

17. The recombinant DNA construct of any one of embodiments 1-16, wherein the first plant expressible promoter is a vegetative stage promoter.

18. The recombinant DNA construct of any one of embodiments 1-17, wherein the first plant expressible promoter is a meristem-preferred or meristem-specific promoter.

19. The recombinant DNA construct of any one of embodiments 1-18, wherein the first plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5% or 100% identical to a polynucleotide sequence selected from the group consisting of SEQ ID NOs: 31, 32, 33, 34, 35, 36, 37, 38, 39, 40, 41, 42, 43, 44, 45 or 48, or a functional portion thereof.

20. The recombinant DNA construct of embodiment 19, wherein the first plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5% or 100% identical to SEQ ID NO: 31, or a functional portion thereof.

21. The recombinant DNA construct of embodiment 19, wherein the first plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5% or 100% identical to SEQ ID NO: 32 or SEQ ID NO: 48.

22. The recombinant DNA construct of embodiment 19, wherein the first plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5% or 100% identical to SEQ ID NO: 44, or a functional portion thereof.

23. The recombinant DNA construct of any one of embodiments 1-22, wherein the first plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, or least 99%, at least 99.5% or 100% identical to a polynucleotide sequence selected from the group consisting of SEQ ID NOs: 49, 50, 51, 52, 53, 54, 55, 56, 57, 58, 59, 60, 61, 62, 63 or 64, or a functional portion thereof.

24. The recombinant DNA construct of embodiment 23, wherein the first plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, or least 99%, at least 99.5% or 100% identical to SEQ ID NO: 49, or a functional portion thereof.

25. The recombinant DNA construct of any one of embodiments 1-24, wherein the second plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5% or 100% identical to a polynucleotide sequence selected from the group consisting of SEQ ID NOs: 49, 50, 51, 52, 53, 54, 55, 56, 57, 58, 59, 60, 61, 62, 63 or 64, or a functional portion thereof.

26. The recombinant DNA construct of any one of embodiments 1-25, wherein the second plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, or least 99%, at least 99.5% or 100% identical to SEQ ID NO: 49, or a functional portion thereof.

27. The recombinant DNA construct of any one of embodiments 1-26, wherein the second plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, or least 99%, at least 99.5% or 100% identical to a polynucleotide sequence selected from the group consisting of SEQ ID NOs: 70, 71, 72, 73, 74, 75, 76, 77, 78, 79, 80, 81, 82, 83, 84, 85, 86, 87, 88, 89, 90, 91, 92, 93, or 94, or a functional portion thereof.

28. The recombinant DNA construct of any one of embodiments 1-27, wherein the first plant expressible promoter is a vegetative stage promoter and the second plant expressible promoter is a late vegetative stage promoter and/or reproductive stage promoter.

29. The recombinant DNA construct of embodiment 28, wherein the first plant expressible promoter is an early vegetative stage promoter.

30. The recombinant DNA construct of embodiment 28, wherein the second plant expressible promoter is a reproductive stage preferred promoter.

31. The recombinant DNA construct of any one of embodiments 1-30, wherein the first plant expressible promoter initiates detectable expression of the polynucleotide sequence encoding the florigenic FT protein at an earlier developmental stage than the second plant expressible promoter initiates detectable expression of the transcribable DNA sequence.

32. A DNA molecule or vector comprising the recombinant DNA construct of any one of embodiments 1-31.

33. A plasmid vector for *Agrobacterium*-mediated transformation comprising the recombinant DNA construct of any one of embodiments 1-31.

34. A donor template molecule for site-directed integration comprising the recombinant DNA construct of any one of embodiments 1-31.

35. A transgenic plant comprising an insertion of the recombinant DNA construct of any one of embodiments 1-31 into the genome of at least one cell of the transgenic plant.

36. The transgenic plant of embodiment 35, wherein the transgenic plant is homozygous for the insertion of the recombinant DNA construct.

37. The transgenic plant of embodiment 35, wherein the transgenic plant is hemizygous for the insertion of the recombinant DNA construct.

38. The transgenic plant of any one of embodiments 35-37, wherein the transgenic plant is a short day plant.

39. The transgenic plant of any one of embodiments 35-38, wherein the transgenic plant is a dicotyledonous plant.

40. The transgenic plant of any one of embodiments 35-39, wherein the transgenic plant is a leguminous plant.

41. The transgenic plant of any one of embodiments 35-40, wherein the transgenic plant is soybean.

42. The transgenic plant of embodiment 41, wherein the transgenic soybean plant produces more pods per node than a control plant not having the recombinant DNA construct.

43. The transgenic plant of any one of embodiments 35-42, wherein the transgenic plant produces more flowers per node than a control plant not having the recombinant DNA construct.

44. The transgenic plant or part thereof of any one of embodiments 35-43, wherein the transgenic plant produces more seeds, bolls, siliques, fruits, nuts or pods per node of the transgenic plant than a control plant not having the recombinant DNA construct.

45. The transgenic plant or part thereof of any one of embodiments 35-44, wherein the transgenic plant flowers earlier than a control plant not having the recombinant DNA construct.

46. The transgenic plant or part thereof of any one of embodiments 35-45, wherein the transgenic plant has more floral racemes per node than a control plant not having the recombinant DNA construct.

47. A transgenic plant part comprising an insertion of the recombinant DNA construct of any one of embodiments 1-31 into the genome of at least one cell of the transgenic plant part.

48. The transgenic plant part of any one of embodiments 44-47, wherein the transgenic plant part is one of the following: a seed, fruit, leaf, cotyledon, hypocotyl, meristem, embryo, endosperm, root, shoot, stem, pod, flower, infloresence, stalk, pedicel, style, stigma, receptacle, petal, sepal, pollen, anther, filament, ovary, ovule, pericarp, phloem, or vascular tissue.

49. A recombinant DNA construct comprising a polynucleotide sequence encoding a florigenic FT protein operably linked to a plant expressible promoter, wherein the polynucleotide sequence comprises a sequence that encodes a target site in a mRNA transcript encoded by the polynucleotide sequence, and wherein the target site of the mRNA transcript is at least 80% complementary to an endogenous RNA molecule.

50. The recombinant DNA construct of embodiment 49, wherein the target site of the mRNA transcript is at least 17 nucleotides in length.

51. The recombinant DNA construct of embodiment 49 or 50, wherein the target site of the mRNA transcript is 17, 18, 19, 20, 21, 22, 23, 24, 25, 26 or 27 nucleotides in length.

52. The recombinant DNA construct of any one of embodiments 49-51, wherein the target site of the mRNA transcript is at least 80%, at least 85%, at least 90%, at least 95%, at least 96%, at least 97%, at least 98%, at least 99%, at least 99.5% or 100% complementary to the endogenous RNA molecule.

53. The recombinant DNA construct of any one of embodiments 49-52, wherein the target site is present in a non-coding sequence of the mRNA transcript.

54. The recombinant DNA construct of any one of embodiments 49-53, wherein the target site of the mRNA transcript is at least 80%, at least 85%, at least 90%, at least 95%, at least 96%, at least 97%, at least 98%, at least 99% or 100% complementary to SEQ ID NO: 95, 96, 97, 103, 104, or 105.

55. The recombinant DNA construct of any one of embodiments 49-54, wherein the target site of the mRNA transcript is at least 80%, at least 85%, at least 90%, at least 95%, at least 96%, at least 97%, at least 98%, at least 99% or 100% complementary to SEQ ID NO: 95 or 103.

56. The recombinant DNA construct of any one of embodiments 49-55, wherein the polynucleotide sequence encoding the florigenic FT protein comprises a sequence that is at least at least 80%, at least 85%, at least 90%, at least 95%, at least 96%, at least 97%, at least 98%, at least 99% or 100% identical to SEQ ID NO: 98, 99, 100, 101, 106, 107, 108, 109 or 110.

57. The recombinant DNA construct of any one of embodiments 49-54 or 56, wherein the target site of the mRNA transcript is at least 80%, at least 85%, at least 90%, at least 95%, at least 96%, at least 97%, at least 98%, at least 99% or 100% identical to SEQ ID NO: 99 or 107.

58. The recombinant DNA construct of any one of embodiments 49-57, wherein the florigenic FT protein comprises an amino acid sequence having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or least 99% identity to a sequence selected from the group consisting of SEQ ID NOs: 2, 4, 6, 8, 10, 12, 14, 16, 18, 20, 22, 24, 26, 28, and 30, or a functional fragment thereof.

59. The recombinant DNA construct of any one of embodiments 49-58, wherein the florigenic FT protein further comprises one or more of the following amino acids: a tyrosine or other uncharged polar or nonpolar residue at the amino acid position of the florigenic FT protein corresponding to amino acid position 85 of SEQ ID NO: 14; a leucine or other nonpolar residue at the amino acid position of the florigenic FT protein corresponding to amino acid position 128 of SEQ ID NO: 14; and a tryptophan or other large nonpolar residue at the amino acid position of the florigenic FT protein corresponding to amino acid position 138 of SEQ ID NO: 14.

60. The recombinant DNA construct of any one of embodiments 49-58, wherein the florigenic FT protein does not have one or more of the following amino acids: a histidine at the amino acid position corresponding to a lysine or arginine at the amino acid position corresponding to position 85 of SEQ ID NO: 14; a lysine or arginine at the amino acid position corresponding to position 128 of SEQ ID NO: 14; and a serine, aspartic acid, glutamic acid, lysine or arginine at the amino acid position corresponding to position 138 of SEQ ID NO: 14.

61. The recombinant DNA construct of any one of embodiments 49-61, wherein the florigenic FT protein comprises an amino acid sequence selected from the group consisting of SEQ ID NOs: 2, 4, 6, 8, 10, 12, 14, 16, 18, 20, 22, 24, 26, 28, and 30, or a functional fragment thereof.

62. The recombinant DNA construct of any one of embodiments 49-62, wherein the polynucleotide sequence is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to a sequence selected from the group consisting of SEQ ID NOs: 1, 3, 5, 7, 9, 11, 13, 15, 17, 19, 21, 23, 25, 27, and 29.

63. The recombinant DNA construct of any one of embodiments 49-62, wherein the plant expressible promoter is a vegetative stage promoter.

64. The recombinant DNA construct of any one of embodiments 49-63, wherein the plant expressible promoter is a meristem-preferred or meristem-specific promoter.

65. The recombinant DNA construct of any one of embodiments 49-64, wherein the plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5% or 100% identical to a polynucleotide sequence selected from the group consisting of SEQ ID NOs: 31, 32, 33, 34, 35, 36, 37, 38, 39, 40, 41, 42, 43, 44, 45 or 48, or a functional portion thereof.

66. The recombinant DNA construct of any one of embodiments 49-65, wherein the plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5% or 100% identical to SEQ ID NO: 31, or a functional portion thereof.

67. The recombinant DNA construct of any one of embodiments 49-65, wherein the plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5% or 100% identical to SEQ ID NO: 32 or SEQ ID NO: 48.

68. The recombinant DNA construct of any one of embodiments 49-65, wherein the plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5% or 100% identical to SEQ ID NO: 44, or a functional portion thereof.

69. The recombinant DNA construct of any one of embodiments 49-68, wherein the plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, or least 99%, at least 99.5% or 100% identical to a polynucleotide sequence selected from the group consisting of SEQ ID NOs: 49, 50, 51, 52, 53, 54, 55, 56, 57, 58, 59, 60, 61, 62, 63 or 64, or a functional portion thereof.

70. A DNA molecule or vector comprising the recombinant DNA construct of any one of embodiments 49-69.

71. A plasmid vector for *Agrobacterium*-mediated transformation comprising the recombinant DNA construct of any one of embodiments 49-69.

72. A donor template molecule for site-directed integration comprising the recombinant DNA construct of any one of embodiments 49-69.

73. A transgenic plant comprising an insertion of the recombinant DNA construct of any one of embodiments 49-69 into the genome of at least one cell of the transgenic plant.

74. The transgenic plant of embodiment 73, wherein the transgenic plant is homozygous for the insertion of the recombinant DNA construct.

75. The transgenic plant of embodiment 73, wherein the transgenic plant is hemizygous for the insertion of the recombinant DNA construct.

76. The transgenic plant of any one of embodiments 73-75, wherein the transgenic plant is a short day plant.

77. The transgenic plant of any one of embodiments 73-76, wherein the transgenic plant is a dicotyledonous plant.

78. The transgenic plant of any one of embodiments 73-77, wherein the transgenic plant is a leguminous plant.

79. The transgenic plant of any one of embodiments 73-78, wherein the transgenic plant is soybean.

80. The transgenic plant of any one of embodiments 73-79, wherein the transgenic soybean plant produces more pods per node than a control plant not having the recombinant DNA construct.

81. The transgenic plant of any one of embodiments 73-80, wherein the transgenic plant produces more flowers per node than a control plant not having the recombinant DNA construct.

82. The transgenic plant or part thereof of any one of embodiments 73-81, wherein the transgenic plant produces more bolls, siliques, fruits, nuts or pods per node of the transgenic plant than a control plant not having the recombinant DNA construct.

83. The transgenic plant or part thereof of any one of embodiments 73-82, wherein the transgenic plant flowers earlier than a control plant not having the recombinant DNA construct.

84. The transgenic plant or part thereof of any one of embodiments 73-83, wherein the transgenic plant has more floral racemes per node than a control plant not having the recombinant DNA construct.

85. A transgenic plant part comprising an insertion of the recombinant DNA construct of any one of embodiments 49-69 into the genome of at least one cell of the transgenic plant part.

86. The transgenic plant part of any one of embodiments 82-85, wherein the transgenic plant part is one of the following: a seed, fruit, leaf, cotyledon, hypocotyl, meristem, embryo, endosperm, root, shoot, stem, pod, flower, infloresence, stalk, pedicel, style, stigma, receptacle, petal, sepal, pollen, anther, filament, ovary, ovule, pericarp, phloem, or vascular tissue.

87. A recombinant DNA construct comprising a transcribable DNA sequence encoding a RNA molecule comprising a targeting sequence that is at least 80% complementary to at least 15 consecutive nucleotides of a polynucleotide sequence encoding a florigenic FT protein, wherein the transcribable DNA sequence is operably linked to a plant expressible promoter.

88. The recombinant DNA construct of embodiment 87, wherein the targeting sequence of the RNA molecule is from about 15 to about 27 nucleotides in length.

89. The recombinant DNA construct of embodiment 87 or 88, wherein the targeting sequence of the RNA molecule is at least 85%, at least 90%, at least 95%, at least 96%, at least 97%, at least 98%, at least 99%, at least 99.5% or 100% complementary to at least 15 consecutive nucleotides of the polynucleotide sequence encoding the florigenic FT protein.

90. The recombinant DNA construct of any one of embodiments 87-89, wherein the targeting sequence of the RNA molecule is at least 80% complementary to at least 15 consecutive nucleotides of a mRNA transcript encoded by the polynucleotide sequence encoding the florigenic FT protein.

91. The recombinant DNA construct of any one of embodiments 87-90, wherein targeting sequence of the RNA molecule is at least 80% complementary to at least 15 consecutive nucleotides of an exonic or coding sequence of the mRNA transcript.

92. The recombinant DNA construct of any one of embodiments 87-91, wherein targeting sequence of the RNA molecule is at least 80% complementary to at least 15 consecutive nucleotides of a non-coding sequence of the mRNA transcript.

93. The recombinant DNA construct of any one of embodiments 87-92, wherein the RNA molecule encoded by the transcribable DNA sequence is a precursor miRNA or siRNA.

94. The recombinant DNA construct of any one of embodiments 87-93, wherein the florigenic FT protein encoded by the polynucleotide sequence comprises an amino acid sequence having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or least 99% identity to a sequence selected from the group consisting of SEQ ID NOs: 2, 4, 6, 8, 10, 12, 14, 16, 18, 20, 22, 24, 26, 28, and 30, or a functional fragment thereof.

95. The recombinant DNA construct of any one of embodiments 87-94, wherein the florigenic FT protein further comprises one or more of the following amino acids: a tyrosine or other uncharged polar or nonpolar residue at the amino acid position of the florigenic FT protein corresponding to amino acid position 85 of SEQ ID NO: 14; a leucine or other nonpolar residue at the amino acid position of the florigenic FT protein corresponding to amino acid position 128 of SEQ ID NO: 14; and a tryptophan or other large nonpolar residue at the amino acid position of the florigenic FT protein corresponding to amino acid position 138 of SEQ ID NO: 14.

96. The recombinant DNA construct of any one of embodiments 87-94, wherein the florigenic FT protein does not have one or more of the following amino acids: a histidine at the amino acid position corresponding to a lysine or arginine at the amino acid position corresponding to position 85 of SEQ ID NO: 14; a lysine or arginine at the amino acid position corresponding to position 128 of SEQ ID NO: 14; and a serine, aspartic acid, glutamic acid, lysine or arginine at the amino acid position corresponding to position 138 of SEQ ID NO: 14.

97. The recombinant DNA construct of any one of embodiments 87-96, wherein the florigenic FT protein comprises an amino acid sequence selected from the group consisting of SEQ ID NOs: 2, 4, 6, 8, 10, 12, 14, 16, 18, 20, 22, 24, 26, 28, and 30, or a functional fragment thereof.

98. The recombinant DNA construct of any one of embodiments 87-97, wherein the polynucleotide sequence encoding the florigenic FT protein is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to a sequence selected from the group consisting of SEQ ID NOs: 1, 3, 5, 7, 9, 11, 13, 15, 17, 19, 21, 23, 25, 27, and 29.

99. The recombinant DNA construct of any one of embodiments 87-98, wherein the plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5% or 100% identical to a polynucleotide sequence selected from the group consisting of SEQ ID NOs: 49, 50, 51, 52, 53, 54, 55, 56, 57, 58, 59, 60, 61, 62, 63 or 64, or a functional portion thereof.

100. The recombinant DNA construct of any one of embodiments 87-99, wherein the plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, or least 99%, at least 99.5% or 100% identical to SEQ ID NO: 49, or a functional portion thereof.

101. The recombinant DNA construct of any one of embodiments 87-100, wherein the plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, or least 99%, at least 99.5% or 100% identical to a polynucleotide sequence selected from the group consisting of SEQ ID NOs: 70, 71, 72, 73, 74, 75, 76, 77, 78, 79, 80, 81, 82, 83, 84, 85, 86, 87, 88, 89, 90, 91, 92, 93, or 94, or a functional portion thereof.

102. The recombinant DNA construct of any one of embodiments 87-101, wherein the plant expressible promoter is a vegetative stage promoter.

103. The recombinant DNA construct of any one of embodiments 87-102, wherein the plant expressible promoter is a late vegetative stage promoter and/or reproductive stage promoter.

104. The recombinant DNA construct of any one of embodiments 87-103, wherein the plant expressible promoter is heterologous with respect to the transcribable DNA sequence.

105. A DNA molecule or vector comprising the recombinant DNA construct of any one of embodiments 87-104.

106. A transgenic plant comprising an insertion of the recombinant DNA construct of any one of embodiments 87-104 into the genome of at least one cell of the transgenic plant.

107. The transgenic plant of embodiment 106, wherein the transgenic plant is a short day plant.

108. The transgenic plant of embodiment 106 or 107, wherein the transgenic plant is a dicotyledonous plant.

109. The transgenic plant of any one of embodiments 106-108, wherein the transgenic plant is a leguminous plant.

110. The transgenic plant of any one of embodiments 106-109, wherein the transgenic plant is soybean.

111. A transgenic plant part comprising an insertion of the recombinant DNA construct of any one of embodiments 87-103 into the genome of at least one cell of the transgenic plant part.

112. The transgenic plant part of embodiment 111, wherein the transgenic plant part is one of the following: a seed, fruit, leaf, cotyledon, hypocotyl, meristem, embryo, endosperm, root, shoot, stem, pod, flower, infloresence, stalk, pedicel, style, stigma, receptacle, petal, sepal, pollen, anther, filament, ovary, ovule, pericarp, phloem, or vascular tissue.

113. A method for producing a transgenic plant, comprising
(a) transforming at least one cell of an explant with the recombinant DNA construct of any one of embodiments 1-31, 49-69 or 87-104; and
(b) regenerating or developing the transgenic plant from the transformed explant.

114. The method of embodiment 113, further comprising:
(c) selecting a transgenic plant having one or more of the following traits or phenotypes: earlier flowering, longer reproductive or flowering duration, increased number of flowers per node, increased number of floral racemes per node, increased number of pods, bolls, siliques, fruits, or nuts per node, and increased number of seeds per node, as compared to a control plant not having the recombinant DNA construct.

115. The method of embodiment 113 or 114, wherein the transforming step (a) is carried out via *Agrobacterium*-mediated transformation or microprojectile bombardment of the explant.

116. The method of any one of embodiments 113-115, wherein the transforming step (a) comprises site-directed integration of the recombinant DNA construct.

117. A method of planting a transgenic crop plant, comprising:
planting the transgenic crop plant at a higher density in the field, wherein the transgenic crop plant comprises an insertion of the recombinant DNA construct of any one of embodiments 1-31, 49-69 or 87-104.

118. The method of embodiment 117, wherein the transgenic crop plant is soybean, and wherein about 150,000 to 250,000 seeds of the transgenic soybean plant are planted per acre.

119. The method of embodiment 117, wherein the transgenic crop plant is cotton, and wherein about 48,000 to 60,000 seeds of the transgenic cotton plant are planted per acre.

120. The method of embodiment 117, wherein the transgenic crop plant is canola, and wherein about 450,000 to 680,000 seeds of the transgenic canola plant are planted per acre.

121. The transgenic plant of any one of embodiments 35-46, 73-84, or 106-110, wherein the transgenic plant has at least 1%, at least 2%, at least 5%, at least 10%, at least 15%, at least 20%, at least 25%, at least 30%, at least 35%, at least 40%, at least 45%, at least 50%, at least 60%, at least 70%, at least 75%, at least 80%, at least 90%, at least 100%, at least 125%, at least 150%, at least 175%, at least 200%, at least 250%, at least 300%, at least 350%, or at least 400% more seeds, pods, bolls, siliques, fruits, nuts or tubers than a non-transgenic control plant.

122. The transgenic plant of any one of embodiments 35-46, 73-84, or 106-110, wherein the transgenic plant has an average of at least 5%, at least 10%, at least 15%, at least 20%, at least 25%, at least 30%, at least 35%, at least 40%, at least 45%, at least 50%, at least 60%, at least 70%, at least 75%, at least 80%, at least 90%, at least 100%, at least 125%, at least 150%, at least 175%, at least 200%, at least 250%, at least 300%, at least 350%, or at least 400% more seeds, pods, bolls, siliques, fruits, nuts or tubers per node than a non-transgenic control plant.

123. The transgenic plant of any one of embodiments 35-46, 73-84, or 106-110, wherein the transgenic plant has an average of at least 2, at least 3, at least 4, at least 5, at least 6, at least 7, at least 8, at least 9, or at least 10 pods, bolls, siliques, fruits, nuts or tubers per node.

124. The transgenic plant of any one of embodiments 35-46, 73-84, or 106-110, wherein the transgenic plant has an average of 2 to 10, 2 to 9, 2 to 8, 2 to 7, 2 to 6, 2 to 5, 2 to 4, 3 to 10, 3 to 9, 3 to 8, 3 to 7, 3 to 6, 3 to 5, 4 to 10, 4 to 9, 4 to 8, 4 to 7, 4 to 6, or 4 to 5 pods, bolls, siliques, fruits, nuts or tubers per node.

125. The transgenic plant of any one of embodiments 35-46, 73-84, or 106-110, wherein the transgenic plant has an average of at least 1, at least 2, at least 3, at least 4, at least 5, at least 6, at least 7, at least 8, at least 9, or at least 10 more bolls, siliques, fruits, nuts or pods per node as compared to a non-transgenic control plant.

126. The transgenic plant of any one of embodiments 35-46, 73-84, or 106-110, wherein the transgenic plant flowers at least 1, at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, or at least 45 days earlier than a non-transgenic control plant.

127. The transgenic plant of any one of embodiments 121, 122, 123, 124, 125 or 126, wherein the transgenic plant is a soybean plant, and the transgenic plant has more pods per node on average than a non-transgenic control plant.

128. A transgenic plant comprising a polynucleotide sequence encoding a florigenic FT protein operably linked to a vegetative stage promoter, wherein expression of the florigenic FT protein is suppressed in a late vegetative and/or reproductive tissue.

129. The transgenic plant of embodiment 128, wherein expression of the florigenic FT protein is suppressed by a small RNA molecule.

130. A recombinant DNA construct comprising a polynucleotide sequence encoding a florigenic FT protein and operably linked to a vegetative stage promoter, and at least one transcribable DNA sequence encoding an RNA molecule comprising a targeting sequence that is complementary to at least a portion of the polynucleotide sequence.

131. A transgenic plant comprising an insertion of the recombinant DNA construct of embodiment 130 into the genome of at least one cell of the transgenic plant.

132. A transgenic plant comprising a recombinant polynucleotide sequence encoding a florigenic FT protein operably linked to a vegetative stage promoter, wherein expression of the polynucleotide sequence is spatially and temporally restricted by a small RNA molecule.

133. A recombinant DNA construct comprising an expression cassette, wherein the expression cassette comprises a polynucleotide sequence encoding a florigenic FT protein operably linked to a plant expressible promoter, wherein the plant expressible promoter comprises a polynucleotide sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to a polynucleotide sequence selected from the group consisting of SEQ ID NOs: 49, 50, 51, 52, 53, 54, 55, 56, 57, 58, 59, 60, 61, 62, 63 or 64, or a functional portion thereof.

134. The recombinant DNA construct of embodiment 130 or 133, wherein the florigenic FT protein comprises an amino acid sequence having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to a sequence selected from the group consisting of SEQ ID NOs: 2, 4, 6, 8, 10, 12, 14, 16, 18, 20, 22, 24, 26, 28 and 30, or a functional fragment thereof.

135. A DNA molecule or vector comprising the recombinant DNA construct of embodiment 130 or 133.

136. A plasmid vector for *Agrobacterium*-mediated transformation comprising the recombinant DNA construct of embodiment 130 or 133.

137. A donor template molecule for site-directed integration comprising the recombinant DNA construct of embodiment 130 or 133.

138. A transgenic plant comprising an insertion of the recombinant DNA construct of embodiment 130 or 133 into the genome of at least one cell of the transgenic plant.

139. The transgenic plant of any one of embodiments 131, 132, or 138, wherein the transgenic plant is homozygous for the insertion of the recombinant DNA construct.

140. The transgenic plant of any one of embodiments 131, 132, 138, or 139, wherein the transgenic plant is hemizygous for the insertion of the recombinant DNA construct.

141. The transgenic plant of any one of embodiments 131, 132, or 138-140, wherein the transgenic plant is a short day plant.

142. The transgenic plant of any one of embodiments 131, 132, or 138-141, wherein the transgenic plant is a dicotyledonous plant.

143. The transgenic plant of any one of embodiments 131, 132, or 138-142, wherein the transgenic plant is a leguminous plant.

144. The transgenic plant of any one of embodiments 131, 132, or 138-143, wherein the transgenic plant is soybean.

145. The transgenic plant of any one of embodiments 35-46, 73-84, 106-110, 131, 132, or 138-144, wherein the transgenic plant produces more seeds, bolls, siliques, fruits, nuts or pods per node of the transgenic plant than a control plant not having the recombinant DNA construct.

146. The transgenic plant of any one of embodiments 35-46, 73-84, 106-110, 131, 132, or 138-145, wherein the transgenic plant flowers earlier than a control plant not having the recombinant DNA construct.

147. The transgenic plant of any one of embodiments 35-46, 73-84, 106-110, 131, 132, or 138-146, wherein the transgenic plant is a soybean plant that has a plant height of at least 700 millimeters at R8 stage.

148. The transgenic plant of any one of embodiments 35-46, 73-84, 106-110, 131, 132, or 138-147, wherein the transgenic plant is a soybean plant that has at least 100 nodes per plant at R8 stage.

149. A transgenic plant part comprising an insertion of the recombinant DNA construct of embodiment 130 or 133 into the genome of at least one cell of the transgenic plant part.

EXAMPLES

Example 1. Soybean Short Day Induction Treatment and Identification of Flowering Locus T (FT) Genes by Transcriptional Profiling This example was previously described in co-pending U.S. patent application Ser. No. 15/131,987, and International Application No. PCT/US2016/028130, which are incorporated herein by reference in their entirety. Methods for the photoperiodic light treatment (i.e., short day induction of flowering in plants) are described in U.S. Pat. No. 8,935,880 and U.S. Patent Application Publication No. 2014/0259905, which are incorporated herein by reference in their entirety. As described further therein, the early short day induction treatment produced soybean plants having altered reproductive traits including an increased number of pods/seeds per plant. Transcriptional profiling experiments were performed using gene expression microarrays to determine if particular transcripts were up-regulated in these light-induced plants to identify genes that may be responsible for mediating the short day induction phenotypes. In these experiments, an analysis of transcripts was conducted on soybean leaf and floral apex tissues collected after 1, 3 and 5 days from plants that received a short day inductive light treatment (Short day) in comparison to tissues from plants that did not receive the inductive treatment (Long day).

As shown in FIG. 2, an increased accumulation of transcripts was observed for a particular Flowering Locus T gene, Gm.FT2a (SEQ ID NO: 1), in leaf tissue harvested at 3 and 5 days after the early short day induction (eSDI) treatment in comparison to samples taken from either (i) floral apex tissues of the same short day induction plants, or (ii) leaf tissues and floral apex tissues of soybean plants that instead received the long day treatment. These data support the conclusion that Gm.FT2a expression is induced in leaf tissue of plants experiencing the eSDI treatment, which was not seen in plants grown under long day conditions. Gm.FT2a expression was also not observed in the floral apex of eSDI treated plants, which is consistent with the model of FT protein expression being induced in peripheral leafy tissues in response to inductive photoperiod conditions and then migrating to its site of action in the meristems to induce flowering. However, additional experiments using a more sensitive RNA sequencing analysis of transcripts did show some Gm.FT2a induction in the shoot apex and axillary buds in response to the eSDI treatment (data not shown).

Example 2. Characterization of the pAt.Erecta Promoter Expression Patterns in Soybean Achieving desirable traits or phenotypes by transgenic approaches may require control of the temporal and spatial patterns of ectopic FT gene expression. Soy physiological experiments identifying Gm.FT2a expression in vegetative tissues following the short day induction treatment (see FIG. 2) indicated that achieving yield positive traits may rely on earlier FT expression during the vegetative stage. On the other hand, even though FT transcripts are not detected in the vegetative apex, FT protein has been shown to move long distance from the leaves to the apical tissue where it triggers a vegetative to reproductive transition. See, e.g., Lifschitz, E. et al., (2006), supra; and Corbeiser, L. et al., "FT Protein Movement Contributes to Long-Distance Signaling in Floral Induction of *Arabidopsis*", *Science* 316: 1030-1033 (2007). Thus, in light of our own observations, we proposed using a vegetative stage promoter that is active in the meristem to control ectopic FT expression in a plant. By expressing the morphogenetic FT signal directly in the meristem at the desired developmental stage, multiple endogenous pathways and regulatory feedbacks (e.g., control of FT transduction in the leaf and long distance translocation of the FT signal) may be bypassed or avoided. Previous experiments with the short day induction treatment (described above in Example 1) revealed up-regulation of the Gm.Erecta gene in the meristems of soybean plants. The pErecta promoter (SEQ ID NO: 31) from *Arabidopsis* had been shown to have weak expression in the meristem(s) of plants during vegetative stages of development. Accordingly, the pAt.Erecta promoter was selected for initial FT expression experiments.

Figure 4A:
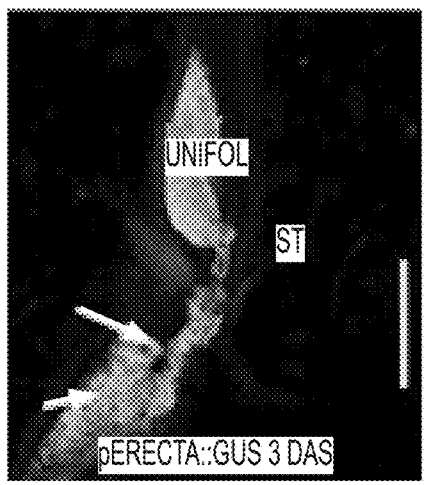
Figure 4B:
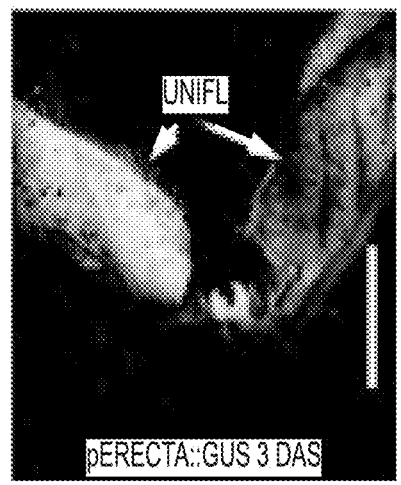
Figure 4C:
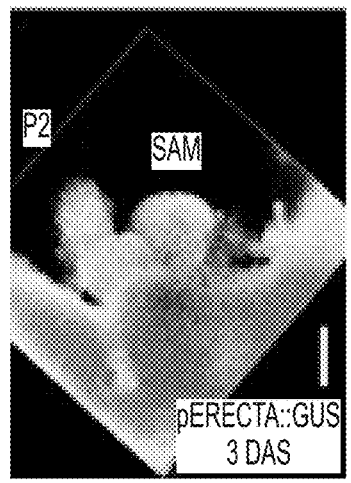
Figure 4D:
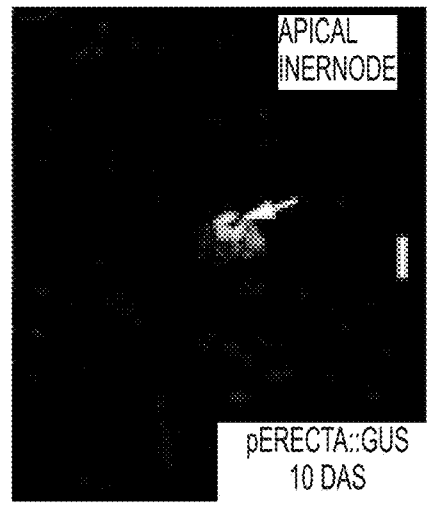
Figure 4E:
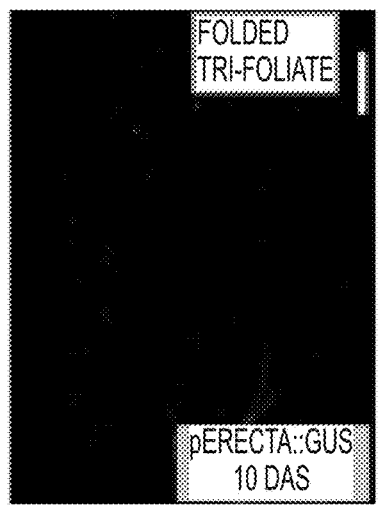
Figure 4F:
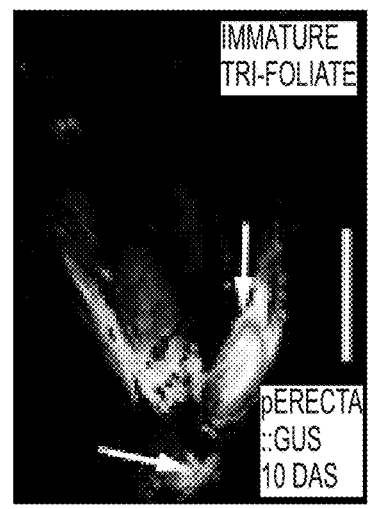
Figure 4G:
Figure 4H:
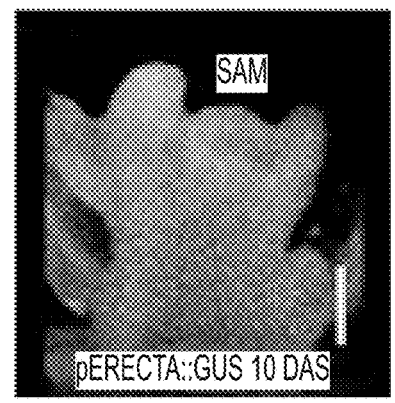
Figure 4I:
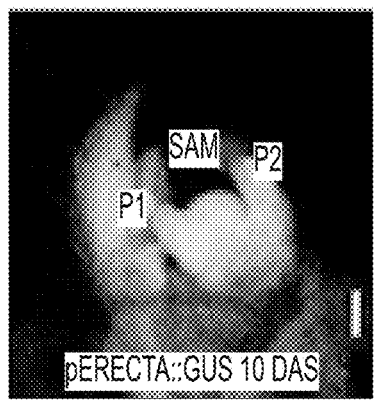

Additional experiments were performed to further characterize the expression patterns of pAt.Erecta fused to a GUS reporter gene in vegetative and floral meristematic tissues. Analysis of GUS expression patterns during the development of soy seedlings indicated that the pAt.Erecta promoter exhibits a temporal and spatial pattern of expression, preferably in the meristematic tissues during the vegetative stage of development. FIGS. 3A to 3O and 4A to 4O and FIGS. 5A to 5F and 6A to 6F include two sets of images to show the pattern of GUS staining. FIGS. 3A to 3O and 5A to 5F provide black and white images of the stained tissues, and FIGS. 4A to 4O and 6A to 6F provide black and white images corresponding to FIGS. 3A to 3O and 5A to 5F, respectively, but color filtered to show the pattern and intensity of blue GUS staining. Thus, the GUS staining pattern of expression can be viewed with these black and white images by comparing the corresponding images of FIGS. 3A to 3O and 4A to 4O or FIGS. 5A to 5F and 6A to 6F. As shown in FIGS. 3A to 3O and 4A to 4O, GUS staining was detected in the soy immature uni-foliate blade and petiole (FIGS. 4A and 4B) at three days after sowing/germination. pAt.Erecta::GUS expression was also broadly detected in the trifoliate primordia, shoot apical meristem (SAM) and axillary meristem sites at this early vegetative stage (FIG. 4C). GUS activity was not detected in the fully expanded uni-foliate and trifoliate leaves at ten days after germination or planting (FIGS. 4D and 4E). However, GUS activity was detected at the proximal part of the immature, unexpanded, but fully developed trifoliate blade, and at the adaxial side of the petiole (FIG. 4F). Detailed observation of the developing apical tissue showed that broad expression was retained in the developing immature leaf primordia, axillary meristems and shoot apical meristems (FIGS. 4G-I).

Figure 4J:
Figure 4K:
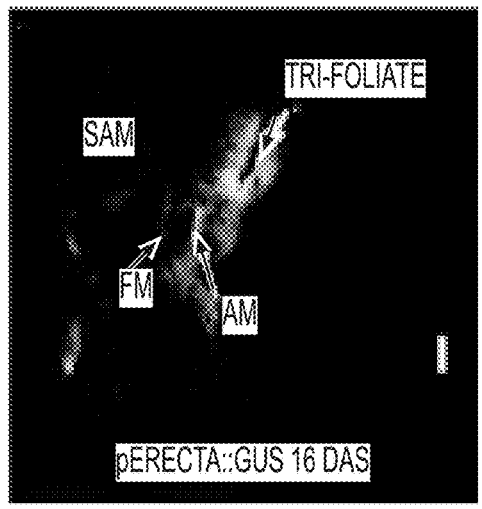
Figure 4L:
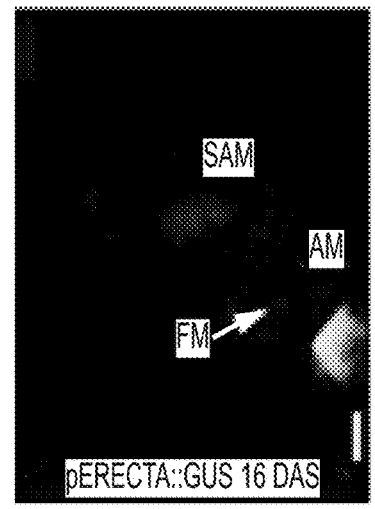
Figure 4M:
Figure 4N:
Figure 4O:
Figure 5A:
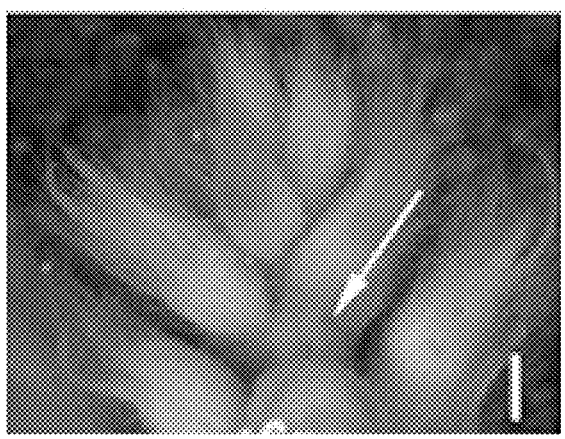
FIGS. 5A to 5F and FIGS. 6A to 6F show the GUS expression pattern with the pAT.Erecta promoter during R1 and floral stages of development (35-40 days after germination).
Figure 5B:
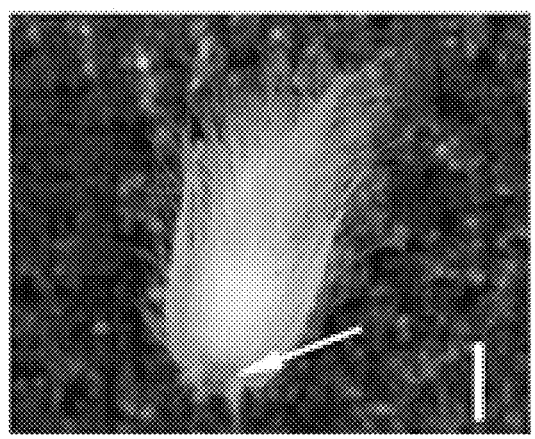
Figure 5C:
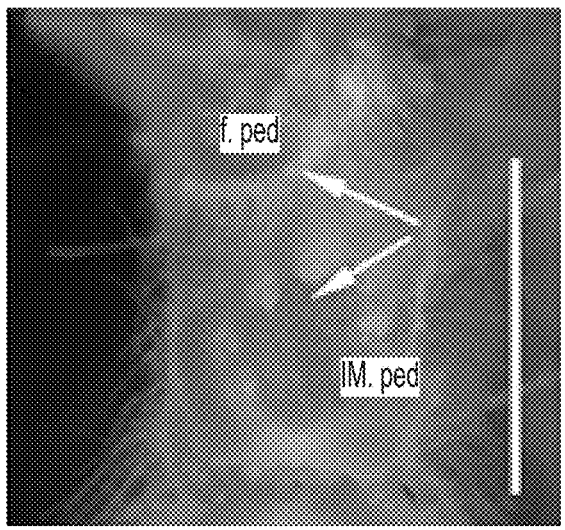
Figure 5D:
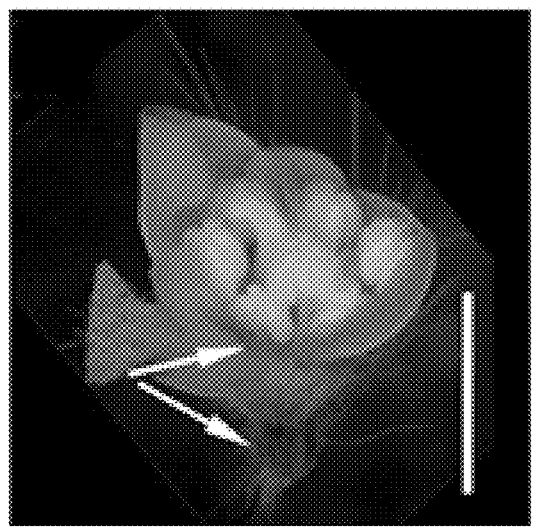
Figure 5E:
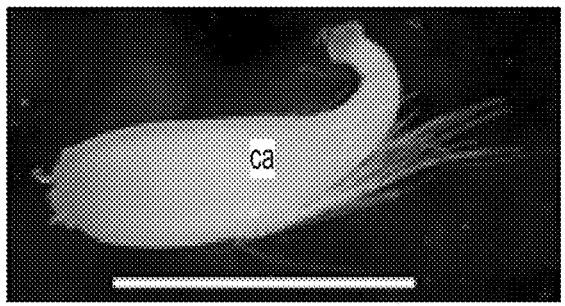
Figure 5F:
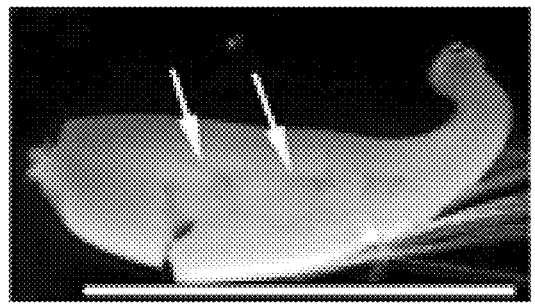
Figure 6A:
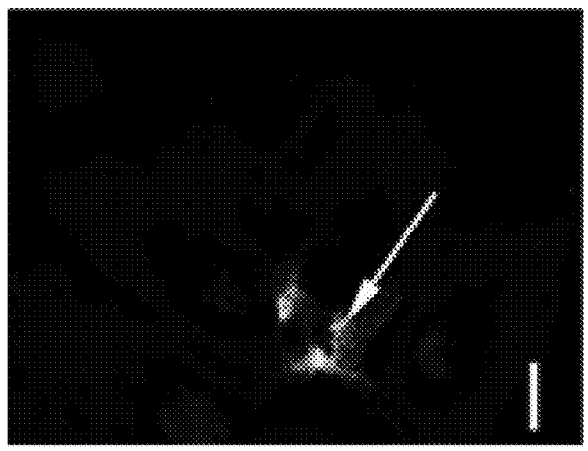
Figure 6B:
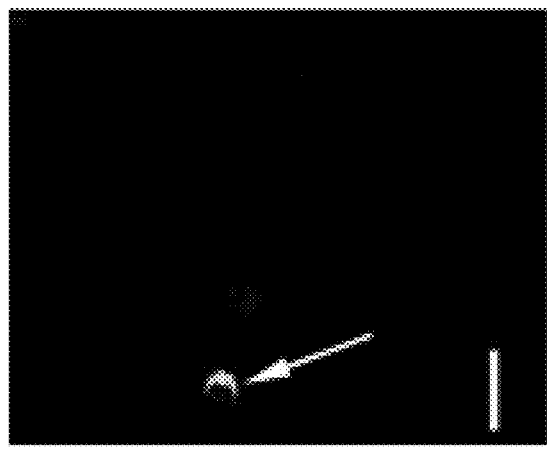
Figure 6C:
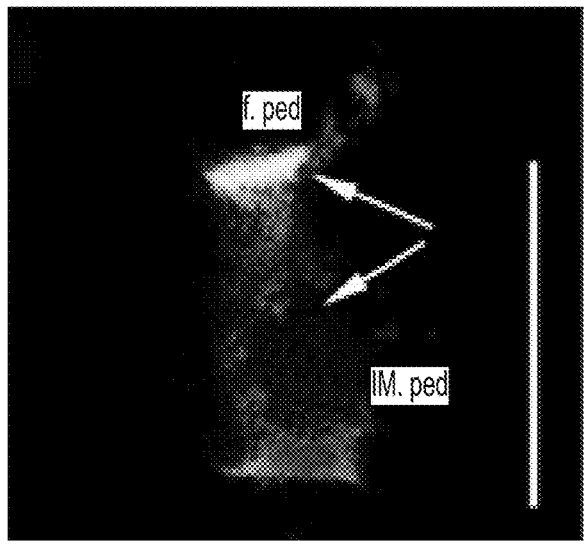
Figure 6D:
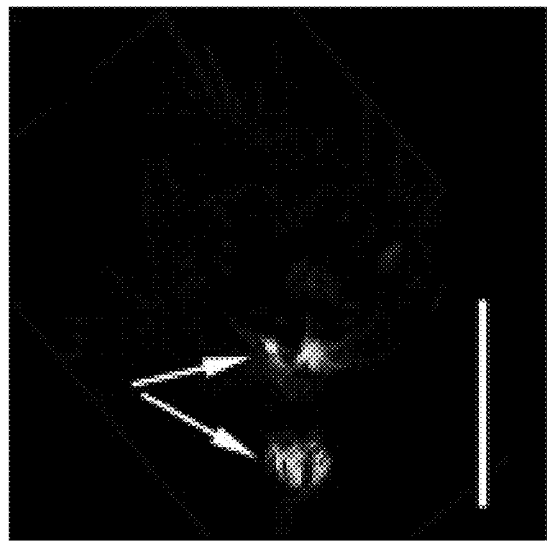
Figure 6E:
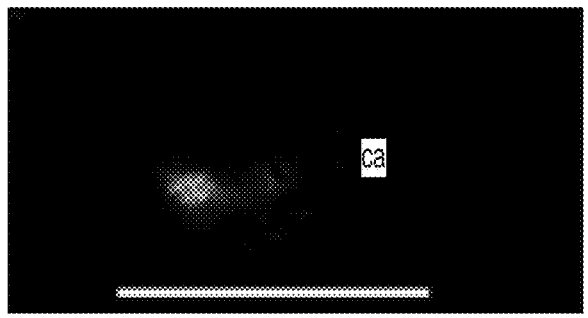
Figure 6F:
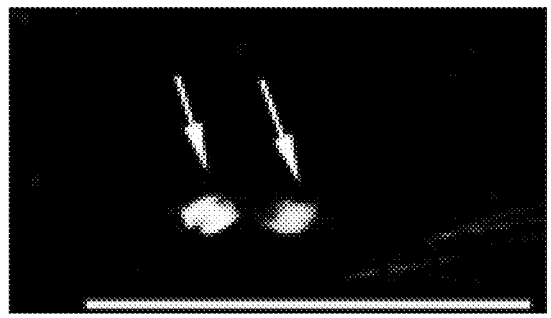

At the early reproductive stage, pAt.Erecta promoter activity was not detected in the mature blade and was reduced in the developing leaf primordia. The GUS signal was not detected in the indeterminate vegetative apex at the shoot apical meristem (SAM) or in the axillary meristem (AM) once these tissues started to form inflorescences (FIGS. 4J-4L). In all later stages, any additional meristematic activity could not be detected in the apex or in the axillaries or flower primordia. However, GUS expression continued in the adaxial side of the petiole and proximal part of the immature leaf blade (FIGS. 4M and 4N), but not in the fully expanded leaf blade (FIG. 4O). GUS expression patterns with the pAt.Erecta promoter were also analyzed at the later R1 stages of development (35-40 days after germination). Similar to earlier stages of development, no expression was detected in the mature leaves or stems. However, strong promoter activity was detected in the inflorescence stems (FIGS. 5A and 6A; see arrow) and floral pedicels (FIGS. 5B and 6B; see arrow). In both tissues, expression was detected in vasculature and parenchyma cells (FIGS. 5C and 6C). At this stage, expression was also detected in the stamen filaments (FIGS. 5D and 6D; see arrows) and in the unpollinated ovules (FIGS. 5E, 5F, 6E and 6F; see arrows in 6F).

Previously, the pAt.Erecta promoter was characterized in *Arabidopsis*. Interestingly, pAt.Erecta expression patterns in *Arabidopsis* were comparable to the patterns observed in soy during the vegetative stage, but not during late reproductive stages. In contrast, the pAt.Erecta expression pattern in soybean is diminished in early reproductive tissues but remerges in some later reproductive organs and tissues, including the inflorescence stems and floral pedicels. See, e.g., Chen, M-K et al., *FEBS Letters* 588: 3912-17 (2014); Yokoyama, R et al.; Shpak, E D et al., *Science* 309: 290-293

(2005); and Yokoyama, R et al., *Plant J* 15(3): 301-310 (1998), the entire contents and disclosures of which are incorporated herein by reference. Thus, the pAt.Erecta promoter provides a novel expression pattern in soybean.

Example 3. Expression of Flowering Locus T Gene, Gm.FT2a, Under Control of a pAt. Erecta Promoter Alters Flowering Time and Pods Per Node in Soybean Transgenic soybean plants were produced by transforming soybean explants with a recombinant DNA molecule (i.e., a T-DNA transformation vector) comprising the pAt.Erecta promoter operably linked to the Gm.FT2a gene via *Agrobacterium*-mediated transformation to generate four pAt.Erecta::Gm.FT2a events that were carried forward for further testing. The effect of FT2a overexpression was immediately seen in $R_0$ plants, which had very early flowering and termination with reduced seed yield (e.g., only about 8 seeds/plant). These transgenic Gm.FT2a plants also had a short plant height and very few, if any, branches. Segregating $R_1$ plants and their progeny were subsequently grown in the greenhouse under long day conditions for initial study and characterization. By growing these plants under long day conditions, the severe dwarf phenotypes observed with Gm.FT2a transgenic $R_0$ plants were improved. In these experiments, both homozygous and hemizygous plants grown in the greenhouse under 16-hour long day conditions (i.e., 16/8 hours of day/night photoperiods) flowered much earlier than wild type null segregants. Gm.FT2a transgenic plants flowered at about 19-22 days after planting or seeding). (see, e.g., FIGS. 9A to 9C). Under these growth conditions, transgenic soybean plants expressing Gm.FT2a further had an increased number of pods per node on the main stem in comparison to wild type controls (see, e.g., FIGS. 10 and 11, discussed further below).

Figure 7:
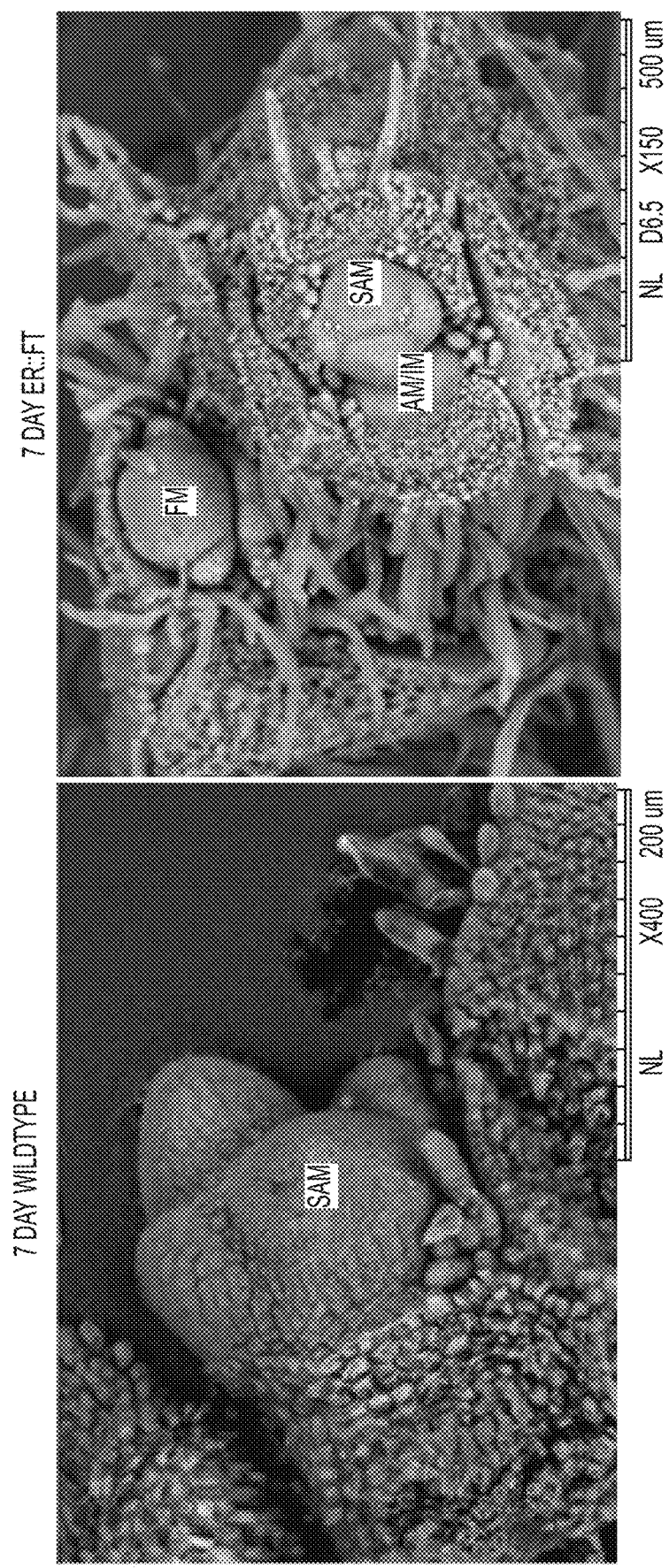
FIG. 7 shows section imaging of the shoot apical meristem (SAM) from wild type versus GmFT2a-expressing transgenic plants at 7 days after planting using scanning electron microscopy (eSEM) analysis.
Figure 8:
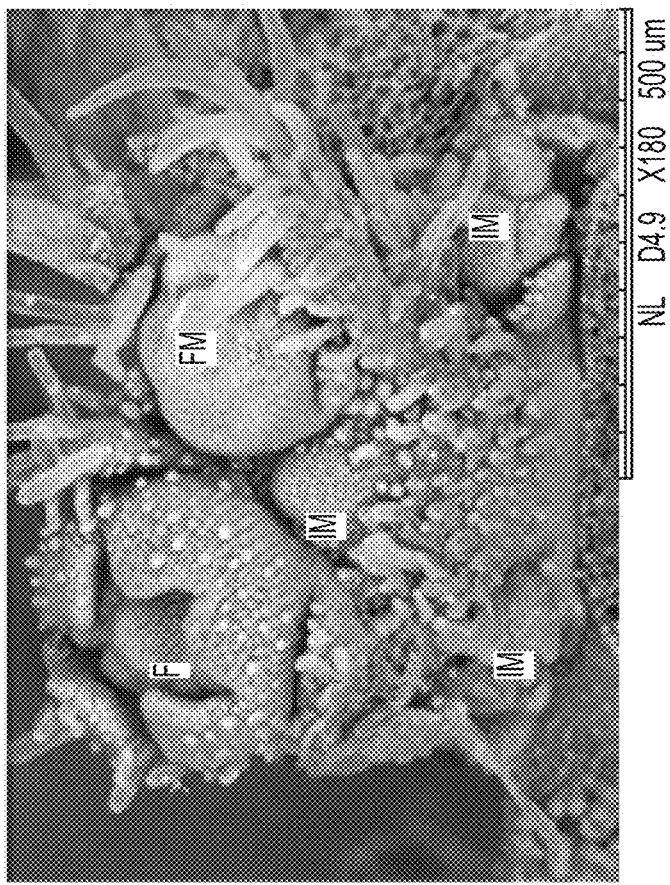
FIG. 8 shows scanning electron microscopy (eSEM) micrographs of an axillary inflorescence primordia from a wild type plant (collected at 27 days after planting), in comparison to an axillary inflorescence primordia from a transgenic event expressing Gm.FT2a (collected at 9 days after planting).
Figure 8:
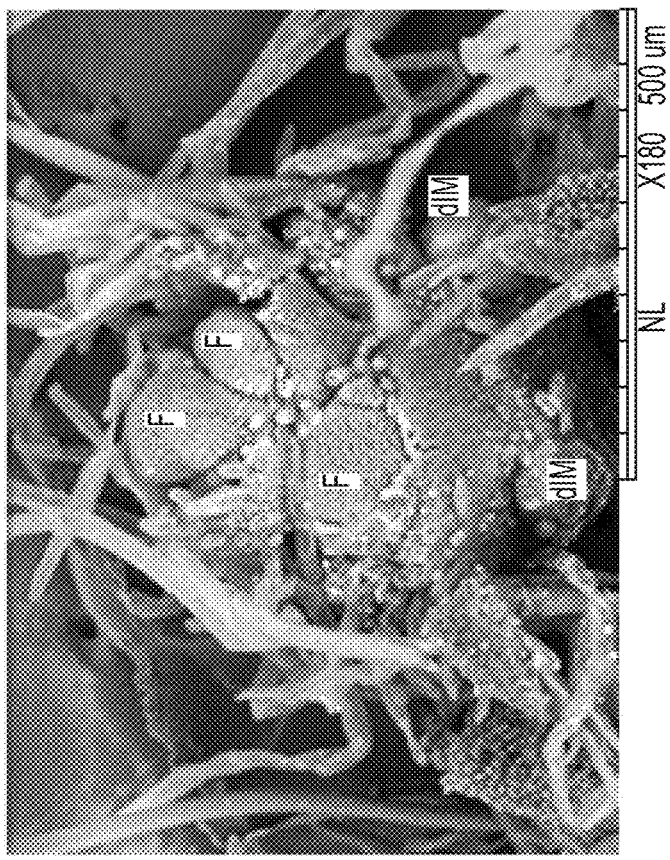
Figure 9C:
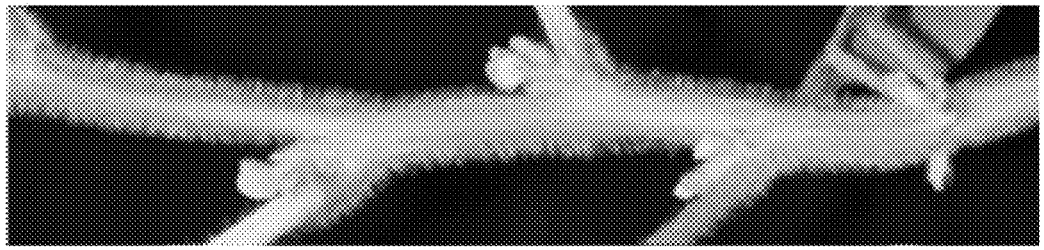
FIGS. 9A to 9C show the effects of Gm.FT2a expression driven by the At.Erecta promoter in soybean.
Figure 9B:
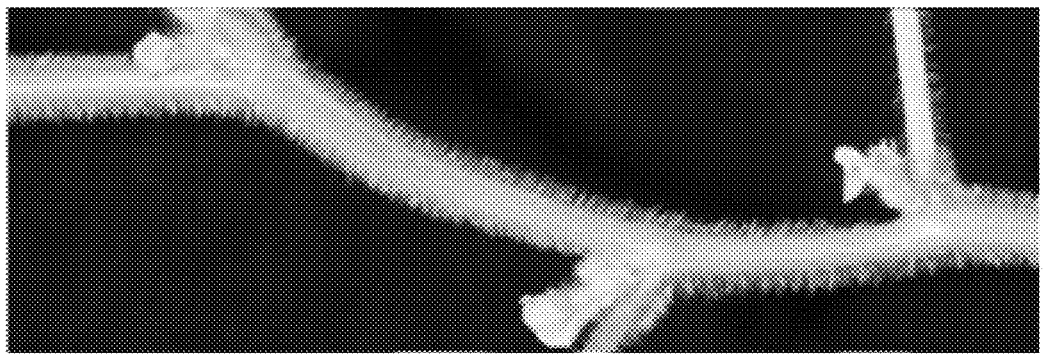
Figure 9A:
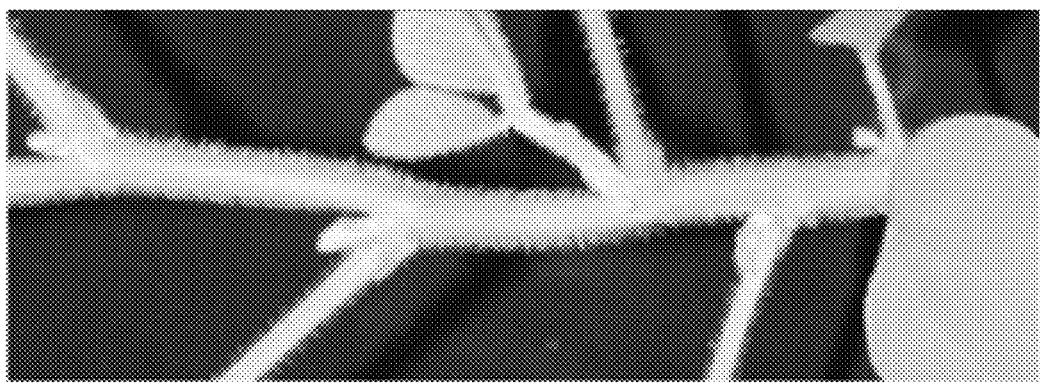

Plants containing one of the pAt.Erecta::Gm.FT2a transgenic events (Event 1) grown in controlled environment conditions were further analyzed via scanning electron microscopy analysis (eSEM). Analysis of the shoot apical meristem (SAM) of these transgenic plants (collected at 7 days after planting) revealed an early transition of the SAM into an inflorescence meristem (IM) and floral meristem (FM) (FIG. 7). In contrast, the SAMs of wild type soybean plants were not differentiated into IM at this growth stage. Similarly, imaging of the axillary meristem of the FT2a transformants (collected at 9 days after planting) indicated the development of dormant inflorescence meristems (dIMs) (or lateral primordial racemes) into IM and FM (FIG. 8), leading to more earlier-developing floral branches (racemes) per node in these transgenic plants. Additional phenotypic characterization revealed early flowering at the V1 stage in Gm.FT2a expressing soybean plants, which was well before the floral transition occurred in null segregating plants (FIGS. 9A to 9C). These data in combination with the pAt.Erecta::GUS expression pattern described above indicate that early flowering, and more particularly the formation of inflorescence and floral meristems, were induced by ectopic expression of Gm.FT2a during the vegetative stage in leaf primordia and the shoot apical and axillary meristems of seedlings. The formation of a higher number of inflorescence and floral meristems is believed to further cause earlier release and elongation of the secondary and tertiary racemes, leading to a greater number of productive flowers and pods being formed per node.

Figure 10:
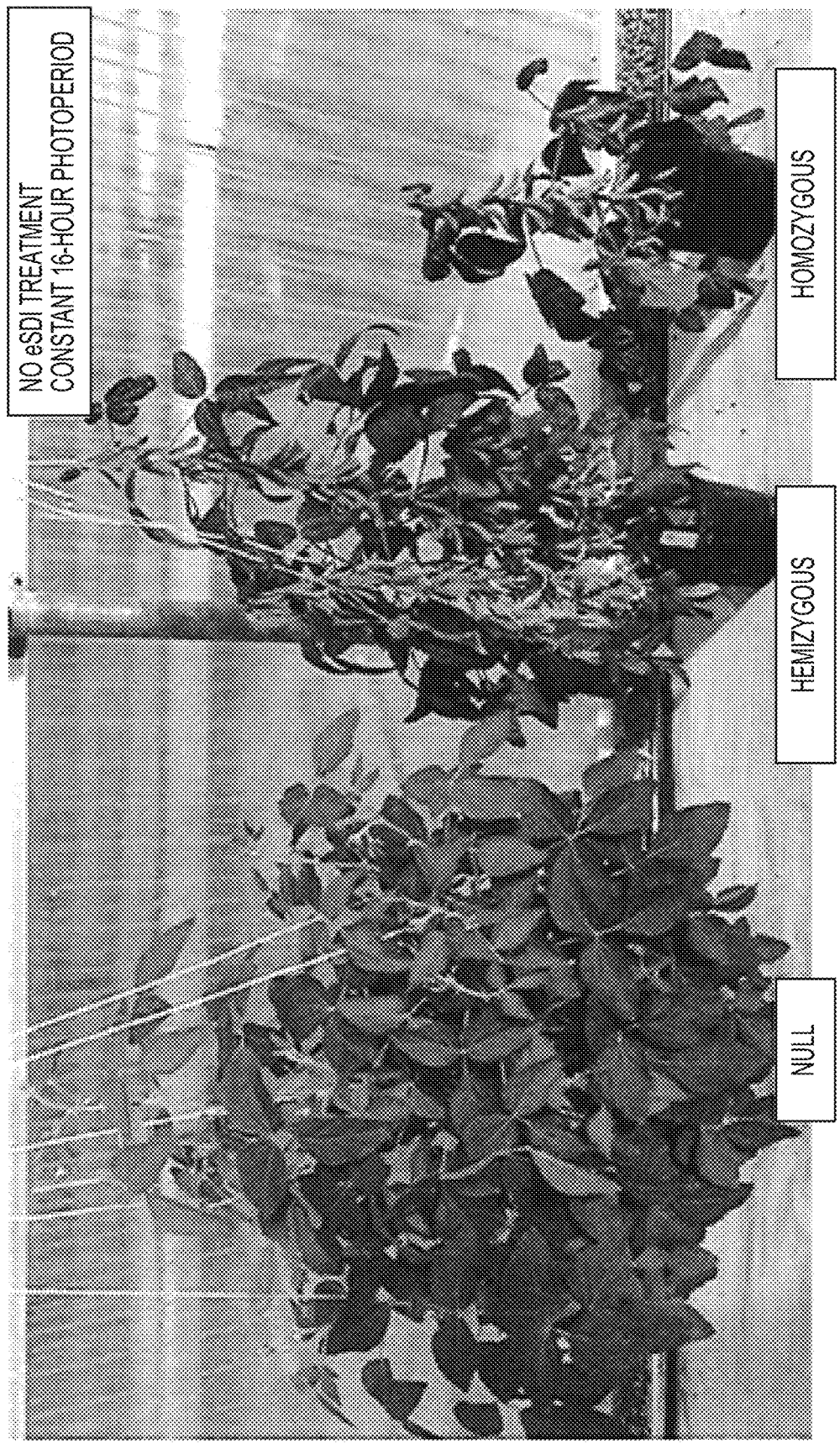
FIG. 10 shows a whole plant image of a wild type null segregant next to plants hemizygous and homozygous for the Gm.FT2a transgene as indicated.

Not only did Gm.FT2a transgenic soybean plants experience earlier flowering and produce more pods per node on the main stem (relative to segregating null plants), the effects of ectopic Gm.FT2a expression in transgenic plants were also found to be dosage dependent. Although both homozygous and hemizygous plants had a reduced height and less branching, plants homozygous for the Gm.FT2a transgene were more severely affected than hemizygous plants, presumably because homozygous plants contain two copies of the transgene (i.e., a higher dosage), as opposed to only one copy (i.e., a lower dosage) in hemizygous plants. Under long day growth conditions, homozygous plants terminated earlier and had a shorter overall height with fewer nodes and branches on the main stem in comparison to plants hemizygous for the transgene (FIG. 10). Unlike homozygous plants, which exhibited a number of sub-optimal dwarf phenotypes including very few (if any) branches on the main stem, hemizygous plants had an intermediate phenotype in terms of their vegetative growth, plant height, and the number of nodes present on the main stem relative to wild type and homozygous plants. Under 16-hour long day conditions, hemizygous plants had a more normal plant height with some degree of branching and a more extended duration of flowering, relative to homozygous plants (FIG. 10). Hemizygous plants also flowered for 40-64 days after initiation of R1, whereas homozygous plants flowered for only 16-24 days due to their earlier termination.

Additional experiments were conducted with plants transformed with the Gm.FT2a construct (3 events) in long day (16 hour) controlled environment conditions to further characterize the dosage response between hemizygous and homozygous plants. Differences in the number of nodes and pods on the main stem and branches, as well as the average number of pods per node and the average height per plant are shown in Table 1 for three homozygous events (Homo-Event 2, Homo-Event 3, Homo-Event 4) and three hemizygous events (Hemi-Event 2, Hemi-Event 3, Hemi-Event 4). These events are distinguished from Event 1 above.

TABLE 1

Event level data for homozygous and hemizygous Gm.FT2a transgenic plants.

| Zygosity-Event # | Avg. # MS nodes per plant | Avg. # BR nodes per plant | Avg. # MS pods per plant | Avg. # BR pods per plant | Avg. Pods per Node | Avg. Height (in) per plant |
|---|---|---|---|---|---|---|
| Homo-Event 2 | 11.8 | 6.9 | 46 | 9 | 2.9 | 17.5 |
| Homo-Event 3 | 12.3 | 6.5 | 66.4 | 9 | 4 | 21 |
| Homo-Event 4 | 12.5 | 6.8 | 49.6 | 9.1 | 3 | 19.5 |
| Hemi-Event 2 | 25.3 | 12.4 | 183.5 | 47.3 | 6.1 | 37.5 |

TABLE 1-continued

Event level data for homozygous and hemizygous Gm.FT2a transgenic plants.

| Zygosity-Event # | Avg. # MS nodes per plant | Avg. # BR nodes per plant | Avg. # MS pods per plant | Avg. # BR pods per plant | Avg. Pods per Node | Avg. Height (in) per plant |
|---|---|---|---|---|---|---|
| Hemi-Event 3 | 23.9 | 13.2 | 200.3 | 28.8 | 6.1 | 40 |
| Hemi-Event 4 | 25.4 | 15.3 | 186.8 | 58 | 6 | 41.5 |

As shown in Table 2, hemizygous plants consistently had a higher number of nodes on the main stem (MS) and branches (BR) and a greater plant height than homozygous plants. Thus, hemizygous plants were generally less affected than homozygous plants and more like wild type plants. Hemizygous plants also had an increased number of pods per node and a higher number of pods on the main stem and branches, relative to homozygous plants. Therefore, hemizygous plants generally had a closer-to-normal plant architecture with a greater number of pods per node (and per plant), presumably due to their lower Gm.FT2a transgene dosage. The relative dosage level of Gm.FT2a based on transgene zygosity was further confirmed by additional experiments showing that Gm.FT2a transcript levels were higher in tissues from homozygous plants, than in tissues from hemizygous plants (data not shown).

Figure 11:
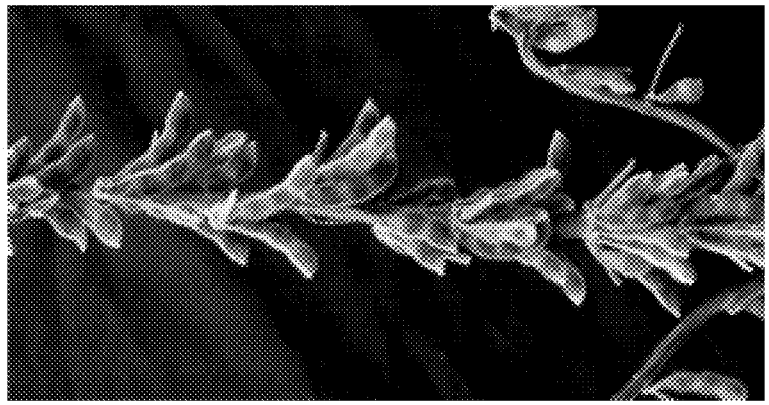
FIG. 11 shows images of the main stem of plants that are homozygous or hemizygous for the pAtErecta-Gm.FT2a transgene in comparison to a null segregant as indicated.
Figure 11:
Figure 11:

The early induction of flowering in these Gm.FT2a transgenic plants was associated with more pods (and seeds) per node on the main stem in both hemizygous and homozygous plants. Homozygous and hemizygous plants containing the Gm.FT2a transgene each had an increased number of pods/seeds per node on the main stem of the plant in comparison to wild type segregants (FIG. 11). The distribution of pods on the main stem was also found to be different between Gm.FT2a transgenic and wild type null plants. Both homozygous and hemizygous plants grown under long day conditions were found to have more pods on at least the lower nodes of the main stem and more pods per node on average, in comparison to wild type null plants (data not shown). Plants hemizygous for the Gm.FT2a transgene contained the highest number of pods per node over the length of the main stem. However, these effects were dependent on the particular growing conditions including day length, etc. In general, experiments performed with soybean under longer day conditions tended to produce greater differences between transgenic and null plants.

The dosage-dependent effects of transgenic Gm.FT2a expression were also observed in field trial experiments. In a field trial experiment, soybean plants hemizygous for two Gm.FT2a events (Events 1 and 2 above) showed an average of about 2.68 pods per node on the main stem, and plants homozygous for these events had about 1.40 pods per node on average, whereas null segregating plants had about 1.63 pods per node. In an earlier field trial, however, plants hemizygous for transgenic Gm.FT2a (Event 2) were found to have an average number of about 3.21 pods per node, as compared to an average of about 3.05 pods per node in homozygous plants and about 2.19 pods per node in null segregating plants. In another micro plot experiment conducted at a different field location, plants hemizygous for the Gm.FT2a transgene (Event 1) were found to have about 2.17 pods per node on average, as compared to an average of about 2.05 pods per node in plants homozygous for the Gm.FT2a transgene (Event 2) and about 1.30 pods per node in null segregating plants. Thus, the number of pods per node on plants containing the Gm.FT2a transgene may depend on a variety of factors including dosage of the FT transgene, environmental and field conditions, and perhaps differences in agronomic practices. However, much like transgenic Gm.FT2a plants grown in the greenhouse, homozygous and hemizygous Gm.FT2a transgenic plants grown under field conditions often had fewer nodes on the main stem, shorter overall plant height, and/or reduced branching in transgenic plants. Indeed, wild type plants typically had more branching and a greater number of total nodes per plant than hemizygous and homozygous Gm.FT2a plants.

Additional physiological data was collected from homozygous Gm.FT2a transgenic plants and wild type (WT) control plants grown in the greenhouse under 14-hour long day conditions (see Table 2). These data provide an average of measurements taken from six Gm.FT2a transgenic plants for each event, or from eight wild type plants.

The following matrices were collected for phenotypic characterization of these plants: Days to flowering at R1 (DOFR1); Days to R7 (DOR7); reproductive duration in days from R1 to R7 (PDR1R7); number of branches per plant (BRPP); total fertile nodes on branches (FNBR); total fertile nodes per plant (FNLP); total fertile nodes on main stem (FNST); number of nodes on branches (NDBR); number of nodes on main stem (NDMS); number of nodes/plant (NDPL); percent fertile nodes on branches (PFNB); percent total fertile nodes (PFNN); percent fertile nodes on main stem (PFNS); number of pods per plant (PDPP); number of pods on main stem (PODMS); number of pods on branches (PODBR); number of pods/node on average; seeds per plant at R8 (SDPPR8); and weight of 1000 seeds (SW1000). Each of these measurements was taken at harvest unless another time point is specified.

TABLE 2

Construct level phenotypic data for transgenic homozygous Gm.FT2a and WT plants.

| | WT | pAtErecta::Gm.FT2a |
|---|---|---|
| DOFR1 | 33.5 | 21.3 |
| DOR7 | 106.9 | 92.9 |
| PDR1R7 | 76.5 | 71.6 |
| BRPP | 20.1 | 1 |
| FNBR | 190.6 | 2 |
| FNLP | 214.6 | 15 |
| FNST | 24.0 | 14.3 |
| NDBR | 211.4 | 3 |
| NDMS | 33.4 | 15.3 |
| NDPL | 244.9 | 16.3 |
| PDPP | 575.8 | 61.2 |
| PFNB | 90.4 | 75 |
| PFNN | 87.8 | 92.0 |

TABLE 2-continued

Construct level phenotypic data for transgenic homozygous Gm.FT2a and WT plants.

|  | WT | pAtErecta::Gm.FT2a |
|---|---|---|
| PFNS | 71.4 | 92.9 |
| PODBR | 487.3 | 3 |
| PODMS | 88.4 | 60.2 |
| Pods/Node | 2.4 | 3.8 |
| SDPPR8 | 1319.6 | 122.1 |
| SW1000 (grams) | 146 | 122.5 |

Consistent with the observations noted above, homozygous Gm.FT2a transgenic plants experienced earlier floral induction than WT plants (DOFR1 about 21 days after planting, instead of about 33-34 days in wild type plants). These measurements further showed that the number of branches (and other measurements related to branching, such as the number of nodes or pods on branches) was greatly reduced. Due to the transgenic plants having a shorter stature with very little branching, the total numbers of nodes or pods per plant were also greatly reduced. However, the number of pods per node on the main stem was increased in transgenic plants (e.g., about 3.8 average pods/node) relative to wild type null plants (e.g., about 2.4 pods/node).

Without being bound by any theory, the larger number of pods per node observed with transgenic soybean plants expressing FT2a in the meristem during vegetative stages of development may be caused at least in part by synchronization of early flowering with early secondary and/or tertiary raceme release and/or better resource utilization to produce more pod-producing flowers per node. Early FT expression in the meristem (see, e.g., FIGS. 3 and 4) may cause early release of the dormant inflorescence meristems to produce a greater number of racemes per node of the plant, such that a greater number of racemes produce mature flowers and fully developed pods at each node. However, subsequent FT expression in reproductive tissues (see, e.g., FIGS. 5 and 6) may terminate floral development of later developing flowers at each node leading to more efficient resource allocation to the earlier developing racemes, flowers and pods. In wild-type soybean plants, a much lower percentage of secondary and tertiary racemes produce flowers and fully developed pods relative to primary racemes, and later developing flowers of the primary raceme typically do not produce mature flowers and/or full-sized pods prior to abscission. Thus, it is theorized that more pods per node may be generated in plants expressing FT proteins in the vegetative meristem by synchronizing early flower development with early release of the lateral racemes at one or more node(s) of the plant. With at least the pAt.Erecta promoter driving FT expression, later developing flowers (that may not otherwise produce fully developed or full-sized pods) may also become terminated by later reproductive-stage expression of FT to direct resources to the earlier developing flowers.

Example 4. Expression of Flowering Locus T Gene, Gm.FT2a, Under Control of Alternative Vegetative Stage Promoters in Soybean Based on the phenotypes observed in the preceding Example 3, two promoters were also proposed to drive Gm.FT2a transgene expression that were considered vegetative-stage, leaf-preferred promoters: pAt.BLS (SEQ ID NO: 46) and pAt.ALMT6 (SEQ ID NO: 47). As used herein, a "leaf-preferred" promoter refers to a promoter that preferentially initiates transcription of its associated gene in leaf tissues relative to other plant tissues. Since FT is believed to function as a mobile florigen, early FT expression during vegetative stages in peripheral tissues, such as in the leaf with a leaf-preferred or leaf-specific promoter, may lead to phenotypes similar to the meristem-preferred pAt.Erecta::Gm.FT2a expression. It was further theorized that FT expression with a vegetative leaf promoter might also attenuate the floral induction signal, and thus mitigate the early termination phenotypes observed with homozygous FT expression in the meristem, and increase plant height and branching.

In these experiments, transformation vectors for pAt.ALMT6::Gm.FT2a and pAt.BLS::Gm.FT2a were constructed and used to transform a soybean line by Agrobacterium-mediated transformation. Expression with the pAt.BLS promoter has been shown to start in leaf primordia number 5 (p5) and is expressed in the source leaf veins only until transition to flowering, and the pAt.ALMT6 promoter is also a vegetative leaf promoter with expression at later developmental stages relative to pAt.BLS. See, e.g., Efroni et al., "A Protracted and Dynamic Maturation Schedule Underlies Arabidopsis Leaf Development," The Plant Cell 20(9): 2293-2306 (2008); and Shani et al., "Stage-Specific Regulation of Solanum lycopersicum Leaf Maturation by Class 1 KNOTTED1-LIKE HOMEOBOX Proteins," The Plant Cell 21(10): 3078-3092 (2009). Transgenic soybean plants were produced for each of these vector constructs and characterized for phenotypes in growth chambers under 14-hour photoperiod conditions in comparison to wild type plants. For each of the pAt.BLS promoter constructs, six transgenic events were tested (5 plants per event), and for the pAt.ALMT6 promoter, seven transgenic events were tested (5 plants per event). For each of these constructs, control data was collected from five wild type plants.

The following matrices were collected for phenotypic characterization of these transgenic plants (Tables 3 and 4). The individual measurements are as defined above, and phenotypic characterization was conducted on plants homozygous for the transgene.

TABLE 3

Construct level phenotypic data for pAt.ALMT6::Gm.FT2a and WT plants.

|  | WT | pAt.ALMT6::Gm.FT2a |
|---|---|---|
| DOFR1 | 35.2 | 38.8 |
| DOR7 | 84.7 | 88.8 |
| PDR1R7 | 49.5 | 50.0 |
| BRPP | 7.7 | 8.9 |
| FNBR | 57.8 | 73.3 |
| FNLP | 69.7 | 85.0 |
| FNST | 12.0 | 11.7 |
| NDBR | 78.9 | 96.0 |
| NDMS | 21.3 | 22.5 |
| NDPL | 100.2 | 118.5 |
| PDPP | 120.2 | 141.1 |
| PFNB | 73.2 | 76.8 |
| PFNN | 71.7 | 72.1 |
| PFNS | 57.9 | 51.7 |
| PODBR | 91.8 | 118.1 |
| PODMS | 28.3 | 22.9 |
| Pods/Node | 1.4 | 1.2 |

TABLE 4

Construct level phenotypic data for pAt.BLS::Gm.FT2a and WT plants.

|  | WT | pAt.BLS::Gm.FT2a |
|---|---|---|
| DOFR1 | 31.3 | 35.2 |
| DOR7 | 78.1 | 82.6 |
| PDR1R7 | 46.9 | 47.5 |
| BRPP | 7.5 | 8.8 |
| FNBR | 65.7 | 81.2 |
| FNLP | 80.5 | 94.0 |
| FNST | 14.9 | 12.7 |
| NDBR | 72.2 | 95.6 |
| NDMS | 21.9 | 22.3 |
| NDPL | 94.0 | 117.9 |
| PDPP | 137.0 | 148.1 |
| PFNB | 92.3 | 85.3 |
| PFNN | 87.4 | 80.1 |
| PFNS | 68.1 | 57.3 |
| PODBR | 100.9 | 123.4 |
| PODMS | 36.1 | 24.8 |
| Pods/Node | 1.7 | 1.3 |

Transgenic plants expressing Gm.FT2a under the control of the alternative pAt.ALMT6 and pAt.BLS promoters were phenotypically more similar to wild type (WT) plants than pAT.Erecta::Gm.FT2a transgenic plants. Plants transformed with the pAt.ALMT6::Gm.FT2a and pAt.BLS::Gm.FT2a constructs had flowering times and vegetative growth traits similar to wild type control plants, perhaps with a slightly increased number of nodes on branches as compared to wild type plants (Tables 3 and 4). These data may be interpreted to indicate that both the timing and location of transgenic FT expression are important for producing reproductive and yield-related traits or phenotypes that differ from wild-type plants. Merely expressing a FT transgene during earlier vegetative stages of development (e.g., in leaf tissues) may not be sufficient to alter the reproductive or yield-related phenotypes of a plant (e.g., pods per node). Thus, according to embodiments of the present invention, a promoter operably linked to a florigenic FT transgene may preferably be a meristem-specific or meristem-preferred promoter in addition to driving expression during the vegetative stages of plant development. However, when the expression profiles for the above two leaf-preferred promoters were tested in soybean plants, no GUS staining was observed in the developing leaf with the pAt.BLS promoter, and the pAt.ALMT6 promoter did not produce detectable GUS expression in the leaf until late vegetative stages with much higher expression during early reproductive stages. Thus, it remains possible that expression of FT transgenes in peripheral (leaf) tissues during early vegetative stages using different tissue-specific promoters may be sufficient in some cases to induce early flowering and/or cause other reproductive or yield-related traits or phenotypes, which may also depend on the particular plant species tested.

Example 5. Identification of Protein Domains of FT Homologs by Pfam Analysis

Gm.FT2a orthologs were identified by sequence analysis and literature review, and a few examples of these FT homologs are listed in Table 5 along with Gm.FT2a. These included other soybean FT genes as well as a few FT genes from other plant species. The amino acid sequences of these FT proteins were analyzed to identify any Pfam protein domains using the HMMER software and Pfam databases (version 27.0). These FT protein sequences (SEQ ID NOs: 2, 4, 6, 8, 10 and 12) were found to have the same Pfam domain identified as a phosphatidyl ethanolamine binding domain protein (PEBP) having a Pfam domain name of "PBP_N", and a Pfam accession number of PF01161. The location of the PBP_N domains in each of these FT protein sequences are also listed in Table 5. The location of the PBP_N domain in other FT proteins can be determined by sequence alignment. It is thus contemplated that any DNA sequence encoding at least an FT protein comprising the PBP_N domain may be used in a recombinant DNA molecule of the present invention, as long as the corresponding FT protein has florigenic activity when ectopically expressed in the meristem of a plant.

TABLE 5

Location of PBP_N (Pfam) domain in FT protein sequences.

| PROTEIN SEQ ID NO. | Gene Name | Domain location |
|---|---|---|
| 2 | Gm.FT2a | 28-162 |
| 4 | Gm.FT5a | 26-157 |
| 6 | Gm.FT2b | 28-162 |
| 8 | Zm.ZCN8 | 26-154 |
| 10 | Nt.FT-like | 25-159 |
| 12 | Le.SFT | 29-161 |

Example 6. Expression of FT Homologs Under Control of pAt.Erecta Promoter in Soybean Additional transformation vectors containing other FT homologs (Table 6) under control of the pAt.Erecta promoter were constructed and used to transform soybeans via *Agrobacterium*-mediated transformation. Transgenic plants generated from these events were characterized for their phenotypes in the greenhouse with a 14 to 14.5 hour natural daylight photoperiod. For each construct, six events were tested (6 plants per event). Six plants were also tested and averaged for wild type (WT) control plants. Different groups of experiments (A-E) were conducted as shown in Table 6 with separate wild type controls.

TABLE 6

List of constructs for some Gm.FT2a and its homologs with their protein sequences.

| Construct Description | Gene Name | PROTEIN SEQ ID NO. | Testing Group |
|---|---|---|---|
| pAt.Erecta::Gm.FT2a | Gm.FT2a | 2 | A |
| pAt.Erecta::Gm.FT2b | Gm.FT2b | 6 | C |
| pAt.Erecta::Gm.FT5a | Gm.FT5a | 4 | E |
| pAt.Erecta::Zm.ZCN8 | Zm.ZCN8 | 8 | B |
| pAt.Erecta::Nt.FT-like | Nt.FT-like | 10 | B |
| pAt.Erecta::Le.SFT | Le.SFT | 12 | D |

The following matrices were collected for phenotypic characterization of plants transformed with each of the constructs listed in Table 6 for expressing other FT homologs with the pAt.Erecta promoter, in addition to data collected for the Gm.FT2a construct as described above. The individual measurements are as defined above, and phenotypic characterization of transformants was conducted on plants homozygous for the transgene.

Phenotypic data was collected for plants expressing the Zm.ZCN8 and Nt.FT-like transgenes under the control of the pAt.Erecta promoter (see Tables 7 and 8). Trait values for each Event in Tables 7 and 8 are an average of all plants tested containing the Event. A column is also provided with an average of the Event values for each trait.

pronounced in the Zm.ZCN8 and Nt.FT-like expressing transgenic plants. Overall, plants expressing the Zm.ZCN8 transgene had shorter plant height and less branching but more pods per node on the main stem. Similarly, plants

TABLE 7

Construct and event level phenotypic data for Zm.ZCN8 and WT plants.

|  | WT | Average | Event 1 | Event 2 | Event 3 | Event 4 | Event 5 | Event 6 |
| --- | --- | --- | --- | --- | --- | --- | --- | --- |
| DOFR1 | 33.5 | 28.6 | 29 | 29.2 | 27.5 | 27 | 30.7 | 28 |
| DOR7 | 106.9 | 93.5 | 97.3 | 89.2 | 88.2 | 93.5 | 100.3 | 92.8 |
| PDR1R7 | 76.5 | 64.1 | 69.8 | 60 | 59 | 59.5 | 71.7 | 64.8 |
| BRPP | 20.1 | 3.2 | 2.8 | 1.3 | 1.5 | 1.3 | 9.5 | 3 |
| FNBR | 190.6 | 26.9 | 32 | 8 | 7 | 2.3 | 95.3 | 17 |
| FNLP | 214.6 | 54.9 | 67.5 | 28 | 40.5 | 20.3 | 132.5 | 40.5 |
| FNST | 24.0 | 28.3 | 35.5 | 22 | 33.5 | 18 | 37.3 | 23.5 |
| NDBR | 211.4 | 30.2 | 32.5 | 9 | 7.5 | 3.5 | 110.8 | 17.8 |
| NDMS | 33.4 | 30.5 | 36.3 | 24 | 34.3 | 20 | 44.8 | 24 |
| NDPL | 244.9 | 60.3 | 68.8 | 30.8 | 41.8 | 23.5 | 155.5 | 41.8 |
| PDPP | 575.8 | 317.5 | 498.3 | 144.8 | 319 | 76.3 | 658 | 208.8 |
| PFNB | 90.4 | 87.2 | 98.6 | 90.3 | 85.4 | 64.6 | 91.1 | 93.2 |
| PFNN | 87.8 | 93.1 | 98.1 | 92.3 | 97.0 | 86.5 | 88.5 | 96.4 |
| PFNS | 71.4 | 93.2 | 97.9 | 92.5 | 97.9 | 90.6 | 82.1 | 98.1 |
| PODBR | 487.3 | 105.4 | 162 | 19 | 18.5 | 3.3 | 384.5 | 45.3 |
| PODMS | 88.4 | 212.9 | 336.3 | 130.5 | 300.5 | 73 | 273.5 | 163.5 |
| Pods/Node | 2.4 | 5.5 | 7.2 | 4.6 | 7.7 | 3.2 | 4.9 | 5.2 |
| SDPPR8 | 1319.6 | 564.7 | 961 | 200.5 | 562 | 136.8 | 1166.3 | 361.5 |
| SW1000 (grams) | 146 | 108.9 | 102.9 | 127.4 | 105.3 | 82.9 | 116.6 | 117.9 |

TABLE 8

Construct and event level phenotypic data for Nt.FT-like and WT plants.

|  | WT | Average | Event 1 | Event 2 | Event 3 | Event 4 | Event 5 | Event 6 |
| --- | --- | --- | --- | --- | --- | --- | --- | --- |
| DOFR1 | 33.5 | 31.5 | 39.3 | 27.7 | 25.3 | 29 | 37.2 | 30.7 |
| DOR7 | 106.9 | 93.9 | 115.8 | 90.7 | 80.7 | 83.7 | 102.2 | 90.2 |
| PDR1R7 | 76.5 | 62.3 | 76.4 | 63 | 55.3 | 54.7 | 65 | 59.5 |
| BRPP | 20.1 | 9.8 | 20 | 8.3 | 2.3 | 5.3 | 17 | 6 |
| FNBR | 190.6 | 108.7 | 190.5 | 95.3 | 11 | 54.3 | 223 | 78.3 |
| FNLP | 214.6 | 131.4 | 212.3 | 118 | 29.5 | 77.8 | 248 | 103 |
| FNST | 24.0 | 23.2 | 21.8 | 22.8 | 21.3 | 23.5 | 25 | 24.8 |
| NDBR | 211.4 | 128.7 | 281.8 | 97 | 11 | 54.5 | 247.7 | 80.5 |
| NDMS | 33.4 | 28.9 | 33.8 | 27 | 23.3 | 24.8 | 35.7 | 28.8 |
| NDPL | 244.9 | 157.1 | 315.5 | 124 | 31.5 | 79.3 | 283.3 | 109.3 |
| PDPP | 575.8 | 462.1 | 638 | 511.3 | 150.8 | 296 | 745 | 431.5 |
| PFNB | 90.4 | 92.5 | 68.0 | 98.6 | 100 | 99.7 | 91.3 | 97.2 |
| PFNN | 87.8 | 89.6 | 67.6 | 95.4 | 93.3 | 98.3 | 88.4 | 94.2 |
| PFNS | 71.4 | 81.9 | 64.7 | 83.3 | 91.3 | 95.2 | 70.6 | 86.2 |
| PODBR | 487.3 | 326.3 | 529 | 342.3 | 22.7 | 147 | 633.3 | 283.5 |
| PODMS | 88.4 | 136.7 | 109 | 169 | 133.8 | 149 | 111.7 | 148 |
| Pods/Node | 2.4 | 3.6 | 2.0 | 4.3 | 4.9 | 3.8 | 2.7 | 4.0 |
| SDPPR8 | 1319.6 | 928.7 | 1359.8 | 965.5 | 382.7 | 591.5 | 1714.3 | 558.7 |
| SW1000 (grams) | 146 | 149.0 | 143.7 | 121.2 | 133.8 | 179.3 | 142.2 | 174.0 |

Transgenic soybean plants expressing the Zm.ZCN8 and Nt.FT-like proteins flowered earlier than wild type control plants and had an increased number of pods per node (similar to plants expressing the Gm.FT2a transgene). Indeed, soybean plants expressing the Zm.ZCN8 and Nt.FT-like transgenes had several phenotypes similar to the Gm.FT2a transgenic plants, including reduced number of days to flowering (DOFR1), reduced number of branches (BRPP), fewer nodes per plant (NDPL), fewer nodes on branches (NDBR), reduced number of pods per plant (PDPP), and fewer pods on branches (PODBR), along with an increase in the number of pods per node and a decrease in the number of seeds per plant (Tables 7 and 8), relative to wild type controls. However, several of the negative phenotypes observed in homozygous Gm.FT2a plants were less pronounced in the Zm.ZCN8 and Nt.FT-like expressing transgenic plants. Overall, plants expressing the Zm.ZCN8 transgene had shorter plant height and less branching but more pods per node on the main stem. Similarly, plants expressing the Nt.FT-like transgene had shorter plant height, reduced branching and increased pods per node on the main stem, relative to wild type control plants.

Two transgenic Zm.ZCN8 events and four Nt.FT-like events from above were also tested in field trials at two different locations. Phenotypic data were collected for plants expressing Zm.ZCN8 and Nt.FT-like transgenes under the control of the pAt.Erecta promoter (Tables 9 and 10). For field measurements, the traits are similar to the ones listed above for the greenhouse data tables, except DOR8 and PDR1R8 are days to R8 and reproductive duration between R1 and R8. In addition, all other traits are measured at harvest (i.e., at R8 stage), instead of at R7 stage. Events 1 and 2 in Table 9 correspond to Events 2 and 3 in Table 7, and Events 1-4 in Table 10 correspond to Events 1-4 in Table 8, respectively. Except for days to flowering at R1 (DOFR1) and reproductive duration in days from R1 to R8 (PDR1R8), all phenotypic measurements were derived based on data collected from two locations. Similar to the observations in the greenhouse, transgenic soybean plants expressing Zm.ZCN8 and Nt.FT-like proteins also flowered earlier than wild-type control plants in the field. The Zm.ZCN8 transgenic plants had an increased number of pods per node, while the Nt.FT-like plants did not clearly show increased pods per node in the field trial.

TABLE 9

Phenotypic data from a field trial for Zm.ZCN8 and WT plants.

|  | WT | Average | Event 1 | Event 2 |
|---|---|---|---|---|
| DOFR1* | 42.4 | 27.9 | 28.0 | 27.7 |
| DOR8 | 110.7 | 95.0 | 92.0 | 98.0 |
| PDR1R8* | 65.7 | 67.1 | 63.5 | 70.7 |
| BRPPR8 | 2.6 | 0.1 | 0.2 | 0.0 |
| NDBRR8 | 9.7 | 0.3 | 0.5 | 0.1 |
| NDMSR8 | 18.3 | 13.6 | 12.5 | 14.7 |
| NDPLR8 | 28.0 | 13.9 | 13.0 | 14.8 |
| PDPPR8 | 44.2 | 35.1 | 30.1 | 40.0 |
| TPBRR8 | 9.5 | 0.3 | 0.5 | 0.1 |
| PODMSR8 | 34.7 | 34.7 | 29.5 | 39.9 |
| Pods/Node | 1.6 | 2.5 | 2.3 | 2.6 |

TABLE 9-continued

Phenotypic data from a field trial for Zm.ZCN8 and WT plants.

|  | WT | Average | Event 1 | Event 2 |
|---|---|---|---|---|
| SDPPR8 | 99.9 | 67.6 | 54.7 | 80.5 |
| SW1000 (ounces) | 5.1 | 4.1 | 3.8 | 4.3 |

(*single location data)

TABLE 10

Phenotypic data from a field trial for Nt.FT-like and WT plants.

|  | WT | Average | Event 1 | Event 2 | Event 3 | Event 4 |
|---|---|---|---|---|---|---|
| DOFR1* | 42.4 | 38.0 | 42.5 | 26.8 | 26.8 | 25.8 |
| DOR8 | 110.7 | 93.3 | 111.3 | 88.2 | 86.6 | 87.1 |
| PDR1R8* | 65.7 | 63.1 | 66.8 | 62.2 | 60.3 | 63.0 |
| BRPPR8 | 2.6 | 0.7 | 2.4 | 0.1 | 0.2 | 0.1 |
| NDBRR8 | 9.7 | 2.7 | 9.2 | 0.5 | 0.8 | 0.3 |
| NDMSR8 | 18.3 | 11.5 | 18.3 | 9.9 | 7.6 | 10.1 |
| NDPLR8 | 28.0 | 14.2 | 27.5 | 10.4 | 8.5 | 10.4 |
| PDPPR8 | 44.2 | 23.5 | 43.0 | 18.9 | 11.6 | 20.3 |
| TPBRR8 | 9.5 | 2.6 | 8.4 | 0.5 | 0.8 | 0.5 |
| PODMSR8 | 34.7 | 20.9 | 34.6 | 18.5 | 10.8 | 19.8 |
| Pods/Node | 1.6 | 1.6 | 1.6 | 1.8 | 1.4 | 1.7 |
| SDPPR8 | 99.9 | 49.9 | 98.6 | 36.3 | 25.0 | 39.7 |
| SW1000 (ounces) | 5.1 | 4.5 | 5.1 | 4.4 | 4.6 | 4.0 |

(*single location data)

Additional phenotypic data was collected for plants expressing the Gm.FT2b transgene under the control of the pAt.Erecta promoter (Table 11).

TABLE 11

Construct and event level phenotypic data for Gm.FT2b and WT plants.

|  | WT | Average | Event 1 | Event 2 | Event 3 | Event 4 | Event 5 | Event 6 |
|---|---|---|---|---|---|---|---|---|
| DOFR1 | 43.7 | 34.6 | 41.2 | 34.3 | 22.7 | 33.2 | 37.2 | 39.3 |
| DOR7 | 105.9 | 100.4 | 100.5 | 100.3 | 99.8 | 100.3 | 98.7 | 102.8 |
| PDR1R7 | 62.2 | 65.8 | 59.3 | 66 | 77.2 | 67.2 | 61.5 | 63.5 |
| BRPP | 13.4 | 4.7 | 7 | 5 | 1.7 | 3.3 | 3.7 | 7.7 |
| FNBR | 103.8 | 32.4 | 52 | 29.7 | 12 | 30.7 | 21.7 | 48.7 |
| FNLP | 125.0 | 46.6 | 68.7 | 41.3 | 24.3 | 45 | 37.3 | 63 |
| FNST | 21.2 | 14.2 | 16.7 | 11.7 | 12.3 | 14.3 | 15.7 | 14.3 |
| NDBR | 108.4 | 34.2 | 54 | 30.3 | 12.7 | 33.7 | 24.7 | 50 |
| NDMS | 30.2 | 18.0 | 18.3 | 15.3 | 15 | 19 | 19.3 | 21 |
| NDPL | 138.7 | 52.2 | 72.3 | 45.7 | 27.7 | 52.7 | 44 | 71 |
| PDPP | 387.4 | 143.0 | 167 | 140 | 96 | 145.7 | 108.7 | 200.7 |
| PFNB | 95.5 | 94.6 | 96.4 | 97.7 | 96.8 | 91.0 | 87.7 | 97.7 |
| PFNN | 90.1 | 89.1 | 94.9 | 90.3 | 88.0 | 86.0 | 86.1 | 89.4 |
| PFNS | 69.7 | 79.2 | 91.5 | 74.5 | 82.5 | 77.0 | 81.1 | 68.7 |
| PODBR | 284.9 | 90.2 | 109.3 | 96 | 43 | 94.7 | 55.3 | 143 |
| PODMS | 102.5 | 52.7 | 57.7 | 44 | 53 | 51 | 53.3 | 57.7 |
| Pods/Node | 2.8 | 2.7 | 2.3 | 3.1 | 3.5 | 2.8 | 2.5 | 2.8 |
| SDPPR8 | 1159.3 | 322.3 | 411.3 | 292.3 | 195.3 | 346.7 | 245 | 443.3 |
| SW1000 (grams) | 174.0 | 154.0 | 170.4 | 156.7 | 154.1 | 155 | 130.2 | 157.8 |

Transgenic soybean plants expressing the Gm.FT2b transgene flowered earlier and had less branching than wild type control plants. Gm.FT2b expressing soybean plants had a reduced number of days to flowering (DOFR1), reduced number of branches (BRPP), fewer nodes per plant (NDPL), fewer nodes on branches (NDBR), reduced number of pods per plant (PDPP), and fewer pods on branches (PODBR) (Table 9). However, transgenic Gm.FT2b plants did not show an increase in the number of pods per node. Overall, plants expressing the Gm.FT2b transgene had shorter plant height and less branching relative to wild type control plants. Transgenic soybean plants expressing four different events of the Gm.FT2b transgene were also tested in field trial experiments. Phenotypic data was collected for plants expressing the Gm.FT2b transgene under the control of the pAt.Erecta promoter (Table 12). Events 1-4 in Table 11 correspond to Events 3, 2, 1, and 4 in Table 12, respectively. Similar to the observations in the greenhouse, Gm.FT2b expressing soybean plants showed a reduced number of days to flowering (DOFR1) in the field. The other phenotypic measurements also exhibited similar traits as observed in the greenhouse relative to wild-type control plants.

Overall, soybean plants expressing the Le.SFT transgene had shorter plant height with less branching and an increased number of pods per node on average relative to wild type plants (Table 13). However, these effects were variable and event-specific. For example, Events 1, 3 and 4 displayed early flowering (DOFR1), while other events were neutral or actually had delayed flowering. In addition, some of the Le.SFT transgenic events showed increased pods per node on average to varying extents, while a couple of the events were neutral in terms of the average number of pods per node. Interestingly, two of the events (Events 5 and 6) had the greatest number of pods per node on average despite having a delay in flowering.

TABLE 12

Phenotypic data from a field trial for Gm.FT2b and WT plants.

|  | WT | Average | Event 1 | Event 2 | Event 3 | Event 4 |
|---|---|---|---|---|---|---|
| DOFR1 | 41.9 | 37.3 | 38.3 | 38.3 | 36.3 | 36.2 |
| DOR8 | 115.4 | 109.2 | 111.1 | 110.6 | 110.6 | 104.6 |
| PDR1R8 | 73.5 | 71.8 | 75.0 | 72.1 | 74.1 | 66.1 |
| SDPPR8 | 188.5 | 95.5 | 99.4 | 81.1 | 117.7 | 83.6 |
| SW1000 (grams) | 153.4 | 137.3 | 144.0 | 129.6 | 134.4 | 141.5 |

Additional phenotypic data was collected from plants expressing the Le.SFT transgene under the control of the pAt.Erecta promoter (Table 13).

Additional phenotypic data was collected from plants expressing the Gm.FT5a transgene under the control of the pAt.Erecta promoter (Table 14).

TABLE 13

Construct and event level phenotypic data for Le.SFT and WT plants.

|  | WT | Average | Event 1 | Event 2 | Event 3 | Event 4 | Event 5 | Event 6 |
|---|---|---|---|---|---|---|---|---|
| DOFR1 | 42.9 | 41.4 | 30 | 44.4 | 30.7 | 28 | 60.2 | 55 |
| DOR7 | 108.6 | 103.8 | 90.7 | 106.2 | 99 | 91.5 | 116.5 | 119 |
| PDR1R7 | 65.5 | 64.0 | 60.2 | 71 | 67 | 65 | 56.4 | 64.2 |
| BRPP | n/a | n/a | n/a | n/a | n/a | n/a | n/a | n/a |
| FNBR | 131.5 | 37.1 | 2.7 | 125.2 | 4.7 | 1 | 47.7 | 41.3 |
| FNLP | 156.8 | 50.7 | 15.7 | 142.6 | 18.1 | 18.3 | 56.7 | 52.7 |
| FNST | 25.3 | 13.7 | 13 | 17.7 | 13.7 | 17.3 | 9 | 11.3 |
| NDBR | 140.2 | 38.9 | 3 | 129.4 | 5.4 | 1 | 51 | 43.7 |
| NDMS | 32.4 | 17.9 | 16 | 25.8 | 16.3 | 21 | 12.3 | 16.3 |
| NDPL | 172.4 | 56.7 | 19 | 154.7 | 21.2 | 22 | 63.3 | 60 |
| PDPP | 473.3 | 201.3 | 53.7 | 432.3 | 69.8 | 85.7 | 279.3 | 287 |
| PFNB | 94.1 | 94.0 | 100 | 96.9 | 83.3 | 100 | 92.9 | 90.7 |
| PFNN | 90.4 | 86.4 | 82.5 | 92.3 | 83.7 | 83.5 | 88.8 | 87.6 |
| PFNS | 77.1 | 76.5 | 81.2 | 69.5 | 84.0 | 82.8 | 72.7 | 68.6 |
| PODBR | 366.2 | 141.8 | 3.7 | 361.5 | 15.5 | 1.3 | 238.5 | 230.7 |
| PODMS | 114 | 60.3 | 50 | 73.6 | 57.1 | 84.3 | 40.7 | 56.3 |
| Pods/Node | 2.7 | 3.6 | 2.8 | 2.8 | 3.3 | 3.9 | 4.4 | 4.8 |
| SDPPR8 | 1247.4 | 476.0 | 136.7 | 1036 | 148.5 | 183 | 655 | 697 |
| SW1000 (grams) | 167.7 | 153.2 | 170.0 | 182.8 | 157.5 | 148.5 | 131.5 | 128.8 |

TABLE 14

Construct and event level phenotypic data for Gm.FT5a and WT plants.

|  | WT | Average | Event 1 | Event 2 | Event 3 | Event 4 | Event 5 |
|---|---|---|---|---|---|---|---|
| DOFR1 | 48.2 | 29.9 | 32.2 | 29 | 28.6 | 29.2 | 30.5 |
| DOR7 | 110 | 92.5 | 96.6 | 90.4 | 91 | 92.8 | 91.8 |
| PDR1R7 | 61.8 | 62.7 | 64.4 | 61.4 | 62.4 | 63.6 | 61.3 |
| BRPP | 12.4 | 2.5 | 7 | 1.7 | 1 | 1.3 | 1.7 |
| FNBR | 105.6 | 7.3 | 20.3 | 4.7 | 3 | 4 | 4.3 |
| FNLP | 126.5 | 24.5 | 41.7 | 20 | 18.7 | 19.3 | 22.7 |
| FNST | 20.9 | 17.2 | 21.3 | 15.3 | 15.7 | 15.3 | 18.3 |
| NDBR | 108.6 | 7.5 | 21 | 5 | 3 | 4 | 4.3 |
| NDMS | 29 | 17.7 | 22 | 15.7 | 16.3 | 16 | 18.7 |
| NDPL | 137.6 | 25.2 | 43 | 20.7 | 19.3 | 20 | 23 |
| PDPP | 304.3 | 131.9 | 214.7 | 111 | 100.3 | 104.3 | 129.3 |
| PFNB | 97.2 | 98.0 | 97.3 | 93.3 | 100 | 100 | 100 |
| PFNN | 98.1 | 97.0 | 95.9 | 90 | 99.1 | 100 | 100 |
| PFNS | 72.1 | 97.0 | 97.1 | 98.1 | 96.1 | 95.8 | 97.9 |
| PODBR | 233.4 | 16.5 | 60.5 | 8 | 4 | 6 | 4 |
| PODMS | 75.1 | 108.6 | 159 | 98.5 | 95 | 92.5 | 98 |
| Pods/Node | 2.2 | 5.2 | 5.0 | 5.4 | 5.2 | 5.2 | 5.6 |
| SDPPR8 | 778.8 | 271.7 | 516 | 232.7 | 175.3 | 182.3 | 252 |
| SW1000 (grams) | 151.6 | 126.0 | 143.7 | 122.4 | 122.2 | 121.8 | 116.8 |

Transgenic soybean plants expressing the Gm.FT5a transgene flowered significantly earlier than wild type control plants and had an increased number of pods per node (similar to plants expressing the Gm.FT2a transgene). Indeed, soybean plants expressing the Gm.FT5a transgene had several phenotypes (similar to the Gm.FT2a transgenic plants), including reduced number of days to flowering (DOFR1), reduced number of branches (BRPP), fewer nodes per plant (NDPL), fewer nodes on branches (NDBR), reduced number of pods per plant (PDPP), and fewer pods on branches (PODBR), along with an increase in the number of pods per node and a decrease in the number of seeds per plant (Table 14). Overall, plants expressing the Gm.FT5a transgene had shorter plant height and less branching, but more pods per node (particularly on the main stem) relative to wild type control plants.

Without being bound by any theory, these data support a model of FT overexpression acting in a dosage-dependent manner with the degree or extent of associated phenotypes (e.g., early flowering, increase in pods per node, and altered plant architecture) depending on (i) the level and timing of FT expression, (ii) tissue specificity of FT expression, and (iii) the relative activity and target specificity of the particular FT protein being expressed. For example, expression of the FT protein orthologs from other plant species in soybean may produce a more attenuated effect relative to overexpression of an endogenous FT protein (Gm.FT2a) in soybean, which may result from the non-native FT protein homologs having a lower activity in soybean. However, expression of some native FT proteins may not produce significant phenotypic effects if they have a different or specialized role in their native state or context. Different FT proteins may also act on different tissue targets and receptors and thus have differential effects on the various plant architecture and flowering traits and phenotypes.

Regardless of the activity level of the particular FT homolog, altered reproductive and plant architecture phenotypes appear to correlate with the timing and location of FT expression. Vegetative-stage expression of FT transgenes may be necessary to induce early flowering and/or cause increased numbers of floral meristems, flowers, pods, etc., per node of the plant. Indeed, FT expression in meristematic tissues during vegetative stages of development is shown with proper dosing of the FT transgene to cause reproductive changes in plants leading to increased numbers of flowers, pods, and/or seeds per node. In contrast, expression of a Gm.FT2a transgene under the control of leaf-preferred promoters produced very little, if any, phenotypic changes, relative to wild type plants. These data indicate that both the timing, and tissue specificity (or tissue preference), of FT expression are important factors that affect reproductive and/or yield-related phenotypic changes in transgenic plants.

The present data suggest that different FT proteins may have different activity levels and/or target specificities despite being expressed using the same pErecta promoter. While several constructs expressing Gm.FT2a, Zm.ZCN8, Nt.FT-like, and Gm.FT5a each caused early flowering and termination in addition to an increased number of pods per node, other constructs expressing Gm.FT2b and Le.SFT had different correlative effects on flowering. Expression of Gm.FT2b did cause early flowering and termination of plants but without a significant increase in the number of pods per node. On the other hand, Le.SFT expression showed increased pods per node and early termination despite a delay in flowering. Interestingly, increased numbers of pods per node in transgenic FT plants did not correlate with an extended reproductive duration (PDR1R7) and was not always aligned with early flowering (DOFR1) as noted above. These data suggest that reproductive changes in response to vegetative-stage expression of FT proteins in the meristem may operate through one or more independent mechanisms or pathways. Increased numbers of pods per node in transgenic FT plants may depend on the number of inflorescent and floral meristems induced from vegetative meristems at each node, which may occur independently of flowering time and/or reproductive duration. As noted above, however, reproductive duration may not necessarily correlate with the duration of flowering.

Example 7. Identification of Additional Vegetative-Stage Meristem Promoters

Having observed phenotypic effects with expression of Gm.FT2a under the control of a vegetative-stage, meristem-preferred promoter, pAt.Erecta, it is contemplated that other vegetative-stage, meristem-preferred (or meristem-specific)

promoters may be used to drive expression of FT proteins to cause reproductive or yield-related traits or phenotypes in plants, such as increased number of pods per node (and/or per plant or main stem). Using the characterized expression pattern of the pAt.Erecta promoter (see Example 2), other vegetative-stage, meristem-preferred (or meristem-specific) promoters were identified from soybean, potato and *Arabidopsis*. Two bioinformatic approaches were utilized to identify candidate genes from other dicotyledonous species including, for example, *Arabidopsis*, soybean, *Medicago*, potato and tomato, having similar expression profiles to pAt.Erecta: BAR Espressolog and Expression Angler. See, e.g., BAR expressolog identification: expression profile similarity ranking of homologous genes in plant species," *Plant J* 71(6): 1038-50 (2012); and Toufighi, K et al., "The Botany Array Resource: e-Northerns, Expression Angling, and promoter analyses," *Plant J* 43(1): 153-163 (2005). The promoter sequences from these genes are thus proposed for use in expressing FT transgenes according to embodiments of the present invention.

Examples of gene promoters identified by this analysis include the following: four receptor like kinase (RLK) genes from soybean, including Glyma10g38730 (SEQ ID NO: 33), Glyma09g27950 (SEQ ID NO: 34), Glyma06g05900 (SEQ ID NO: 35), and Glyma17g34380 (SEQ ID NO: 36). Additional examples include receptor like kinase (RLK) gene promoters from potato, PGSC0003DMP400032802 (SEQ ID NO: 37) and PGSC0003DMP400054040 (SEQ ID NO: 38). It is possible that these RLK genes may be related structurally and/or functionally to Erecta and Erecta-like genes from *Arabidopsis* and other species since they are also RLK genes. Other vegetative stage, meristem-preferred promoters from *Arabidopsis* genes include the following: At.MYB17 (At.LMI2; At3g61250) (SEQ ID NO: 41), Kinesin-like gene (At5g55520) (SEQ ID NO: 42), AP2/B3-like genes including At.REM17 (SEQ ID NO: 43) or At.REM19, and Erecta-like 1 and 2 genes, At.Erl1 (SEQ ID NO: 44) and At.Erl2 (SEQ ID NO: 45). Each of these promoters and similar functional sequences may be operably linked to a FT gene to cause ectopic expression of FT genes in one or more meristem(s) of plants at least during vegetative stage(s) of development.

With regard to the At.MYB17 (At.LMI2) gene, see Pastore, J L et al., "LATE MERISTEM IDENTITY 2 acts together with LEAFY to activate APETALA1," *Development* 138: 3189-3198 (2011), the entire contents and disclosure of which are incorporated herein by reference. With regard to the Kinesin-like gene, see Fleury, D et al., "The *Arabidopsis thaliana* Homolog of Yeast BRE1 Has a Function in Cell Cycle Regulation during Early Leaf and Root Growth," *Plant Cell,* 19(2): 417-432 (2007), the entire contents and disclosure of which are incorporated herein by reference. With regard to the REM17 and REM19 *Arabidopsis* genes, see Mantegazza, O et al., "Analysis of the *Arabidopsis* REM gene family predicts functions during flower development," *Ann Bot* 114(7): 1507-1515 (2014), the entire contents and disclosure of which are incorporated herein by reference. Further, with regard to the At.Erl2 gene, see "Special Issue: Receptor-like Kinases," *JIPB* 55(12): 1181-1286 (2013), and particularly Shpak, E., "Diverse Roles of ERECTA Family Genes in Plant Development," *JIPB* 55(12): 1251-1263 (2013), the entire contents and disclosures of which are incorporated herein by reference.

Example 8. Expression of Flowering Locus T Gene, Gm.FT2a, Under Control of a pAt.Erl1 Promoter Alters Flowering Time and Pods Per Node in Soybean A transformation vector containing Gm.FT2a under control of the vegetative stage, meristem-preferred pAt.Erl1 promoter (SEQ ID NO: 44) was constructed and used to transform soybeans via *Agrobacterium*-mediated transformation. Transgenic plants generated from these events were characterized for their phenotypes in the greenhouse with a 14 to 14.5 hour natural daylight photoperiod. For each pAt.Erl1::Gm.FT2a construct, six events were tested (6 plants per event) in the greenhouse. Six plants were also tested and averaged for wild type (WT) control plants. Four events were also tested in the field with 12 replicate field plots per event, and compared to WT controls in the same field. The following matrices were collected for phenotypic characterization of these plants and expressed as an average for each Event (as well as the wild type plants) grown in the greenhouse (see Table 15) and in the field (Table 16). A column providing an average for all the Events per trait is further provided.

TABLE 15

Phenotypic data for pAt.Erl1:Gm.FT2a and WT plants grown in the greenhouse.

|  | WT | Average | Event 1 | Event 2 | Event 3 | Event 4 | Event 5 | Event 6 |
| --- | --- | --- | --- | --- | --- | --- | --- | --- |
| DOFR1 | 46.1 | 32.6 | 40.0 | 32.3 | 34.0 | 29.3 | 28.2 | 31.8 |
| DOR7 | 115.1 | 99.0 | 109.7 | 99.0 | 99.0 | 93.0 | 91.7 | 101.7 |
| PDR1R7 | 69.0 | 66.4 | 69.7 | 66.7 | 65.0 | 63.7 | 63.5 | 69.8 |
| BRPP | 23.5 | 7.4 | 16.0 | 6.0 | 9.7 | 1.3 | 4.3 | 7.3 |
| NDBR | 277.6 | 80.8 | 215.7 | 51.7 | 139.3 | 3.3 | 18.0 | 56.7 |
| NDMS | 29.8 | 32.3 | 30.7 | 33.7 | 32.7 | 30.7 | 32.7 | 33.3 |
| NDPL | 307.4 | 113.0 | 246.3 | 85.3 | 172.0 | 34.0 | 50.7 | 90.0 |
| PDPP | 605.8 | 346.4 | 447.3 | 349.7 | 493.7 | 240.7 | 194.7 | 352.3 |
| PODBR | 503.1 | 173.7 | 332.3 | 164.7 | 323.3 | 8.3 | 42.7 | 171.0 |
| PODMS | 103.0 | 172.7 | 115.0 | 185.0 | 170.3 | 232.3 | 152.0 | 181.3 |
| Pods/Node | 1.9 | 4.0 | 2.1 | 4.1 | 2.9 | 7.1 | 3.8 | 4.0 |
| SDPPR8 | 1290.0 | 747.5 | 1129.0 | 603.5 | 881.0 | 577.0 | 432.3 | 862.3 |
| SW1000 (grams) | 157.6 | 157.3 | 187.7 | 142.6 | 173.8 | 144.3 | 144.9 | 150.3 |

TABLE 16

Phenotypic data for pAt.Erl1:Gm.FT2a and WT plants grown in the field.

|  | WT | Average | Event 1 | Event 2 | Event 4 | Event 6 |
|---|---|---|---|---|---|---|
| DOFR1 | 37.0 | 27.4 | 32.3 | 26.7 | 25.3 | 25.5 |
| DOR8 | 114.9 | 110.6 | 113.8 | 110.4 | 107.9 | 110.5 |
| PDR1R8 | 77.9 | 83.2 | 81.4 | 83.8 | 82.7 | 85.0 |
| BRPPR8 | 2.1 | 0.8 | 1.5 | 1.2 | 0.3 | 0.3 |
| NDBRR8 | 8.0 | 3.2 | 5.6 | 5.2 | 1.0 | 0.9 |
| NDMSR8 | 19.8 | 19.8 | 19.5 | 19.1 | 19.5 | 21.1 |
| NDPLR8 | 27.8 | 23.0 | 25.1 | 24.4 | 20.5 | 22.0 |
| PDPPR8 | 56.1 | 57.8 | 57.4 | 60.6 | 53.1 | 60.2 |
| PDMSR8 | 47.9 | 53.8 | 50.9 | 53.0 | 52.2 | 59.2 |
| TPBR8 | 8.3 | 4.0 | 6.6 | 7.4 | 0.9 | 1.0 |
| Pods/Node | 2.0 | 2.5 | 2.3 | 2.6 | 2.6 | 2.7 |
| SDARR8 | 344.3 | 349.9 | 374.1 | 338.4 | 317.8 | 369.2 |
| SW1000 (ounces) | 5.4 | 5.4 | 5.4 | 5.3 | 5.3 | 5.5 |

Transgenic soybean plants expressing a pAt.Erl1::Gm.FT2a construct flowered earlier than wild type control plants and had an increased number of pods per node (similar to plants expressing the Gm.FT2a transgene under control of the pAt.Erecta promoter). Indeed, soybean plants expressing pAt.Erl1::Gm.FT2a had several phenotypes similar to the pAt.Erecta::Gm.FT2a transgenic plants, including reduced number of days to flowering (DOFR1), reduced number of days to R7 (DOR7), reduced number of branches per plant (BRPP), fewer nodes per plant (NDPL), a reduced number of pods per plant (PDPP), along with an increase in the number of pods per node (Table 15), relative to wild type control plants. However, several phenotypes observed in pAt.Erecta::Gm.FT2a plants, such as number of pods on main stem (PODMS), number of pods on branches (PODBR), and weight of 1000 seeds (SW1000), were less pronounced in the pAt.Erl11::Gm.FT2a expressing transgenic plants. Early results in a second year of field testing also show early flowering indicating similar reproductive traits. As may be inferred, these trait measurements may be abbreviated differently, such as PDPP or PODPP for pods per plant, PDMS or PODMS for pods on the main stem, PDBR or PODBR for pods on braches, TPBR for total pods on branches, etc.

The expression pattern for the *Arabidopsis erecta*-like 1 promoter (pAt.Erl1) in soybean as measured by GUS staining is more restricted than the expression pattern of pAt.Erecta in soybean as described above. pAt.Erl1 drives GUS expression in vegetative axillary meristems and in early floral meristems derived from axillary tissue. However, GUS staining is not observed in the shoot apical meristem at any stage where it can be distinguished from other meristematic tissues of the developing plant. Expression of the GUS reporter under the control of the pAt.Erl1 promoter is not observed in leaf tissue, stem or root at any stage (data not shown). Given that FT expression under the control of either the pAt.Erecta or pAt.Erl1 promoter induced early flowering and increased pods per node, vegetative expression of an FT transgene at or near the meristem(s) of a plant may generally be sufficient to induce these reproductive and yield-related phenotypes or traits.

Example 9. Expression of an miRNA Targeting Gm.FT2a for Suppression

It is hypothesized that reducing the expression level of a Gm.FT2a transgene under the control of a vegetative stage promoter in reproductive or floral tissues via RNA suppression may extend reproductive duration in soybean plants. To test whether suppression of an endogenous Gm.FT2a impacts reproductive or morphological phenotypes of soybean plants, a transformation vector comprising a transcribable DNA sequence encoding a miRNA molecule (miRNA-FT2a; SEQ ID NO: 67) that targets an endogenous Gm.FT2a expression under control of a late vegetative and/or reproductive stage promoter, either pAt.AP1 promoter (SEQ ID NO: 49) or pSl.MADS-RIN promoter (SEQ ID NO: 72), was constructed and used to transform soybean plants via *Agrobacterium*-mediated transformation. Transgenic plants generated from these events were characterized in the greenhouse under 14 to 14.5 hour daylight photoperiod conditions. Six plants per event were tested and compared on average to wild type (WT) control plants. Average phenotypic data collected from the pAP1::miRNA-FT and wild-type plants in the greenhouse is provided in Table 17. Table 18 provides phenotypic observations collected from transgenic pMADS-RIN::miRNA-FT and wild-type plants in the greenhouse and expressed as an average for each Event and as an average across Events and wild-type plants.

TABLE 17

Phenotypic data for pAP1::miRNA-FT2a and WT plants grown in the greenhouse.

|  | WT | pAP1::miRNA-FT |
|---|---|---|
| DOFR1 | 40 | 37 |
| DOR7 | 89 | 89 |
| PDR1R7 | 49 | 52 |

Under greenhouse conditions, the timing and onset of flowering in plants expressing the pAP1::miRNA-FT2a construct was about the same as WT control plants. Transgenic plants expressing the pAP1::miRNA-FT2a or the pMADS-RIN::miRNA-FT2a construct were also grown under field conditions. Six plants comprising four different events of the pAP1::miRNA-FT2a construct were tested and compared on average to wild type (WT) control plants. For field experiments, measurements were made at harvest (R8 stage), except as otherwise indicated. SDARR8 is seeds per area (i.e., per square foot) at R8 stage. Average phenotypic data collected from field grown plants is provided in Table 18 for the pAP1::miRNA-FT2a construct and Table 20 for the pMADS-RIN::miRNA-FT2a construct.

TABLE 18

Phenotypic data for field-grown pAP1::miRNA-FT2a and WT plants.

|  | WT | Average | Event 1 | Event 2 | Event 3 | Event 4 |
|---|---|---|---|---|---|---|
| DOFR1 | 42.4 | 44.7 | 46.7 | 41.0 | 43.7 | 47.2 |
| DOR8 | 110.7 | 114.5 | 115.0 | 111.6 | 114.4 | 116.8 |
| PDR1R8 | 65.7 | 67.0 | 64.5 | 67.7 | 68.8 | 66.8 |
| BRPPR8 | 2.6 | 2.7 | 2.7 | 2.7 | 2.7 | 2.7 |
| NDBRR8 | 9.7 | 11.0 | 10.9 | 10.7 | 10.5 | 11.9 |
| NDMSR8 | 18.3 | 19.3 | 19.5 | 18.4 | 19.3 | 19.9 |
| NDPLR8 | 28.0 | 30.3 | 30.4 | 29.2 | 29.7 | 31.8 |
| PDPPR8 | 44.2 | 39.7 | 37.2 | 43.2 | 40.5 | 37.8 |
| PODMSR8 | 34.7 | 31.7 | 30.4 | 33.5 | 32.5 | 30.5 |
| TPBR8 | 9.5 | 8.0 | 6.8 | 9.8 | 8.0 | 7.3 |
| Pods/node | 1.6 | 1.4 | 1.3 | 1.5 | 1.4 | 1.2 |
| SDARR8 | 282.7 | 251.6 | 247.1 | 259.0 | 264.8 | 235.5 |
| SW1000 (ounces) | 5.1 | 5.2 | 5.2 | 5.1 | 5.2 | 5.2 |

Under field conditions, soybean plants transformed with the pAP1::miRNA-FT2a construct again had about the same flowering and reproductive traits on average as WT control plants, although transgenic pAP1::miRNA-FT2a plants may have had slightly fewer pods (PDPPR8, PDMSR8, TPBR8, Pods/node) compared to WT control plants at the R8 stage.

Example 10. Modification of Gm.FT2a Expression by an Artificial miRNA Driven by a pAP1 Promoter Alters Reproductive Phenotypes Under Greenhouse Conditions To show that suppression of Gm.FT2a in late vegetative and/or reproductive tissues following initial ectopic expression of transgenic Gm.FT2a may extend reproductive duration in soybean plants and/or counteract early termination, a transformation vector comprising Gm.FT2a under control of the vegetative stage, meristem-preferred pAt.Erecta promoter (SEQ ID NO: 31) with either an Apx or Lhcb2 terminator region (T-Apx and T-Lhcb2), and a transcribable DNA sequence encoding an artificial miRNA (SEQ ID NO: 67) targeting Gm.FT2a for suppression and under the control of a pAt.AP1 promoter (SEQ ID NO: 49) with a GAPDH terminator region (each construct designated pAt.Erecta:: Gm.FT2a|pAP1::miRNA-FT2a) was constructed and used to transform soybean via *Agrobacterium*-mediated transformation. Transgenic plants generated from these events were characterized in the greenhouse with a 14 to 14.5 hour daylight photoperiod. For each pAt.Erecta:: Gm.FT2a|pAP1::miRNA-FT2a construct, six events were tested (6 plants per event) and the data was averaged. The average data for each construct was also averaged across all events. Six wild type (WT) control plants were also tested and averaged as a control. Tables 19 and 20 provide the phenotypic data collected for the six events as well as the average for WT and pAt.Erecta::Gm.FT2a|pAP1::miRNA-FT2a plants with the two different terminator regions (T-Apx and T-Lhcb2).

TABLE 19

Phenotypic data for pAt.Erecta::Gm.FT2a::T-Apx | pAP1::miRNA-FT2a::T-GAPDH and WT plants under greenhouse conditions.

|  | WT | Average | Event 1 | Event 2 | Event 3 | Event 4 | Event 5 | Event 6 |
|---|---|---|---|---|---|---|---|---|
| DOFR1 | 33.5 | 28.5 | — | 30.0 | 28.0 | 28.0 | 28.0 | 28.3 |
| DOR7 | 106.9 | 99.7 | 106.8 | 98.8 | 98.3 | 91.3 | 102.7 | 100.3 |
| PDR1R7 | 76.5 | 70.1 | — | 68.8 | 70.3 | 65.0 | 74.2 | 72.0 |
| BRPP | 20.1 | 13.0 | 20.3 | 16.7 | 13.0 | 6.7 | 9.7 | 12.0 |
| FNBR | 190.6 | 160.2 | 231.5 | 192.7 | 155.3 | 89.7 | 147.0 | 145.0 |
| FNPL | 214.6 | 191.5 | 263.8 | 226.7 | 184.3 | 122.0 | 176.0 | 176.3 |
| FNST | 24.0 | 31.3 | 32.3 | 34.0 | 29.0 | 32.3 | 29.0 | 31.3 |
| NDBR | 211.4 | 177.1 | 268.8 | 210.0 | 170.0 | 90.0 | 168.3 | 155.3 |
| NDMS | 33.4 | 36.3 | 38.0 | 37.3 | 36.3 | 34.0 | 35.7 | 36.7 |
| NDPL | 244.9 | 213.4 | 306.8 | 247.3 | 206.3 | 124.0 | 204.0 | 192.0 |
| PDPP | 575.8 | 647.5 | 642.8 | 732.0 | 645.8 | 569.7 | 653.7 | 641.0 |
| PFNB | 90.4 | 92.7 | 87.4 | 92.1 | 91.6 | 99.7 | 91.3 | 93.9 |
| PFNN | 87.8 | 91.3 | 86.9 | 92.0 | 89.7 | 98.4 | 89.0 | 91.9 |
| PFNS | 71.4 | 86.0 | 84.9 | 91.7 | 80.4 | 95.3 | 78.8 | 84.7 |
| PODBR | 487.1 | 486.2 | 519.8 | 567.3 | 497.3 | 368.3 | 493.3 | 471.3 |
| PODMS | 88.4 | 161.3 | 123.0 | 164.7 | 148.5 | 201.3 | 160.3 | 169.7 |
| Pods/Node | 2.4 | 3.3 | 2.2 | 3.0 | 3.2 | 4.7 | 3.6 | 3.4 |
| SDPP8 | 1319.6 | 1197.2 | 1508.0 | 1163.0 | 1184.8 | 750.8 | 1170.0 | 1406.8 |
| SW1000 (grams) | 146.0 | 158.8 | 149.2 | 169.9 | 144.3 | 172.6 | 163.5 | 153.2 |

TABLE 20

Phenotypic data for pAt.Erecta::Gm.FT2a::T-Lhcb2|pAP1::miRNA-FT2a::T-GAPDH and WT plants under greenhouse conditions.

|  | WT | Average | Event 1 | Event 2 | Event 3 | Event 4 | Event 5 | Event 6 |
|---|---|---|---|---|---|---|---|---|
| DOFR1 | 33.5 | 28.2 | 28 | — | 28 | 28 | 29.2 | 28 |
| DOR7 | 106.9 | 99.5 | 98.3 | 95.8 | 101 | 99.8 | 99.5 | 102.7 |
| PDR1R7 | 76.5 | 71.7 | 68.6 | — | 73 | 71.8 | 70.3 | 74.7 |
| BRPP | 20.1 | 9 | 5.8 | 8.5 | 8.5 | 6.3 | 15 | 10.3 |
| FNBR | 190.6 | 97.8 | 79.8 | 45.5 | 92 | 84.8 | 149.8 | 135.3 |
| FNPL | 214.6 | 130.5 | 112.3 | 80 | 126.5 | 117 | 184.3 | 162.8 |
| FNST | 24 | 32.6 | 32.5 | 34.5 | 34.5 | 32.3 | 34.5 | 27.5 |
| NDBR | 211.4 | 106.2 | 84.5 | 45.5 | 97.5 | 91 | 164 | 154.8 |
| NDMS | 33.4 | 36.9 | 36.5 | 37 | 37.8 | 35 | 39.3 | 35.8 |
| NDPL | 244.9 | 143.1 | 121 | 82.5 | 135.3 | 126 | 203.3 | 190.5 |
| PDPP | 575.8 | 558.5 | 543.8 | 454 | 566.8 | 534.8 | 633.5 | 618 |
| PFNB | 90.4 | 93.7 | 94.6 | 100 | 94.7 | 94.5 | 91.4 | 86.8 |
| PFNN | 87.8 | 92.3 | 94.1 | 96.7 | 93.6 | 93.5 | 90.7 | 85 |
| PFNS | 71.4 | 88.5 | 88.2 | 94.1 | 91.3 | 92.1 | 87.7 | 77.4 |
| PODBR | 487.3 | 329.7 | 309.5 | 157 | 344 | 304.8 | 446 | 417 |
| PODMS | 88.4 | 228.8 | 234.3 | 297 | 222.8 | 230 | 187.5 | 201 |
| Pods/node | 2.4 | 4.3 | 4.9 | 5.9 | 4.2 | 4.7 | 3.1 | 3.2 |
| SDPP8 | 1319.6 | 778.9 | 728.5 | 644.3 | 832 | 964.8 | 699.5 | 804.5 |
| SW1000 (grams) | 146 | 155.5 | 158.1 | 182 | 158.7 | 128.4 | 169.8 | 135.8 |

Figure 12:
FIG. 12 shows whole plant images of plants transformed with either pAt.Erecta::Gm.FT2a or pAtErecta::Gm.FT2a/pAP1::miRNA-FT2a::T-Apx.

In this greenhouse experiment, transgenic soybean plants comprising either of the pAt.Erecta::Gm.FT2a|pAP1::miRNA-FT2a constructs had an earlier onset of flowering (DOFR1) and an increased number of pods per node (and per main stem) relative to WT control plants (Pods/node, PODMS). Transgenic plants with the combined pAt.Erecta::Gm.FT2a pAP1::miRNA-FT2a construct had increased plant height and branching as well as an increased number of nodes per plant (and per main stem) and increased pods per plant (and per main stem), relative to soybean plants with only the pAt.Erecta::Gm.FT2a transgene without the miRNA suppression cassette (see, e.g., Table 2). FIG. 12 provides whole images of plants homozygous for either pAt.Erecta::Gm.FT2a or pAt.Erecta::Gm.FT2a/pAP1::miRNA-FT2a showing that additional suppression of the Gm.FT2a transgene is effective at mitigating the early termination phenotypes observed with the pAt.Erecta::Gm.FT2a transgene alone, including short plant height and reduced branching.

This data indicates that suppression of Gm.FT2a in later vegetative and/or reproductive tissues following an earlier ectopic dosage of the Gm.FT2a transgene is effective at triggering early flowering and maintaining an increased number of pods per node, while mitigating the early termination phenotypes observed in plants having the Gm.FT2a transgene alone. Interestingly, the increased number of pods per node in these plants was observed without an apparent increase in reproductive duration.

Example 11. Modification of Gm.FT2a Expression by an Artificial miRNA Driven by a pAP1 Promoter Alters Reproductive Phenotypes Under Field Conditions Three or four transformation events (depending on the year) of the pAt.Erecta::Gm.FT2a::T-Apx pAP1::miRNA-FT2a::T-GAPDH construct described in Example 10 were grown and tested under field conditions for two consecutive years. For each of the events and WT control, phenotypic data was collected and averaged (events are numbered for consistency). Tables 21 and 22 provide the average phenotypic data collected from these plants, as well as an average across three events.

Four transformation events of the pAt.Erecta::Gm.FT2a::T-Lhbc2|pAP1::miRNA-FT::T-GAPDH construct described in Example 10 were grown and tested under field conditions for two consecutive years. For each event and the WT control, phenotypic data was collected and averaged from multiple plants. Tables 23 and 24 provide the average phenotypic data collected from these plants, as well as an average across the four events.

TABLE 21

Phenotypic data for pAt.Erecta::Gm.FT2a::T-Apx | pAP1::miRNA-FT::T-GAPDH and WT plants grown in the field (Year 1).

|  | WT | Average | Event 2 | Event 3 | Event 4 |
|---|---|---|---|---|---|
| DOFR1 | 42.4 | 32.5 | 35.7 | 31.2 | 30.7 |
| DOR8 | 110.7 | 112.5 | 115.1 | 113.3 | 109.2 |
| PDR1R8 | 65.7 | 78.2 | 76.6 | 80.2 | 77.7 |
| BRPPR8 | 2.6 | 0.9 | 1.1 | 1.0 | 0.5 |
| NDBRR8 | 9.7 | 2.6 | 3.7 | 2.9 | 1.1 |
| NDMSR8 | 18.3 | 19.7 | 20.1 | 19.8 | 19.2 |
| NDPLR8 | 28.0 | 22.3 | 23.8 | 22.8 | 20.2 |
| PDPPR8 | 44.2 | 45.8 | 43.6 | 45.6 | 48.1 |
| PDMSR8 | 34.7 | 43.7 | 40.8 | 43.4 | 47.0 |

TABLE 21-continued

Phenotypic data for pAt.Erecta::Gm.FT2a::T-Apx | pAP1::miRNA-FT::T-GAPDH and WT plants grown in the field (Year 1).

|  | WT | Average | Event 2 | Event 3 | Event 4 |
|---|---|---|---|---|---|
| TPBR8 | 9.5 | 2.0 | 2.8 | 2.2 | 1.1 |
| Pods/node | 1.6 | 2.1 | 1.8 | 2.0 | 2.4 |
| SDARR8 | 282.7 | 268.6 | 259.1 | 288.7 | 257.9 |
| SW1000 (ounces) | 5.1 | 4.8 | 4.9 | 4.7 | 4.7 |

TABLE 22

Phenotypic data for pAt.Erecta::Gm.FT2a::T-Apx|pAP1::miRNA-FT::T-GAPDH and WT plants grown in the field (Year 2).

|  | WT | Average | Event 2 | Event 3 | Event 4 | Event 6 |
|---|---|---|---|---|---|---|
| DOFR1 | 37.0 | 30.6 | 32.6 | 32.0 | 28.3 | 29.3 |
| DOR8 | 114.9 | 117.6 | 120.7 | 118.9 | 116.0 | 114.8 |
| PDR1R8 | 77.9 | 87.0 | 88.1 | 86.9 | 87.7 | 85.5 |
| BRPPR8 | 2.1 | 0.9 | 1.2 | 2.0 | 0.2 | 0.3 |
| NDBRR8 | 8.0 | 4.7 | 7.5 | 8.1 | 1.5 | 1.5 |
| NDMSR8 | 19.8 | 20.8 | 21.4 | 20.4 | 20.1 | 21.1 |
| NDPLR8 | 27.8 | 25.4 | 28.9 | 28.6 | 21.6 | 22.6 |
| PDPPR8 | 56.1 | 64.2 | 65.5 | 66.0 | 63.2 | 62.2 |
| PDMSR8 | 47.9 | 58.3 | 55.3 | 56.3 | 61.1 | 60.5 |
| TPBR8 | 8.3 | 5.9 | 10.2 | 9.7 | 2.0 | 1.6 |
| Pods/Node | 2.0 | 2.6 | 2.3 | 2.2 | 3.0 | 2.8 |
| SDARR8 | 344.3 | 365.1 | 359.5 | 380.9 | 340.6 | 379.5 |
| SW1000 (ounces) | 5.4 | 5.4 | 5.4 | 5.6 | 5.4 | 5.4 |

TABLE 23

Phenotypic data for pAt.Erecta::Gm.FT2a::T-Lhbc2|pAP1::miRNA-FT::T-GAPDH and WT plants grown in the field (Year 1).

|  | WT | Average | Event 1 | Event 2 | Event 3 | Event 4 |
|---|---|---|---|---|---|---|
| DOFR1 | 42.4 | 31.8 | 31.2 | 30.8 | 33.0 | 32.3 |
| DOR8 | 110.7 | 110.2 | 110.6 | 109.5 | 111.3 | 109.2 |
| PDR1R8 | 65.7 | 76.2 | 77.3 | 77.7 | 76.3 | 73.5 |
| BRPPR8 | 2.6 | 0.6 | 0.4 | 0.4 | 0.6 | 1.0 |
| NDBRR8 | 9.7 | 1.0 | 0.4 | 0.3 | 1.8 | 1.5 |
| NDMSR8 | 18.3 | 19.6 | 19.9 | 19.6 | 19.4 | 19.6 |
| NDPLR8 | 28.0 | 20.7 | 20.2 | 20.0 | 21.2 | 21.2 |
| PDPPR8 | 44.2 | 49.5 | 49.0 | 49.8 | 48.8 | 50.5 |
| PODMSR8 | 34.7 | 48.4 | 48.5 | 49.2 | 46.9 | 48.8 |
| TPBR8 | 9.5 | 1.2 | 0.5 | 0.6 | 1.9 | 1.7 |
| Pods/node | 1.6 | 2.4 | 2.4 | 2.5 | 2.4 | 2.3 |
| SDARR8 | 282.7 | 287.0 | 285.6 | 288.6 | 272.7 | 300.9 |
| SW1000 (ounces) | 5.1 | 4.9 | 5.0 | 4.9 | 4.9 | 4.6 |

TABLE 24

Phenotypic data for pAt.Erecta::Gm.FT2a::T-Lhbc2|pAP1::miRNA-FT::T-GAPDH and WT plants grown in the field (Year 2).

|  | WT | Average | Event 1 | Event 2 | Event 3 | Event 4 |
|---|---|---|---|---|---|---|
| DOFR1 | 37.0 | 28.7 | 28.4 | 28.5 | 28.6 | 29.3 |
| DOR8 | 114.9 | 114.6 | 114.7 | 113.7 | 115.0 | 114.9 |
| PDR1R8 | 77.9 | 85.9 | 86.3 | 85.2 | 86.4 | 85.6 |
| BRPPR8 | 2.1 | 0.7 | 0.3 | 0.3 | 0.6 | 1.3 |
| NDBRR8 | 8.0 | 1.8 | 0.8 | 1.2 | 1.4 | 3.8 |
| NDMSR8 | 19.8 | 21.7 | 21.9 | 21.2 | 22.0 | 21.5 |
| NDPLR8 | 27.8 | 23.5 | 22.9 | 22.5 | 23.4 | 25.2 |

TABLE 24-continued

Phenotypic data for
pAt.Erecta::Gm.FT2a::T-Lhbc2|pAP1::miRNA-FT::T-GAPDH
and WT plants grown in the field (Year 2).

|  | WT | Average | Event 1 | Event 2 | Event 3 | Event 4 |
|---|---|---|---|---|---|---|
| PDPPR8 | 56.1 | 63.6 | 60.6 | 68.3 | 59.4 | 66.0 |
| PDMSR8 | 47.9 | 60.9 | 58.8 | 65.5 | 58.0 | 61.2 |
| TPBR8 | 8.3 | 2.1 | 1.5 | 1.3 | 1.4 | 4.3 |
| Pods/Node | 2.0 | 2.7 | 2.6 | 3.1 | 2.5 | 2.7 |
| SDARR8 | 344.3 | 358.9 | 316.1 | 355.2 | 365.5 | 398.6 |
| SW1000 (ounces) | 5.4 | 5.5 | 5.6 | 5.6 | 5.5 | 5.2 |

Soybean plants having either of the pAtErecta::Gm.FT2a|pAP1::miRNA-FT2a constructs (with either terminator) flowered earlier (DOFR1) and had a slightly more extended reproductive duration (in days) between R1 and R8 stages (PDR1R8) and an increased number of pods per node (and per plant) at the R8 stage (PDPPR8, Pods/node) when grown under field conditions relative to WT control plants. However, soybean plants having the pAt.Erecta::Gm.FT2a pAP1::miRNA-FT2a::T-GAPDH construct also had reduced branching (BRPPR8) relative to WT control plants. Early results in a third year of field testing of plants with the pAt.Erecta::Gm.FT2a pAP1::miRNA-FT2a::T-GAPDH construct also show early flowering indicating similar reproductive traits.

These field results indicate that both of the pAt.Erecta::Gm.FT2a|pAP1::miRNA-FT2a::T-GAPDH constructs with the different terminators are able to enhance yield traits and mitigate early termination phenotypes under field conditions (see, e.g., Example 3 above), which is consistent with the greenhouse data provided in Example 10 above. This data further supports the model that suppression of the Gm.FT2a transgene helps to lessen or mitigate the early termination and plant architecture phenotypes, including reduced plant height, branching and nodes per plant (or per main stem), as compared to expression of the Gm.FT2a transgene alone.

Example 12. Modification of Gm.FT2a Expression by an Artificial miRNA Driven by a pSl.MADS5 Promoter Alters Reproductive Phenotypes Under Greenhouse Conditions In addition to the pAP1 promoter, other reproductive stage promoters were used to express a miRNA molecule that targets the Gm.FT2a transgene for suppression. In one set of experiments, a transformation vector comprising Gm.FT2a under control of the pAt.Erecta promoter and a transcribable DNA sequence encoding an artificial miRNA that targets Gm. FT2a for suppression and under the control of a *Solanum lycopersicum* MADS5 promoter (pSl.MADS5; SEQ ID NO: 71) was constructed and used to transform soybeans via *Agrobacterium*-mediated transformation. Transgenic plants generated from these events were characterized in the greenhouse for their phenotypes in the greenhouse with a 14 to 14.5 hour daylight photoperiod. For the pAt.Erecta::Gm.FT2a::T-Lhcb2|pSl.MADS5::miRNA-FT2a::T-GAPDH construct, six events were tested (6 plants per event). Six plants were also tested and averaged for wild type (WT) control plants.

Table 25 provides the average phenotypic data for each event and WT plant, and an average for each trait across all events tested. ("--" means data not collected.)

TABLE 25

Phenotypic data for pAt.Erecta::Gm.FT2a::T-Lhcb2|pSl.MADS5::miRNA-FT::T-GAPDH and WT plants under greenhouse conditions.

|  | WT | Average | Event 1 | Event 2 | Event 3 | Event 4 | Event 5 | Event 6 |
|---|---|---|---|---|---|---|---|---|
| DOFR1 | 33.5 | 28.0 | 28.0 | — | — | — | — | 28.0 |
| DOR7 | 106.9 | 87.1 | 83.3 | 86.7 | 89.7 | 87.5 | 88.3 | 87.2 |
| PDR1R7 | 76.5 | 58.5 | 56.0 | — | — | — | — | 61.0 |
| BRPP | 20.1 | 2.1 | 1.0 | 1.5 | — | 4.0 | 2.0 | 2.0 |
| FNBR | 190.6 | 7.9 | 3.0 | 5.0 | — | 16.5 | 7.7 | 7.3 |
| FNPL | 214.6 | 29.6 | 11.0 | 33.5 | 31.5 | 41.8 | 24.3 | 35.5 |
| FNST | 24.0 | 25.8 | 10.3 | 31.0 | 31.5 | 33.5 | 18.5 | 30.0 |
| NDBR | 211.4 | 8.4 | 3.0 | 6.0 | — | 17.0 | 8.0 | 8.0 |
| NDMS | 33.4 | 26.6 | 10.8 | 31.5 | 32.3 | 33.8 | 19.8 | 31.5 |
| NDPL | 244.9 | 30.6 | 11.5 | 34.5 | 32.3 | 42.3 | 25.8 | 37.5 |
| PDPP | 575.8 | 252.4 | 34.8 | 244.0 | 265.3 | 253.3 | 157.8 | 559.5 |
| PFNB | 90.4 | 94.6 | 100.0 | 87.5 | — | 98.1 | 95.2 | 92.1 |
| PFNN | 87.8 | 96.6 | 95.8 | 97.5 | 97.8 | 99.0 | 94.9 | 94.9 |
| PFNS | 71.4 | 96.8 | 95.8 | 98.5 | 97.8 | 99.2 | 94.5 | 95.1 |
| PODBR | 487.3 | 12.0 | 3.0 | 5.5 | — | 33.0 | 9.7 | 8.7 |
| PODMS | 88.4 | 246.8 | 34.0 | 241.3 | 265.3 | 236.8 | 150.5 | 553.0 |
| Pods/Node | 2.4 | 7.6 | 3.1 | 7.1 | 8.2 | 6.3 | 6.4 | 14.6 |
| SDPP8 | 1319.6 | 335.3 | 38.0 | 321.3 | 359.3 | 527.8 | 305.8 | 460.0 |
| SW1000 (grams) | 146.0 | 178.6 | 180.8 | 167.2 | 173.0 | 183.3 | 182.3 | 185.0 |

Similar to the previous examples, limiting the ectopic expression of Gm.FT2a using an artificial miRNA expressed in reproductive tissues resulted in soybean plants that flowered earlier (DOFR1) than WT control plants. However, transgenic soybean plants comprising the pAt.Erecta::Gm.FT2a::T-Lhcb2|pSl.MADS5::miRNA-FT2a::T-GAPDH construct have fewer pods per plant (PDPP), fewer nodes per plant (NDPL), reduced number of branches (BRPP), fewer seeds per plant at R8 stage (SDPP8), and a reduced reproductive duration between R1 and R7 stages (PDR1R7), as compared to WT control plants, although these transgenic plants did have a greater number of pods per node (and per main stem) relative to WT control plants (Pods/Node, PODMS), and improved plant architecture phenotypes relative to pAt.Erecta::Gm.FT2a expression alone (see, e.g., Table 2).

This data further supports the model that suppression of the Gm.FT2a transgene helps to lessen or mitigate the early termination phenotypes with the Gm.FT2a transgene alone, but expression of a miRNA-FT2a with the pMADS5 promoter may not be as effective as the pAP1 promoter at mitigating the early termination phenotypes.

Example 13. Modification of Gm.FT2a Expression by an Artificial miRNA Driven by a pSl.MADS5 Promoter Alters Reproductive Phenotypes in the Field Transgenic plants comprising three or four events of the pAt.Erecta::Gm.FT2a pSl.MADS5::miRNA-FT2a construct described in Example 12 were grown and tested under field conditions for two consecutive years. Data was collected for six plants for each event and WT control (events are numbered for consistency). Tables 26 and 27 provide the average phenotypic data collected from each event and WT control, and an average for each trait across all events.

TABLE 26

Phenotypic data for pAt.Erecta::Gm.FT2a::T-Lhcb2 | pSl.MADS5::miRNA-FT2a::T-GAPDH and WT plants grown in the field (Year 1).

|  | WT | Average | Event 2 | Event 3 | Event 4 |
|---|---|---|---|---|---|
| DOFR1 | 42.4 | 27.6 | 27.7 | 27.5 | 27.7 |
| DOR8 | 110.7 | 100.8 | 100.3 | 101.8 | 100.2 |
| PDR1R8 | 65.7 | 73.1 | 73.2 | 74.0 | 72.0 |
| BRPPR8 | 2.6 | 0.1 | 0.1 | 0.0 | 0.1 |
| NDBRR8 | 9.7 | 0.2 | 0.2 | 0.1 | 0.3 |
| NDMSR8 | 18.3 | 15.2 | 14.5 | 15.7 | 15.3 |
| NDPLR8 | 28.0 | 15.4 | 14.7 | 15.8 | 15.6 |
| PDPPR8 | 44.2 | 43.2 | 41.7 | 45.4 | 42.5 |
| PDMSR8 | 34.7 | 43.0 | 41.4 | 45.3 | 42.2 |
| TPBR8 | 9.5 | 0.2 | 0.3 | 0.0 | 0.3 |
| Pods/Node | 1.6 | 2.9 | 2.9 | 2.9 | 2.8 |
| SDARR8 | 282.7 | 243.7 | 233.8 | 264.4 | 233.0 |
| SW1000 (ounces) | 5.1 | 4.6 | 4.4 | 4.7 | 4.7 |

TABLE 27

Phenotypic data for pAt.Erecta::Gm.FT2a::T-Lhcb2|pSlLe.MADS5::miRNA-FT2a::T-GAPDH and WT plants grown in the field (Year 2).

|  | WT | Average | Event 2 | Event 3 | Event 4 | Event 5 |
|---|---|---|---|---|---|---|
| DOFR1 | 37.0 | 24.5 | 24.3 | 24.7 | 24.3 | 24.8 |
| DOR8 | 114.9 | 106.7 | 106.3 | 106.8 | 106.2 | 107.7 |
| PDR1R8 | 77.9 | 82.2 | 82.1 | 82.1 | 81.8 | 82.9 |
| BRPPR8 | 2.1 | 0.3 | 0.3 | 0.2 | 0.5 | 0.2 |
| NDBRR8 | 8.0 | 1.1 | 0.8 | 0.8 | 2.0 | 0.7 |
| NDMSR8 | 19.8 | 15.2 | 15.4 | 15.3 | 15.4 | 14.7 |
| NDPLR8 | 27.8 | 16.2 | 16.2 | 16.1 | 17.3 | 15.1 |
| PDPPR8 | 56.1 | 45.7 | 46.4 | 48.9 | 50.1 | 37.4 |
| PDMSR8 | 47.9 | 44.0 | 45.2 | 47.6 | 46.3 | 37.0 |
| TPBR8 | 8.3 | 1.8 | 1.2 | 1.4 | 3.8 | 1.0 |
| Pods/Node | 2.0 | 2.8 | 2.9 | 3.0 | 2.9 | 2.5 |
| SDARR8 | 344.3 | 254.9 | 280.4 | 236.5 | 267.9 | 235.0 |
| SW1000 (ounces) | 5.4 | 5.3 | 5.1 | 5.5 | 5.4 | 5.0 |

Soybean plants having the pAt.Erecta::Gm.FT2a|pSl.MADS5::miRNA-FT2a construct flowered earlier (DOFR1) and had a slightly more extended reproductive duration (in days) between R1 and R8 stages (PDR1R8) and an increased number of pods per node at the R8 stage (Pods/node) under field conditions, relative to WT control plants. However, soybean plants having the pAt.Erecta::Gm.FT2a|pSl.MADS5::miRNA-FT2a construct also had reduced branching (BRPPR8) relative to WT control plants.

Example 14. Modification of Gm.FT2a Expression by an Artificial miRNA Driven by a pSl.NOD Promoter Alters Reproductive Phenotypes Under Greenhouse Conditions A third promoter (pSl.NOD) controlling expression of a miRNA-FT2a was also tested under greenhouse conditions. A transformation vector comprising Gm.FT2a under control of the pAt.Erecta promoter (SEQ ID NO: 31) and a transcribable DNA sequence encoding a miRNA-FT2a (SEQ ID NO: 67) under the control of a *Solanum lycopersicum* NOD promoter (pSl.NOD; SEQ ID NO: 70) was constructed and used to transform soybeans via *Agrobacterium*-mediated transformation. Transgenic plants comprising six events of this pAt.Erecta::Gm.FT2a pSl.NOD::miRNA-FT2a construct (six plants per event) were grown in the greenhouse with a 14 to 14.5 hour daylight photoperiod. Data was collected from six plants for each event and wild type (WT) control. Table 28 provides the average phenotypic data collected from each event and WT control, and an average for each trait across all events.

TABLE 28

Phenotypic data for greenhouse-grown pAt.Erecta::Gm.FT2a|pSl.NOD::miRNA-FT2a and WT plants.

|  | WT | Average | Event 1 | Event 2 | Event 3 | Event 4 | Event 5 | Event 6 |
|---|---|---|---|---|---|---|---|---|
| DOFR1 | 40.0 | 20.4 | 20.3 | 20.4 | 20.8 | 20.7 | 20.0 | 20.2 |
| DOR7 | 107.3 | 90.9 | 87.2 | 86.0 | 96.8 | 86.0 | 86.0 | 99.6 |
| PDR1R7 | 67.3 | 70.5 | 66.8 | 65.6 | 76.0 | 65.4 | 66.0 | 79.4 |
| BRPP | 17.9 | 3.3 | — | 2.0 | 7.7 | 1.5 | 2.0 | — |
| FNBR | 182.3 | 34.3 | — | 19.0 | 106.0 | 4.5 | 7.5 | — |
| FNPL | 205.9 | 44.2 | 20.0 | 27.7 | 132.3 | 20.8 | 21.0 | 19.0 |
| FNST | 23.6 | 20.2 | 20.0 | 21.3 | 26.3 | 18.5 | 16.0 | 19.0 |
| NDBR | 231.0 | 37.3 | — | 20.0 | 114.0 | 5.5 | 9.5 | — |
| NDMS | 34.4 | 22.6 | 21.3 | 22.3 | 31.0 | 20.3 | 18.7 | 20.7 |
| NDPL | 265.4 | 48.5 | 21.3 | 29.0 | 145.0 | 23.0 | 25.0 | 20.7 |
| PDPP | 703.0 | 228.3 | 133.3 | 188.0 | 563.7 | 108.0 | 139.7 | 142.3 |
| PFNB | 78.9 | 85.6 | — | 95.0 | 93.3 | 75.0 | 78.9 | — |
| PFNN | 77.5 | 90.8 | 94.3 | 96.1 | 91.3 | 90.3 | 84.5 | 91.8 |

TABLE 28-continued

Phenotypic data for greenhouse-grown pAt.Erecta::Gm.FT2a|pSl.NOD::miRNA-FT2a and WT plants.

|  | WT | Average | Event 1 | Event 2 | Event 3 | Event 4 | Event 5 | Event 6 |
|---|---|---|---|---|---|---|---|---|
| PFNS | 69.8 | 89.7 | 94.3 | 95.2 | 84.8 | 91.1 | 85.8 | 91.8 |
| PODBR | 584.8 | 126.5 | — | 100.0 | 390.3 | 5.0 | 10.5 | — |
| PODMS | 115.1 | 141.7 | 133.3 | 154.7 | 173.1 | 105.5 | 132.7 | 142.3 |
| Pods/Node | 2.7 | 5.6 | 6.3 | 6.5 | 3.9 | 4.8 | 5.9 | 6.8 |
| SDPP8 | 1413.0 | 437.0 | 307.5 | 409.7 | 973.0 | 243.5 | 282.7 | 276.3 |
| SW1000 (grams) | 126.2 | 113.4 | 120.5 | 117.5 | 83.6 | 137.5 | 118.4 | 109.8 |

Soybean plants comprising the pAt.Erecta::Gm.FT2a|pSl.NOD::miRNA-FT2a construct flowered earlier (DOFR1) than WT control plants and had a shorter reproductive duration (PDR1R7), fewer branches per plant (BRPP), fewer nodes per plant (NDPL), and fewer pods per plant (PDPP), in the greenhouse as compared to WT control plants. However, these transgenic plants did have a greater number of pods per node (and per main stem) relative to WT plants (Pods/Node, PODMS), and improved plant architecture phenotypes relative to pAtErecta::Gm.FT2a expression alone (see, e.g., Table 2).

This data further supports the model that suppression of the Gm.FT2a transgene helps to lessen or mitigate the early termination phenotypes, but expression of a miRNA-FT2a under the pSl.NOD promoter may not be as effective as the pAP1 promoter at mitigating the early termination phenotypes, although these transgenic plants did have a higher number of pods per node (and per main stem) than WT control plants (Pods/Node, PODMS).

Example 15. Modification of Ectopic Gm.FT2a Expression with a Heterologous miR172 Target Site Alters Reproductive Phenotypes Under Greenhouse Conditions As an alternative approach to suppressing Gm.FT2a, constructs were made comprising a Gm.FT2a transgene and an engineered miRNA target or binding site (or sensor) that is recognized by an endogenous miRNA in soybean, which serves to attenuate and/or refine the ectopic expression of the Gm.FT2a transgene. Transformation vectors comprising a Gm.FT2a transgene under control of the pAt.Erecta promoter (SEQ ID NO: 31) with either an Apx or Lhcb2 terminator region (T-Apx or T-Lhcb2), and further comprising a sequence (SEQ ID NO: 98) encoding a miR172 miRNA target site (SEQ ID NO: 99) in the transgenic Gm.FT2a mRNA were constructed and used to transform soybean via *Agrobacterium*-mediated transformation. Transgenic plants generated from these events were characterized for their phenotypes in the greenhouse with a 14 to 14.5 hour daylight photoperiod. For each of the two pAt.Erecta::Gm.FT2a with miR172 binding site constructs, six events were tested (6 plants per event). Six plants were also tested and averaged for wild type (WT) control plants. Tables 29 and 30 provide the average phenotypic data collected from each event and WT control for each of the two constructs, and an average for each trait across all events tested.

TABLE 29

Phenotypic data for pAt.Erecta::Gm.FT2a::T-Apx/miR172 target site and WT plants.

|  | WT | Average | Event 1 | Event 2 | Event 3 | Event 4 | Event 5 | Event 6 |
|---|---|---|---|---|---|---|---|---|
| DOFR1 | 33.5 | 28.0 | — | 28.0 | — | — | — | — |
| DOR7 | 106.9 | 88.3 | 91.3 | 89.7 | 86.3 | 89.0 | 88.2 | 85.3 |
| PDR1R7 | 76.5 | 64.5 | — | 64.5 | — | — | — | — |
| BRPP | 20.1 | 3.9 | 1.5 | 4.0 | — | 11.5 | 1.5 | 1.0 |
| FNBR | 190.6 | 21.6 | 4.0 | 21.3 | — | 75.0 | 3.3 | 4.5 |
| FNPL | 214.6 | 37.0 | 39.0 | 50.3 | 26.5 | 64.3 | 16.5 | 25.5 |
| FNST | 24.0 | 26.8 | 37.0 | 34.3 | 26.5 | 26.8 | 13.3 | 23.3 |
| NDBR | 211.4 | 26.8 | 4.0 | 25.3 | — | 96.5 | 3.5 | 4.5 |
| NDMS | 33.4 | 28.8 | 38.0 | 38.0 | 26.8 | 32.0 | 14.3 | 23.8 |
| NDPL | 244.9 | 41.3 | 40.0 | 57.0 | 26.8 | 80.3 | 17.8 | 26.0 |
| PDPP | 575.8 | 227.9 | 294.0 | 331.5 | 201.8 | 297.0 | 68.0 | 175.3 |
| PFNB | 90.4 | 93.1 | 100.0 | 83.7 | — | 88.3 | 93.8 | 100.0 |
| PFNN | 87.8 | 95.0 | 97.6 | 91.5 | 99.1 | 90.7 | 93.5 | 97.9 |
| PFNS | 71.4 | 93.4 | 97.4 | 90.9 | 99.1 | 82.2 | 93.4 | 97.7 |
| PODBR | 487.3 | 60.8 | 4.5 | 82.0 | — | 206.0 | 5.0 | 6.5 |
| PODMS | 88.4 | 198.8 | 291.8 | 270.0 | 201.8 | 194.0 | 63.0 | 172.0 |
| Pods/Node | 2.4 | 6.4 | 7.4 | 6.7 | 7.5 | 6.1 | 3.9 | 6.8 |
| SDPP8 | 1319.6 | 330.0 | 443.8 | 460.0 | 368.5 | 409.3 | 47.8 | 250.8 |
| SW1000 (grams) | 146.0 | 169.5 | 166.8 | 176.3 | 177.7 | 171.8 | 152.7 | 172.1 |

TABLE 30

Phenotypic data for pAt.Erecta::Gm.FT2a::T-Lhcb2/miR172 target site and WT plants.

|  | WT | Average | Event 1 | Event 2 | Event 3 | Event 4 | Event 5 | Event 6 |
|---|---|---|---|---|---|---|---|---|
| DOFR1 | 40.3 | 27.2 | 28.0 | 25.0 | 25.0 | 33.3 | 26.3 | 25.3 |
| DOR7 | 116.5 | 99.9 | 96.6 | 88.0 | 97.0 | 123.0 | 102.4 | 92.7 |
| PDR1R7 | 76.3 | 73.0 | 70.8 | 63.0 | 70.8 | 89.3 | 76.6 | 67.3 |
| BRPP | 17.5 | 5.3 | 3.0 | 1.3 | 1.5 | 13.5 | 6.3 | 6.3 |
| FNBR | 162.5 | 48.6 | 33.0 | 3.8 | 4.5 | 153.5 | 46.3 | 50.3 |
| FNPL | 185.8 | 65.7 | 69.0 | 24.3 | 32.0 | 128.3 | 70.3 | 70.3 |
| FNST | 23.3 | 27.8 | 36.0 | 20.5 | 27.5 | 26.0 | 24.0 | 32.5 |
| NDBR | 249.5 | 55.1 | 37.0 | 5.5 | 7.0 | 173.5 | 50.8 | 56.7 |
| NDMS | 33.5 | 31.9 | 38.3 | 21.8 | 28.5 | 36.7 | 31.8 | 34.3 |
| NDPL | 283.0 | 74.9 | 75.3 | 27.3 | 35.5 | 152.3 | 82.5 | 76.8 |
| PDPP | 628.5 | 317.3 | 407.0 | 132.0 | 198.5 | 433.3 | 338.3 | 394.8 |
| PFNB | 65.2 | 81.9 | 85.3 | 87.5 | 67.8 | 87.7 | 77.5 | 85.5 |
| PFNN | 65.7 | 85.3 | 93.8 | 91.6 | 90.2 | 69.2 | 73.9 | 93.2 |
| PFNS | 69.0 | 86.4 | 94.5 | 94.7 | 96.4 | 66.4 | 71.3 | 95.1 |
| PODBR | 504.8 | 158.8 | 131.7 | 8.0 | 8.5 | 478.5 | 150.5 | 175.3 |
| PODMS | 123.8 | 192.4 | 275.3 | 124.0 | 190.0 | 114.3 | 187.8 | 263.3 |
| Pods/Node | 2.2 | 4.8 | 6.3 | 5.1 | 5.6 | 2.2 | 3.6 | 6.2 |
| SDPP8 | 1261.3 | 559.5 | 712.0 | 118.8 | 655.7 | 593.3 | 603.5 | 673.5 |
| SW1000 (grams) | 135.0 | 128.8 | 105.2 | 144.5 | 122.6 | 120.2 | 175.9 | 104.6 |

Soybean plants comprising either of the two pAt.Erecta::Gm.FT2a/miR172 target site constructs flowered earlier (DOFR1), but had reduced branching (BRPP) and fewer pods and nodes per plant (PDPP, NDPL), as compared to WT control plants. However, these transgenic plants did have a greater number of pods per node (and per main stem) relative to WT control plants (Pods/Node, PODMS), and improved plant architecture phenotypes relative to pAt.Erecta::Gm.FT2a expression alone (see Table 2).

Figure 13:
FIG. 13 shows whole plant images of plants transformed with either pAt.Erecta::Gm.FT2a alone or pAt.Erecta::Gm.FT2a+miR172 target site.

This data supports the hypothesis that suppression of the Gm.FT2a transgene via a target site for an endogenous miR172 is effective at lessening or mitigating the early termination observed with expression of the Gm.FT2a transgene, but suppression of the Gm.FT2a transgene via an engineered miR172 target site may not be as effective (at least in some cases) as expression of an artificial miRNA to suppress Gm.FT2a using a late vegetative and/or reproductive stage promoter, such as the pAP1 promoter, at mitigating the early termination phenotypes, although Gm.FT2a transgenic plants containing the miR172 target site did have a higher number of pods per node (and per main stem) than WT control plants (Pods/Node, PODMS) with improved plant architecture phenotypes relative to Gm.FT2a expression alone. FIG. 13 provides whole images of plants homozygous for either pAt.Erecta::Gm.FT2a or pAt.Erecta::Gm.FT2a/miR172 target site showing that additional suppression via the endogenous miR172 target site is effective at mitigating the early termination phenotypes observed with the pAt.Erecta::Gm.FT2a transgene alone, including short plant height and reduced branching.

Example 16. Modification of Ectopic Gm.FT2a Expression with a miR172 Target Site Alters Reproductive Phenotypes Under Field Conditions Transgenic plants comprising four events of the pAtErecta::Gm.FT2a::T-Apx/miR172 target site construct described in Example 15 were grown and tested under field conditions. Events 1-4 in Table 29 correspond to Events 1-4 in Table 31, respectively. Data was collected for six plants for each event and WT control. Table 31 provides the average phenotypic data collected from each event and WT control, and an average for each trait across all events.

TABLE 31

Phenotypic data for field-grown pAt.Erecta::Gm.FT2a::T-Apx/miR172 target site and WT plants.

|  | WT | Average | Event 1 | Event 2 | Event 3 | Event 4 |
|---|---|---|---|---|---|---|
| DOFR1 | 42.4 | 26.8 | 26.5 | 27 | 27.3 | 26.3 |
| DOR8 | 110.7 | 91.9 | 93.7 | 92.5 | 91.3 | 90.1 |
| PDR1R8 | 65.7 | 66.1 | 68.5 | 66.4 | 65.2 | 64.2 |
| BRPPR8 | 2.6 | 0.1 | 0.2 | 0.1 | 0.1 | 0.1 |
| NDBRR8 | 9.7 | 0.3 | 0.5 | 0.2 | 0.3 | 0.3 |
| NDMSR8 | 18.3 | 10.8 | 12.5 | 11.2 | 10.7 | 8.9 |
| NDPLR8 | 28.0 | 11.1 | 13 | 11.3 | 11.0 | 9.1 |
| PDPPR8 | 44.2 | 23.2 | 30.1 | 25.0 | 21.7 | 15.8 |
| PDMSR8 | 34.7 | 22.7 | 29.4 | 24.7 | 21.3 | 15.3 |
| TPBR8 | 9.5 | 0.5 | 0.7 | 0.2 | 0.4 | 0.5 |
| Pods/Node | 1.6 | 2.1 | 2.4 | 2.1 | 2.0 | 1.7 |
| SDARR8 | 282.7 | 130.3 | 148.7 | 155.3 | 129.3 | 88.1 |
| SW1000 (ounces) | 5.1 | 4.6 | 4.7 | 4.5 | 4.6 | 4.6 |

Similar to the greenhouse data, soybean plants with the pAt.Erecta::Gm.FT2a::T-Apx/miR172 target site construct flowered earlier (DOFR1) and had an increased number of pods per node (and per main stem) at the R8 stage (PDPP8, Pods/node) under field conditions, relative to WT control plants. However, these soybean plants with the pAtErecta::Gm.FT2a::T-Apx/miR172 target site construct also had reduced branching (BRPPR8) and reduced pods and nodes per plant (PDPPR8, NDPLR8) relative to WT control plants.

Example 17. Modification of Ectopic Gm.FT2a Expression with a Truncated pAt.Erecta Promoter and a Heterologous miR172 Target Site Alters Reproductive Phenotypes Under Greenhouse Conditions A truncated pAt.Erecta promoter was used to drive an attenuated level of expression of a Gm.FT2a transgene, and coupled with a miR172 miRNA target site to possibly further attenuate and/or refine the ectopic expression of the Gm.FT2a transgene. Transformation vectors comprising a Gm.FT2a transgene under control of a truncated pAt.Erecta promoter (SEQ ID NO: 32) with a Lhcb2 terminator region (T-Lhcb2) and further comprising a sequence (SEQ ID NO: 98) encoding a miR172 target site (SEQ ID NO: 99) were constructed and used to transform soybean plants via *Agrobacterium*-mediated transformation. Transgenic plants generated from these events were characterized for their phenotypes in the greenhouse with a 14 to 14.5 hour daylight photoperiod. For the pAt.Erecta_truncated::Gm.FT2a with miR172 target site construct, six events were tested (6 plants per event). Six plants were also tested and averaged for wild type (WT) control plants. Table 32 provides the average phenotypic data collected from each event and WT control, and an average for each trait across the events tested.

TABLE 32

Phenotypic data for pErecta_truncated::Gm.FT2a::T-Lhbc2/miR172 target site and WT plants under greenhouse conditions.

|  | WT | Average | Event 1 | Event 2 | Event 3 | Event 4 | Event 5 | Event 6 |
|---|---|---|---|---|---|---|---|---|
| DOFR1 | 40.3 | 33.4 | 32.5 | 25.0 | 34.7 | 35.7 | 38.7 | 33.8 |
| DOR7 | 116.5 | 107.1 | 105.5 | 92.2 | 109.4 | 107.7 | 116.8 | 111.3 |
| PDR1R7 | 76.3 | 74.1 | 73.0 | 67.0 | 75.0 | 72.0 | 80.0 | 77.6 |
| BRPP | 17.5 | 14.2 | 15.3 | 2.0 | 14.8 | 15.8 | 20.8 | 16.8 |
| FNBR | 162.5 | 148.3 | 171.3 | 5.7 | 180.5 | 156.8 | 177.3 | 198.5 |
| FNPL | 185.8 | 175.0 | 201.3 | 36.5 | 207.0 | 180.0 | 203.0 | 222.3 |
| FNST | 23.3 | 26.9 | 30.0 | 32.3 | 26.5 | 23.3 | 25.8 | 23.8 |
| NDBR | 249.5 | 211.9 | 220.8 | 5.7 | 256.0 | 258.0 | 281.8 | 249.5 |
| NDMS | 33.5 | 38.2 | 39.0 | 33.3 | 36.0 | 35.0 | 48.3 | 37.8 |
| NDPL | 283.0 | 249.9 | 259.8 | 37.5 | 292.0 | 293.0 | 330.0 | 287.3 |
| PDPP | 628.5 | 635.0 | 752.5 | 324.8 | 727.8 | 615.0 | 676.3 | 713.8 |
| PFNB | 65.2 | 75.7 | 77.8 | 100.0 | 70.1 | 62.3 | 63.0 | 81.0 |
| PFNN | 65.7 | 74.8 | 77.8 | 97.5 | 70.5 | 62.8 | 61.5 | 78.5 |
| PFNS | 69.0 | 72.1 | 78.0 | 97.0 | 74.3 | 67.2 | 53.0 | 63.2 |
| PODBR | 504.8 | 469.6 | 577.3 | 12.7 | 581.5 | 508.0 | 531.5 | 606.8 |
| PODMS | 123.8 | 165.9 | 175.3 | 315.3 | 146.3 | 107.0 | 144.8 | 107.0 |
| Pods/Node | 2.2 | 3.5 | 2.9 | 8.7 | 2.5 | 2.1 | 2.1 | 2.6 |
| SDPP8 | 1261.3 | 1144.0 | 1550.3 | 691.5 | 1053.8 | 984.0 | 1107.3 | 1477.3 |
| SW1000 (grams) | 135.0 | 114.1 | 126.5 | 116.6 | 96.0 | 98.0 | 115.3 | 131.9 |

Soybean plants comprising the pAt.Erecta_truncated::Gm.FT2a/miR172 target site construct flowered earlier (DOFR1), but had slightly reduced branching (BRPP) and fewer nodes per plant (NDPL), as compared to WT control plants. However, these transgenic plants did have a greater number of pods per node (and per main stem) relative to WT control plants (Pods/Node, PODMS), and improved plant architecture phenotypes relative to the pAtErecta::Gm.FT2a expression alone (see, e.g., Table 2).

This data further supports the hypothesis that suppression of the Gm.FT2a transgene with a target site for an endogenous miR172 is effective at lessening or mitigating the early termination observed with expression of the Gm.FT2a transgene, and/or that expression of the Gm.FT2a transgene with a truncated pAt.Erecta promoter may further mitigate early termination phenotypes with Gm.FT2a expression alone.

Example 18. Modification of Ectopic Gm.FT2a Expression with a Truncated pAt.Erecta Promoter and a miR172 Target Site Alters Reproductive Phenotypes in the Field Transgenic plants for three events of the pAt.Erecta_truncated::Gm.FT2a::T-Lhbc2/miR172 target site construct described in Example 18 were grown and tested under field conditions. Events 1, 2, and 5 in Table 32 correspond to Events 1-3 in Table 33, respectively. Data was collected for six plants for each event and WT control. Table 33 provides average phenotypic data for each event and WT control, and averages for each trait across all events.

TABLE 33

Phenotypic data for pErecta_truncated::Gm.FT2a::T-Lhbc2/miR172 target site and WT plants in the field.

|  | WT | Average | Event 1 | Event 2 | Event 3 |
|---|---|---|---|---|---|
| DOFR1 | 42.4 | 30.4 | 29.8 | 27.7 | 33.8 |
| DOR8 | 110.7 | 105.3 | 108.1 | 99.8 | 108.0 |
| PDR1R8 | 65.7 | 74.3 | 77.0 | 73.8 | 72.2 |
| BRPPR8 | 2.6 | 0.7 | 1.0 | 0.0 | 1.1 |

TABLE 33-continued

Phenotypic data for pErecta_truncated::Gm.FT2a::T-Lhbc2/miR172 target site and WT plants in the field.

|  | WT | Average | Event 1 | Event 2 | Event 3 |
|---|---|---|---|---|---|
| NDBRR8 | 9.7 | 1.6 | 1.5 | 0.2 | 3.0 |
| NDMSR8 | 18.3 | 17.3 | 17.8 | 14.8 | 19.2 |
| NDPLR8 | 28.0 | 18.8 | 19.3 | 15.0 | 22.2 |
| PDPPR8 | 44.2 | 43.9 | 45.5 | 41.4 | 44.7 |
| PDMSR8 | 34.7 | 42.4 | 43.9 | 41.1 | 42.1 |
| TPBR8 | 9.5 | 1.6 | 1.6 | 0.4 | 2.7 |
| Pods/Node | 1.6 | 2.4 | 2.4 | 2.7 | 2.1 |
| SDARR8 | 282.7 | 263.4 | 278.2 | 242.7 | 269.2 |
| SW1000 (ounces) | 5.1 | 4.9 | 5.0 | 4.5 | 5.1 |

Similar to the greenhouse data, soybean plants with the pAt.Erecta_truncated::Gm.FT2a/miR172 target site construct flowered earlier (DOFR1) and had an increased number of pods per node (and per main stem) at the R8 stage (PDMSR8, Pods/node) under field conditions, relative to WT control plants. However, soybean plants with the pAt.Erecta_truncated::Gm.FT2a/miR172 target site construct also had reduced branching (BRPPR8) and reduced nodes per plant (NDPLR8) relative to WT control plants.

Example 19. Modification of Ectopic Gm.FT2a and Native Gm.FT2a, Gm.FT5a and Gm.FT5b Expression in Soybeans by an Artificial miRNA Alters Reproductive Phenotypes A transformation vector was constructed and used to transform soybean plants via *Agrobacterium*-mediated transformation, wherein the vector comprised the Gm.FT2a transgene as described above under control of the vegetative stage, meristem-preferred pAt.Erecta promoter (SEQ ID NO: 31) with the Lhcb2 terminator region (T-Lhcb2), and a transcribable DNA sequence encoding an artificial miRNA (SEQ ID NO: 102) that targets not only Gm.FT2a (ectopic and endogenous), but also the endogenous Gm.FT5a and Gm.FT5b genes, for suppression, wherein the transcribable DNA sequence encoding the miRNA is under the control of a pAt.AP1 promoter (SEQ ID NO: 49) with a GAPDH terminator region. Transgenic plants generated from these events were characterized in the greenhouse under 14 to 14.5 hour daylight photoperiod conditions. Data was collected for six plants for each event and WT control. Table 34 provides the average phenotypic data collected from each event and WT control, and an average for each trait across all events.

TABLE 34

Phenotypic data for pAt.Erecta::Gm.FT2a::T-Lhbc2|pAP1::miRNA-FT2a/FT5a/FT5b::T-GAPDH and WT plants grown in the greenhouse.

|  | WT | Average | Event 1 | Event 2 | Event 3 | Event 4 | Event 5 | Event 6 |
|---|---|---|---|---|---|---|---|---|
| DOFR1 | 39.3 | 32.2 | 34.0 | 32.0 | 33.0 | 30.3 | 31.7 | 32.3 |
| DOR7 | 107.0 | 98.0 | 104.2 | 99.3 | 97.8 | 93.7 | 94.5 | 98.5 |
| PDR1R7 | 67.7 | 65.8 | 70.2 | 67.3 | 64.8 | 63.3 | 62.8 | 66.2 |
| BRPPR8 | 16.8 | 9.9 | 13.8 | 12.7 | 12.2 | 1.8 | 9.0 | 9.7 |
| NDBRR8 | 225.8 | 60.9 | 64.3 | 72.3 | 93.8 | 9.2 | 55.3 | 70.7 |
| NDMSR8 | 29.7 | 29.7 | 34.8 | 33.8 | 33.5 | 15.8 | 33.3 | 27.2 |
| NDPLR8 | 255.5 | 90.7 | 99.2 | 106.2 | 127.3 | 25.0 | 88.7 | 97.8 |
| PDMSR8 | 74.8 | 177.2 | 212.8 | 222.2 | 161.8 | 92.3 | 218.8 | 155.2 |
| PDNDBRR8 | 1.8 | 2.6 | 3.2 | 3.4 | 2.6 | 1.8 | 2.6 | 2.2 |
| PDNDMSR8 | 2.3 | 6.0 | 6.2 | 6.6 | 5.2 | 5.4 | 6.6 | 5.7 |
| Pods/Node | 1.9 | 4.2 | 4.3 | 4.5 | 3.6 | 4.5 | 4.5 | 4.0 |
| PDPPR8 | 482.7 | 349.0 | 411.3 | 470.8 | 418.2 | 111.8 | 346.3 | 335.5 |
| PHTR8 | 1016.3 | 955.5 | 1133.5 | 1156.3 | 1032.5 | 475.5 | 1049.3 | 885.8 |
| SDPDR8 | 2.1 | 1.9 | 1.9 | 1.8 | 1.9 | 1.6 | 2.3 | 1.9 |
| SNUM | 1012.5 | 694.9 | 798.3 | 825.3 | 814.2 | 220.3 | 789.0 | 722.3 |
| TPBR8 | 407.8 | 171.8 | 198.5 | 248.7 | 256.3 | 19.5 | 127.5 | 180.3 |
| SW1000 (grams) | 141.2 | 135.4 | 144.3 | 150.8 | 141.5 | 107.1 | 149.5 | 119.4 |

Some additional trait measurements are provided in Table 34 including PDNDBRR8 (pods per node on branches) and PDNDMSR8 (pods per node on main stem) at R8 stage, PHTR8 (plant height at R8 stage in millimeters), SDPDR8 (seeds per pod at R8), and SNUM (number of seeds per plant). Soybean plants expressing the pAt.Erecta::Gm.FT2a cassette with combined suppression of Gm.FT2a, Gm.FT5a, and Gm.FT5b flowered earlier (DOFR1) and had a significantly increased number of pods per node (and increased pods on the mainstem), but decreased branching, relative to WT control plants.

Example 20. Expression of Ectopic Gm.FT2a Under Control of a pAP1 Promoter Alters Flowering Time and Pods Per Node in Soybean A transformation vector comprising Gm.FT2a under the control of a pAt.AP1 promoter with a Lhcb2 terminator region was constructed and used to transform soybean via *Agrobacterium*-mediated transformation. Transgenic plants generated from these events were characterized in the greenhouse with a 14 to 14.5 hour daylight photoperiod. Data was collected for six plants for each event and WT control. Table 35 provides the average phenotypic data collected from each event and WT control, and an average for each trait across all events.

TABLE 35

Phenotypic data for pAt.AP1::Gm.FT2a::T-Lhbc2 and WT plants in the greenhouse.

|  | WT | Average | Event 1 | Event 2 | Event 3 | Event 4 | Event 5 | Event 6 |
|---|---|---|---|---|---|---|---|---|
| DOFR1 | 38.3 | 27.4 | 26.7 | 26.7 | 29.3 | 28.2 | 27.0 | 26.5 |
| DOR7 | 106.7 | 94.0 | 91.2 | 92.8 | 96.7 | 93.7 | 94.2 | 95.7 |
| PDR1R7 | 68.3 | 66.6 | 64.5 | 66.2 | 67.3 | 65.5 | 67.2 | 69.2 |
| BRPPR8 | 26.2 | 8.5 | 3.3 | 6.3 | 17.2 | 10.0 | 6.7 | 7.7 |
| NDBRR8 | 352.5 | 90.5 | 14.7 | 75.2 | 175.3 | 106.8 | 91.2 | 79.7 |
| NDMSR8 | 31.5 | 31.8 | 28.8 | 34.5 | 34.3 | 31.7 | 27.5 | 33.8 |
| NDPLR8 | 384.0 | 122.2 | 43.5 | 109.7 | 209.7 | 138.5 | 118.4 | 113.5 |
| PDMSR8 | 69.3 | 165.8 | 122.5 | 212.3 | 120.7 | 182.0 | 158.7 | 198.3 |
| PDNDBRR8 | 1.7 | 3.2 | 1.7 | 4.2 | 2.5 | 4.3 | 2.7 | 4.1 |
| PDNDMSR8 | 2.1 | 5.2 | 4.2 | 6.1 | 3.5 | 6.3 | 5.2 | 5.8 |
| Pods/Node | 1.7 | 3.9 | 3.4 | 4.9 | 2.6 | 4.8 | 3.1 | 4.6 |
| PDPPR8 | 645.2 | 433.9 | 148.8 | 513.5 | 544.5 | 485.7 | 394.2 | 517.0 |
| PHTR8 | 1197.0 | 1153.4 | 1065.3 | 1280.5 | 1240.8 | 1177.5 | 961.1 | 1195.0 |
| SDPDR8 | 2.4 | 2.4 | 2.3 | 2.4 | 2.5 | 2.4 | 2.5 | 2.4 |
| SNUM | 1522.7 | 1059.9 | 349.7 | 1221.7 | 1363.7 | 1172.8 | 985.3 | 1266.3 |
| TPBR8 | 575.8 | 268.4 | 26.3 | 301.2 | 423.8 | 303.7 | 236.8 | 318.7 |
| SW1000 (grams) | 196.7 | 180.3 | 213.4 | 170.0 | 181.6 | 171.9 | 174.0 | 171.0 |

Soybean plants expressing the pAt.AP1::Gm.FT2a::T-Lhbc2 cassette flowered earlier (DOFR1) and had a significantly increased number of pods per node (and increased pods on the mainstem), but decreased branching, relative to WT control plants. Early field results with this construct also show early flowering, thus indicating that similar reproductive traits will be observed in plants grown under field conditions.

Example 21. Expression of Ectopic Gm.FT2a Under Control of a pSl.Nod Promoter in Soybean A transformation vector comprising Gm.FT2a under the control of a pSl.Nod promoter with a Lhcb2 terminator region was constructed and used to transform soybean via Agrobacterium-mediated transformation. Transgenic plants generated from these events were characterized in the greenhouse with a 14 to 14.5 hour daylight photoperiod. Data was collected for six plants for each event and WT control. Table 36 provides the average phenotypic data collected from each event and WT control, and an average for each trait across all events.

In these experiments, no significant change was observed between pSl.Nod::Gm.FT2a::T-Lhbc2 and WT plants. Early field results with this construct further indicate no change in the onset of flowering.

Example 22. Modification of Gm.FT2a Under Control of a pAt.Erl1 Promoter with an Artificial miRNA Driven by a pSl.MADS-RIN Promoter in Soybean To test the hypothesis that suppression of Gm.FT2a in late vegetative and/or reproductive tissues following initial ectopic expression of transgenic Gm.FT2a may extend reproductive duration in soybean plants, a transformation vector comprising Gm.FT2a under control of the vegetative stage, meristem-preferred pAt.Erl1 promoter (SEQ ID NO: 44) with GAPDH terminator region (T-GAPDH), and a transcribable DNA sequence encoding an artificial miRNA (SEQ ID NO: 67) targeting Gm.FT2a for suppression and under the control of a pSl.MADS-RIN promoter (SEQ ID NO: 72) with a T-Apx terminator region was constructed and used to transform soybean via Agrobacterium-mediated

TABLE 36

Phenotypic data for pSl.Nod::Gm.FT2a::T-Lhbc2 and WT plants in the greenhouse.

|  | WT | Average | Event 1 | Event 2 | Event 3 | Event 4 | Event 5 | Event 6 |
|---|---|---|---|---|---|---|---|---|
| DOFR1 | 38.3 | 38.1 | 37.5 | 37.0 | 38.3 | 38.8 | 39.5 | 37.7 |
| DOR7 | 107.8 | 106.4 | 105.2 | 105.0 | 105.5 | 109.2 | 104.7 | 108.8 |
| BRPPR8 | 25.3 | 25.3 | 29.3 | 23.8 | 25.2 | 23.8 | 24.3 | 25.3 |
| NDBRR8 | 312.7 | 337.9 | 373.5 | 315.2 | 336.5 | 333.0 | 317.0 | 352.3 |
| NDMSR8 | 38.2 | 36.4 | 34.7 | 37.2 | 37.2 | 39.3 | 36.3 | 33.8 |
| NDPLR8 | 350.8 | 373.3 | 401.8 | 352.3 | 373.7 | 372.3 | 353.3 | 386.2 |
| PDMSR8 | 89.5 | 91.3 | 89.3 | 96.7 | 100.0 | 97.8 | 93.2 | 70.5 |
| PDNDBRR8 | 2.0 | 1.8 | 1.8 | 1.8 | 1.8 | 1.9 | 1.8 | 1.7 |
| PDNDMSR8 | 2.3 | 2.3 | 1.7 | 2.6 | 2.7 | 2.5 | 2.6 | 2.0 |
| Pods/Node | 2.0 | 1.9 | 2.0 | 1.9 | 1.8 | 1.9 | 1.8 | 1.7 |
| PDPPR8 | 700.8 | 677.5 | 750.8 | 664.3 | 681.5 | 676.7 | 640.8 | 650.7 |
| PDR1R7 | 69.5 | 68.3 | 67.7 | 68.0 | 67.2 | 70.3 | 65.2 | 71.2 |
| PHTR8 | 1324.2 | 1256.6 | 1136.6 | 1220.8 | 1315.2 | 1321.7 | 1295.3 | 1249.8 |
| SDPDR8 | 2.5 | 2.4 | 2.1 | 2.4 | 2.4 | 2.4 | 2.5 | 2.5 |
| SNUM | 1713.3 | 1591.3 | 1517.7 | 1584.5 | 1642.7 | 1600.8 | 1588.7 | 1613.7 |
| TPBR8 | 611.3 | 586.2 | 661.5 | 567.7 | 581.5 | 578.8 | 547.7 | 580.2 |
| SW1000 (grams) | 187.6 | 188.0 | 197.5 | 187.2 | 189.4 | 185.2 | 187.6 | 181.3 | transformation. Transgenic plants generated from these events were characterized in the greenhouse with a 14 to 14.5 hour daylight photoperiod. Data was collected for six plants for each event and WT control. Table 37 provides the average phenotypic data collected from each event and WT control, and an average for each trait across all events.

TABLE 37

Phenotypic data for pAt.Erl1::Gm.FT2a::T-GAPDH|pSl.MADS-RIN::miRNA-FT2a:: T-Apx and WT plants grown in the greenhouse.

|  | WT | Average | Event 1 | Event 2 | Event 3 | Event 4 | Event 5 | Event 6 |
|---|---|---|---|---|---|---|---|---|
| DOFR1 | 39.3 | 33.8 | 33.0 | 34.0 | 35.7 | 35.0 | 33.3 | 31.5 |
| DOR7 | 107.5 | 99.9 | 98.7 | 98.5 | 99.0 | 105.8 | 101.0 | 96.5 |
| PDR1R7 | 68.2 | 66.2 | 65.7 | 64.6 | 63.3 | 70.8 | 67.7 | 65.0 |
| BRPPR8 | 16.5 | 14.4 | 13.3 | 14.2 | 13.2 | 17.8 | 16.0 | 12.0 |
| NDBRR8 | 180.2 | 131.8 | 100.3 | 128.8 | 124.5 | 187.0 | 141.2 | 108.8 |
| NDMSR8 | 31.7 | 32.2 | 31.0 | 32.2 | 28.8 | 36.3 | 31.7 | 33.0 |
| NDPLR8 | 211.8 | 163.9 | 131.3 | 161.0 | 153.3 | 223.3 | 172.8 | 141.8 |
| PDMSR8 | 100.7 | 127.3 | 135.7 | 136.0 | 106.0 | 112.3 | 116.7 | 157.0 |
| PDNDBRR8 | 2.2 | 2.3 | 2.6 | 2.3 | 2.2 | 1.9 | 2.3 | 2.6 |
| PDNDMSR8 | 3.2 | 4.0 | 4.4 | 4.3 | 3.7 | 3.1 | 3.8 | 4.8 |
| Pods/Node | 2.3 | 2.7 | 3.4 | 2.7 | 2.5 | 2.1 | 2.6 | 3.1 |
| PDPPR8 | 480.0 | 423.9 | 420.2 | 419.2 | 388.2 | 449.5 | 429.0 | 437.5 |
| PHTR8 | 1122.5 | 1118.6 | 1081.3 | 1152.5 | 1114.2 | 1185.5 | 1063.3 | 1114.9 |
| SDPDR8 | 2.2 | 2.3 | 2.3 | 2.3 | 2.3 | 2.3 | 2.4 | 2.4 |
| SNUM | 1060.8 | 983.4 | 980.5 | 954.7 | 894.7 | 1023.3 | 1003.7 | 1043.4 |
| TPBR8 | 379.3 | 296.6 | 284.5 | 283.2 | 282.2 | 337.2 | 312.3 | 280.5 |
| SW1000 (grams) | 152.2 | 154.1 | 163.6 | 151.6 | 159.8 | 148.4 | 153.7 | 147.3 |

Soybean plants expressing the for pAt.Er11::Gm.FT2a::T-GAPDH|pSl.MADS-RIN::miRNA-FT2a cassettes flowered slightly earlier (DOFR1) and had a slightly increased number of pods per node (and slightly increased pods on the mainstem), and a moderate decrease in branching, relative to WT control plants. Early field results with this construct also show moderately early flowering, indicating that similar moderate changes in reproductive traits will be observed with this construct in plants grown under field conditions.

Example 23. Modification of Ectopic Gm.FT2a Expression with a pAt.Er11 Promoter and a miR156 Sensor Alters Flowering Time A transformation vector comprising Gm.FT2a under control of the vegetative stage, meristem-preferred pAt.Er11 promoter (SEQ ID NO: 44) with a miR156 target site (SEQ ID NO: 106) and GAPDH terminator region (T-GAPDH) was constructed and used to transform soybean via *Agrobacterium*-mediated transformation. Transgenic plants generated from these events were tested in the field. Data was collected for six plants for each event and WT control. Early field results with this construct show early flowering, indicating that moderate changes in reproductive traits including increased pods per node will likely be observed with this construct in plants grown in the field or greenhouse.

Example 24. Modification of Ectopic Gm.FT2a Expression with a Truncated pAt.Erecta Promoter Alters Flowering Time A transformation vector comprising Gm.FT2a under control of a shorter truncated pAt.Erecta promoter (SEQ ID NO: 48) with a Lhcb2 terminator region (T-Lhcb2) was constructed and used to transform soybean via *Agrobacterium*-mediated transformation. Transgenic plants generated from these events were tested in the field. Data was collected for six plants for each event and WT control. Early field results with this construct show slightly earlier onset of flowering, indicating that slight or moderate changes in reproductive traits including slightly increased pods per node will likely be observed with this construct in plants grown in the field or greenhouse. Thus, more attenuated reproductive phenotypes and mitigated early termination effects may be achieved with this more minimal, truncated pAt.Erecta promoter (compare Examples 3 and 17).

Having described the present disclosure in detail, it will be apparent that modifications, variations, and equivalent embodiments are possible without departing from the spirit and scope of the present disclosure as described herein and in the appended claims. Furthermore, it should be appreciated that all examples in the present disclosure are provided as non-limiting examples.

What is claimed is:

1. A recombinant DNA construct comprising a first expression cassette and a second expression cassette, wherein the first expression cassette comprises a polynucleotide sequence encoding a florigenic Flowering Locus T (FT) protein comprising an amino acid sequence that is at least 90% identical to SEQ ID NO: 2 operably linked to a first plant expressible promoter, wherein the first plant expressible promoter is a vegetative stage promoter, and the second expression cassette comprises a transcribable DNA sequence encoding a RNA molecule comprising a targeting sequence that is at least 90% complementary to at least 21 consecutive nucleotides of the polynucleotide sequence of the first expression cassette, and wherein the transcribable DNA sequence is operably linked to a second plant expressible promoter, wherein the second plant expressible promoter is a late vegetative stage promoter and/or reproductive stage promoter.

2. The recombinant DNA construct of claim 1, wherein the transcribable DNA sequence comprises a sequence that is at least 90% complementary to SEQ ID NO: 65, 68, or 69.

3. The recombinant DNA construct of claim 1, wherein the florigenic FT protein further comprises one or more of the following amino acids: a tyrosine or other uncharged polar or nonpolar residue at the amino acid position of the florigenic FT protein corresponding to amino acid position 85 of SEQ ID NO: 14; a leucine or other nonpolar residue at the amino acid position of the florigenic FT protein corresponding to amino acid position 128 of SEQ ID NO: 14; and a tryptophan or other large nonpolar residue at the amino acid position of the florigenic FT protein corresponding to amino acid position 138 of SEQ ID NO: 14.

4. The recombinant DNA construct of claim 1, wherein the florigenic FT protein does not have one or more of the following amino acids: a histidine at the amino acid position corresponding to position 85 of SEQ ID NO: 14; a lysine or arginine at the amino acid position corresponding to position 128 of SEQ ID NO: 14; and a serine, aspartic acid, glutamic acid, lysine or arginine at the amino acid position corresponding to position 138 of SEQ ID NO: 14.

5. The recombinant DNA construct of claim 1, wherein the polynucleotide sequence is at least 90% identical to SEQ ID NO: 1.

6. The recombinant DNA construct of claim 1, wherein the first plant expressible promoter comprises a polynucleotide sequence that is at least 95% identical to a polynucleotide sequence selected from the group consisting of SEQ ID NOs: 31, 32, and 48.

7. The recombinant DNA construct of claim 1, wherein the second plant expressible promoter comprises a polynucleotide sequence that is at least 95% identical to SEQ ID NO: 49.

8. The recombinant DNA construct of claim 1, wherein the first plant expressible promoter is an early vegetative stage promoter.

9. The recombinant DNA construct of claim 1, wherein the second plant expressible promoter is a reproductive stage preferred promoter.

10. The recombinant DNA construct of claim 1, wherein the first plant expressible promoter initiates detectable expression of the polynucleotide sequence encoding the florigenic FT protein at an earlier developmental stage than the second plant expressible promoter initiates detectable expression of the transcribable DNA sequence.

11. A transgenic plant comprising an insertion of the recombinant DNA construct of claim 1 into the genome of at least one cell of the transgenic plant.

12. The transgenic plant of claim 11, wherein the transgenic plant is soybean.

13. The transgenic plant of claim 12, wherein the transgenic soybean plant produces more pods per node than a control plant not having the recombinant DNA construct.

14. The transgenic plant of claim 12, wherein the transgenic soybean plant produces more flowers per node than a control plant not having the recombinant DNA construct.

15. The transgenic plant of claim 12, wherein the transgenic soybean plant produces more seeds or pods per node of the transgenic plant than a control plant not having the recombinant DNA construct.

16. The transgenic plant of claim 12, wherein the transgenic soybean plant flowers earlier than a control plant not having the recombinant DNA construct.

17. The transgenic plant or part thereof of claim 11, wherein the transgenic plant has more floral racemes per node than a control plant not having the recombinant DNA construct.

18. The recombinant DNA construct of claim 1, wherein the targeting sequence of the RNA molecule is at least 95% complementary to at least 21 consecutive nucleotides of the polynucleotide sequence of the first expression cassette or an mRNA encoded by the polynucleotide sequence of the first expression cassette.

19. The recombinant DNA construct of claim 1, wherein the targeting sequence of the RNA molecule is 100% complementary to at least 21 consecutive nucleotides of the polynucleotide sequence of the first expression cassette or an mRNA encoded by the polynucleotide sequence of the first expression cassette.

20. The recombinant DNA construct of claim 1, wherein the amino acid sequence is at least 95% identical to SEQ ID NO: 2.

21. The recombinant DNA construct of claim 1, wherein the amino acid sequence is 100% identical to SEQ ID NO: 2.

22. The recombinant DNA construct of claim 1, wherein the first plant expressible promoter comprises a polynucleotide sequence that is 100% identical to a polynucleotide sequence selected from the group consisting of SEQ ID NOs: 31, 32, and 48.

23. The recombinant DNA construct of claim 1, wherein the second plant expressible promoter comprises a polynucleotide sequence that is 100% identical to SEQ ID NO: 49.

* * * * *

SEQUENCE LISTING

<160> NUMBER OF SEQ ID NOS: 110

<210> SEQ ID NO 1
<211> LENGTH: 531
<212> TYPE: DNA
<213> ORGANISM: Glycine max

<400> SEQUENCE: 1

```
atgcctagtg gaagtaggga tcctctcgtt gttggggag taattgggga tgtattggat      60 cctttgaat attctattcc tatgaggtt acctacaata acagagatgt cagcaatgga     120
tgtgaattca aaccctcaca gttgtcaac caaccaaggg taaatatcgg tggtgatgac     180
ctcaggaact tctatacttt gattgcggtt gatcccgatg cacctagccc aagtgacccc     240
aatttgagag aatacctcca ttggttggtg actgatatcc cagcaacaac aggggctagt     300
ttcggccatg aggttgtaac atatgaaagt ccaagaccaa tgatgggat tcatcgtttg     360 gtgtttgtgt tatttcgtca actgggtagg agaccgtgt atgcaccagg atggcgccag     420
aatttcaaca ctaaagaatt tgctgaactt tacaaccttg gattgccagt tgctgctgtc     480
tatttcaaca ttcagaggga atctggttct ggtggaagga ggttatacta a              531
```

<210> SEQ ID NO 2
<211> LENGTH: 176
<212> TYPE: PRT
<213> ORGANISM: Glycine max

<400> SEQUENCE: 2

```
Met Pro Ser Gly Ser Arg Asp Pro Leu Val Val Gly Val Ile Gly
1               5                   10                  15

Asp Val Leu Asp Pro Phe Glu Tyr Ser Ile Pro Met Arg Val Thr Tyr
                20                  25                  30

Asn Asn Arg Asp Val Ser Asn Gly Cys Glu Phe Lys Pro Ser Gln Val
            35                  40                  45

Val Asn Gln Pro Arg Val Asn Ile Gly Gly Asp Asp Leu Arg Asn Phe
        50                  55                  60

Tyr Thr Leu Ile Ala Val Asp Pro Asp Ala Pro Ser Pro Ser Asp Pro
65                  70                  75                  80

Asn Leu Arg Glu Tyr Leu His Trp Leu Val Thr Asp Ile Pro Ala Thr
                85                  90                  95

Thr Gly Ala Ser Phe Gly His Glu Val Val Thr Tyr Glu Ser Pro Arg
            100                 105                 110

Pro Met Met Gly Ile His Arg Leu Val Phe Val Leu Phe Arg Gln Leu
        115                 120                 125

Gly Arg Glu Thr Val Tyr Ala Pro Gly Trp Arg Gln Asn Phe Asn Thr
    130                 135                 140

Lys Glu Phe Ala Glu Leu Tyr Asn Leu Gly Leu Pro Val Ala Ala Val
145                 150                 155                 160

Tyr Phe Asn Ile Gln Arg Glu Ser Gly Ser Gly Gly Arg Arg Leu Tyr
                165                 170                 175
```

<210> SEQ ID NO 3
<211> LENGTH: 519
<212> TYPE: DNA
<213> ORGANISM: Glycine max

<400> SEQUENCE: 3

```
atggcacggg agaaccctct tgttattggt ggtgtgattg ggatgttct caaccctttt      60
```

```
acaagctccg tttctttgac tgtttcaatc aataatiaggg cgattagcaa tggcttggaa    120
ctcaggccct ctcaagttgt taatcgccct agggttactg ttggtggtga agacctaagg    180
accttctaca ctctggttat ggtggatgca gatgcaccta gccctagcaa ccctgtcttg    240
agggaatacc ttcactggat ggtgacagat attccagcta ccacaaatgc aagctttggg    300
agagaggttg tgttttatga gagcccgaac ccttcagtag ggattcatcg aatcgtgttc    360
gtattgttcc agcaattggg cagagacact gtcatcaccc cagaatggcg ccataatttc    420
aattccagaa actttgctga aattaataac cttgcacctg ttgcagcagc ttatgccaac    480
tgccaaagag agcgtggttg cggtggaagg agatattaa                           519
```

```
<210> SEQ ID NO 4
<211> LENGTH: 172
<212> TYPE: PRT
<213> ORGANISM: Glycine max

<400> SEQUENCE: 4

Met Ala Arg Glu Asn Pro Leu Val Ile Gly Gly Val Ile Gly Asp Val
1               5                   10                  15

Leu Asn Pro Phe Thr Ser Ser Val Ser Leu Thr Val Ser Ile Asn Asn
            20                  25                  30

Arg Ala Ile Ser Asn Gly Leu Glu Leu Arg Pro Ser Gln Val Val Asn
        35                  40                  45

Arg Pro Arg Val Thr Val Gly Gly Glu Asp Leu Arg Thr Phe Tyr Thr
    50                  55                  60

Leu Val Met Val Asp Ala Asp Ala Pro Ser Pro Ser Asn Pro Val Leu
65                  70                  75                  80

Arg Glu Tyr Leu His Trp Met Val Thr Asp Ile Pro Ala Thr Thr Asn
                85                  90                  95

Ala Ser Phe Gly Arg Glu Val Val Phe Tyr Glu Ser Pro Asn Pro Ser
            100                 105                 110

Val Gly Ile His Arg Ile Val Phe Val Leu Phe Gln Gln Leu Gly Arg
        115                 120                 125

Asp Thr Val Ile Thr Pro Glu Trp Arg His Asn Phe Asn Ser Arg Asn
    130                 135                 140

Phe Ala Glu Ile Asn Asn Leu Ala Pro Val Ala Ala Ala Tyr Ala Asn
145                 150                 155                 160

Cys Gln Arg Glu Arg Gly Cys Gly Gly Arg Arg Tyr
                165                 170
```

```
<210> SEQ ID NO 5
<211> LENGTH: 531
<212> TYPE: DNA
<213> ORGANISM: Glycine max

<400> SEQUENCE: 5
atgcctcgtg gaagtaggga ccctctagtt gttgggcgtg tgattgggga tgtattggac     60
ccttttgaat gttctattcc tatgagggtc acctacaata caaagatgt cagcaatgga    120 tgtgaattca aaccctcaca agttgtcaac caaccaagaa taaatatcgg tggtgatgat    180
ttcaggaact tctacacttt gatcgcggtt gatcctgatg cacctagccc aagtgatccc    240
aatttcagag aatacctcca ttggttagta actgacattc agcaacaac ggggcctact    300 ttcggtcatg aggttgtaac atatgaaaat ccacgaccca tgatgggat ccatcgtata    360 gtctttgtgt tatttcgtca acagggtaga gagacagtgt atgcaccagg atggcgccaa    420
```

```
aatttcatta ctagagaatt tgctgaactt tacaatcttg gattgccagt tgctgctgtc    480
tattttaaca tccagagaga atctggttgt ggtggaagaa ggctatgtta a             531
```

<210> SEQ ID NO 6
<211> LENGTH: 176
<212> TYPE: PRT
<213> ORGANISM: Glycine max

<400> SEQUENCE: 6

```
Met Pro Arg Gly Ser Arg Asp Pro Leu Val Val Gly Arg Val Ile Gly
1               5                   10                  15

Asp Val Leu Asp Pro Phe Glu Cys Ser Ile Pro Met Arg Val Thr Tyr
            20                  25                  30

Asn Asn Lys Asp Val Ser Asn Gly Cys Glu Phe Lys Pro Ser Gln Val
        35                  40                  45

Val Asn Gln Pro Arg Ile Asn Ile Gly Gly Asp Asp Phe Arg Asn Phe
    50                  55                  60

Tyr Thr Leu Ile Ala Val Asp Pro Asp Ala Pro Ser Pro Ser Asp Pro
65                  70                  75                  80

Asn Phe Arg Glu Tyr Leu His Trp Leu Val Thr Asp Ile Pro Ala Thr
                85                  90                  95

Thr Gly Pro Thr Phe Gly His Glu Val Val Thr Tyr Glu Asn Pro Arg
            100                 105                 110

Pro Met Met Gly Ile His Arg Ile Val Phe Val Leu Phe Arg Gln Gln
        115                 120                 125

Gly Arg Glu Thr Val Tyr Ala Pro Gly Trp Arg Gln Asn Phe Ile Thr
    130                 135                 140

Arg Glu Phe Ala Glu Leu Tyr Asn Leu Gly Leu Pro Val Ala Ala Val
145                 150                 155                 160

Tyr Phe Asn Ile Gln Arg Glu Ser Gly Cys Gly Gly Arg Arg Leu Cys
                165                 170                 175
```

<210> SEQ ID NO 7
<211> LENGTH: 528
<212> TYPE: DNA
<213> ORGANISM: Zea mays

<400> SEQUENCE: 7

```
atgtcagcaa ccgatcattt ggttatggct cgtgtcatac aggatgtatt ggatcccttt     60
acaccaacca ttccactaag aataacgtac aacaataggc tacttctgcc aagtgctgag    120
ctaaagccat ccgcggttgt aagtaaacca cgagtcgata tcggtggcag tgacatgagg    180
gctttctaca ccctggtact gattgacccg gatgccccaa gtccaagcca tccatcacta    240
agggagtact tgcactggat ggtgacagat attccagaaa caactagtgt caactttggc    300
caagagctaa tattttatga gaggccggac ccaagatctg gcatccacag gctggtattt    360
gtgctgttcc gtcaacttgg caggggggaca gttttttgcac cagaaatgcg ccacaacttc    420
aactgcagaa gctttgcacg gcaatatcac ctcagcattg ccaccgctac acatttcaac    480
tgtcaaaggg aaggtggatc cggcggaaga aggtttaggg aagagtag                528
```

<210> SEQ ID NO 8
<211> LENGTH: 175
<212> TYPE: PRT
<213> ORGANISM: Zea mays

<400> SEQUENCE: 8

```
Met Ser Ala Thr Asp His Leu Val Met Ala Arg Val Ile Gln Asp Val
1               5                   10                  15

Leu Asp Pro Phe Thr Pro Thr Ile Pro Leu Arg Ile Tyr Asn Asn
            20                  25                  30

Arg Leu Leu Leu Pro Ser Ala Glu Leu Lys Pro Ser Ala Val Val Ser
                35                  40                  45

Lys Pro Arg Val Asp Ile Gly Gly Ser Asp Met Arg Ala Phe Tyr Thr
50                  55                  60

Leu Val Leu Ile Asp Pro Asp Ala Pro Ser Pro Ser His Pro Ser Leu
65                  70                  75                  80

Arg Glu Tyr Leu His Trp Met Val Thr Asp Ile Pro Glu Thr Thr Ser
                85                  90                  95

Val Asn Phe Gly Gln Glu Leu Ile Phe Tyr Glu Arg Pro Asp Pro Arg
            100                 105                 110

Ser Gly Ile His Arg Leu Val Phe Val Leu Phe Arg Gln Leu Gly Arg
                115                 120                 125

Gly Thr Val Phe Ala Pro Glu Met Arg His Asn Phe Asn Cys Arg Ser
130                 135                 140

Phe Ala Arg Gln Tyr His Leu Ser Ile Ala Thr Ala Thr His Phe Asn
145                 150                 155                 160

Cys Gln Arg Glu Gly Gly Ser Gly Gly Arg Arg Phe Arg Glu Glu
                165                 170                 175
```

<210> SEQ ID NO 9
<211> LENGTH: 525
<212> TYPE: DNA
<213> ORGANISM: Nicotiana tabacum

<400> SEQUENCE: 9

```
atgccaagaa tagatccttt gatagttggt cgtgtggtag agatgttttt agatccattc    60
acaaggtctg ttgatcttag agtggtttac aataataggg aagtcaacaa tgcatgtggc   120
ttgaaacctt ctcaaattgt tacgcaacct agggttcaaa ttggagggga tgatcttcgc   180
aactttacta ctctggttat ggtggatcct gatgctccaa gcccaagcaa ccctaacctg   240
agggagtatc tacactggct ggtcacagat atcccagcaa ctacagatac aagctttgga   300
aatgaagtta tatgctacga gaatccacaa ccatcattgg gaattcatcg ctttgttttc   360
gtgttgtttc gacaattggg tcgcgaaact gtgtatgcac aggttggcg tcagaatttc    420 agcacaagag actttgcaga agtttacaat cttggtttgc ccgtttctgc tgtttacttc   480
aattgccata gggagagtgg tactggtggc cgccgcgcat attaa                    525
```

<210> SEQ ID NO 10
<211> LENGTH: 174
<212> TYPE: PRT
<213> ORGANISM: Nicotiana tabacum

<400> SEQUENCE: 10

```
Met Pro Arg Ile Asp Pro Leu Ile Val Gly Arg Val Val Gly Asp Val
1               5                   10                  15

Leu Asp Pro Phe Thr Arg Ser Val Asp Leu Arg Val Val Tyr Asn Asn
            20                  25                  30

Arg Glu Val Asn Asn Ala Cys Gly Leu Lys Pro Ser Gln Ile Val Thr
                35                  40                  45

Gln Pro Arg Val Gln Ile Gly Gly Asp Asp Leu Arg Asn Phe Tyr Thr
50                  55                  60
```

Leu Val Met Val Asp Pro Asp Ala Pro Ser Pro Ser Asn Pro Asn Leu
65                  70                  75                  80

Arg Glu Tyr Leu His Trp Leu Val Thr Asp Ile Pro Ala Thr Thr Asp
            85                  90                  95

Thr Ser Phe Gly Asn Glu Val Ile Cys Tyr Glu Asn Pro Gln Pro Ser
        100                 105                 110

Leu Gly Ile His Arg Phe Val Phe Leu Phe Arg Gln Leu Gly Arg
    115                 120                 125

Glu Thr Val Tyr Ala Pro Gly Trp Arg Gln Asn Phe Ser Thr Arg Asp
130                 135                 140

Phe Ala Glu Val Tyr Asn Leu Gly Leu Pro Val Ser Ala Val Tyr Phe
145                 150                 155                 160

Asn Cys His Arg Glu Ser Gly Thr Gly Gly Arg Arg Ala Tyr
                165                 170

<210> SEQ ID NO 11
<211> LENGTH: 534
<212> TYPE: DNA
<213> ORGANISM: Solanum lycopersicum

<400> SEQUENCE: 11
atgcctagag aacgtgatcc tcttgttgtt ggtcgtgtgg taggggatgt attggaccct      60
ttcacaagaa ctattggcct aagagttata tatagagata gagaagttaa taatggatgc     120
gagcttaggc cttcccaagt tattaaccag ccaagggttg aagttggagg agatgaccta     180
cgtacctttt tcactttggt tatggtggac cctgatgctc caagtccgag tgatccaaat     240
ctgagagaat accttcactg gttggtcacc gatattccag ctaccacagg ttcaagtttt     300
gggcaagaaa tagtgagcta tgaaagtcca agaccatcaa tgggaataca tcgatttgta     360
tttgtattat tcagacaatt aggtcggcaa acagtgtatg ctccaggatg gcgtcagaat     420
ttcaacacaa gagattttgc agaactttat aatcttggtt tacctgttgc tgctgtctat     480
tttaattgtc aaagagagag tggcagtggt ggacgtagaa gatctgctga ttga           534

<210> SEQ ID NO 12
<211> LENGTH: 177
<212> TYPE: PRT
<213> ORGANISM: Solanum lycopersicum

<400> SEQUENCE: 12

Met Pro Arg Glu Arg Asp Pro Leu Val Val Gly Arg Val Val Gly Asp
1               5                   10                  15

Val Leu Asp Pro Phe Thr Arg Thr Ile Gly Leu Arg Val Ile Tyr Arg
                20                  25                  30

Asp Arg Glu Val Asn Asn Gly Cys Glu Leu Arg Pro Ser Gln Val Ile
            35                  40                  45

Asn Gln Pro Arg Val Glu Val Gly Gly Asp Asp Leu Arg Thr Phe Phe
        50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ser Ser Phe Gly Gln Glu Ile Val Ser Tyr Glu Ser Pro Arg Pro
            100                 105                 110

Ser Met Gly Ile His Arg Phe Val Phe Val Leu Phe Arg Gln Leu Gly
        115                 120                 125

```
Arg Gln Thr Val Tyr Ala Pro Gly Trp Arg Gln Asn Phe Asn Thr Arg
        130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Ser Ala
                165                 170                 175

Asp

<210> SEQ ID NO 13
<211> LENGTH: 528
<212> TYPE: DNA
<213> ORGANISM: Arabidopsis thaliana

<400> SEQUENCE: 13
atgtctataa atataagaga ccctcttata gtaagcagag ttgttggaga cgttcttgat      60
ccgtttaata gatcaatcac tctaaaggtt acttatggcc aaagagaggt gactaatggc    120
ttggatctaa ggccttctca ggttcaaaac aagccaagag ttgagattgg tggagaagac    180
ctcaggaact tctatacttt ggttatggtg gatccagatg ttccaagtcc tagcaaccct    240 caccteegag aatatctcca ttggttggtg actgatatcc ctgctacaac tggaacaacc    300
tttggcaatg agattgtgtg ttacgaaaat ccaagtccca ctgcaggaat tcatcgtgtc    360
gtgtttatat tgtttcgaca gcttggcagg caaacagtgt atgcaccagg gtggcgccag    420
aacttcaaca ctcgcgagtt tgctgagatc tacaatctcg gccttccegt ggccgcagtt    480 ttctacaatt gtcagaggga gagtggctgc ggaggaagaa gactttag                 528

<210> SEQ ID NO 14
<211> LENGTH: 175
<212> TYPE: PRT
<213> ORGANISM: Arabidopsis thaliana

<400> SEQUENCE: 14

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
                20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
        50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175
```

```
<210> SEQ ID NO 15
<211> LENGTH: 528
<212> TYPE: DNA
<213> ORGANISM: Arabidopsis thaliana

<400> SEQUENCE: 15
atgtctttaa gtcgtagaga tcctcttgtg gtcggcagtg ttgttggaga tgttcttgat      60
cctttcacga ggttggtctc tcttaaggtc acttatggcc atagagaggt tactaatggc     120
ttggatctaa ggccttctca agttctgaac aaaccaatag tggagattgg aggagacgac     180
ttcagaaatt tctacacctt ggttatggtg atccagatg tgccgagtcc aagcaaccct      240
caccaacgag aatatctcca ctggttggtg actgatatac ctgccaccac tggaaatgcc     300
tttggcaatg aggtggtgtg ctacgagagt ccacgtcccc cctcgggaat tcatcgtatt     360
gtgttggtat tgttccggca actcggaaga caaacggttt atgcaccggg gtggcgccaa     420
cagttcaaca ctcgtgagtt tgctgagatc tacaatcttg gtcttcctgt ggctgcctct     480
tacttcaact gccagaggga gaatggctgt gggggaagaa gaacgtag                  528

<210> SEQ ID NO 16
<211> LENGTH: 175
<212> TYPE: PRT
<213> ORGANISM: Arabidopsis thaliana

<400> SEQUENCE: 16

Met Ser Leu Ser Arg Arg Asp Pro Leu Val Val Gly Ser Val Val Gly
1               5                   10                  15

Asp Val Leu Asp Pro Phe Thr Arg Leu Val Ser Leu Lys Val Thr Tyr
            20                  25                  30

Gly His Arg Glu Val Thr Asn Gly Leu Asp Leu Arg Pro Ser Gln Val
        35                  40                  45

Leu Asn Lys Pro Ile Val Glu Ile Gly Gly Asp Asp Phe Arg Asn Phe
    50                  55                  60

Tyr Thr Leu Val Met Val Asp Pro Asp Val Pro Ser Pro Ser Asn Pro
65                  70                  75                  80

His Gln Arg Glu Tyr Leu His Trp Leu Val Thr Asp Ile Pro Ala Thr
                85                  90                  95

Thr Gly Asn Ala Phe Gly Asn Glu Val Val Cys Tyr Glu Ser Pro Arg
            100                 105                 110

Pro Pro Ser Gly Ile His Arg Ile Val Leu Val Leu Phe Arg Gln Leu
        115                 120                 125

Gly Arg Gln Thr Val Tyr Ala Pro Gly Trp Arg Gln Gln Phe Asn Thr
    130                 135                 140

Arg Glu Phe Ala Glu Ile Tyr Asn Leu Gly Leu Pro Val Ala Ala Ser
145                 150                 155                 160

Tyr Phe Asn Cys Gln Arg Glu Asn Gly Cys Gly Gly Arg Arg Thr
                165                 170                 175

<210> SEQ ID NO 17
<211> LENGTH: 540
<212> TYPE: DNA
<213> ORGANISM: Oryza sativa

<400> SEQUENCE: 17
atggccggaa gtggcaggga cagggaccct cttgtggttg gtagggttgt gggtgatgtg      60
ctggacgcgt tcgtccggag caccaacctc aaggtcacct atggctccaa gaccgtgtcc     120
aatggctgcg agctcaagcc gtccatggtc acccaccagc ctagggtcga ggtcggcggc     180
```

| | |
|---|---|
| aatgacatga ggacattcta caccottgtg atggtagacc cagatgcacc aagcccaagt | 240 |
| gaccctaacc ttagggagta tctacattgg ttggtcactg atattcctgg tactactgca | 300 |
| gcgtcatttg gcaagaggt gatgtgctac gagagcccaa ggccaaccat ggggatccac | 360 |
| cggctggtgt tcgtgctgtt ccagcagctg ggcgtcaga cagtgtacgc gcccgggtgg | 420 |
| cgtcagaact tcaacaccaa ggacttcgcc gagctctaca acctcggctc gccggtcgcc | 480 |
| gccgtctact tcaactgcca gcgcgaggca ggctccggcg caggagggt ctaccctag | 540 |

<210> SEQ ID NO 18
<211> LENGTH: 179
<212> TYPE: PRT
<213> ORGANISM: Oryza sativa

<400> SEQUENCE: 18

Met Ala Gly Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
    130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Arg Arg
                165                 170                 175

Val Tyr Pro

<210> SEQ ID NO 19
<211> LENGTH: 525
<212> TYPE: DNA
<213> ORGANISM: Populus trichocarpa

<400> SEQUENCE: 19

| | |
|---|---|
| atgtcaaggg acagagatcc tctgagcgtt ggccgtgtta tagggacgt gctggacccc | 60 |
| ttcacaaagt ctatctccct cagggtcact tacagctcca gagaggtcaa caatggttgc | 120 |
| gagctcaagc cctctcaggt tgccaaccag cctaggggttg atattggcgg ggaagatcta | 180 |
| aggaccttct acactctggt tatggtggac cctgatgcac ccagcccaag tgaccccagc | 240 |
| ctaagagaat atttgcattg gttggtgact gatattccag caacaactgg ggcaagcttt | 300 |
| ggccatgaaa ctgtgtgcta tgagagcccg aggccgacaa tgggaattca tcggtttgtt | 360 |
| ttcgtcttgt ttcggcaact gggcaggcaa actgtgtatg cccctgggtg cgccagaac | 420 |
| ttcaacacca gagactttgc tgaggtctac aatcttggat cgccagtggc tgctgtttat | 480 |

```
ttcaactgcc agagggagag tggctctggt ggtaggaggc gataa              525
```

<210> SEQ ID NO 20
<211> LENGTH: 174
<212> TYPE: PRT
<213> ORGANISM: Populus trichocarpa

<400> SEQUENCE: 20

```
Met Ser Arg Asp Arg Asp Pro Leu Ser Val Gly Arg Val Ile Gly Asp
1               5                   10                  15

Val Leu Asp Pro Phe Thr Lys Ser Ile Ser Leu Arg Val Thr Tyr Ser
                20                  25                  30

Ser Arg Glu Val Asn Asn Gly Cys Glu Leu Lys Pro Ser Gln Val Ala
            35                  40                  45

Asn Gln Pro Arg Val Asp Ile Gly Gly Glu Asp Leu Arg Thr Phe Tyr
        50                  55                  60

Thr Leu Val Met Val Asp Pro Asp Ala Pro Ser Pro Ser Asp Pro Ser
65                  70                  75                  80

Leu Arg Glu Tyr Leu His Trp Leu Val Thr Asp Ile Pro Ala Thr Thr
                85                  90                  95

Gly Ala Ser Phe Gly His Glu Thr Val Cys Tyr Glu Ser Pro Arg Pro
                100                 105                 110

Thr Met Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Arg
        130                 135                 140

Asp Phe Ala Glu Val Tyr Asn Leu Gly Ser Pro Val Ala Ala Val Tyr
145                 150                 155                 160

Phe Asn Cys Gln Arg Glu Ser Gly Ser Gly Arg Arg Arg
                165                 170
```

<210> SEQ ID NO 21
<211> LENGTH: 519
<212> TYPE: DNA
<213> ORGANISM: Glycine max

<400> SEQUENCE: 21

```
atggcacggg agaaccctct tgttattggg ggtgtgattg ggatgttct caatccttt      60 acaatctccg tttcttttac tatttcaatc aataataggg cgattagcaa tggcttggaa   120
ctgaggccct ctcaagttgt taatcgccct agagtcactg ttggtggtga agacctaagg   180
accttctaca cactggttat ggtggatgca gatgcaccta gccctagcaa ccctgtcttg   240
agggaatacc ttcactggat ggtgacagat attccagcta ccacaaatgc aagctttggg   300
agagaggttg tgttttatga gagcccgaac ccttcagcag ggattcatcg acttgtgttc   360
atattattcc agcaactggg cagagacact gtcatcaccc cagaatggcg ccataatttc   420
aattccagaa actttgctga attaataaac cttgcacctg ttgcagcagc ttatgccaac   480
tgccaaagag agcgtggttg cggtggaagg agatattaa                           519
```

<210> SEQ ID NO 22
<211> LENGTH: 172
<212> TYPE: PRT
<213> ORGANISM: Glycine max

<400> SEQUENCE: 22

```
Met Ala Arg Glu Asn Pro Leu Val Ile Gly Gly Val Ile Gly Asp Val
```

```
            1               5                  10                 15
Leu Asn Pro Phe Thr Ile Ser Val Ser Phe Thr Ile Ser Ile Asn Asn
                    20                 25                 30

Arg Ala Ile Ser Asn Gly Leu Glu Leu Arg Pro Ser Gln Val Val Asn
            35                 40                 45

Arg Pro Arg Val Thr Val Gly Gly Glu Asp Leu Arg Thr Phe Tyr Thr
        50                 55                 60

Leu Val Met Val Asp Ala Asp Ala Pro Ser Pro Ser Asn Pro Val Leu
65                  70                 75                 80

Arg Glu Tyr Leu His Trp Met Val Thr Asp Ile Pro Ala Thr Thr Asn
                85                 90                 95

Ala Ser Phe Gly Arg Glu Val Val Phe Tyr Glu Ser Pro Asn Pro Ser
                100                125                110

Ala Gly Ile His Arg Leu Val Phe Ile Leu Phe Gln Gln Leu Gly Arg
            115                120                125

Asp Thr Val Ile Thr Pro Glu Trp Arg His Asn Phe Asn Ser Arg Asn
        130                135                140

Phe Ala Glu Ile Asn Asn Leu Ala Pro Val Ala Ala Ala Tyr Ala Asn
145                 150                155                160

Cys Gln Arg Glu Arg Gly Cys Gly Gly Arg Arg Tyr
                165                170
```

<210> SEQ ID NO 23
<211> LENGTH: 525
<212> TYPE: DNA
<213> ORGANISM: Gossypium hirsutum

<400> SEQUENCE: 23

```
atgcctagag acagagatcc tttggttgtt ggtagggtta taggagatgt gttggaccct      60
tttacaaggt ctatttcact tagggtcact tatgctacta gggatgttag caatggtgtt     120
gagcttaagc catctcaagt tgttaaccaa ccaaggggtg atattggtgg ggatgatctg     180
aggaccttct acaccttggt tatggtggat cctgatgctc caagtccaag tgacccaaac     240
ctcagggaat acttgcactg gttggttact gatattccag ccacaactgg tgcaagcttt     300
ggtcaagagg tggtctgcta tgagagccca cgaccaacgg tcggtatcca tcgttttgtg     360
ttcgtgctgt tccggcaact tggaaggcaa acggtgtacg ctccagggtg cgccaaaac      420
ttcaacacta gggactttgc tgagctttac aacctcgggt tgccggtggc tgctgtttac     480
tttaactgcc agagggagag tggatccggt ggccgtagga catga                    525
```

<210> SEQ ID NO 24
<211> LENGTH: 174
<212> TYPE: PRT
<213> ORGANISM: Gossypium hirsutum

<400> SEQUENCE: 24

```
Met Pro Arg Asp Arg Asp Pro Leu Val Val Gly Arg Val Ile Gly Asp
1               5                  10                 15

Val Leu Asp Pro Phe Thr Arg Ser Ile Ser Leu Arg Val Thr Tyr Ala
                20                 25                 30

Thr Arg Asp Val Ser Asn Gly Val Glu Leu Lys Pro Ser Gln Val Val
            35                 40                 45

Asn Gln Pro Arg Val Asp Ile Gly Gly Asp Asp Leu Arg Thr Phe Tyr
        50                 55                 60

Thr Leu Val Met Val Asp Pro Asp Ala Pro Ser Pro Ser Asp Pro Asn
```

```
                65                  70                  75                  80
Leu Arg Glu Tyr Leu His Trp Leu Val Thr Asp Ile Pro Ala Thr Thr
                    85                  90                  95

Gly Ala Ser Phe Gly Gln Glu Val Val Cys Tyr Glu Ser Pro Arg Pro
                100                 105                 110

Thr Val Gly Ile His Arg Phe Val Phe Val Leu Phe Arg Gln Leu Gly
                115                 120                 125

Arg Gln Thr Val Tyr Ala Pro Gly Trp Arg Gln Asn Phe Asn Thr Arg
            130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Arg Arg Thr
                165                 170

<210> SEQ ID NO 25
<211> LENGTH: 528
<212> TYPE: DNA
<213> ORGANISM: Brassica napus

<400> SEQUENCE: 25
atgtctttaa gtaatagaga tcctcttgtg gtagggagag ttgtaggaga cgttcttgaa      60
tgtttcacaa gatcaatcga tctaaggggtt acttatggcc aaagagaggt gacaaatggg    120
ttggatctaa ggccttctca agttctcaac aagccaagag ttgagattgg tggagaagac    180
ctaaggaact tctatacttt ggttatggtg gatccagatg ttccaagtcc tagcaatcct    240
cacctccgag aatatcttca ctggttggtg actgatatcc cagcgacaac tggaacaaac    300
tttggcaatg agattgtgtc ttacgagagt ccaaggccca actcgggtat tcatcgtatc    360
gtgctcgtat tgttccgaca gctcggtagg caaacagtgt atgaaccagg atggcgccaa    420
caattcaaca ctcgtgagtt tgcttcccta caatctcg gccttcccgt ggctgcggtt       480
ttctacaatt gtcagaggga gagtggctgc ggaggacgaa aagttag                   528

<210> SEQ ID NO 26
<211> LENGTH: 175
<212> TYPE: PRT
<213> ORGANISM: Brassica napus

<400> SEQUENCE: 26

Met Ser Leu Ser Asn Arg Asp Pro Leu Val Val Gly Arg Val Val Gly
1               5                  10                  15

Asp Val Leu Glu Cys Phe Thr Arg Ser Ile Asp Leu Arg Val Thr Tyr
                20                  25                  30

Gly Gln Arg Glu Val Thr Asn Gly Leu Asp Leu Arg Pro Ser Gln Val
            35                  40                  45

Leu Asn Lys Pro Arg Val Glu Ile Gly Gly Glu Asp Leu Arg Asn Phe
        50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Asn Phe Gly Asn Glu Ile Val Ser Tyr Glu Ser Pro Arg
                100                 105                 110

Pro Asn Ser Gly Ile His Arg Ile Val Leu Val Leu Phe Arg Gln Leu
            115                 120                 125

Gly Arg Gln Thr Val Tyr Glu Pro Gly Trp Arg Gln Gln Phe Asn Thr
```

```
              130                 135                 140
Arg Glu Phe Ala Ser Leu Tyr Asn Leu Gly Leu Pro Val Ala Ala Val
145                 150                 155                 160

Phe Tyr Asn Cys Gln Arg Glu Ser Gly Cys Gly Arg Arg Ser
                165                 170                 175

<210> SEQ ID NO 27
<211> LENGTH: 543
<212> TYPE: DNA
<213> ORGANISM: Triticum aestivum

<400> SEQUENCE: 27
atgtcggcag cggatccatt ggttgtggct catgttttac aagatgtgct tgatccattt      60
acatcaactg ttccgctcag gatagcctac aacaataggc tagttctggc aggtgctgag     120
ctaagaccat ctgcaattgt aagcaagcca cgagttgata tcggtggcag tgacatgaga     180
gtcctctata ccctgatatt ggtggatcca gacgccccaa gcccaagtca cccatcacta     240
agggagtact tgcactggat ggtgtccgac atccctggaa caactagtgg cagcttcggc     300
caagagcttg tagtttatga agaccagaa cccagatctg gtattaccg atggtatt         360 gtgctgttcc agcaactagg caggggaaca gttttgcac cagatgtgcg acacaatttc      420
agctgcagaa actttgcacg gcagtaccac ctcaacattg tggctgcctc atatttcaac     480
tgtcaaaggg aaggtggatc tggcggaaga aggtttaggc cagaaagttc tcaaggggag     540
tag                                                                    543

<210> SEQ ID NO 28
<211> LENGTH: 180
<212> TYPE: PRT
<213> ORGANISM: Triticum aestivum

<400> SEQUENCE: 28

Met Ser Ala Ala Asp Pro Leu Val Val Ala His Val Leu Gln Asp Val
1               5                   10                  15

Leu Asp Pro Phe Thr Ser Thr Val Pro Leu Arg Ile Ala Tyr Asn Asn
            20                  25                  30

Arg Leu Val Leu Ala Gly Ala Glu Leu Arg Pro Ser Ala Ile Val Ser
        35                  40                  45

Lys Pro Arg Val Asp Ile Gly Gly Ser Asp Met Arg Val Leu Tyr Thr
    50                  55                  60

Leu Ile Leu Val Asp Pro Asp Ala Pro Ser Pro Ser His Pro Ser Leu
65                  70                  75                  80

Arg Glu Tyr Leu His Trp Met Val Ser Asp Ile Pro Gly Thr Thr Ser
                85                  90                  95

Gly Ser Phe Gly Gln Glu Leu Val Val Tyr Glu Arg Pro Glu Pro Arg
            100                 105                 110

Ser Gly Ile His Arg Met Val Phe Val Leu Phe Gln Gln Leu Gly Arg
        115                 120                 125

Gly Thr Val Phe Ala Pro Asp Val Arg His Asn Phe Ser Cys Arg Asn
    130                 135                 140

Phe Ala Arg Gln Tyr His Leu Asn Ile Val Ala Ala Ser Tyr Phe Asn
145                 150                 155                 160

Cys Gln Arg Glu Gly Gly Ser Gly Gly Arg Arg Phe Arg Pro Glu Ser
                165                 170                 175

Ser Gln Gly Glu
            180
```

<210> SEQ ID NO 29
<211> LENGTH: 531
<212> TYPE: DNA
<213> ORGANISM: Pisum sativum

<400> SEQUENCE: 29

```
atggcaggta gtagcaggaa tcctctcgct gttggtcgtg taattggtga tgtgatagac      60
ccctttgaaa attcggttcc tctccgagtc acctatggta gtagagatgt gaataatggt     120
tgtgagctta aaccctctca cgttggaaat caacccagag tgaatgttgg tggaaacgat     180
ctcaggaaca tttatactct agttcttgtg acccagatt cacctagccc aagcaaccct      240
acttttaggg agtaccttca ttggttggtg actgatattc cagctactac tgaggtcagt     300
ttcggtaacg aaattgtgag ctatgaaagg ccacgaccca cctcagggat ccatcgtttc     360
gtgtttatac tattccgtca gcagtgtaga caaagggttt acgctccagg atggcgacag     420
aatttcaata caagagaatt tgctgaactt tacaatcttg gatcaccagt tgctgctgtt     480
ttcttcaact gtcaaaggga gagtggctct ggtggaagaa catttagata a              531
```

<210> SEQ ID NO 30
<211> LENGTH: 176
<212> TYPE: PRT
<213> ORGANISM: Pisum sativum

<400> SEQUENCE: 30

```
Met Ala Gly Ser Ser Arg Asn Pro Leu Ala Val Gly Arg Val Ile Gly
1               5                   10                  15

Asp Val Ile Asp Pro Phe Glu Asn Ser Val Pro Leu Arg Val Thr Tyr
            20                  25                  30

Gly Ser Arg Asp Val Asn Asn Gly Cys Glu Leu Lys Pro Ser His Val
        35                  40                  45

Gly Asn Gln Pro Arg Val Asn Val Gly Gly Asn Asp Leu Arg Asn Ile
    50                  55                  60

Tyr Thr Leu Val Leu Val Asp Pro Asp Ser Pro Ser Pro Ser Asn Pro
65                  70                  75                  80

Thr Phe Arg Glu Tyr Leu His Trp Leu Val Thr Asp Ile Pro Ala Thr
                85                  90                  95

Thr Glu Val Ser Phe Gly Asn Glu Ile Val Ser Tyr Glu Arg Pro Arg
            100                 105                 110

Pro Thr Ser Gly Ile His Arg Phe Val Phe Ile Leu Phe Arg Gln Gln
        115                 120                 125

Cys Arg Gln Arg Val Tyr Ala Pro Gly Trp Arg Gln Asn Phe Asn Thr
    130                 135                 140

Arg Glu Phe Ala Glu Leu Tyr Asn Leu Gly Ser Pro Val Ala Ala Val
145                 150                 155                 160

Phe Phe Asn Cys Gln Arg Glu Ser Gly Ser Gly Gly Arg Thr Phe Arg
                165                 170                 175
```

<210> SEQ ID NO 31
<211> LENGTH: 901
<212> TYPE: DNA
<213> ORGANISM: Arabidopsis thaliana

<400> SEQUENCE: 31

```
aaaccgaccg gagccaacca aaccggttaa catcctaaaa ccaatcatat tttattaagt      60
tttgtgttga tgctaaacca aaaatcattg gcatgcatat ttctaaattt agtaataaac     120
```

```
aaaaacactt agaaatcaca cgttcactat actaaaaaac gttgacaaaa acacaacaac    180
tatactaata attaaagaag agaaaactga accaaacttt ttgtaaactc ctgaatttaa    240
attagtaatt gaagtaagaa gatgaagaag aacatgttaa gcaaacaaaa aaattacact    300
aaaatcatat aaaaatacat aattacaaaa gtacccataa gatggattta ttgatatggg    360
tcatctgtga aacaagccac agagagacaa agactcgtaa gtattgggca acgaaagcga    420
cctcctttat tcaccactgc cattaacatg ttcttcttct ccttcttctt ctacatttta    480
tgaccgtttt acccttcaag agagagaaac aaaatcactc cctctcactc actctatctc    540
tctcttctgc aaagcttcag aactctggca gagagataaa agatgatggg gttttaact    600 ttatcctccc caaataattc ttcttccctt catctctctc tcttacacaa caggtcccta    660
catttgtaca atctcctctc tttaaagact ctctctcttt ctctctccat ctctatctta    720 ctctgtatt ctgtcgtctg agcactcaat gaaaccactg taaatttccg ccagaatttg    780
atgtgatgga acgataaaaa tcatttttc tcggttaaag taaaaaaaca aaaacaaatt    840
tctgtagaaa tcataataaa agaaagaaaa aaaatctaat gtcggtacat aatacggttc    900
t                                                                    901

<210> SEQ ID NO 32
<211> LENGTH: 507
<212> TYPE: DNA
<213> ORGANISM: Arabidopsis thaliana

<400> SEQUENCE: 32
aaaccgaccg gagccaacca aaccggttaa catcctaaaa ccaatcatat tttattaagt     60
tttgtgttga tgctaaacca aaaatcattg gcatgcatat ttctaaattt agtaataaac    120
aaaaacactt agaaatcaca cgttcactat actaaaaaac gttgacaaaa acacaacaac    180
tatactaata attaaagaag agaaaactga accaaacttt ttgtaaactc ctgaatttaa    240
attagtaatt gcacaacagg tccctacatt tgtacaatct cctctcttta aagactctct    300
ctctttctct ctccatctct atcttactct gtatttctgt cgtctgagca ctcaatgaaa    360
ccactgtaaa tttccgccag aatttgatgt gatggaacga taaaaatcat ttttctcgg    420 ttaaagtaaa aaacaaaaa caaatttctg tagaaatcat aataaagaa agaaaaaaaa    480 tctaatgtcg gtacataata cggttct                                        507

<210> SEQ ID NO 33
<211> LENGTH: 2000
<212> TYPE: DNA
<213> ORGANISM: Glycine max

<400> SEQUENCE: 33
catgagcaag taagtaaaca ttttatctct gttacactcc aaacacatac actaacttaa     60
gcagagtcct ttttcggcta ttcactccat caccaaagaa tgagctcatc cataaaaaca    120
tatacatgtc aacatgtcga agatgtaga acctggtaac aataataaag aatgataatt    180
tttttatttt taaaacgaag cactaaaata gatttaatta tatttatcat ataaaattac    240
caattaatca tatatctagt gaaatgatca cttcaagtat aaaaaaagat tttatacttt    300 tcgtcttct gtatttagaa atattagcaa agtcttggat aaaaagtgg tcgtagcctg    360 tccctgtagt ttccttgtta gtcttgatga acaagaagtt ctcagttctc cccaccctat    420
tctgattcgg tttacatgga agtagtaagt aaccatacac cattatagaa ataatacgat    480
```

| | |
|---|---:|
| aaccacacgc catgtcttac ctcatgcgtt tactgaagtt gttttcttct tttattttc | 540 |
| tttgatggag ttatggtatt aatattcaat attagattgg aacttgcaga tcaacttcaa | 600 |
| gaggcactct tgataagga tacccaggc attgcttttt gacataacgc caaaaccctc | 660 |
| ctaaaaaacc cttcattttc tatctcttag ttccatttta tgcaatgaaa taaaacttct | 720 |
| caaatagtgt caaagcccga aaattgccta ccatatattt atcacgattc atgaagggta | 780 |
| tcttaattcc ttttttttt ttttcctgaa atgttttttt tgaaggaatt ttcttgaaat | 840 |
| gttttaatgc ctttttttt actcaagaaa tgtcttaatg cttgtttact tacataaagt | 900 |
| aatatcgttt gtctttttt acgcaatatt atattctagt actctgtctc tccaatctta | 960 |
| ttattttaa aattttctt ccttcctatc ctattatgca caaaaggtg taattttaac | 1020 |
| atttttctac tagtaaaaaa cctacaaact ttttctattg ttaaaattaa atataaaagt | 1080 |
| aattatttt attttatata aaaatacaaa gattttatgg aaaaatatgt aagatataaa | 1140 |
| aatatgatta attattttac tttcatctta acttagcaaa tactttctga tcagtgcctt | 1200 |
| atctcgcaca atccacaaac attatctcgc acaagccaca aacacgcgct tcatgatcca | 1260 |
| aaattgtacg agcgacgctg tccatgtctc ctagaacgcg cgtagtaaga ataagtgtc | 1320 |
| cctttgattt catgttgcat agttaatttt tagtttaaga ttaattttag atagttttcc | 1380 |
| atatttttaa ttttatatta aagataaagt caaaattaat gtttagaatt aattgagttt | 1440 |
| aagtcatttt aggtacctt tggataaga aatttaaatt aaattttaat tcaaaattaa | 1500 |
| tataaaccaa aattattaaa acataaatca tattacttta aaattaattt ttcgaaaaag | 1560 |
| cacattcaaa gctccactaa aaattgtctt tgattaatag ccgtggatga gatttgattt | 1620 |
| attagtgaga aaagacaaag aggtttaagc gcacgcgaag agaggcgcgt aagtaaatag | 1680 |
| gagaaacttt agctgtcaaa tatgctggga acggcgagt acgaatgacg gcggctacca | 1740 |
| cccttatatt acagtgacag tctcactctc acctatctag cctaacgtcg cttcaccgcc | 1800 |
| gtttcccatt cttattctct ctcttcataa cactcttcct atttacagtt cacgccaaat | 1860 |
| gcctgcactc tttctctact attaccaagc attggccaca ccaacaccaa cgaataaccct | 1920 |
| ttgttattgt aactaataac cactgcattt ttcccatact cgttgatctc ttccactaag | 1980 |
| tgctgtggtt ggtgaccgca | 2000 |

<210> SEQ ID NO 34
<211> LENGTH: 2479
<212> TYPE: DNA
<213> ORGANISM: Glycine max

<400> SEQUENCE: 34

| | |
|---|---:|
| ttggattgtg tagaagaaaa aaattgaaaa aaaatatgac atccatgtta atttttgaaa | 60 |
| ttttcttata ataattttcc gtcttcaacc aaaccagact cctattaagt atagtaaata | 120 |
| ctattatatt tttgtggact tcttaataaa tagtagtaat attttgaaaa gcttttttat | 180 |
| ttttacgaaa gtcataataa attataaaca aacttataaa aaatattaaa tcttatagta | 240 |
| ctacttttat ataataataa taataataat aataataata ataataataa taaaacgtgt | 300 |
| tcaaaattat taatattcct cttgaagttc cgtttcatat tctgtaaaaa aaagttgcgt | 360 |
| ttgatattaa aatataacag tactaaaaaa acaacataaa aagaaaatc atgtttgatg | 420 |
| aaagaaaata caaatatatt ttcataaaga gaacttcaca attactcgca atgctgtgtg | 480 |
| aaatagggat ataaccttta tccaagacac gttcccatca ttgaagtata attaaatctt | 540 |
| ttacggttaa ttataatgaa atcatttggg atttgctttt gcctattatc acttttcaca | 600 |

```
cgatgatact taattattca tagacctttt tgtcgagtaa gagggggaaat gctaaacttt    660 tctgcttaga ttttttggca tagttaatgg atttttagcct tttctttct tattaatttt    720 tttctttcat aagcatagtc ccggtaaaat tctcactttc agttgatact ttacctcctc    780
cgaaaagttt cccatattag agactcaatg gcgtataaaa tcatcttaaa catttactta    840
taatgaatgg aaataaaatc taaaagtta gctactaatt ctttcacggc cattacgaag     900
actttgctta aaaatggaaa aaagcaaaa tataaaagag tgtacattgt ctattttat     960 aattgacttg gctctgtatg tattatgtaa ttaattttta atcttatatt ttgattattt    1020
atagagatat aaaatgaatt tgatagttaa agaaagaaaa gaagagatga aaaattgtgt    1080
gttcgatcct ctaataaaac taacatttta ataaattaat atttatcatt tttttaatta    1140
tttgagtttt ggaagtgtaa tgagtcgagt aatttttattt gatggttgtt tggttcactt    1200
atctatgttg atcaagtaat cgatcaattt atctccatga ataatgatga ttttttaagaa    1260 tatttaacat ttgaccatca attccttaaa tcatgtaatt attttttgtca accatgcaac    1320 ctctataaat ataggtccta catatgtttg acattcatca tagtgtgtaa tgtattttt     1380 ttattaaaaa aaacagagat gatgaactcg tgataaagaa tcacctaaca cattactgat    1440
actctctata aatatcacat gacaaccttta aacaaatacg cacaattcat atatcaatat    1500
ccattacttt gtcatattct aatttgagtg taaaagtctt tattattaca gtcttttaag    1560
ttggtttaga gcaatttgag ttaatatctt tatacaaaaa taacttaatt ttttaatatt    1620
atttttaaga catatttctc ataaaaaatc acataaatta gtttataatt tttaatttaa    1680
tattatcttc atttttattt ataaaattta attacctaat tcatcaatat taaaaaaata    1740
aattaattta attaatatca ataaatttat cctaaactta taaacattat cattaatgct    1800
cttctctctt aaatgtttat ggatataact tctttttattt aattaaaatg tttatttaa     1860 attaaattaa tgtaagaaat aatacaaatt gaatattgta taaaggaaca aacataattt    1920
tgttttgtat tagaccataa gtaatactcc atattagatt atatatataa cttttattt     1980 aaaattatag agtatacttt ttttagagga aattatagag caaactacat tcatatgatt    2040 tctctttttat aaatattgaa aacaaaatag ggatatgcaa cagcaaacga gggaggtttg    2100
aggagagagg gagagagaga gaatgtaggc gcgtgtggca cagttatgag ttaagactta    2160
ggagaagtac acattggcat aggcattgtt attggattat tgtagagtc cgatagacta    2220 gaatgacggc tactagttac tactctctct cttcataaac acaccattta tgttttccc    2280 ttcccttcac gccaaacgcc tgcactctac actctactct ctcgtgctct gtgactactg    2340
tcactctctc ataaaccaaa catgcccctta atccattttc catagtagtt agtgttgtta    2400
ctcatctctt ccatcttcaa tctctcttct ttccttattg ttgctcacca aggtgggggtt    2460 ttttgtacgt gtggtggca                                                2479
```

```
<210> SEQ ID NO 35
<211> LENGTH: 2000
<212> TYPE: DNA
<213> ORGANISM: Glycine max

<400> SEQUENCE: 35
cattaaataa ttctaaaaaa gatataaatt tttgtataca aatctatatt taagaaactt    60
ttaatctaga tgtcgatttt aaaaaatatt atttaattaa aaaatattag atggtgtaat    120
aattaatcaa aattatatca agataatctg attcctttct atacacacat aatattttt    180
```

```
catccttagt ccctaatatt ttcaattctc attttgttac cagacttgta ccgaacaaaa      240
acaaaatatc taatcatagt tttcattcaa caaaaatgat ttttaactca atttgaaaca      300
cttttcattc attttaaaaa ctaagaaaaa atttgtgatt tattttata attttgaaaa      360 acattctacc atcattatta ttgtttctac taccatcatt attaatgtta ctactatcac      420
cttcctagtt ataaccgtaa gcattatata ttttattat tattgttatt atgttatttt      480
gttaatatat ttattttgt tctaaaaaat tattattttt tcatatcttt cactattttt      540
gttattattt tagcaagttt gattattttt tattttaaat attttatgt gtcactttt      600 atatcacatt atttaacagt gtgaatcgat aaaaaatata ataattatct ttaatttgta      660
agaatttttt caaaattaaa actgatttta gttcttgaaa aatgtaaaac taaaaatgaa      720
aaccacctaa cggggcctta gtaattagga catggtctcc ctggttaccc acgggatttt      780
ttcacatcaa agaagacctg gtatttcat tttcatgaga ttttgcata tcgaacaagg      840 cattaagaca ggggttgtca ttgtcgtgat agtataattt acatggtcga agtgatagaa      900
actttaacca tcatttacct tgtaccttac ataacacaa aatactacga tttccaaaca      960
ctagatcgcg cgcttatgtt ttcagacaca ttattcttct tcattcataa ataaatttgc     1020
agctagtata tgataattgt accaatttat gtaagttttt tacaaaggac attcttatct     1080
caataaaaaa ctaaatgttt aaaatattct ctagcacatt ttttaaatac attttgtcta     1140
attaattaaa attaaaagag gatataaaaa atatgctgct aacatcttga acatttccgc     1200
aatcaataat ttctcaatct atctgaatat ttttgcaact gtatacaaaa atctcagaac     1260
agaaaattat tgattaaact ggaagaattt aataacattt gattcacgtt tgtttagtga     1320
ttaaaaaatc ataacattac actatctaac aaatgcagca tccataacta ccaaacatta     1380
aacaagagaa acagacaaag tccaataatc acagagacac gcagtgacaa agaaaagaaa     1440
gagggaacgg taaagagaaa ggtgtctctg tcatctcaaa tagattgcca taactccctc     1500
cttctctctc acaagctctt gcagagtgaa agcgaccact ttccgatctc aattaaaagt     1560
atggcataat ttgcaatggc ggaactgaac gaataataat aagagatacc atagttaaga     1620
gagagaaaca caaacatgga aaaagctggg cctcactccc tgggtacaca tagatagaga     1680
ctatggtgca gtgttgcagg ttgtagcaga agctctgcca aatagtgtta actttattcg     1740
agaaaattat tattattatt attattatta ttattctctc tctctagtct attatcagtg     1800
gtaattcagt aatgttgttg cattatagag agagcgtggt ctatgtgcca gggtgatgtg     1860
atgtcatttc actaccttca aagccagaaa aatgcaacag aaaaagcttt catcccatca     1920
catcatttga accatgaatc atgaactagt tttctaaact aaaactataa caacaccttc     1980
ggttgttgtt gttgttggct                                                 2000
```

<210> SEQ ID NO 36
<211> LENGTH: 2000
<212> TYPE: DNA
<213> ORGANISM: Glycine max

<400> SEQUENCE: 36

```
aacatttaag atcttaaaga tgccaagagc ttcatatgaa aatgtacaaa agagatttta       60
aaggcaatat caatgctgtg acgccatatt aaaataaaag ggatggtttc tcctgtatat      120
tgagcaattt gtattactta tatacacaaa atctaaattg attcttaaca aatatgtaaa      180
gaaattaata atatgatcaa gttacctgaa gaagctaaaa taaaatagaa aattaagtaa      240
aagaaatgag gagtagaata taagataaca tcaaaaaatt atttcagcat attttaagaa      300
```

```
catcaaattt accttctcatc aaaattaatc ttaaaagact aaaacattta attaagttta    360
taaatactca cacaaaatat taattattt tgtaattat attttttata ttttattta       420 ctattgcctc aaaatttgca ctaaacaaga gaccctagag atttcgttag aacaataata    480
gacacggtat taaataatta aattaatacg aggatgcata actaccaaac aaatgcgata    540
aataaatgag acgacgagag agcacaacgc gggaatgaga taattaagaa aaaaaatcta    600
ataaattagg aaaaaaaaga cataatatca taagcttgaa tccaatgtac aaagagaggt    660
tggcaataaa gagaaagaga aaagacgtcc ctgtcacctc aaatggattg cattactcat    720
tgaaaaggac attattactt ccgactttt atattaactt actaattata aaatatataa     780
aaaaatactt caaagatgca tatattttat tttatacat aattacataa cagaataata    840
taaaataatg taactacaca ttaaaacatt aaaatagtga ttggagtagt ggtataagag    900
gacgttgaat tcacgcggaa gagaaggata tatttcatgt ttaatttgtt gtcatgccta    960
gttcaatgta atctaataag taaaaataaa atacaaacaa aataaagatt ttggtttctt   1020
aacaaaagta cttttacttt aaatatatat ttttatctgg tttttaaaca tgcacatatt   1080
taacataaaa gttcatatta aacttttttcc tacatacttg gatcaaatag tcacgtattg  1140
caggtaaaaa ataatagtgt agcttataga aatcgtagaa ataagtctat aaaccagaag   1200
aaaaaaaaca ttaaaataat agtatagaaa tctatatcag tgtccccagt tcttacattc   1260
atgacccatt tccccataaa ctctttgcag ataatgcaat ggcaaaacca cacagaaagt   1320 gaccctggg aatcaaaagt taaaaccaat ggcacagcat agcacagtgt acagtgttta    1380
tttactatat agcaaaacac tcactggcat aacactttag ggagagagag agtgaaaaca   1440
agtgtaaaaa gagagaaagt taggaggggg atagagagtg tgtgtgtgtg cagagtttgc   1500
aggcttgtag cagaaatggt ggcagatggt tttaactta tgtgtgaaat aattttcttc    1560
tatctctttt ctctttagtg ttttctctct ctctctctct cttctttttc ttcctgcatc   1620
ttcttgtgtt tagggagtgt gatgttttgt ggcagaagaa cgatgtgatt ggacacagcc   1680
aaagctgtgg acttgttctg ttactacttt gtaattgtaa tcacataaaa ggctagaggg   1740
tatgaagagt gcacagaaaa atactagtac tagtttcaaa caaaactcac cttactacta   1800
cccttccatc tcaagccata gttgagttga gtggtgcaca gtgtcactat acataccact   1860
aacacccttt tttggttctt gttctgtggc tccttgtgct ttgagcaaga gcttttttgag 1920 aaagagcttg gtggtggtgg ttgttgttga gtggtttcat ggttaggctg ttgttaagtt   1980
gaagttcatc agttgcagct                                               2000
```

<210> SEQ ID NO 37
<211> LENGTH: 1399
<212> TYPE: DNA
<213> ORGANISM: Solanum tuberosum

<400> SEQUENCE: 37

```
aacgaaaaat ttagaaacta ttagtgatcc aaatgttcgt gattacctgc aacgagaaca     60
acaacgaata cttgaaaaaa gaaatcgaca atcacaacca caaccataat cgcaacaatt    120
ctcagaatca tatcctaatt ttttttcgaa tagtgctaaa tttgaaaacg acctaccgaa    180
tttctaaatt attgttgtga tcaattaatt attatgttat gtattgtatt ttatcttgta    240
tttaaattat tatgttatgt attgtattgt tatcttgtat ttaaattatc atatcatgta    300
ttgtattttt aaattaattt tttttgcata ttctttataa tgaaaattaa taataaaaca    360
```

| | |
|---|---:|
| attttattat tcacgaaaat tagaaaaaaa gttaaaatac tattaatttg aaattaaaat | 420 |
| agtatatatt aaataatatt tttaaaaata ttatattata tttaaaaaga attatgaata | 480 |
| ttagatattt aattaatgga attatatgta aaataatatg ttaattagaa agtaatagaa | 540 |
| aaataataaa ataatgaaaa agtagaaata gagagtgtga atagtagaat ttggagaact | 600 |
| attcaactct ctaaatttga agaatatagg gtgatttgga ggtgggttgg agtgtccatt | 660 |
| ctctatttta ctctcaaaat atagagaatg gagagaaaaa tagaggtgga ttggagatgg | 720 |
| tcttagtgac attttttgatt ccgccaatgc tcagttggcg tagtcgctgt caaacttgag | 780 |
| aaaggattac ccctttaggc ttgcacagac agtgacttat gatgaaatga agccagagaa | 840 |
| ggcactctgt tataacactt aaatgaaaat acatgtgtat ggactagcaa taaaaggggc | 900 |
| actagtaatt ttagtaattg aaaagcaagt gtatagagag agataatgag agagaaagag | 960 |
| taagtacact actactgcta ctatcccata tagctgtaat gttgcaggtc tgattttttgc | 1020 |
| agttgcagac cccctttcttg gcacaagctc ttttaacttt tatcttctca ataattctc | 1080 |
| tctctctctc tctctcttt ttctcttttt acattgtgag gaaactgaat acccattgta | 1140 |
| tgtattagtg tgaggcctat ctgccacaag gatgtgatgg aacactatgc ttcctctgct | 1200 |
| aaaaccccac aaccccaaaa ctcttttttca cttcacattt aatcacaatt cctcagtgaa | 1260 |
| attattctgt tgctctctct aatttcaatt tcaatgtcgg taagtccaag aactggtttt | 1320 |
| tcaattcaaa ggagctgagt tagtgcaaac acttgaggtt tgagttttg acagagactt | 1380 |
| gagtctcaga gaaactacc | 1399 |

<210> SEQ ID NO 38
<211> LENGTH: 2000
<212> TYPE: DNA
<213> ORGANISM: Solanum tuberosum

<400> SEQUENCE: 38

| | |
|---|---:|
| accttatata agttacaatt tagttatgta tataagttaa aattaaatta aaagacattt | 60 |
| cgaaataata tgattatacc atttcgaaat taattagaga gagaaataag atctcgcaaa | 120 |
| attaagtgtc ttcttgaaat taagaaccat ttttaggaga taattatgta ttttttcatt | 180 |
| tttaatttga cacgtatgca tatccactat tttgttttat tccaaagtga cccctacttc | 240 |
| ttttggtaat ttcttttgagt attttaaact ctagtcccc tttctcaagc aaaaaggctc | 300 |
| actcgcgcac gcgcgaagag acattgtgac gcgctggatg gaaaatccag aagcgtaact | 360 |
| gtcaaaaaat agaacaactt tgggaaacgg ggtgacggcc gctgccacca ctttttttcat | 420 |
| ttccaaacac tcattaacta acgtcgtttc accgccgttt actgcttaat gagtatgaat | 480 |
| tacactctaa tagtctattt ttacttattt ttaatgtgtt tatcaaatta tattttaaa | 540 |
| tataatactt taaaatatat atcatcaata ataagagtaa attaaaaaat aaatgacaaa | 600 |
| ttgttttctta aattgttaaa ttaaacaatt aaaactgaat attttacaaaa tacctcttaa | 660 |
| cttgctaaat taaacaattg aaactatatt tatattaata aattgaactg acaaaaataa | 720 |
| ataaaggaac tatatatttt ctcaattata tcttttttact aaaatattat ttttctaata | 780 |
| ctagttaaac tttttaaaaaa catctaataa agaaaaagaa tttgttcaat tatactttag | 840 |
| aagctttttat tattattatt attattagta gtagtagtag tagtaataaa ttagattaaa | 900 |
| ttaaagagag aagtattcaa aactcccaaa actattgtat tagttttatt tcagaactat | 960 |
| tgacaatctt aattttttttt tttttaattt gactaggtga acttaaatat acttcatttt | 1020 |
| ttgcaaaaca agtgaagtac actcttaaat tttcatcaag tttagaaatg ttttcaacaa | 1080 |

```
tttactagac tctttattaa gaacttcatg ttctttcaag agtttatgag cacttgctat    1140
gtcatgttac agatcaagaa tatctacaga gtgtatctaa atttagtact agtaaagtag    1200
aaaatgtatt actatctct caaacaatag gtattcatta tactattttg agatgtccaa     1260
caattttttt tcactttatg aaatcaatga ataatttaac acttagttcc taattcccag    1320
taagcattaa ttatagttat ttacttatta tatttttcaa cacattatat tgaaaaagtg    1380
atatagtaaa tctatctttt tattttatta tttcttaaaa tttgtacaaa cttaataata    1440
gacaaatatt gttgaatagg aataataatt tacattaaat ccaatatatt tttcaatagt    1500
tgtcactaaa tgaaaatact tcatctgttt caatttatgt gatagttttc atttttcaaa    1560
agtcagacaa ttatatattt ataaattaag taaaaaatat tataagtcac actaattaac    1620
aattcgaaat attcggtacg gaggaactaa cacttatgtt tttagaccat attagtcttt    1680
tctctctatt tattatataa tattgagagg agagtgcaac caccatggca actttctctg    1740
tcttcataaa acgcagctga cattaaaaac acagacacac acttcgcatt tcatatccct    1800
ctcactacac gccaaatgcc tgctcttcct atttctcttc ttcttctttt tcttcttctc    1860
tctcattcac ataacacaca ttcttgtact aactctgcat cataaactct accccacttt    1920
cttcttcttc tccggtcata ttgctctgaa actccactta ttgctctctc ccggcattta    1980
tttttagttt ctcagaaata                                                2000

<210> SEQ ID NO 39
<211> LENGTH: 471
<212> TYPE: DNA
<213> ORGANISM: Arabidopsis thaliana

<400> SEQUENCE: 39
taataagaga cgaaaaaaaa ataactaact gatcattacc atccataaat aaatagttgc     60
tgccataaac caaacacatt gtgcttatca aaagaagaa atttgtactt aatgaaacat     120
tcattattag caaagtgtaa aaccaaagaa aaacaaactt tatttctcat tttattagta    180
aaagtgaaga agagtaaaga aaagagaga ctgagatgag gctgagagcc tgagtctgcg     240
ggtggagaga gagagaaaga aagcctcttt acacgtgatt tttaaaagag accaaaaccc    300
caaaagcaaa cctcttttgc atgcgtcctt aaaagacata aatttctctc aaaattttct    360
acatcacaaa atcaatcttt ttctcttctt cttcgtcttc atcatcatca tcatcatctt    420
cctctttctc ttcctactga gatattttct ccacattgag aggaaagcta t              471

<210> SEQ ID NO 40
<211> LENGTH: 1231
<212> TYPE: DNA
<213> ORGANISM: Arabidopsis thaliana

<400> SEQUENCE: 40
aggataaatt tcatctatta agatatcagt caattataat gtgttacgtg attcgataaa     60
aaaaaaagac caaaaaaaaa aagaagataa ctattggtaa gcgtaagaaa tgtgtttaca    120
ttttggcatt ttgccaaaac acataaagat ggttagtgat gagacgagac gagtcatgcg    180
ctacttttaa aacaaaatga aaaacatcat taagctaaca aaccaaacac acttgttttg    240
ataacatgtt ctagggaact agttatgcca aatctaatcc gcataagaag actaagtcac    300
aacataattc agtaatttgg ttgagattaa atcctataaa tatgatttta aggtataaga    360
gagaagagac tcttttgatc aacacaatca aacatctaca aagaaaatta tctcacatag    420
```

```
ctacttctta atctaattt ttcattaatc cattttattt taaatgtgaa gaatcgcatc      480
tagatgtgac ctctcatgat aaaaaattaa accattgtaa aaaaaatgtt gtgtaaaact      540
aaatataata aattattaaa aaaatacaaa ttcaatccac taggttaaaa actcctatgt      600
agaacatttt tttatattaa aatgtaaata catgaatctt attttcgaa aaactaaaga      660
catcttttt ttatatatta attaccaaaa caaaataaga cgacaaaaat attctttgat      720
atagtaaaag aaaactagaa aactagaaaa caataaatta ccaaaacaat ctagaaaaca      780
ataaatccta ctttgcatta ctttattata aaatcccgaa atgaatctat aaatgtagaa      840
aatattatac aaaagttgta agagatttta atatacataa ttacatatat atacaagtaa      900
atacaccgta tatacatacg aaggagtaaa cagtattatt tggtatatag ttacgtctct      960
atatacgaag ggttcaaact tcaaagtaat aatttaatca acaatgtgta catattgata     1020
agtagtagta tatatgtaaa ggtctcacgt ctctataata aagtatgact cgtcacgtga     1080
cctcctcttc ttcgcagaga cagagatagg atgagacaga aagaaaccaa caaaaccaaa     1140
cccccaaaacc caagaaaaag agaaaaacac tctcttctct tctctctctc tctttctatt     1200
taagagactt cactgtctct ctcagtcttt t                                   1231

<210> SEQ ID NO 41
<211> LENGTH: 1548
<212> TYPE: DNA
<213> ORGANISM: Arabidopsis thaliana

<400> SEQUENCE: 41
ttcacgtgtt tatttattta tttgggttat taaacataaa tcatgtaaat ctgaatcctg       60
tggagatctc tccctagttg atgaatagat atgatgaatt taattctttc atgaaataaa      120
aatatatgaa acatatgtag cagaaaaaga agcatatcta tgaaacaaca aacattcaaa      180
aaaaaaagga aaacggaaaa ttattaatat gaaaactacg gctttgactt gtagctgact      240
acatttacga catatatata taaatggacc ccactgagtg tctgcaaggt ctttacacaa      300
cagtatcttc ttctgtttct ttgactcttt gtgatcccta agcctaccca taatacgtgt      360
ctacatttta ttggattgtt tcgtgactct gtaatctttt ttataagaaa acaagtaata      420
gtgaaattga agtaaatagc tcagcacaga aacttcgaca aaaataactc acagattaga      480
aaagaaaata tatgcataaa tagccatggt tcatttatga acaatttatt cgttttttta      540
gtttataatt tcattaaaac atgtttgtca catcacattt catgtccttc ggctcctact      600
acaacaacaa gtcactgtca tctccattac ttccacttct gctccttct ttattaactt      660
gttcaaaaac aattctaaga taaataacaa taaatgttgg tctctctta ttatttcccg      720
gctaaagaag gaggatgtct cgtattatcc gccatcaatg ctcttttgtt tcctgttct      780
tgcaatttga atccctgaga atcctagccc acttatttac tactttgcct tagctgtttt      840
cgacatcaaa attttggtca tatgactcat atcaatcttc aaatttgata aaatatgttc      900
ccaattcaca aaaacaaaaa agttttcgaa agctcaaaaa cctttaccat tcaatagta      960
gataggattc ttttagattt gcatttcacg aaaagagaag aaaaaaaatc gaaaatatt     1020
tgcaatcatg attttttgtt tctgaaggag acctgtagtt gctgtcatga acattaaata     1080
caaatctaat aaatgttgta cgaattttgc gtgtaataaa tggtcagggc cggctcgaag     1140
ctcgctgatc gtcctttttt cgtgtctcta tagcaacaca caatcgtatt tatttcaaac     1200
tttttttact ttgtttccca tccatcaaat ataagtataa aaatgtaaag aatcatcata     1260
tatagatcgt aaaattcattg cttcctttgg cttttattt catctagacg acgttaaaac     1320
```

```
cagaccagac caaatacatt tatcattttt ccctttttc taaaattctc tctttgattc    1380
ctatcttctt ctctttattt tcactttgtg ctttctctgt ctctcctatt atgagtctaa    1440
aagtctacta gctgttcaat agttttgtct ttctgtgttt cttcttcttc aaaaccgaaa    1500
gaaattcaaa aagagtcttt cgctgcttgt tagtggggtg aggaacaa                 1548

<210> SEQ ID NO 42
<211> LENGTH: 440
<212> TYPE: DNA
<213> ORGANISM: Arabidopsis thaliana

<400> SEQUENCE: 42
aaacccgaac ccgaaccaaa cccgaaccaa aatcttaaat tacccgaatg ggtcttaaat      60
ttctaaatcc gaaaaacccg aacccaaaat acccaacccg aatctgaccc gaatatccga    120
acgcctaatt tttctatgtt aatgaaatca attatatgac atgtttataa agagaaataa    180
attacggtga gaattaagcc catttacgtt acggaaataa acacccatt taaaaaagcc     240 caacacgtga agcccatttc cgagtgcgtc ccacatttac tccaacggtc gaatcgactc    300
aaacattcaa aatacaaaaa cgctatcttt atcgtcttcc tctgtctctc tctcacaaca    360
cataacgttc aaatcctctc tctctctatc tcgtctctta tctctagatc taaaaatctc    420
ttctttcctc aatctctgtt                                                440

<210> SEQ ID NO 43
<211> LENGTH: 317
<212> TYPE: DNA
<213> ORGANISM: Arabidopsis thaliana

<400> SEQUENCE: 43
acagacattt acttatacgg ttattgaggt tgaactggac cggagtagca ataaattatc      60
ggttcagttt gggagatcaa accgtttaaa agaaaataat ttgaaatggc cacgcagaat    120
acgagggtct gaggattgta cctcctttct ctgcaaaaac ttaaacgttg atttgactca    180
agcgtcaagg taaggtactc tctcttcata caacatttta gctttacttt ttctctttac    240
tcttctctct ctctttctct ttctctttct ctttcactcg ttctctctca ctcactctct    300
tcacacacag atccaag                                                   317

<210> SEQ ID NO 44
<211> LENGTH: 3912
<212> TYPE: DNA
<213> ORGANISM: Arabidopsis thaliana

<400> SEQUENCE: 44
acaccaataa aaatacacag caataaaatc gctacgtata tatatatata atatgtatta      60
tctattacaa gatagtaata gagtatagca agttgtatca tctaacaaac tatgcgaata    120
aaatttgaac attgtgacat gtagatgtag tgtaatttag ctaagtgctt atcatcagta    180
acatagaccg acttaacttt ttacgaaaaa aaaaagtaa catagaccga aaaatgcat     240 atcgtaaatt taatggaaaa cacaatttac gataagtaaa aaacaaaag aaattacgat    300 aagtcgagaa aaatgcaaca aattgagata agtattgat aaaaccatga aagtgtcggc    360
gtatgtaaat gcggtgatta atgtgatcat tagagcgtgt gtgttaaacg cggcggtttt    420
agtggagatt gatcagctga taacactctt accgggacga atctaattcc atattcatgg    480
cttgttaaaa cctaagacat acgcaatctc taatttgcta gtatagttag ttctatatta    540
```

```
tttttcgact aataatgtaa acatatgatt attaagtcgc aaaaagagtg cttaacaacc    600
aaaaagtgga ttaattaact tggtgggaaa agttacaaaa cctttaatga ttactctttg    660
taccaagaat agtggcgaag cactataaga gcagagaaaa gaagctcaat aatgtactaa    720
aagttgtaga tttttacagc ttaaatacac caaaattaat agaaaagttg gtaattttt     780
aattcatggc tactgattta gattttagaa acaatagta gtatcattgt cacatcttaa     840
acacacaata ggtatgtttt aaatcaaagg ccgtagttaa tttgtcaaaa atgtatgcat    900
ttggtatttg gatgtctccg aaaggatgga tatatggact tgttagataa tttcatacct    960
cagtatcaat agtcatggag cccaaattgc tcaaaaacat atttttaatt ccaagacttt   1020
gatgaagacg taataatgag tccaatgggc catcagatac aatgttcgga atttaacggg   1080
tttgttagtt ataagtattg ggcttgacct atctggttca atgatatgta ggaacaaccc   1140
aatttgcaaa gctttattaa aagactctt agttgtcgtc aaggtttaac ttgtagtagt   1200
tggtaagaaa ttctacgtga aataggcaac attacaaaaa caaaaatcaa ttcgaaatca   1260
tacaaaacga aaccaagtag taaccaacta cactattatg acattaatga ttagacattc   1320
ccaaatcata caagttcctg tcatgaagga acaatggtc cgtatttgca aacgattaca   1380
aaaattcaaa ccaaaaatga aaaaacgagt taaattattt ggtttataaa aatagtaatg   1440
tcaacagaag actagattgg gaaacctgaa gcgaacagag cttttaaaaa cgagtttgaa   1500
cggctgggat catttggtac aatacccacc gtaagtttgt ttaccctagg gatgcaagcc   1560
aaaggcccaa atcagttact acttactgct acaaccatcg tctcagcttt tgtctcagc    1620
tttttactaa tgaagcatac aatttcttgg gcatgtcaca tctcgacacg tgtccactat   1680
tctcttctct tattggctac tcgttcgtag gcttctgtta atagatgatc tctctataac   1740
tctaacagtc ttttctttct ctttatttcg ttttggtatt ttaagtttca aattgaaaat   1800
aataggagga aaagtctagt tttaaatatt gttttttac aagtgaacgt gaaccaattt   1860
acctcttttt ttttatatat cctatcggct aatctggtta gtatcggtag aaatgcaccg   1920
aggtgctaca gagattaatg ctagggatag tcagaccgct tgtatttctg actatcaagt   1980
aaatctacgc ccaactcaca tatttcccaa acaaatgtga ttttttttt tttttttt     2040
tttttttttt ttttgtaaca aatgtgattt tgttttcaag gaaaatagaa cttacgtttg   2100
ggaatttcac ccttcactaa agcttccttc tgccattaga ccacaaaggc ttgggcaatt   2160
taccattttt gtaaaagtag aaaacaaaat gcctaaaatg ttcatacttc attacatcaa   2220
caaggttatg cccacgatat agaggcatgt aacatttata tatatagtgg aagaagccta   2280
cgagctttat taataagtat aaactctgat tattaggtaa ataaattact taaaacgatt   2340
actcaactga caaaaccgta gttgaataat aaggttacta tgaataccga ttgaatattg   2400
caaagccgga attgaaaaat atataacaga tcaaatgttc aagtgtggtc ataattctca   2460
cataggtcat atagctgaac ccatgcatct atttactagt ctatagaaag tactagagac   2520
gcatacagct gaacctactc tattcttta ttaattttgg ttctcgtgga tacaaaattc    2580
ctccaacatt tattagaacg aataaaacca atatgatgat gattagttat tggtaaacat   2640
ataaacgttg agtaaacttc aaaatagatt gaagtactat taagacttgc atttttccc    2700
cttgggttat attcttgaat cgtttcgaag tattttaact ttcaagaata gaaggttcct   2760
caactataaa caattacatt aatcaaaacc atttctatgt aaacaacata attttttgtat  2820
atttagtct tccccaaaag tttgaccgat agggcggttt agaccgtata gtacgactgt    2880
acaacaaaaa ggactctgga gacctaaaga tccaaaacta tgcaaaataa agatacggtc   2940
```

```
ggaccaattt aatctaacaa aaccaaatcc ttatactaaa ctatttaccg atacatttcc    3000
atataacaca gtacacacaa ttaaatcaaa cattattgga agaacaagat agaatattgg    3060
cttaatctcg aacgattaga gttatcctag agcctcggag cttttgtcac atataatata    3120
aactatggta tatataaaca tgactctcat ttgtatttat cgcaaggtac aattccacca    3180 attttttcg tcccactcat acagctttaa ttgtgaaatc aatccataaa aaaccaacat    3240
gtgacatggt ctctataact ataactataa gatagtaaaa aattcacatc aacataaaag    3300
aaaaccaatc atattggcta aaaaaaacta acggtcgaaa aacgtataac cacaaaacca    3360
aaccggtcca accggtgtcc ccaatcacta tcaaagcatt aactaacttt cacaaggaaa    3420
agcatagttc agtttctcta catcgcttcc catcctctta accctgttta ctcgaatcat    3480
ccaccgttgg atcaaacacg cgctacaaat ctagcgcgtg accgaggttt ttacacagtg    3540
gaatattacc atgcattgga aagcggcgtc tacaacaaac ggcgggtcat gtcaccgtca    3600
aaatcaacct ttcttaattc ctaacgccgt tacttatctc cgtttactaa aaatgttaat    3660
gcgtgtgaga gtgaagatca tatactaatt agaagtggct aatgttttaa cgtgacatta    3720
ttatcatagt taatggttcg atcagagttt taagtagtaa atgatataag tgtgtgtata    3780
taattgcata catatatact ctcacactct gacagatttg tcgtggtctt agtattctct    3840
ttcatggcta gttatatagg gctctagtac attatctctc tctccccatt tctctgtctc    3900
tctcttcttt aa    3912

<210> SEQ ID NO 45
<211> LENGTH: 2000
<212> TYPE: DNA
<213> ORGANISM: Arabidopsis thaliana

<400> SEQUENCE: 45
atctttatgg tcaccgagtc tactgatata attttactgt cgcagtttgt ttccactact      60
taagtttcta taatttcaca gtttgaaaga aaaattactg gttattcagc taaattacaa     120
agattagttt aattagttta gccagtataa tgttttagta aagtattaaa cggcattttt     180
cgttgggaga attatgttat ggtataatct actaatacat acttttacac atatatcaaa     240
aagtttgacc atagtaggta gtacaacata gaagaatcaa gatcggaacc agcaaggaag     300
aagatacggt cggtccatat taagctaaga ggaccaacgt aactcgatat atatttttct     360
gttctctacg ttaccaccat ataaatttta atattgaaaa aatcatcttt tggcattgtg     420
tttgatgtcg gattcggaat atggaaagag gagagatatg agattttggc acaaaggaag     480
ctgccaaagc attagggcaa ccgagtagta acgagatcaa acatcgtttc aatcggacgg     540
tcggggtttg accaatattt ctcggatatc ttttggaccc tacgttctga cttgaacttg     600
atcagtcact tcagtacctt agttttcatt ttcaatgtga tcatgagttt tttttacat     660 gttagcttca aaacaaatac taatattcat taactatgga tcggcatagt tttcatgtaa     720
tcagctgagc gtttatcata ttgattgaag ctaacatgta aaattctcat gatcacattg     780
acttttgcct acaaatttta aaagagtata caaataattg cttaatgaag atagcttcca     840
tagagaaaga gtaacagctt tatacggagg catagcttta gacacgatct ctgctcttgt     900 gtttttgtt taacactgaa tccacagtga aattactgct cattttttt cattttttat     960 tacattttt tttttacttt tttatttatt acaatctaca gttctaccaa cttattcaac    1020
ctagtggtac catatcgacc ccaaaattaa tcaatctaat tacaaggtag aaatagaaag    1080
```

| | |
|---|---|
| attttatcaa aggagacaac tctgatcgat aatatgttgc aataaaacca tgaaaaactg | 1140 |
| taaaaaatat tgaaagctga agaaaaattt tcaaatcgat aaaaggatag tactaaacca | 1200 |
| atccggtttg tggcatcttt ttcacccaat cactatcaaa gcattaacta aaaatcacaa | 1260 |
| ggaagagcat aatttgattc tctacatcgc agtccacgat aggatttctc tatccaccgt | 1320 |
| tggatcaaat ttaataatga tgcacgcgcg cgtcaacggg attttaccca gcaaggaat | 1380 |
| gtcttttcac cggactctta aaagacgttc ttctttttc acctttgcat tggaaaacgg | 1440 |
| cgtttcttct tagaaccgtc gccgtcaaat catacggcct aataaatctc cgtttaacgc | 1500 |
| cgttacttta ccgttaagta ctaaaaaac aaaaaaaat catttcgatc actgtctcat | 1560 |
| taagatgatc ggagatgttt tagcagggtt taacaagtga tgatagtaat gtatgtatat | 1620 |
| atgttactga cattattttg tcgttgtcta ataggagggt actaaagttt ctctctctca | 1680 |
| tggcgtcgga gctcagcctc tagtaatgta gactgtcctc tcttctctc tctcttcttt | 1740 |
| aaacatctct gctctgtttt ccttccagtt cacgctaatc tcctgtgtcg gtccctctc | 1800 |
| tcttttcctt tggtctctcc caacaatggc agaacgactt tgtacccttc ttttgctctt | 1860 |
| tgtttgaatt tcgtttcttg ctacaaagct tcaaaggatc tgacttttcc ctaaacagaa | 1920 |
| aaagaggtct ttaaccaaaa aaggttgtta cttgttttct gggtttcgtg gtgttactct | 1980 |
| tgaggaagaa gaagaagaag | 2000 |

<210> SEQ ID NO 46
<211> LENGTH: 1470
<212> TYPE: DNA
<213> ORGANISM: Arabidopsis thaliana

<400> SEQUENCE: 46

| | |
|---|---|
| ctacctaata taactagcta gggatttcta ctcttgtttt cataatcgat ctacggacat | 60 |
| ttctcggaac gtggtcaaga ttcatgagtc ttctgttttt tatgtctctg ttcaatttgg | 120 |
| tttagagatt agtatgctta tttgtttatt tcatatatgg ttatgagagg agaggctaat | 180 |
| ggcatatact ctgatgtttg tgatggctgc taatatcgtt gaggagttat tcacgttgtt | 240 |
| tcatgcgcaa aaatcaacag aaaaaattct gattatgagc caactctgtg aacccttata | 300 |
| gtgcgcccag aggtttgcga ggcaaaatcc cgatgaacca gaaggaattt tagatctcta | 360 |
| tcaacaataa ctatgatgga gctcgtttaa attcatcaca gcgacaacat cattaggctg | 420 |
| cccaacgtct atgtctcctg gaggtgatgg tacttgatct ctcaaccaat tttcttgaaa | 480 |
| atatcatgcc ttgtgagcgc tttcatattg cgcctaaaat acccaatacg caatgaacct | 540 |
| acttccaaag gcatagaaaa aaaactgata atgataatga gatttgtcac tatacttatc | 600 |
| ctatccctac ataggagccg tttgattgtt tagtccatgt tttcatttg tttagtctaa | 660 |
| tgctatataa cttttcttta tcagtctatt gttatatgac ttatatatat ctcaagagat | 720 |
| aaggccaata aatcttcttc ttaattatat ctgaagactc aaaacatatt ttgagtttaa | 780 |
| taaaataaat aacgtccaaa tgctacatac aaacggacca aattcatgga ggtataaatt | 840 |
| taaattattt tttgttccaa agtgtatgca gtgatttatt gatgaatgcg atagagcggc | 900 |
| gaaagagaat aatcgtcacc tagaagacaa attgatcggc cgtacatata tacataaata | 960 |
| caaacctgcc acttcacatg tcacccacct ttaagcaccc ccttcacata catactttct | 1020 |
| ataacaaaaa tatcagcttc tagttcatat ttatgttaca ataactcgag tgaatcatac | 1080 |
| taaaaaaatg taatgctttc tctaaatagg agataaaatg caccctccga cctaactaaa | 1140 |
| gattccttat tttagctatt taagacatat tgcacatgta tagagataca taaacacata | 1200 |

```
tgcaatatgc acatcttcta tacattgaaa aaagctgatc ttgcaaatat ttgtcttaca   1260
caacacaagc gaccaaagcg atgcgtttcc caatgataag gttacgacat acttacacga   1320
ctctctctat tgtctcgtct cttcctttcc tcatccctct cctttgtctc ctttcactct   1380 attttttcact tttcagaata cttttacgta aaaatcatgg acatgtcatt gtctccaccc   1440
tactatactc ttttttttgtt cttttttgttt                                   1470
```

<210> SEQ ID NO 47
<211> LENGTH: 1793
<212> TYPE: DNA
<213> ORGANISM: Arabidopsis thaliana

<400> SEQUENCE: 47

```
ttggttgtct ggcatcatca ttttgtaccg tttctcccaa agtaagaaac ggtacaatct     60
tctcttatat agatttcata ccccaaaacc ctaaattcat tagggttttc aaaaaaaaaa   120
atcacgttta cctctaaacc aatcttctct tatatagata aatcataacg tttgtttgat    180
ttttcagttt tctacttaac caatattaaa ctaaagtcga attgagatga gtggtagcaa    240
accacagttt aattaagaag ttaattatag gccacatgat tgagcaagcc ttttttgtttt   300 gtaacacatc ttatcagctg cttaaaattt tggctgcctc ccattggcca actggtctaa    360
acatcattgc attggcattc tcataatcaa tcaatctaat gagaaacttt gaatatttat    420
gaaaaactga ataacaacat aacataaacg aacaatgtaa aaagaaaaa cacaaaaaaa    480 aaaacacttt aaaaaacaaa aaccaaaaac tcttaaacta taaactcatg aacacttagt    540
gatgaggtct gaaagggtgt aaccaccacc tgttgtcaat aggtgacaac ttcttcttgg    600
gaacattcgg gaaagtgaag gcttaggtga cggttgtctt aaaagtctct tttagttaat    660
tcatcgtatt ttcgatgggc attacgtttg atgcataaag gcccatatgg gctatacatg   720
tactgcgttt gagtggcttt ctaaggattg atgtattgtc tctatgagag tattcgttta    780
actcatggag atctactctc cacgatattt tctgtaaact ttctttttg ttgattagat     840 aaatagaaaa ttgtgtagag cgaaactttt aatgaattaa aatgcggaag cgattaaagc    900
atgaatagat aaattggaca agagattaaa cgagggatca tctagttttt acactgatca    960
ctagtcatct gcttgcagaa gaagtatatc attaatcaag caaaacgagg gcataaattt   1020
cttacaaata actttacag taggttaatg atttttttaat aacttgtcca tttcacatgc   1080
atgtgtatct ttgtactata catgctaagt gtttcattaa tcaagataaa cgtgtctacg   1140
aataacttaa aacagtacaa cttccctaaa aaattcatta atgaaaggt ttttatagat    1200 tatacattgc acggtacggt tcggttacca ttcgaagtct aaaaagagaa tgacggttct   1260
gataatgctt ttaatcgctt ttgtattgta aatcattaaa acagtaagcc ggataccgaa   1320
ttactaatca gacccaaaaa agaatctata ggaaaaatat caactgaaga gcgggtaggc   1380
ttgaccttga aggaagaat ggtgagcgag cggtggatag atatgtaata aattgtaacg    1440
ctttcaaaat gtcaaagtca caagtcacat tactcacgag ccaacactaa ccatgcaact   1500
tttgttttga cattttccta aactttaggt ataaaatacc cgcgtaataa ataacctctt   1560
cataattggg tccacccact cacaggtcca cataagga accgaaaaag gtaaaattca   1620
aaaacttaca aagtttttta gagatgatgt ggtgaagtat tgcattaatg gaataatggg   1680
aaaagaaagt aattgcaacg tacgtataga ttaatccatt gacacaaatg aaaagtttct   1740
ttctatttaa tgtacacaac aaaggttctc ttcagagtaa tttaggggaa aaa          1793
```

<210> SEQ ID NO 48
<211> LENGTH: 257
<212> TYPE: DNA
<213> ORGANISM: Arabidopsis thaliana

<400> SEQUENCE: 48

| | | | | | |
|---|---|---|---|---|---|
| acacaacagg | tccctacatt | tgtacaatct | cctctcttta | aagactctct | ctctttctct | 60 |
| ctccatctct | atcttactct | gtatttctgt | cgtctgagca | ctcaatgaaa | ccactgtaaa | 120 |
| tttccgccag | aatttgatgt | gatggaacga | taaaaatcat | ttttctcgg | ttaaagtaaa | 180 |
| aaaacaaaaa | caaatttctg | tagaaatcat | aataaaagaa | agaaaaaaaa | tctaatgtcg | 240 |
| gtacataata | cggttct | | | | | 257 |

<210> SEQ ID NO 49
<211> LENGTH: 1787
<212> TYPE: DNA
<213> ORGANISM: Arabidopsis thaliana

<400> SEQUENCE: 49

| | | | | | |
|---|---|---|---|---|---|
| aagggatatt | taatgggaag | aaaagaaggg | tggagatgta | acaaaggcga | agataatgga | 60 |
| tattcttggg | atgttgtctt | caaggccacg | agcttagatt | cttttagttt | tgctcaattt | 120 |
| gttaagtttc | tactttcct | tttgttgctt | actacttttg | ctcatgatct | ccatatacat | 180 |
| atcatacata | tatatagtat | actatcttta | gactgatttc | tctatacact | atcttttaac | 240 |
| ttatgtatcg | tttcaaaact | caggacgtac | atgtttaaat | ttggttatat | aaccacgacc | 300 |
| atttcaagta | tatatgtcat | accataccag | atttaatata | acttctatga | agaaaataca | 360 |
| taaagttgga | ttaaaatgca | agtgacatct | ttttagcata | ggttcatttg | gcatagaaga | 420 |
| aatatataac | taaaaatgaa | ctttaactta | aatagatttt | actatattac | aattttttct | 480 |
| ttttacatgg | tctaatttat | ttttctaaaa | ttagtataat | tgttgttttg | atgaaacaat | 540 |
| aataccgtaa | gcaatagttg | ctaaaagatg | tccaaatatt | tataaattac | aaagtaaatc | 600 |
| aaataaggaa | gaagacacgt | ggaaaacacc | aaataagaga | agaaatggaa | aaaacagaaa | 660 |
| gaaattttt | aacaagaaaa | atcaattagt | cctcaaacct | gagatattta | aagtaatcaa | 720 |
| ctaaaacagg | aacacttgac | taacaaagaa | atttgaaacg | tggtccaact | ttcacttaat | 780 |
| tatattgttt | tctctaaggc | ttatgcaata | tatgccttaa | gcaaatgccg | aatctgtttt | 840 |
| tttttttttt | gttattggat | attgactgaa | aataaggggt | tttttcacac | ttgaagatct | 900 |
| caaaagagaa | aactattaca | acggaaattc | attgtaaaag | aagtgattaa | gcaaattgag | 960 |
| caaaggtttt | tatgtggttt | atttcattat | atgattgaca | tcaaattgta | tatatatggt | 1020 |
| tgttttattt | aacaatatat | atggatataa | cgtacaaact | aaatatgttt | gattgacgaa | 1080 |
| aaaaaatata | tgtatgtttg | attaacaaca | tagcacatat | tcaactgatt | tttgtcctga | 1140 |
| tcatctacaa | cttaataaga | acacacaaca | ttgaacaaat | ctttgacaaa | atactatttt | 1200 |
| tgggtttgaa | attttgaata | cttacaatta | ttcttctcga | tcttcctctc | tttccttaaa | 1260 |
| tcctgcgtac | aaatccgtcg | acgcaataca | ttacacagtt | gtcaattggt | tctcagctct | 1320 |
| accaaaaaca | tctattgcca | aaagaaaggt | ctatttgtac | ttcactgtta | cagctgagaa | 1380 |
| cattaaatat | aataagcaaa | tttgataaaa | caagggttc | tcaccttatt | ccaaaagaat | 1440 |
| agtgtaaaat | agggtaatag | agaaatgtta | ataaaaggaa | attaaaaata | gatattttgg | 1500 |
| ttggttcaga | ttttgtttcg | tagatctaca | gggaaatctc | cgccgtcaat | gcaaagcgaa | 1560 |
| ggtgacactt | ggggaaggac | cagtggtccg | tacaatgtta | cttacccatt | tctcttcacg | 1620 |

-continued

```
agacgtcgat aatcaaattg tttattttca tatttttaag tccgcagttt tattaaaaaa    1680
tcatggaccc gacattagta cgagatatac caatgagaag tcgacacgca aatcctaaag    1740
aaaccactgt ggttttttgca aacaagagaa accagcttta gcttttc                1787
```

<210> SEQ ID NO 50
<211> LENGTH: 1731
<212> TYPE: DNA
<213> ORGANISM: Arabidopsis thaliana

<400> SEQUENCE: 50

```
atttctctta aaataactaa attatatgaa gaaaaaacaa gagagataac gacgatcttg      60
atctaattag gaaagttttc taatgatggt aatgtgaaag agtgcttctt tcactcttta     120
tttaaagaag agatattttg gaaatagcgg tttgaaagaa agctataact tggtattggg     180
gaaggaaata aaccagagtt ggtttctagg atgtgttgtc gacttctcat tggtctgatt     240
agacttccat tgcctaatgt cgagtctatg ttttctcgta tataattttc aataagtgga     300
acattgataa aaaaaataac aataattgat tatcgacgtc tagtgacgtg aaaatgggtt     360
agctagacaa gtgaaatatg cacagaccac agacttcaga gcttcccaa gtgtcgcatt      420
cgatttgcat tgacggcgga tatttcttaa ataatttct ttcatttct aactatatta       480
ttggttgttg atatatattt tttgtaaata aaatgtaat aatgtaacca agtagttata      540
gaggttttaa ttgctcggcg gtaagaacag tgaagtacat atagatgttt cttggtagag     600
ttgaacttca attgacaact gtgtattttg ttgagtcaat agatttcacg ttggatataa     660
agatacagca gaagaaaatt aatttttgaag tttgggttaa ttaaggaaat atccaaaata   720
caaattacca taagtttttt ttgtactact aagcaaatta tatactcaac ttttcttttt    780
gctaaaattt gtctttgatg gaattctagg gaataaatta agagaactac gtattataga   840
ttaatacacc atgatcactt taagcagacc aaatgataat aacttattga acacgattta    900
ttcatgtagt acgtacatag atccaaagat cggaataaga tacgagagaa aatggttacc   960
ccatttattt atgtggagat aagaagcaag caactaaagc aattaaaagt accaaagaag  1020
aacatttaga gcaaactaaa agaatctaaa gctcgtgccc ttggcgacac tatccgctga  1080
tctccattat caacactttt cgtacatatg cagtacttcc tcctttgtcc attattaaaa  1140
tttagcatat atgtttgaat cgttgccgct ttcaattttt ttttttttttg agtatattgt  1200
tttgagtgtt gtatatccgt caacatatta cacatctata ttttcaact ttttggatga   1260
atttactaag ttggcataaa ttatcaaaaa acaaattggt aaatgatctg ttattaaatt   1320
gtgattaaaa taacattttg accaaaacaa acctcgcatc acacataatt atgatatttt  1380
attatatggt gcatgcaata tctgttaact aagatgctat ttgaatgtta atttcaatgt   1440
gtcatccaat ccaatcgagt ttttttttct tttaaaaaa acaacaaaat tcatggtcac   1500
tataaatact ctttttattct taagaatttt tttctcctgt attttccaaa aataatagtc  1560
cattttttacc ttatttatct cccgaagaaa ttggatcgat caatgaagga agaaatcaa   1620
atggtcttat gatcaaagca acattgagaa attcaatcta caaaaagcag acacatctcg  1680
acgtaagaaa gaagaaatta tcatagtgat caaaagtacg taaaatcgga a            1731
```

<210> SEQ ID NO 51
<211> LENGTH: 2001
<212> TYPE: DNA
<213> ORGANISM: Arabidopsis thaliana

<400> SEQUENCE: 51

```
atagaaaaaa gtggttatcc aagctacaca aacttttag acttatttct ctcattcttc      60
tagagatttt taatgaaatt tgtatatact tgaaatgcat ataaaataaa taagaaaaca     120
atatctactt aatgtcctgt tcaagaatta ttaagaaatt tcactacgtt gttaagtcca     180
ttttactcca ccttctccac tggagttaga ctctactaag tcgcgttatc ctgcagagta     240
aagattgact atgcattgga ccttgtcgat gtgaaaatgt taaaaagata attattatga     300
aatctctact ataacatatt tggtttcctc aattttaaaa tacctatttt tttctcagtt     360
taccattaac caatctattc cgtgatattt aatgtttaaa cccttcttca attctattta     420
acctacattc taaacaaggt gtcctcattt tcaaaatcct aaactcatct tcatctatat     480
ttctattttc tgccaaaatc ataccacaaa aacatatac gaaaaatgac cacggaaatt      540
gtcttttatt gtttatttcc aaagtcaacc aagttgactg ttctttatat aatgattttt     600
ttttaaaaaa ttatatattg agctaagaaa atattaagtg taattttcaa aaagagaaaa     660
tatatttatt ataaaaatct atagtggtgg atcaaaattc tggtttaaat tattgtatca     720
attttgaggt tcaaattta ggatggaaga gaaacgtaga atgcacttaa agttctgtcg      780
attttttgtta gtacataatc cctcatataa ccatacatat acttattgca ataaccatac     840
gttaagaata gggaccaact tcatcggtgc ttctgttaga catttcaaga atgatatatc     900
acattcatgt atctccgtat atgtattaag accaatgact aaactcagcc attgtagata     960
tagttcaggt aaaactgtca attgtggatc agtatgttga aaattgttaa ctatggttcg    1020
cttgtaacag aatataaata taataataat atataatact aatagtaata tatataataa    1080
taataaaaag caagcactaa ttattttata gaaacacttt aaaaagtatt aaaatctcat    1140
ttaaaacaac tctccaagtt ggtagtccat tgatctacaa gacagctcca cctgaaccac    1200
atccacaatg taaaatttaa ccgtacacat aaaccatgat cataagatgc aacatggtaa    1260
aatctctggt gaagttttcg taatcgatga tgaatatata tatatatata tatatatata    1320
tatatatata tatatatata tatatatata tatatataca atataatttt atttttcaatc   1380
tatttagtaa gtacatattt gttatgaaag tacaaaaata acattgtaat aggtcaagct    1440
ctttgtggtg gtttacattg taataggtca agctctttat tattatttta ctatatgtat    1500
cttcttatcc attcttatat tttatatcat atatggtcaa aagaaccaat cgtatcacag    1560
cagcatttgt taatagaact ttgatcttgg taattacagg ttctatattg aaatcgcagg    1620
agccaaacca gcaacttggg ttaattatta acttcattca ccataataa taattgatcg     1680
tcaagactat ttcggacaca aagacataaa tacttgtttt ctgctctccc tttccctaaa    1740
tgtatcattt gatactttct ctttttccct ccatatgcct tttgtgtgta taaatatatg    1800
tatatgaata agttcacaaa aatagaaaat taaatcaaat cttcgcgtaa tttctcatca    1860
aactccactt tcttcttttt taagagaatc tagggtttct tctactactt cttctttctt    1920
ctttaggtgg tcaaatttcc aagttcttct tttagctctc tcttttgttt ccaagaaacc    1980
tgagaagaat ttttgtagat a                                              2001
```

<210> SEQ ID NO 52
<211> LENGTH: 1814
<212> TYPE: DNA
<213> ORGANISM: Arabidopsis thaliana

<400> SEQUENCE: 52

```
tctacagtga cgtaagtgat gtggtataaa tacggtatgt gacgtgaata catagacgat       60
```

```
gatatttgtg gaaaaaaaag aaagaaaaaa aaaacacaaa agctacatac gagtggaaga      120
agagaccaga gtggagataa agttttaagg gctgtttggg aaataaacca tttgatgtgt      180
tgtcgagtcc tcattggcta cttttttactg tgcttgtaac tcgttcgtta gttttgtgcc    240 tcccttttagc ttacattgtt tccgtaccgt acggactttt gttattgttt ttaaggttaa    300
gaaatcagac caagaactc aatagatatt aaaggagaat aatctttaac tccttaatac     360
tttctacagt aacactataa cgactatata tagggtttaa atattctttc aaaatgcaaa    420
ttgtattttg gtttttttaat ttttcttttt gcatggagac aagtttttttt ctggttaaat  480 gcacggagaa attttaattt tatttaaggt gactttctgt ttttccttta aacagggaga    540
aacattgtgc ttacaatttc aaagatatat atattagata aaattaaata tagtgtgttt    600
taataagtac acgaaagaat ttgacccaat tgtaataaaa ccttaggaaa aatagtaatt   660
ttataattgc aaacacaaaa ataacacgga acattttaca atattttatc ctgctaaatt   720
ggaaggaaaa aaactaaaat gatgtccttt tcttcaattt caagttaagt atcgatcttc    780
tctttgctct ggaaattgat gaacctacaa agtggaagct aggctgaaat ttagctgctg    840
aaccaacaaa actcttaaca tcaaatgaag catgttctat agatcgtggc gttgatcttt     900
ttggaccaac caatatgcaa aatgcatata ttgttgtaaa aaaaatgcct atattccata  960
acttattcac ttgatatact ataattttttc ttttgaccgg gaaaaagtgg cctatttatg   1020
ggaagagaat ctcaaacgta tgatactctc aatgtaggaa aagtctctag actaccattt   1080
tcttttactc ctttagaccc attggatttg ggtagatgga tttattaaat acaatgtaag   1140 gagttttttaa atgaaatata aagatacttt aatgattaac tggtaactgg taaattggta   1200
atgtactact attgtagtca atgtaagaaa atagttacga aaataaaacc ttttctgtca   1260
attaataact cactactata attttttgtag gattaacaca tcacactaag ctatttttatg  1320 actaaataag taaatataat ttcttccgaa ggttcaactt tttgagtggt tattgaatag   1380
ggaacgtgtt ccgataagaa gttaacaaaa caacattcat gtcggtccca tgactattat   1440
atgtctgact ctgtgtgata tcgatatata cataacatat attggtctga aaagtggaaa    1500
atctatttta agatttggta actgatcaat gaattgataa ctgatagtct gataccaaac  1560
ataaactagt tttgtacact aacaaaataa gaatgaaata tcaaattttg taagaattgg   1620
taactgatat aatgaatcat cgtaactgat tattttctttt taccttccga cgtaaatttg   1680
tttatgttgc tcttaattat gttcgtacct taattgatca taaacacata aattttagtg   1740
attccttatg tcgagttgtc aatggtttgg aagattggta gctcctgaca tttcatcgga  1800
atttcttctc tcca                                                      1814
```

<210> SEQ ID NO 53
<211> LENGTH: 2001
<212> TYPE: DNA
<213> ORGANISM: Glycine max

<400> SEQUENCE: 53

```
tttcgtgtgt gtgaacaaaa taaatgatct gcacatgtat catggttata gtaacaagtc      60
ccagctccca agggtagtag ctgcttaaag acacacggaa accctcgagg ataatggtgg    120
agagagagtg ttgaaatttc aaccatctca ctttttttctt ctaccttatt ctttagccga    180
aaattaagtt ctaactttaa aatacagatt tgcttcagaa gttgattttt taggtttttt     240
tttttctgga agaccaatat taatttgtga tagttagtta aaaaaattat attatgtttt    300
```

```
gtgatagtta gttgaaaaaa ttatattgtg ttttgctact aatttacttt caaaatataa      360
atatccaaat atatatataa atcttatcac ttgaaaatag atggtgggta tatggactca      420
aatctatgga tcggtctgtt taacccacga attttgcaga taacaagcct ttttttaaaa      480
gaaaattcgc ataactatat ccaagttttt cttagttcgg tccattaagc tagcacatct      540
agtagtcttt atccatggac atattattaa tttgttatgt taaaattttg attttttaatc     600 tagtggtata ttttagtatg atagatttta acttaaaaaa tgaagtcaat ttttttattac    660 taatttata  cattttcac  ttttaaaaaa tatttatttc ataagaaata ttttaaatt      720 actatttggg tccatggatc aatttattta tctgagtttt tatgggctag atacaaatct      780
tggaaaaaag ccaatttatt tcatggattg gcttatttga tccgtctaaa atgcaagctt     840
cacaagacaa accttaaaca taccatacca tccttttatc tatctctact tcaaaatcaa     900
tttttgcaac attcactcaa tggtgcactt aattaacaaa ccctcatcca tatacacata    960
tttagagatc aacaatatga ttatctatca aaaatacaca aaatcagtgt gtgtttgggt    1020
aggcgttgac aaaaattagt tttgaatgaa attgatttta taattttttt tttgttaaaa    1080
ttgattttga agtaatatta tttatgtttg gatgttttat taaaaaatta agttatgaat    1140
aaaatgaagt acataatttt ggaccaaaaa ttattcaaaa ttatttcaac ccaaaattaa    1200
ttctgtatcc aaagtcaatt ttaaattttt ctttgatgtg aaactaaaca tgtaaaaatg    1260
tatttaaatt aaaattaatt ttagacttat aattaattct ctgtggtcaa tccaaataca    1320
cactcacact tagaatgtat gaaatttcaa ttttttaactt tctcatctat gagctgttcc    1380
tattcctcct tcccctccta tgccctcact agggagccag ccagccatat tccaaaagcc    1440
cttattatca cacatgggtc cctccatagt caaaataaaa ataatatcat gatcactgtt    1500
tggccataaa gagctatacg acacacatgg acacagtagt acactgccca accaatcaca    1560
cgtcgacagc acaccgttcc caaactactt cacctttccc aaaccagaaa ccaaaaccac    1620
ttgtcatcaa acccctgccc agatagtttt tctccatttc aatattttac ttcaccttt     1680 gaggctttgt gggtactaca aaacataaca caattgaact cactgtgctt tcccatgaca    1740
cacatctata cttgtccaga agaagaaaga tccatgaact aacattccca cacgctcgct    1800
tcaccatatt tgccacccctt ttaaccctca cttcttgggt ttattttgct ccttttttt    1860 ttccttgttt ggggtttgca ttttttcctgg ttgaaaaagg gaagaacttg aactaattgg    1920
ttaagttacc tatctatcta tctatctagg gtataatatt ttatatcagt tattaaagga    1980
aagaaagaaa gaaacgaaga t                                              2001
```

<210> SEQ ID NO 54
<211> LENGTH: 2001
<212> TYPE: DNA
<213> ORGANISM: Glycine max

<400> SEQUENCE: 54

```
tcactagggt agtagttgct taaagacaca cggaaacatt taaggataat tgtggagaga      60
gagtgttgaa atttcaatca tctctctctc taccacggta tacttcaata aaaaaaatta     120
aggactaatt ttaaaataca gagatttatt ctagaggttg attcttttag tgtgtttgat    180
tttatgttaa tacctcaaac atacatttag aatcccacaa aattagtttg gtatcatgtt    240
tggattttca aaagttaatt ttgtaacgta cgtttgggat aaacctaggt ttgggtttgg    300
atcagaccaa caaatttgta gcttttaaag tgaaattact ttttatttgt atatttagga    360
tagaaacatg catgaagtaa aaatactttt gattagtata tatccaaaca aatatcaaca    420
```

-continued

```
cttttgaaca aaaagggtaa tcatgttcta ttaatatttt ttttttttgt gataaagaag        480
tagctgaagc ttcttatttg acaattaaat aattcttctc ctatcggatt ggtccatttt        540
taaagtaaaa tgatacctca aattgtgact atatacacaa gccgtgaatc aaatcttaga        600
ccttggttaa aagactcaag tgctaagtca tttgtaccaa taacttttgg tataagtaaa        660
ctcatttttt acaacatact tttgattcaa acttatgttc gcaaacttta tacaaatatg        720
cacttagtgt gtttggatat ttcctagaat gaattttgag tgccaaatca aggtggaaat        780
attgcaaagg ttaaagtaaa tatttgttac tttgaccttt tcaagttacc atgttattga        840
taaagagtat ttatcgattt ttattaatga ttaatctttg tcaaaaaatt tagttagtta        900
gttttagcgg gatttttttcc tcctaattat attttttttca tccacaatac ttgaatttga        960
caccttcatt aaaaggatta agtctgtatt actcagattg ttactttgcc tgctttaagt       1020
tgattttgat aagattgaaa gctaatccaa atatatattt tcacattaaa aatttttattg       1080
catttaaaat taattggctt aaaaataaat tttgaattat atatatatat tgaatttgtt       1140
ataacttta gcaagaaaaa atatttaaac acagaccaca ttatctcaaa ataaattttta       1200
attaaaatta ttttattcaa aaatcaattt ttatcaatat tcacccaaac acacaaactt       1260
aatttaaaaa aaaatcctca tttatattag agatccacaa tatagttatc tatatatcaa       1320
ccatacacaa aatcataacg taagaaattt caattttcaa ccatctcatg tgatctatgc       1380
atgctattat tcctcctacc cctcctattc cctcactagg gagccagcca tattccaaaa       1440
gctcttaaca cacatgggtc cctccatagt cataataaaa ataatatcat catcactgtg       1500
tggccataaa gagctacaag acacacatgg acacagtagt acactgccca accaatcaca       1560
cgtcgacagc acaacgatcc caaactactt cacctttccc aaaccagaaa ccaaaaccac       1620
ttgtcaccaa accccagtcc cagatagttt tctcaccatt tccgtatttt acttcacctt       1680
tagtgggtag tggttacatg atatcagcac actttcactc actgtgcttt cccgtgacac       1740
gcatctatac ttgtccagaa gaagtaagat ccatgaacta acattcccac acgctcgctt       1800
caccatattt gccacccttt taacctcact tcttagggtt attttgctcc ctttttccttg       1860
tttgggaatt gggtttggtt tggttttttct tggttgtaaa aggtaaagaa gaactaattg       1920
gttaagttac tatatatcta gctagggtat ataatattat ataattattg ttattaaagg       1980
aaacaaagaa agaactaaga t                                                 2001
```

<210> SEQ ID NO 55
<211> LENGTH: 2001
<212> TYPE: DNA
<213> ORGANISM: Glycine max

<400> SEQUENCE: 55

```
acaaaagatc acaaaattga acaataatga caatacctcg cattgaagta gttcaataca         60
tattctgagt atgactcgcg agtacatgta tctcatgttt cagtttttaa ccacagctgg        120
atgccatgga cacttttaat tctattcttt taaatgagat acctggccta tcaattttaa        180
gggtaaatta aaactcagaa atcaacatac taaaaaattg catgcatgtc cgcaaaagaa        240
aatgtttaag gcagtatata ttcactagtg cacaaagttt tgaccttaaa tattgaaata        300
gtgaccatac gagtgtaatg tttcagatat atataatgct aattatggac taattaatta        360
aaatagagga ttgctttcaa taggaaaata gtagtgtaat ggaaccggaa agtgaacta        420
gaaagaaatg ttaaaaatgg tctagggaaa aagttaagga gaaatggat tatacataat        480
```

| | |
|---|---|
| gtcaaaaatt ttataccgct gattataatt tatatattat gtaggaaaaa tttattaaat | 540 |
| tttaaaataa ttaaaattat aatttatgat tgaatgatat tataaaacaa ttttacacaa | 600 |
| tcaatttata aatattaaac ttaaaagata aacctaaaaa atactatttt tctttatcat | 660 |
| aatattagta taaaataatt ctactaaaaa aaataattaa tatttataaa aatacatata | 720 |
| aaataaatat ttttttttata acataattta ttttatatat aaaaattaat caaatatttt | 780 |
| aactttggat tacttaatta aaaaatgatt cctaaaaaag accatttgaa tattatttgg | 840 |
| tggacgaagg gatggaccag agttcaatac tcgtgggttt tggcggcgtc aatgagagga | 900 |
| tgcacgtaat gttcgggtcc gtacggcatt gccactgttt aaaccatcgg acacttgaaa | 960 |
| gctcaaagca gtgactgtga tgagcagctc gcaatagaga atccaaaatt cccaaaagca | 1020 |
| aaaacaaaac ccaaaaagca aaagagatat cattgtgtgg ctgttagata ccacagacag | 1080 |
| caacatggta actgaccacc caatccgggc tcgacagcgc aacgttagca aaaccgccct | 1140 |
| ggttttttcc caaccagaa accactttat cgccaaaccc caatgtgatt agagtgttgc | 1200 |
| taggtgcacc tactgttatt gctggtgcac ccaaccttct ttgataatga taaaattatc | 1260 |
| cgtcttcttt ttcccttta c ggatcaagtt gatccgcaag ttgatttta agacttacag | 1320 |
| atcaagttaa tcgtaagtc ttttatggat caacttgatc cgtaagtctt aaaaattaat | 1380 |
| ttaccaatca acttgatccg taagaagctt gcagatcaag ttgatccata aaagacttaa | 1440 |
| aaatcaattt gcggatcaac ttgatccgta agaagcttac gaatcaagtt gatccgtaaa | 1500 |
| agacttacgg atcaacttga tccgtaagtc ttaacaatct acttgcggat caacttgatc | 1560 |
| cgtaagaaac ttgcagatca tctatatcaa ctgtagatca actaaaacat atgcggatcg | 1620 |
| actcattaca tatgtggacc aacctgaatg agctaggtgc acaaaaatat ttttaaaaat | 1680 |
| acatagggat atttttgtct tttcatgtta agtgttaggt gcccaacaac aataatgctg | 1740 |
| ggtgcactta gtaacaccca tgtgattagg gatatataac aacatagcat actcacacta | 1800 |
| ctactcactg cggttttttt ctcctccaga agaagaaga tccttaaatc aacattctct | 1860 |
| ctccctccct tggttataat agcaagcttt tcaagcatat ttccggggtt tgttcccttt | 1920 |
| tccttgttta gggttttctt tggaaaaaaa aggtaattag gtataataat ataattaaag | 1980 |
| caaaaaaaaa aaaaataaca t | 2001 |

```
<210> SEQ ID NO 56
<211> LENGTH: 1162
<212> TYPE: DNA
<213> ORGANISM: Glycine max

<400> SEQUENCE: 56
```

| | |
|---|---|
| agcgcaccgg gaaccaaaac gcgtgtacgc gtaccacgta tcccaattcc ataagaaatt | 60 |
| ctaaaaccc acacgaacca ttttgggcag gaacaaaatc ccccagacga cgacacctca | 120 |
| gaaagttagg ggcatttttgg tactttctgc atgtgttaga gccttgtttg tataaaggat | 180 |
| atagatattt gtctaaggtg tatattgtaa acaaaatatg actttcctat tcttacatgg | 240 |
| tcttttgtct tataaaagat gatagtgacc gagttgataa ttgttcacaa taataatatg | 300 |
| tgtaaagtga tagtcagtta acaagtgtcg actacccgtc gattccgtac aagatagtaa | 360 |
| tcatacgagt gtaaagtttc ctatagagag agagacatga atactaaggg ggattattta | 420 |
| attaaaatag aggattgttt taaataggta aataataata ataataataa taataataat | 480 |
| aataataata ataataataa taataagcaa aggagaaaga gatgttaaaa atggtggaag | 540 |
| gaaaagata accctaaaaa ggaacatttg aatatttggt ggacgaaggg atggaccaga | 600 |

-continued

```
gttcaatact cgtgggtcgt ggcgccgtca acgtaaggat gcacgtaatg ttctggttca    660
tatacgacat tgacactgtt taaaccatca gacacttgaa agcaaagcag tgagtgtgac    720
tgtgagagag cagcaataga gaatccaaaa tcccgaaaat caaaaacaaa acccaaaaag    780
caaaagagat atgattgtgt ggctgttagt taccacgaca acaacatggt aactgacaag    840
ccaatcaggg atcgacagcg caacgttaag aaaactaccc cggtttttcg taaaccagaa    900
accacttgtc gccaaacccc aatgtgatta gtgatatata ataacatagc atactcacac    960
taccactcac tgcggttttt ctcctccaga agaagaaaga tccgtaaatt aacattctct   1020
ccctcccttc gctataatag caagcttttc aagcatattt ctggggtttg gtcccttttc   1080
cttgtttggg gttttcttgg gaaaaaagaa gtaattaggt ataataatag tataactaaa   1140
gcaaaaaaaa agacagtaat at                                            1162
```

<210> SEQ ID NO 57
<211> LENGTH: 2001
<212> TYPE: DNA
<213> ORGANISM: Solanum lycopersicum

<400> SEQUENCE: 57

```
atctttcaaa gagacggatt tagagcgagt tctaatctaa taaaaaatta ttcaataaca     60
ccatacttga aattaataac gtttacaatt actttttttt gaaacgtagg ggcatgtgaa    120
attaaaatta aagcgtaaat gaaaattcac aatgtctaaa ttcggaacta acagatgcta    180
tgcaggagag caacaaaaga agaaacccta attgctaaat ggaaaaaagt gcaaggaaaa    240
atcaagtttc tatatgtgtc ttttaagtca attattcatg gtgtcaactg tcaatatata    300
cggggataat gcacaaatac ctctcaactt atgcccgaaa tctcaaagac acacttatac    360
tatactaagg tcctattatt atttttgtta ataatttttt atccctttc tgcttacgtg    420
gcactaaatt gtgggaccaa cgttgattgg ctttttttc caagctagtg tcacgtaggc    480
cgaaaagggg cagaaaatta ttaataaaaa taagtttagg ggtaatagga ctttagtata    540
atataaatat gtctctggga tttcgggcat aagttgaggg atacttgtgc actatatgcg    600
gtatttttat ttaggggtgg tttggtttga agaaagttat gatgctatga ttagttattt    660
tttagtgaat gtttgatttg ttgcattaaa aataatatgt atggcataat ttttaagaat    720
aatttatttc ttcgattttc ttcgtaaatg tgaaagtgat aatataaaaa tagcttaaga    780
ggaaaatttt gtttaactat ttttccagtt atctcatcat taattcatta ttactcgact    840
caagacaata ataactcaaa attatagggt cctttggtgc gagggatcaa aaataacgat    900
aatgtgataa aaaaaaaaat cttgtttagt tgtcatgttt agaataactt atccaccatt    960
tacattatag tgatgagata tgttattcgt aaataactac cttcaaaata acctatcctg   1020
taataactta ttcccaacga tagtaataaa aatttatgtt acgattattt ttctttatcc   1080
atcactggac taaacgtgtt ggaagaactt taatttagag ttggtgggct aactgtcgtt   1140
attgggaaac ctgtatgcat attgaaaaag taaaaaaaag acaaagagtg ttgtttgtag   1200
gtacaattgg tgtcgaatag taattggaga gtactgctgt gaagtgactc tagttgttta   1260
actgtttctt cactatgaac cacacgatga caaacgtagt acaatcgaag ccaaaaatag   1320
attcaaggtt attacaaaac ttaaataaca aaaccacaaa cactgcaatt atactaccta   1380
gtatattagt actagcagtg agactgtttc gtttttgatc aaaaatttcg cgctcgagtt   1440
taatataggt tgtatcaatg gtgaagctat ctcacccttg atcagaaatt tcgagttttg   1500
```

| | |
|---|---|
| aatataaaaa aaaattatat taagagcacc actcagaatg aattttgcag tgtacgattc | 1560 |
| aaatttaatt gggggctcta atacgaaatt ccgcattggg tggaaaagga aaaagaaaaa | 1620 |
| gctatgatca atctactctc cactgttgca gtttaccctg ctatgttgta ctaaattgta | 1680 |
| ttcttgcatg aatctcaaag gataatattt gattttcttt taattataag tatttaaaat | 1740 |
| tatatccaaa aaaaaatata gcttatttgt gattccgaga tctgtgagta gaaaatccta | 1800 |
| aaaactattt cgagccaatt tttgagaact atgaaaatat ttaaagtaaa aaattatacc | 1860 |
| atttgatgaa tataactaaa atagatattt aaaagattaa ttatcaacgt ttaattcaaa | 1920 |
| aattgatgac caagcactag attggtcata tagttttgag attataactt cttaattatt | 1980 |
| gggtattgtt aaactttcaa c | 2001 |

<210> SEQ ID NO 58
<211> LENGTH: 2001
<212> TYPE: DNA
<213> ORGANISM: Solanum lycopersicum

<400> SEQUENCE: 58

| | |
|---|---|
| cccacccttt ggttcttcga acccctacc cgcacccctt tcttcttctt tttcttcggt | 60 |
| gatctcgtcc cccgtccccc cccctcaccc ccgcctcctc ctttcttctt tttcggaaca | 120 |
| ccctcaccta tttcttcatt tcaaattatt cttacttatt cttaaaagtg atgaataaga | 180 |
| aaaaaatgaa aaacccaaca acttgttaca tatcgaaggg tttgttgatt atgatgaact | 240 |
| tgaaacattt tttaataaaa aaatttgtaa tttcttcatc tcaaattagt ttttttaattt | 300 |
| atattattta tttattttga taatgtgttt taaaaattga tgtttctagt tttgaatacg | 360 |
| ttagagtttg attttatttt tataatcttg gattaattca taattttctt ttctgttttt | 420 |
| atctttctaa aaacgtataa ataaaaataa ataaaaaaga attaaaaaaa gtcaaaattt | 480 |
| ttaattttca atgtggcact gacgtgacac taatgtgaca ataaaatgac gcgtgtgtaa | 540 |
| tacacttgct actgtgagac tggtattgta gtattagggt tgaaaaaaat cactttaaag | 600 |
| atgttaaggg ataatttaaa cgctagtgta gtttaagtgc taaagtaagt tttgcagcca | 660 |
| agttcgagag aacttttatg tattttctct ttaaatatat actcttctca ctgacgatta | 720 |
| tcgatgtaat gatctgactg ttctttaatt ttcttcaaag ttttatttgg attagtgatt | 780 |
| aaatggctaa gacttaattg tcaaagtaac tccctaacca tgatatttct tttatttttct | 840 |
| ttttaaaatt gatctctttta ttggcttatt tctcctattt tatttcacct ctttcttccc | 900 |
| tatttcctct aagacgcaat aaaaagagtg ctttgaaaga aataaagaaa attgtatgct | 960 |
| taaaaaagta ttaggaagag aactattccc aatatttatg gacaagatag tatattgcta | 1020 |
| agatggcgga atttcaataa ttttttaatga aatatataat gtatttatga actaaattag | 1080 |
| aattgaagat ttatttttat acaattaaat tttaattatt aatttaattt atatcatgta | 1140 |
| tcactagttc aagtaaaaat ttagagaaaa tggaagaaaa ataaacgaag aagagccaaa | 1200 |
| tctaattagg catatgctac aatggaaccg cattaacaaa caaaaatatt taaaactact | 1260 |
| cctaaaataa aggaggaaaa catatattat aaatcacaaa aatattagt atcacaaaaa | 1320 |
| tgaacctgag ggacatatta tgaacttttt atataaagta ataataatca aattttagaa | 1380 |
| tttaaattag ccaagtgaaa tatatacctt taattataat tttattttta ttaaaaaaac | 1440 |
| gatgtcatat atgaaatgta gagagtacta catagtgcag aagtactgaa tgtcctagga | 1500 |
| ccttagcata taaggagtat atactaaaaa taagaatgac gtaaacacc atcaatgcaa | 1560 |
| ctattatacg aataaaaact caataagtat ggcccaacca ttacctgcca acccgttgaa | 1620 |

```
atctcgatta atttaaattt acgtacaaaa taaataaaaa tttcaaacta aaactatcta    1680
atcacatttt gtctggtggt atgtagcata attttgtggc tcttaaccac cagatactag    1740
cagtgtgtac gttttatcca atcacaaatc gacaacgcaa cacccttaa tgcttaaacc     1800 actcttgtat caggttatta ttattccctt tcactcaatc aatcaaaaat caacaaataa    1860
aacctccccc cccaaccctc aatcatgctt cttcttccat atagtctctc aattagtcca    1920
aacaaacctc tctatctatg ctaggtagct tatatgattt aatagttcga ttaatttaaa    1980
tacgcattaa agatagagga t                                              2001
```

<210> SEQ ID NO 59
<211> LENGTH: 1812
<212> TYPE: DNA
<213> ORGANISM: Solanum lycopersicum

<400> SEQUENCE: 59

```
tttcgtcaaa agtgttgtca aatttctatt ggttcacaat actcttcaac tcatttaact      60
tttactcacc gtttcaaaaa caattaactc tagtctgact tgattgacta gacacggagt     120
ttaagagtat aaagaagatt tttaaatata taattgtaaa ctaaaacata tttagaaaaa     180
ttgagatagt aataattaac aaaaacggac tcactctctc ccttttctca ttattactcg     240
gccgcaaact cttaaaaata cacgccttaa ttaatactct tgcctaatag agtattcatt     300
tagcacattt ttaagaaaat tgtaaattac taaggatatg attttttata taatggacaa     360
ttgttattaa aaagacgaag atattttta aaacttttat tcgaaacaaa tatgagaaaa      420
ttggaaaaaa aattcagaaa atgttttttt cataccaaac acactcctaa gtttaagtag     480
ggaaaatcgt ctgatatacc tctcaacttt gtcatttagg gttgatatac cccttgttat     540
gaaagtggct catatatacc cctacttgta aacaaatggc tcacatatac ccttttctc      600 taacggaaat gaaacaaaa taattttagt ctaaattttt attatttttt tctaaaaaat      660
ataatcccat atgaataaat ttaatcctcg tcaaacatat ttttttttac tttattttgt    720
ttcaataact aatttataat tattatttg atgataaaat ttatttatgt ttcactaata     780
ttcttgtaaa acttattgta gatgatcaaa ttttttcttc gaatccgaaa ttaaattaca    840
atacacatac agaaaaatag tttaattttt tattctttaa actaagaaat gaaagaaaaa    900
aacaaaataa gataagaaat tcaaataatt ataataaaag aagtcaaaaa ataatttatg    960
tatgaaaaaa aattaaaata taccttgaac tttgatagaa gaatcatatt taccccctaaa  1020 taattttttt ttaaaaatta gaagtaataa atataaattt aaaattaatt ttttaaaatt    1080
tgttaaatga agggtatatg cgagccattt tgtaacggca ggggtatatg ttagccgttt    1140
gtataacggt aagggcatag atgagccact tttataacga ggggtatata agctccaaat    1200
gacaaagttg agaggtatat caaacccttc tcctatttaa gtatttagca tatcatttaa    1260
tagaataaat taaataaata cttatatgaa gaaaattgaa aaaaaaaatt caaaaatgt     1320 tttccttcat actaaacaca cttctaatct aagtatttag catatcattt aatagaataa    1380
attaaataaa tactttagat gaatattaat tggtatcttg atttagatag ataattggga    1440
cgggacctca tgttcaaatt ttaagagaga taaaatatt aaatgattct tttcattgtt     1500
ttagtgttgt tgaatagaat tatttaatac attttattaa aggatgatga taattatttt    1560
atcaaaatta atctaactgt acgaaagatc atcaaaatat taattagtat catccaaaaa    1620
acaatttctt aaaaatcagg caacaagata tggaaataag atcttttgtt ttttcttata    1680
```

```
tttgaataaa agaaaaagac tacgtatttta atatctcata tgtaatatat aatgaataat   1740
cttttttttt taataaaagt atcataaaat tatagagcac tagaaaaatc atttctttt   1800 gactaatatg gc   1812

<210> SEQ ID NO 60
<211> LENGTH: 1880
<212> TYPE: DNA
<213> ORGANISM: Solanum lycopersicum

<400> SEQUENCE: 60
atctgaaata acttttgttg ggcaaaatat cccagatgtg aagagagag aatatagtgg     60 ttttaaaaa accagagtgg tttcgtcaaa tgtgttgtcg attttcatt ggacagagaa    120 gatggattat tgttatgtg tctcaataaa acccacaagt ttttttttgt acagtagaca    180
atagccgtgc gcatcttgta gccaggtgat gcgaaacaat ggaataacgc ccaccatctt    240
tttgaaattt cggtgaaaat agtagcttcg tcacgaatta atatttgata aatattatta    300
tacattcata atcactgctt cttttaaata aaatatttt ttcgttttat atcaattgat    360
tttttttata tgtttattga aaaaaaatta taagtaagaa gatgatattg ctaattccac    420
acatattact tttagtatga tgataaacta atataaaact gagggagtag attatttgtt    480
ataataagat agagatactg ttaaaaaata tgatatagta aatgaagttg gtataataaa    540
aaatattaaa aggaaatgct tcactaatga ggccttatat agcacgattt ttttttatga    600
tagattatat atattatagt tagggaatta catggctttg agacatattg gcctctacat    660
agtttcgaag cctattggct tccacgtatt ttttatatat tagttattac ggctaccttta    720 tcaaaacatg ctaatttaat acaaattatt cttaaaacga gcctagtaga tataactctc    780
tgttggtcat cttttacaag cgccatagta tgctcggagg ggtagatagt atagtaattt    840
gggaggacga tgttagcgtg gtacctagtc ttgacaaaaa ctctgcttca tggtatatat    900
aacttaagac tgatgtttt atataattgg tatagtttaa tttatgattc cattacgttt    960
aattgtgtga ttgtatattt aaaacttaaa tttctataac agtttataaa attttgtatt   1020
gctattaaat atattttta aaataaaaca aaagaaatta ataaggaagt atgtcttttt   1080
tattcggaca tgatgattca taaactggga taaagattta aatagattg tagggtaaat   1140 cttatattta ggtatttcat tttcttataa ttttatcag ctgtatataa gtttcaatgg   1200
tttaatttat tgtagtaata ggttattgtt ggtgcttctg ttgaataaat aacaaaatca   1260
agcattatgg gtatatagtt gtttataatt tctttgatac gatggtacaa aattatctta   1320
tgacttgagg ggggtgtttg gtaggcaata tttcggagga atatttcaaa attaaatttt   1380
aaataaattt atagttactc tcttcttaat tatttgttga tatttaatt taaaattgtc   1440 tcaattattt ataaaaattt taaattctta attaatttaa ttcataatta ataaagataa   1500
aataataaat tactatatca actatcattt tttaataata tattatttaa aaattgaata   1560
aatatttaaa aataaaaaaa tttatattta attgataata tatcaatcaa acgcaatata   1620
aatttaattc gcaaaaatca aagcgtaaag ttaaccaatt cattggctgg gtggatagca   1680
gtcgtttgta tggacaagaa ttaatgtacg gctaatacta ttggttaatt tattgagcaa   1740
attgtgtggt ccaactggat attcactctc ttatcccttt cgttttcctc ttttagtatt   1800 ttattttttca ccccatagta attgttattt tttaaatgtg cattggataa atttatatat   1860
atatatatat gtaataatta   1880
```

```
<210> SEQ ID NO 61
<211> LENGTH: 2001
<212> TYPE: DNA
<213> ORGANISM: Zea mays

<400> SEQUENCE: 61
cccgccgagc aagtcaatcg ccccatcatg cggacttgct cggcaaatgg gctagagaga      60
ggtttatggg cctcgccttg ggtaccctgt tcccggtacc cgacaatgac cttcctcgga     120
tgctgatagg tcaattaaag aaacaacaat ggatatatat ggataggtat agaggtgtaa     180
ggctatctct agaacgttgc ctattcttat acccatattc aaactttatt gataaaatgt     240
tggacaggtc tggtgccctt ggaacaagtg ttgtttccat tctccagagt ggactacttc     300
ttgcgctgat ttgtttggtg agttaccgaa ggagatttag gggaagaaaa acagggcact     360
tataagtgat atattgttta tctcagatgt attgatcact tctctggtat tggtgcaatg     420
tattggggta ccgatcactg agtaatcacg caatgtattg gggtactaaa tcctctctgg     480
tatcgattat tcatgcaatg tattgacgat tttaataagt gaatcgccaa tgtatatgat     540
atttccactg gcggtgtact aatacagcc gccagtgtat atacatcatt tccactgacg     600
gttcagttaa gtgaaccgca agtgtatatg acatttccac tggcggtgta ctttatagaa     660
ccgccagtgt atatacatcc tttacactga cggttcagtt aagtgaacca ccagtgtata     720
tgatatttcc actggcggtg tacttaatac agctgccagt gtatatacat cctttatact     780
gacggttcag ttaagtgaac cgacagtgta tatgatattt ccactgccgg tgtacttaat     840
acagctgcca gtgtatatac atcctttata ctgacggttc agttaagtga accgccagta     900
tatattatat ttccactggc ggtttactta ataaaaccgc aagtgtaaat acatcattta     960
cactgacagt tttgttaagt gaaccaccag cgtatatata tttacactgc cggttcgtta    1020
agacgggccc gtctgttttt ttcactggcg tgctgtaact gaaaccgcca ttataaattt    1080
ctacgtgccg ccaccttaga gctcttttct actagtgtta acttcttttc ttgtagacca    1140
tttggaaaac aggaaacaac gcggtactgt attcaacaac agatggttgt ccacacctat    1200
gacaatcatg gcgtcaatgc agtagtaagt ttgtcgtttt tgtgtgtgtg tgtttattag    1260
ccgtttcttt gttttttttc ttctgttgag ctccaacttt atgaaacgtc gtaagctggt    1320
aattatgaaa tgtaaggatt tggagagaga aaaaaaacgg gagggaaaac catgcatgct    1380
gctgacgcga cggccggacg cagacgcaac aatgcccccg gtgcggcgtt gtcgagcagc    1440
cactgcacca ccccacgcat cacctgcagt aatctagcga cgggttttttc ttatttattt    1500 atttatttat ttatttttct tctctcccctc cctccctcag atttgttttc gtttcatta    1560 atcgttatta ccagcaatta attaactttta tctattgatt taccaaaccg caataaagaa    1620
tatatatatt cttttattaa ggtccagtaa taagcagcac agaagcgcag gtgcagcagc    1680
agcagcgtca gcgcccgagg cgcgcacgag agaaacagag gctgacgagg tggggcccgt    1740
gcgggccttg accaatcgga gttcgacaac agcctggcca cccacaaaca cacactcctt    1800
cgcctcgcgc cggccgtcgt cgcctccctc caccgaacga tccctcctcc tcctcctcct    1860
cctcctcctc gcatcccacc ccaccccacc ttctccttaa agctacctgc ctacccggcg    1920
gttgccgccg ccgcaatcga tcgaccggaa gagaaagagc agctagctag ctagcagatc    1980
ggagcacggc aacaaggcga t                                              2001

<210> SEQ ID NO 62
<211> LENGTH: 1610
<212> TYPE: DNA
```

<213> ORGANISM: Zea mays

<400> SEQUENCE: 62

```
tagtgttatc catggccaca ttattttgtt tgtttgagtt agtttcatta ttcaagcaac      60
agtccattga tgcaataatt gacatataac agttgtacac attatcttgc taaaaccgga     120
actattgttt ccagtatcaa aaaatataa cctgataatg aattttccat tggattttat     180
gcaatatcca gattctcaag atctcttggg aaccaaacgc cgccaaaaat cggttccaca     240
aacgaattcg ataaagcaag tgacaacaac gatttcagtg agatttttttt taaaatacac     300
tactctactc caggaatgac taggacaaca tagatagata gtgaagggaa aaatagtggc     360
tgcccttgcc aacatctttt ggttatgata gcaagtgtaa taaggtgatg tagatggact     420
acatgagacg ccacgtcaga tttaaaaatg tggaacaaag agaagtggag aaaaaaattg     480
ggttgctcgc tagtagccaa ctgagagtgg gttggacacg gactccaaag actccctgtt     540
agagagagag aggggttgac caaatattaa atatacaacc ggtatcctcg aagagttatt     600
atacaaatga ttgtctatac gtgacatgac aacatcacaa accaactata gactacatat     660
tactctatct atactaaaat ataattcatt ttaacgctaa ttacatattt attaattaac     720
ttatgaatgt attttgtatg tatatctaca ttcattatct tctattcgaa tgtagataga     780
aaaagagcaa tagaactata ttttgggaca gaagaagtat taattagaga gtatttggtt     840
tctaaagact tagtccctca attttattct tattcagtcc ctaaattgac aaatacaaaa     900
actgaaatta agttttagat tttatatttg acaatttat actataataa aatagagaga     960
ttaaaaatta atacctagaa atcaaatata ctcttaaact tcacttcgtg ccagaggcta    1020
gctgcgacta gctgcgagat tggaatggat ccggtttcga ccgtacgagg aaggacgctg    1080
gcccaggcag tggggccttg tgatgggaga tgcggtgggg cccgacgggt ccggccgcgg    1140
ggcatcggct aatgggagtt cgacaacggc agcctcggaa cccatcccgg tttcgcgata    1200
cccccctcact gctccagtgc tccctcctcc cctcccctcc gatcaagtcg gggcaacgcg    1260
catcactcgc tttaaatccg cacctcccgg ccggtcccct tatcacctca ccttctcctt    1320
tgagtcctct ctctccgccg ccgcagctag ctgtgacgtt atgctctcgc cggcgccata    1380
gcgccagcgc ctaccgtcta caactatcca gccttaggct tacctatccc gtcaatcaag    1440
cctctcgtaa ggaacaagga aggtagctag ctagttctat agctgctgtc gtcgtcgtca    1500
tcggcggcgg cggcgcctgt tcttagagga taaggttgtc ctagcggaga gggagctagc    1560
caggatttcg gttgagatca agagggggag caggcggcgg cggcggcgat                1610
```

<210> SEQ ID NO 63
<211> LENGTH: 2001
<212> TYPE: DNA
<213> ORGANISM: Zea mays

<400> SEQUENCE: 63

```
cccccctcta ggcgactatc aaggatccct atccaaacgg ccctaagtgc gagacgggta      60
tggactagag gtcggtgccg aggaggtagc agggaggtgc gagattctgt tacagagatc     120
gcggggtgct cggccacac aacgcagcg cgaggcgttt ggcatggtcc gccaaactcg     180
cgaagacgac gaccgggagg cgtgggcccc actgcgcagc gtgatagttt ggtcgcgcag     240
cgggtgcggt gagcggctga cgagagggtc ccgcccgcca gcgagccggg gtgtgcgatg     300
ggccagcgag cgcgagaacg tagttgggcc gcgcgaagcg aggagttggc tcgaaattgg     360
gccgaataga gtggaattgg cccatgaagc cttttttattc tttttctttttt atattttctg     420
```

```
ttttctgttt tcttttcttt ttattttttt caattcccaa tttgaacttc aaaatatgag      480
tatgaaacta gtacccaatt tgaagttcaa gtatgacttt gaatttgtac tcaaattaga      540
tttttaatca taccagtatg gttaagtttg tgtatttata aactttgttt tatattttat      600
tttatccctt tctttctttt tttcctcaaa tactcttctc attatcattt ttatttaatt      660
catattatta ttgattttaa tgcacaaaca aaaaatccaa tatgatgcaa tggtttatt      720 gtgtcttatt aaggatctac ttttttttac atgagtggtc acatgtaatg ataactagag     780
gtacacatac atatataaag gaaacaattt ctccttttat tcttccttac aaagtgggta     840
ttacaatcct ttcatttgca ctttcttcga tgcattgatt gttgattatc ccatgtttct     900
atacctctta gaggttggac attgctcctt tatataaaaa cacacctaga acgagtgacc     960
ttagagttgt tctccatctt tggatgctga ataagttgca tgttagaagc tcattagccg    1020
atgaagtgta aacatctcta gtgtgaatac tttatggtgg aaagtgtttc tgttgctttg    1080
ttgattgtca cagtttgtgt cccatgtaat tctaactcta gccatggact tttttcttcg    1140
gtctattagc ttgagtgcta tgttaggttg ctaccaagac aaaatacact cacttgtgag    1200
tgttgaagtt ggattttgtt cctttagggc tagcttgaaa cttaaatccc ctccagagtt    1260
tttggggatt gagtgaaaaa tgagctattt tcctactcaa tcttcgagaa ttatagaggg    1320
aatttaagtt tttaaactag ccattgtcta aaaaatgtca tcttcttccc cgtgtctaac    1380
tcggccatgt cgctcgtgct aggggaggtt cgactgttgt aacacccaaa atttctattt    1440
tgagaatcaa ttaaatttct ttaaaaatat ttgaattaat tcttttatgt gtattatact    1500
gctaaaaata tcttcttctt ctcggccgta caagtaggtc gctttccaat atatattctc    1560
gttttacaat attttcaacg cattttttcc ttttattaag gtccaagtaa taagtagtag    1620
taccggtggg gaaagagaaa gagagagaag cgcggccgca gcgagcagcg tcgtcagcgg    1680
ttggggcgcg gacgagagtg agaggctgac gaggtgggcc cgtgcgagcc ttgaccaatc    1740
ggagttcgac agcagcctgc ccccaaaccc acgcacgctc atcacacaga cacacacact    1800
ctctgtgtct ctcgcgtcgc gcccggccgt cgcctcccct ccctccctgc accgaccgat    1860
ccctcccctg aaccctcct cacatcctac cacctcttta aagctaccca gctacctgcc     1920
tgcctcgcct caacctcgcc ggcggccgca gccgcataga ccggaagaga aaggaagcag    1980
agatcggagg caggcgaaga t                                               2001

<210> SEQ ID NO 64
<211> LENGTH: 1589
<212> TYPE: DNA
<213> ORGANISM: Zea mays

<400> SEQUENCE: 64
ggtttcgctc gtcccgctgt cgtgttttga ttggacgcgg gggttttgga gcggcgtgga      60
ggcagctaga ccgtcggatc atgacgggga tcgttattgc gggccagaag gatgggccta    120
gcgaggccgg cgttcgagtg atgcgctcgt cagggcgcgc ggggcaggga ttggtcgagc    180
ctggcgtggg ccggaagggt gcggttcagt ggtgagatat ggttttttcc attttgcttg    240
ttccagttcc agtccagcct tcagggtcg gtcgggcaca agggagcgag atggcaagtc     300
aaacgtcgcg tttgctgcag ggcgtctggc tgatgggtcc acacgggtgt aggaccggat    360
gtctgtgagg ctattatcaa taaaagtttt atgggagttt catgcacatt taatggtatg    420
tcacgtcagc attttggacg ttatgccata tcatttaaaa tgaatgggtt tcagagataa    480
```

```
aattagtttg atgtggatga aatcatgtca acccgttttc aaagtcttgg aaactatgtg      540
aaatgtccat tgatagtggt ttgtttaatc ttaccatatt ttactaacat ctattggtta      600
tttagttgca tcatttaatt agtatattaa tctatgaaaa tgaagtttg cattgagaag       660 tattatttca tttttagttt cataacactt ttgatgatgt ggcattgttg gaaagagcga      720
tatgaaatcc ctattgtgaa cagcctgagt gtcctcccct gtttcttttt ccctcggaga      780
aactgtgatt gagggttttg aataacaagg aattttagcc cactcaatac cgtttaattc      840
tctttgtcca aacaaatcat tattgtagat tattcattat tattaggaaa gattcaggtt      900
accctccata cctattaggc tttatttgga tactttgtat agtgttttat atattataat      960
ttgtggcttc tgtacagtgt tatatcatca ctagatgtgt ggtttctgta ttgtcaccaa     1020
ataacatggg ggtcatgtgt ggttttgta gaataatttt atagtacgat gttgtcatga      1080
ctctacaagg gaactttaca tgaattaaac ctgcacaaaa tttacaagct tttgagcctc     1140
tgtcatgaat gtacaatgtt atagaaatac aagaagtgta gccttgcata tttgtataaa     1200
ttgtttgggg gaaagaatct atgcttcaaa aaatgtggcc ttgtagcttg cacaaagtac     1260
atgttgtaca atgctacaga agaaacatgt cttgccgctc agccaaaagg accgaccgtg     1320
agaatcagag cactgcccct gagtctaagt aaacagaaaa agaggacaaa atgagttatt     1380
acaatacaga gaggcaaaga ttcttggaac tatagaccac aaactttagg gtcgtcaacc     1440
ccaccaccca cccgtgcccc tcgcacgcgg gcccgcctcc ttgcgcacta ccaccggacc     1500
atggtccctt ttaaatactt caccgccacc cactccccct ttttgcgatg acctcattgt     1560
catctttccg gtaaactagg cacctctttt                                      1589
```

<210> SEQ ID NO 65
<211> LENGTH: 21
<212> TYPE: DNA
<213> ORGANISM: Glycine max

<400> SEQUENCE: 65

```
tgtaggtaac cctcatagga c                                                 21
```

<210> SEQ ID NO 66
<211> LENGTH: 21
<212> TYPE: RNA
<213> ORGANISM: Glycine max

<400> SEQUENCE: 66

```
uguagguaac ccucauagga c                                                 21
```

<210> SEQ ID NO 67
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
ggcagagccg tgcccgtctc atcccctgcc cgtgcaagca gctaggtagg acgatttgag       60
cgtggtgtta ggccgaaccg ctgaaggaag attgctccac tgttgactgc attgtaggta     120
accctcatag gacaaatgta ttgcttatat tcagcaatat aatgttcgtc ctatgatttt     180
tacctacaat atagtcgata gtggaagaac ggtaacatat gtggtttgca gcaggtgagc     240
aggatgggtg tggatgattg aatatctctg ttcagtgttt tcatcatctg actgaacact     300
```

```
gaatcagctt gctgacgtta gaggttag                                         328

<210> SEQ ID NO 68
<211> LENGTH: 21
<212> TYPE: RNA
<213> ORGANISM: Glycine max

<400> SEQUENCE: 68
guccuaugag gguuaccuac a                                                 21

<210> SEQ ID NO 69
<211> LENGTH: 21
<212> TYPE: DNA
<213> ORGANISM: Glycine max

<400> SEQUENCE: 69
gtcctatgag ggttacctac a                                                 21

<210> SEQ ID NO 70
<211> LENGTH: 3058
<212> TYPE: DNA
<213> ORGANISM: Solanum lycopersicum

<400> SEQUENCE: 70
aatcataaac acaaatataa gaaaaaattt tgtgatagat taataattaa cgtaaaactc        60
atcaatttac aaaaatctct tagaataatc agtgaacgat tcatataatc gaccctaact       120
gctcctaatt ggtgtgttat cattgttata agctaaaagt agttatgatg aactatacat       180
tatgtggtaa acaaattact tcaaaccata atatattgtg gggcttgatg ggattttgtc       240
aatttcatca agaattttg ttttgggcca ctttgacatt atgcatccaa aaaggtccaa        300
tagataacta gcccacttaa taagttcatt tactcctctt gctgattttg gactaaacag       360
aagagccaga aatcacagac ttatccattt tgtggtccag actgtgtcac caccttttgag     420 aaaaggtaac aacgacgaca tattcagtga agttgcacga gtagagtttt aaaaggagag       480
cgtgtacatt gtcttacgaa aaaaatttgt gttacatagc gcgtcatttg aatgagacct       540
aatgaggtac aaattcaaaa taatcagact ctaaatataga aaacatgata aatacttgat      600
ttatcccata ctatgtgata cattttaata tatagtttat tttaaaagat atgatacata       660
tatcacataa actgaaacgt cggaatgaat aaaaaaatgtt gttattacta ggtttcttgt     720
gactaataat ctaaagctcc tttgaagaag taattcctag aaattaggtt tacctaccac       780 tactttttc tttttttttg acacaagtga aggtataagt tgaaacaatg accaattact        840
catgggaagt tgtttattag cccacaggtc tcattggcca cttatatttt agcatagtta       900
cttcgagaga tcaatcaaaa aacttacaaa aatatttatt cagtgagtc gatagtaaat        960 atttatcatt caccatcgta tgatatacat ttgatatata ttttaggtgt tgattttctc      1020
atacatacaa gttgtataat ataacataca cttcagatac atatagtttg aagtcaaaat      1080
ttatatgcaa aatatgaggt atgttaacac gtgatctctc cataaagcta aataatttat      1140
gtatatattt tttaaatata catataatat tatattctaa tttgttttgc cctttttttag    1200 tggtacaatt atattttaa aattttaaat tcgtctctag ctaacttgca catatagttt       1260
gaagtcacat acacttggta ctctcttcac ctacattcaa cttctgcttt gaaaacatac      1320
atacatagac ataatatatt cgtataattt taataaaaaa atatcgtata cacgcaaata     1380
tattatttta ttttaaaga aaatgaaaat ccaaatatg acaatcccaa gtttgtggcc       1440
aggtgttaaa cacttgtgga ctaaacatat atatttatatt tttcaattta tccataggac    1500
```

| | |
|---|---|
| acacacttag aaaaaatggg catttcccca tagttttggc ctaaagttcc taaaaaccac | 1560 |
| tggcttcttc tgcattctcc aaaactgtgg aaccaaaaga cttataagta ctgtttcttg | 1620 |
| gtttaattat ttttacgtat tttattttta aagaatataa tatttaaatt ttaatatttt | 1680 |
| attaaaatta tgtatcgtct tttaaatcat ataattatat tgaaagttga aattaaaaaa | 1740 |
| cttactaaat ataaataaaa atgcttaaat taaaacagaa ggagtaatat ctaaaatgag | 1800 |
| ttatatatat atatataaaa gcttatttta atacgaatat tttattcata tagtgtgagc | 1860 |
| tcataaaatt tattcataat ttgagaatag ttaatgactt attttcgat ataatattgt | 1920 |
| tattctcttc tcaaaagatt tactagtaat gcgaggactg ttaatgacgt attctttaag | 1980 |
| ctcgaatgat ttagatttaa cctttatata aatatttaat gacttttatg aaatatatca | 2040 |
| agatattcga aatggtaagt atcaaatata tattttgttg cataaagttt ttttctaaac | 2100 |
| taaagtgcag agaactttat acactatagg agtaatattt actacttata taagtagtac | 2160 |
| aatattgagt aatatttact gtttattaat tattatatta tattaatata ctccctatcc | 2220 |
| aagaataact cgactttacc aataaaaagt cactgtaatt tctctttgct cctgagttaa | 2280 |
| atatttttat tcggttattc tcgtagccga ttaaagttat atagatatta agaaaatata | 2340 |
| tttaggcttt ttatattata tttaaagtt aattatgttt attttagtta tttatcaaat | 2400 |
| attatcttat accctgcgta taaactaaag taaaatcac attaaattta cgtatagtaa | 2460 |
| aagtaatgtg attattaatt ataaattt tattaaatat gtgaataatt tagctcctga | 2520 |
| tctactatca aacgaattat tatagtatta gtgacggagc catcatattt ttaagggttt | 2580 |
| attcgaacct tcttcagcga aaaattatac tatttctata tgattaaaat aactttttag | 2640 |
| atatatacaa taaatgtcaa accccattca atcattttaa gtatttattt cttcaaatta | 2700 |
| tcgaactctt ttatcgaaaa ttttgaatcg accgctatat actaatattt tatttaaaac | 2760 |
| cacagattta tcattcatga accgacaaat gtatttaaat ttactgacca taacagaa | 2820 |
| cctgataaca cataaactac ttattattat tattattatt attgttatta taatcatagt | 2880 |
| accaaaaaaa atataaaaat aatattactc acgtactgag aattaaataa taaataaata | 2940 |
| aataaagtga taaacaaaaa caagtgactg gaacattgga aattatccaa aaccatcaaa | 3000 |
| acaaaatatc tataaataga tagaaattca ttcttatttc ttacttcact tacaaaaa | 3058 |

<210> SEQ ID NO 71
<211> LENGTH: 2245
<212> TYPE: DNA
<213> ORGANISM: Solanum lycopersicum

<400> SEQUENCE: 71

| | |
|---|---|
| tcttgtcaat atgatctcaa ataacaaata attctatgac aatatgtatt aaccatttta | 60 |
| aaacatcgat cttatgttct ttcaattata attaatttac taaatattaa ttatatttta | 120 |
| caacatcgta taatatatat gtgatacaca tgtcaaagca cgtgcggtga agctaaatat | 180 |
| ttaaataact ttaaagtaac tttcaattaa tattagtttg aattaaaaaa aataatgaat | 240 |
| tagtcatgag atttgcgtac tcttactttt gaagagtgtg ttatcactct tataataggt | 300 |
| aaaagggaaa agggtctgat ataccctca actttgtcat ttggagctga tataccccctc | 360 |
| gttataaaag tggctcatat atgcccttac cgctatataa acggctcaca tataccccctg | 420 |
| ccgttacaaa atggctcaca tataccctt attaacgga agttaaaaca ttagtttaa | 480 |
| atttatattt attacttcta atttttaaa aaaaattatt tagggggtata tatgattctt | 540 |

```
ctatcaaagt tcaaggttta ttgtaatttt tttcatacat aaattatttt ttgacttctt      600
ttattatagt tatttgaatt tcttattctt attttgtttt ttttctttca ttccttagtt      660
taaagaataa aaaattaaac tattttttg tgtgtattgt aatttaattt cgtattcgaa       720
gaaaaaattt ggtcatctat aataagtttt acaagaatat tagtgaaaca taaataaatt     780
tgattatcaa ataataatt ataattaat cattgaaaca aaaaaagtca aaaaaatatg       840
tttgacgagg attaaattac tcatatggga ttatatttt tagaaaaatt attatttttc     900
atttccgtta gaggaaaatg gtatatgtga gtcatttgtt tacaagtagg ggtatatatg    960
agtcactttc ataacaaggg gtatatcagc tctaaatgac aaagttgagg ggtatatcag    1020
acccttttcc ctatgtaaaa tctaaaatta agtttgaact cacataaaat tatataggcc    1080
gtaacctact taacccattg tcatcactaa ttatatagag atcttgattt gatatattaa    1140
aagtaaatgc atcacatatt ttttttaaaa attatttatt tgtaaaaata aggtcgacaa    1200
atactgtgaa atcaatgtga aaaggtttt gatcgttgag tgtatcttta actatggtga    1260
tgcacaacgt aacgaaatca ttttcattac caatattatg aattttttaca ttatatataa   1320 aataagatat ataactaata tccatatatt atattacata tataaattaa aaatatataa    1380
cgaacaaaaa tactacaaaa ttaatggaat acactctatg aatccagcat acacaaatag    1440
agcctctacg taagccagtt gttatctaat ctgtttagtc actatgacat cagataagat    1500
atctgtttag ggtacccgtt tacacatcag cttttaaggt ttcctactta ccaaacactt    1560
ctccttcacc aaattgtttc tccaatctca ttcaaacaaa cacacaacta ggtggttcga    1620
acaaactcaa taatttttt ttaaaaaaaa tttatattta tactaaaaat taaataaata    1680
tacatgtaca tttgtttctt aactcataac aaaattaatt aacgactcag tgggatcgtg    1740 aaaatgttt ttacggctaa agttatgaat ttaaaccata gtatccacaa aaagttaagt    1800 ttccatttt tttcccaaag aaaatttaaa ataacaaact cttaatttca aaatatggtg   1860
cacaaaatat aaggggaaag ggttaaattg agataatccg gtgtcatttt aaagcgaaca    1920
aaattgattt tttctaaaac taaaaatcaa gaaacaaaat agaaacatat caaataagac    1980
aacaaaagtg tgtaacgtga caatgtgata taatacgaaa tacccctagga ataattgaac   2040 acataaaatt cactataaaa ggacaatgtc ataattaatt tttgtaaata aaatattcac    2100
cactttacat gatacgtaat tggtatttgg tacaaaattt gagtaatagt aagataaatg    2160
tagtagtagt gtggtactta ctatggttat gtctatatat acatattgca tatgtatata    2220
taaaaagatt gaaacaaaga aaaaa                                          2245
```

<210> SEQ ID NO 72
<211> LENGTH: 2234
<212> TYPE: DNA
<213> ORGANISM: Solanum lycopersicum

<400> SEQUENCE: 72

```
tatgatcttt ttcaatgaag tgattcagtt caatggaact caaatttat atgtggtagg     60 aattttatat caagtcacta atttattttg ataaccatcg agttagtagt taaaattatg   120
atattgatat gttttaagat agaattgaat acataaaagg tagatctggt acataaacta   180
ttgtgcttat gtagaatttg gggaagaaac gtcaaggaat ataatgtaaa gtatagtaga  240
caatttattt tatcgtatac atattaataa ttattttcac gattcgaata tatataaccg  300
atagatcaca caataataaa tattagtgtt gctcatcgaa aactccgatg cactaatgtt  360
tgccactaat tcttaagata gataacaaac acatctaaac attattaatt aagtgtatat  420
```

-continued

```
atacaacata ttttaaactt attctataac tggatttcaa tttaaaaaaa ataatgatgt      480
gtcatgtccc aaagttagtt gcactctaaa aaaagttaaa aggtttttaa ccaaaaataa      540
cttcttgact ataacaaatt agagttggaa ttaataatca aaacatataa aaattgatat      600
ttttaaacaa gttttacacc ataatgtagc aatccatcct gttagtgata ttgtctgctt      660
taaatctagg aatgtacgtc tttaaaatgc gtcattagtg ggtaagacat gcttacttaa      720
aacacgtcat taatgaataa gatttgttta cttatatact caacatctct catatatttt      780
actgatgtga aattagttat cttaaaccgg aatgtcagta cacttcattt gtatcttttt      840
ttatatgagc cattatcatt tacatgtaaa agtgcacctt aaagctggtt aagcttataa      900
actataaatt gttcattttt tctcgtttaa taatcaatat ctacttaaca aggcctgttt      960
aatagatgat aatagtttaa gtagaaaaat gaaattgtaa ctttttttacg acttttaaca     1020 tttcaactat cagttagtaa tatgctcatc cattacatat tttaaagaga acaaagaacc     1080
attaaaaggt taaaaactta ttataaagtt aaatattttt tcagtatata tgaaaggacc     1140
ttacaagtta caactaaatc ttttgaaaga aaagtatcgg tcactactaa gttttccaag     1200
aaaaacaaca acaaaggaac aatctttttc taccacaagg ggatgtgact attgatagaa     1260
tccattcatt ttaatgggag ggcaattttt ttttaagcgg attcaaaata taaaaaagta     1320
aatatacgga caaaaaaaaa taagaaaatt tatcaacgta tacataagaa aagttgcata     1380
cttccaaata gacatgatac ataaacatga tctttaactt gacgtcagtt ggcaactata     1440
tgtgcacaag taggcactta aacttgtata agattgaaca attgacacat tcatcctaca     1500
ggcaccctac atgaaaattt tgtgtcctgc gtggcgtcct acgtgtatca tgtcatgcat     1560
gacatgtgtg gctacttgtt caattttata caagagtaag tgcctacttg tgcgcatcca     1620
aagttgaggg tcatagttac cgactgacgt caagttaaga gtcatgttta tgtattatgc     1680
cctccaggta acatagattt gaagaagcat ggaatgcatg tagatcttac ttctcgtgaa     1740
aatggttttc aaatacgaat agattagtct cggctcaagt aaaacatttt aaaagtaagt     1800
acttaagaca aaataataca ataataaaaa agttatgata atattaaata ataaaaacta     1860
tagcaaaata taatatatta tcgaagcaaa cataaatgtc taattcaagc ctcgataaat     1920
gaaaaaaata atctaatttg aacaccgcaa cttttctttta aatgggccct ccacgacact     1980
tcatgatata tagtaaaaca aaaagtcttt tattctcttt tcttcttgac tagggaacca     2040
ttagatttta aagacattaa atctattacc cttaccctaa gaataagaag atgtaaagta     2100
gaagagaaaa caaccaaaac catatatata catatatata attacattat attgtcttat     2160
aacatatagt cttttaagga aaaacaaatt tagaaaaaaa taatattatt ttacattttt     2220
tttcttcata caat                                                       2234
```

<210> SEQ ID NO 73
<211> LENGTH: 1302
<212> TYPE: DNA
<213> ORGANISM: Arabidopsis thaliana

<400> SEQUENCE: 73

```
actatatacc ctccaattat tgtgtaccaa agaccctcat aggatttatt caaatattgc       60
aaaattgaaa gaaaaaatgt taattaccct atccatgctt agatattttc aaacctaaaa      120
atttggtgca ttttttgtgtt tatacataat tagtaaagga gagaaattag agttccactc      180
tcaccaacac tttattctag ctagtggttt aattttttcaa tttcagtcca tatttagttt      240
```

| | |
|---|---|
| agagaaaaat gtgattctgc caagaaagtt tgatgctttt ttacttagtt catcgaatta | 300 |
| tagagattaa taattgaaaa tcctacaaaa aaccctaaca tttaaaacca tttttattta | 360 |
| atacgttgag agagacagag atattaaaat cgtatgattc gtaagagtgt gatgttgaaa | 420 |
| atgagagatt aataatggaa ggtggagatg gcgcgtgtgc gatgagtgat tgcaacccta | 480 |
| aacagaaaat agtagggcaa tgaatgagtt tggacacgtg tcgacatctc gatggtaggg | 540 |
| tctgataaat ccacctgatt tttttatata aaaaattttg atttttataaa tttttctttt | 600 |
| ttacttataa aatcgagttc agggaatcat gtgacctaac cttaactagg tgaagcctcg | 660 |
| tacgattttc ccaacttacg gaactaccct tgtgattggt taaaaatgta aagtaaaaca | 720 |
| ctactcgttt gtgatgtttt catgatatct aaaactctta ctgctagttt tgataaatct | 780 |
| tactgctaga tttgcttttc cttttccaat ctatagtact gctaagatta ttttttgttag | 840 |
| tgaaattaac agaaatgtct tttgtattag tctactttat aaaccaccat tttgatgtgg | 900 |
| ccaaaaaaaa aaccatgttg ataaattcag tttggtaaga gagtctgatg agacacaaaa | 960 |
| aaaattatgg gaaagaaaga aaacataaat ggataaaata aacagagatt tgaatataag | 1020 |
| atatagttta ttttggttat cttagggttc gtccgatgtt agagatcatg tctgaccgaa | 1080 |
| agtcttagtg cttttttggtt gcagacgtaa ttgcttatt ctgaccggta agtaggtgat | 1140 |
| ggacacaaag gtatgattca attagaaaaa ctaaacatag cattattatt ctgtttggtt | 1200 |
| atatttaaac ccattagctt cttttctctt ttgatttgca cattgaatcg cttattaatc | 1260 |
| tcacttggtc atggtctcat agaagcattt taagcaaatt tg | 1302 |

<210> SEQ ID NO 74
<211> LENGTH: 2001
<212> TYPE: DNA
<213> ORGANISM: Arabidopsis thaliana

<400> SEQUENCE: 74

| | |
|---|---|
| aataaaaaac tactagatta cagctcttga ttggttgata acttgatatc atatatcgtg | 60 |
| tttgtagttg aagatgtaaa gatttatcat cttgtatttg aattttgcac aatatataat | 120 |
| gtgatgattc tatgtttgtt tgtaaactta tgtgcaaatg ggcgataact aaacgttcgt | 180 |
| aaaatagtta catgtactaa ttaatcgaag cacataaata ttatatatat atatatgtat | 240 |
| atatatgaaa cgattcattg attttaagta tttaatttat tttttaagat tttagttgtc | 300 |
| ttaacctcgt acgaagaaga aggatatata ctatttaact cgtggagatg atgaggttcg | 360 |
| gatattttc cttaagacca caagacactg acacgccgac tgatcgataa aaaaagttaa | 420 |
| ggcctacaat acaaaagagt agcagattcc cttacacgtg tttcatttat gatctgttaa | 480 |
| ttaactccat tgagcttcaa tatctcatta gccgaaaatt aacttgacgt tttccattga | 540 |
| actgtcgaaa aaatttgtag aaaaagtgaa atgtccccta tttaacttcc aagtttaaaa | 600 |
| cctaaaatta attagttacc gttttgatga ataacgttga agaatcgtc aacatatcaa | 660 |
| atgatgcaga tacaacaagg gacaaaaaca tcaaaaaatt gattaaaaat aatcattcag | 720 |
| atattagcaa ttaaactgta agtaaatgat tgcatatata tatatgaatg aatacatata | 780 |
| tatgtatcaa actgtaagta aataacatat acatatatat atatatatat aggaaaatat | 840 |
| ctcatttttc aatcatttc agaggtaaac attttaaag acaattttac ctaacccaac | 900 |
| atcttactat atttaaccag ctctgcgaga gcttcaaaac aatgatgaat ttctgcccc | 960 |
| ttttcattga ccaaataaaa gttcacaaat ttgtaaaacc aatcagcatt aatttcgcac | 1020 |
| gtagtttact tcgtccgatt ttagatcaag tagacatttt aaccaaacat attgaatcac | 1080 |

```
ggttcaatca agatacatgg ttgcgagtat aatatatcaa tccttcaccg cattagaaaa    1140
ccaaattttc tatttaattt agcgtgttct tttaatgaac gcagcgtcag cgacaacaaa    1200
gaagaaaaac agatctgcgg cgagaaaaaa tacattgatt agagaagaac tgccgcaaaa    1260
gatgtacgat gatgaagatt gacgtgacgc tgcttaattt cagcgattca tttgatgcaa    1320
ttgcaattca tcggctatca tcggcgactc atccgaaatt gttattttca agctttaatg    1380
tcgttttact tacctactac ttctcatgac acgtcgtttc agtccgctat tgccgctggc    1440
gcagcatcaa ataaaagaac acgctaggat agcttgaaaa gggtacaata actagttata    1500
gaagaacatg agccataaca tttggaaaca aaatgagtta gtttgaattt gaaacatcgc    1560
gctctatgta aaaaagcaa aaagaaaag aaaagagtcc taataattaa aagagaaaa    1620 taaaaggaat tttcaatggt ccgactgtta caagtagatt tccatttta ggaatctagc    1680 tataacgatg aagacagagt tatcattttg ttccatcaaa tatatgacga tatttatatt    1740
taatttcttc aacaacaaat atctcatttg ttggtgccac tttcacatac ttaggacgac    1800
taataattaa ttaaaaagga tttatgtaat aacgcaccat attaacctgt aacaagaaga    1860
attgaaagta atacaagttt atatatatag caacacattt atcgtgtacg atactttatt    1920
ccttttatct attcttgaaa aaaagttacc aattcttgag aagaagaaga aatcagaatc    1980
aagagaagga gagagaaaga t                                              2001

<210> SEQ ID NO 75
<211> LENGTH: 1597
<212> TYPE: DNA
<213> ORGANISM: Arabidopsis thaliana

<400> SEQUENCE: 75
tacaatatct ctctctctac ttctttactc tttctctctc ttccatcttt tacacagaaa      60
gtaaaaaaca ttctcacacc ttctctccca agtgcgtgcc acgcagacac cattatttgc     120
catgagtagt tagttgctag ttgctactaa ttaagaaaaa tgaattaagt ttttaaaaca     180
aacgttgtct agttatataa tccatgtcca tatacatcta gatatatgac ttagatacca     240
atgtttcgac tcttttaggt ctacacgtac gttgcccaaa cttcatattt gagacatctt     300
tatttatttg tcaacagaaa tattgaaaca tgcatggatc ttgatattct aaaggtgcct     360
gaattaaaat agaacgataa cgttttaaaa cctaattccc aatttgtagt ttatatattt     420
cttgtttgat ccatattatt acaagcctat atatagtgta tataaaactc aattaagctt     480
caaaaagtca gaaactcat caatagctca agttccacta attaatgccc gaatttaaag     540
ttcatctcta tagtttaaaa tttgttcgta gctagatttt gcatcttgga gtggttagtt     600
atgtttatta gacacttgga atgcttttga atgtacaatg tccggaaaaa aaaactaata     660
ctgaaagggg atttgtcca agtggtggta gataggagga ggcgcgtgag attggggaaa     720
cattggtttc ttctgcaatg aatgaaacga aagcagctat catcattttc tttttcttac     780
ttcacaagcc gcagaaaagc ctctcctacc ttaaaatgga catgtacgtg tcgcttttct     840
attgcttcct atctattcga caacattgaa gttttgttct attactttcg tattcaattt     900
ttaatttttg tttgagaata ccaattttgt tttggatcta aactcgttct aatgtaaaaa     960
ataataatca gccgcagtat atcaatatgt tacattgtat ctggacgtgg gatatctgac    1020
catgtctcca tgaatccatg atgattgaca gatttatagg gataagtatc ctggtttagg    1080
taatccataa gtatttatga atattatgaa ataaatttc gatcagaaag attaattagt    1140
```

```
taagactatg atgtagggta ttttaaaata ttgctaaaaa ttttgcgcgc tttcagtatg    1200
tatatttatt ttactagttt tcggttgata tatgatttct tgaagtaatt aaggttatta    1260
gctaaatgga agagaacgtg aggaatataa cacatatgtg atcacatacg aatatatgta    1320
ggtttaactt aattggttcg ttgattattc tttataaaag tgaaagtaga tttaaatttg    1380
ttttccaatc ttctatgttt ggccattgtt tgcaagagtt ttgggaatta aagtcttttt    1440
aggtgagacc aagaagggta aaatatgagt ttttgggtct agaatttata agttaaatag    1500
tttattctca tttctaatta ttgttgacca aaaaaaaaaa aaactgtttg gttttgaggt    1560
ttaattactt attgtatatg tacactctca atcataa                             1597

<210> SEQ ID NO 76
<211> LENGTH: 1552
<212> TYPE: DNA
<213> ORGANISM: Arabidopsis thaliana

<400> SEQUENCE: 76
tttactttca ttcccacgct ctctttaagc acgtgtgata cagtcaccaa ataattggct      60
cttgtgatac aattaccaat taaacttgta tatatgtt tatatgttat ttaaaggata     120 aattttt att tcgtattact tactttagag ttttcattat agggttatta tttaatttga    180
acatctatgt gtttctcctc aggtagaatt catgtttgtg tatatatggg tgtctactat    240
ttatggaata tttatacaaa acatctaaac atatcattgc ttgaaaattc tatgtttata    300
tcataatagc aaattgttta tgtttagtta tatataacac aacaatagta ctctaagaaa    360
aacagcatca tgcacgtttg atggttgact agtaactaga cacacgaggc acaaaggtta    420
tcagttgatt aacatgtgta tgtatatacg gtctttcact tatcacatta caaacttgaa    480
agtaaaattt gtttagcgat attaagaaag tttatatata gagacctcgt actagctgga    540
aatgtatatc taaaatgaaa gtacactccc tcttacatac agtttaatat attttcaaca    600
taaaacatat gtacatagta ctagcttatt ttttaaccaa aacttttggg tttgatagtt    660
taacaactcg gtcaagaatc tcatattttc ttacttcaaa taattgccaa tatattctag    720 ttcttttttgt ttttaaatta tacctggtaa ttttctaacg agagtctcat aattgcaagt    780
tgtagtagtc ttgcagctgg atatgaagcg cgtgaattaa aactaaataa tacttacaat    840
aaatgaaagc aacgtatcat atcattttct agttgttttc agaagccgca gaaaagcatc    900
ttctacctta aaatgggttt ccatgtgtcg atgccttatt ggatcatact ttcttacttt    960
ttaattcagt ttaaaataaa ttgaaaaatg agataaacat ttaagtggtt caattatcat   1020
aaaaaacact aaaactgata aaatagccac ataatatagg tcatatcaaa taaatgagaa   1080 ataaatttg tatgcctaaa tcaagttatc catgtttgaa ggtgtttgca gtgaggtata   1140
tatgtttttg tctaataaag attacagtta tgattatgta acataaatta gataatattt   1200
acagctcgcg atacactaca attgaaacgt ggttaattag tgaaactgaa atttgaagaa   1260
gaggatgaaa tatgaatgat attcgttaaa atgatctctt agattgtata gtcattgtcc   1320
cccattgcca aaagatcaac cacttacata agtaaaacg catcttttagt taaaagctaa   1380 ccaaaagagt ggaacatatt tattttttgga ttgcatttgc gaatttcatc aatatatggt   1440
tttgttcaat tgggaaattt aaataactcc actaaaatgt acaaagtaat ttttttttcga   1500 caaagaatct atgaagctaa aaaatctacc cataagtcac ttttagcaga aa             1552

<210> SEQ ID NO 77
<211> LENGTH: 2001
```

```
<212> TYPE: DNA
<213> ORGANISM: Arabidopsis thaliana

<400> SEQUENCE: 77
catcaatcta tatgttgcat gttgtaaggt cacaacttgg aaccataaaa gaatggtgga      60
ggatagcaag tgcgtagaag ataaggatca ttttacatga taatctggat aagacatgcg     120
catatacatc aagtttccat caacaagatt tatagtaccc aaaagaaaga aagaaaaaaa     180
ctaatattcc atcgatctat agaagttgaa caaaataact aaggtaccaa gtgaaatatg     240
agtcagcaag caaagttaaa aaaaagttg  tgtgagacat atcacatgag taaattaaca     300
acaaccatca tcatcatgat gtagatagta taagatgcca tgagaagaag tgaggaaaaa     360
caaattaacc tgacaagaag catcctaaaa aattaacctg tcaaacaatt accaaccttt     420
aaagtgaaaa aaaagttga  aaacactaag gctttgagag cttaaatgtt cataaacaat     480
tttccttttt cttgccaaga tcaatctgca attttgtgt  caagcatgta cgagttattg     540
ttataaataa atctagagtc gttatgtgag ttctactgta ttttatgaaa atcgattaac     600
tagtaaaata catcagtctt cttaagaaga gaacctaaac acgaaaccct ctaataaatg     660
ctagattgca tattcttaca catctatatt agtgtcaaaa acatgattgg actgattta     720
tagtattgaa caagaacgtg actaaatttt cagaaattgg aaagaaaaca aaaacatgat     780
atatttcaat atctaaattt caccatatat atataaaaag acatagtgca tgtgagacgt     840
aaaaaccttt gtaaataaat tttctcttta aatagtaaat agtaccatat cagattaacc     900
atttcagagt gacataattt gtttgtaacc gtatagatcc gttttatgca ttaaaacgat     960
cgtgaagtag ctgtcatacg aaagaacttg tcggcaagag aagcaaagca taagcagaaa    1020
aaaacatatc ttttagaagc ctatcatttt cttactttta ttcacaaaca cacacaatat    1080
acattataag tgttatctac ataatctaaa cgtgtcaata cctgaaaaaa caacaaaact    1140
ttatttgcac ttctttcatt tcatgaacaa tacataacca gatattagat aggacttgga    1200
cttgtgaata tgctctattt aaggcatctt tataggttat atttagaatc ttttttcttat   1260
ttctttttg  agcatattat taaactatgg actagatctg atgaaagaaa gcaatctatt    1320
tatatattat ggtgtaaata ttatcttta  aaaatccaat ggaggagagt gaaagagaaa    1380
agttgaagca ttttgtttgg actatagaga gagagaaaaa aagatcttaa ctctccttag    1440
aaaagtacta ggaatcaatt tttatttct  gcaaaaacaa aagtgtaaaa gaaaattaat    1500
aataatatat attccctgat gaagtaagac taaaataatg taactacaca aaaatacttt    1560
ttagaattta taatatttta tattaatttt taaaaaagga aagttgataa gattggatat    1620
aagtttggaa gcatttattt ggccaagaat ggcttagcat ctctgcaaaa ccaacacaaa    1680
gctatattct cttaaaaatc agttcaacaa aagaagaacc tgaacacagt tggcccacca    1740
ccaccactac cacaatctcc tcctccacca ccaccaccta gtcaccggaa accaattcat    1800
gccctagatt aagaaccaga atccttttga gacaagatct atatatacac tctacacatt    1860
tacttataca ctttatctag atatagatgt gtgtgtgtat aaaggttctt tttcattact    1920
tgttggttta gtgataaaaa ggaggagagt tttcagttgg gttttggttt cttggtgaga    1980
gaagagagaa aaagagagga t                                              2001

<210> SEQ ID NO 78
<211> LENGTH: 1558
<212> TYPE: DNA
<213> ORGANISM: Glycine max
```

<400> SEQUENCE: 78

```
acacgtaaag tggacctaag gatatactta taataaattt ttataattta tatttttttc    60
catcacatca ctacttatat ctattttttt tcttttatt ctaatctttc tcgtaattaa   120
aatgtaaaat ttaatgtatg agtaacattg tatattaaat tttaaaagta aattaaaatt   180
attttatca gcaaaataaa ttttattaaa cttgggtaaa ggggtgccac aacttatgcc   240
catagtatca tgtcattacc ttcagtccta gtaccagatt ttcatatatt ctctaaacat   300
attttcattg tggattcaat catggatcaa ccgttagttg atgttttcgt acttttcgtg   360
ggagacattc ttcgtatcat aaaacaattt cctttattat cttcttaaac tctgttcttt   420
tttttaaaa aaaaaaatct gttaaataac tatttttagg agatgaatag taattgaatt   480
acatataatt ataagaaaat gattttacaa ataattaccct tgagaacaat gattaagaaa   540
tcgataaata aaaaattagg taagatgcag tagaaacatt aattaaatgt caatatatat   600
atatactaat ttcttaacaa ttgatcaatc tcaataatac tgtcaaatgt gcatatcaat   660
tggcattaga tggtttagt ttagatagtg atattgagtt ttttttttta tgcaagtgat   720
attgagtctg tacatatggc ctctaaaaat aacactcaat gattaacaaa attgtattt   780
actggtgaaa tggaagtatt attattaaat ataattcag ggtattaaat taagaaaatt   840
gttgaattaa gtgactccgt tttatgtcat aaagcactaa taatacatac attaattttt   900
aatgaataaa ttttacgtct ctagtttaat attaattatg tactaatagt gttaggattg   960
ctatcaagga gagtctaaat atatcattta aggaaataaa agtacaaagt ttttctggta  1020
aaagatagca tttattatgt caaaaattaa tgaaactcgt ctaattaatg cataatttgt  1080
taagtgattt aaaatcttta atatggtgta tttaatattt attaactact atccttaatt  1140
agcaggacac tacttaacaa gaccgtaata gttcaaaatt acgtcataga aagtttaaag  1200
aataatggga gaaatcataa attatgttag gattgatgaa aatatgattg attagaacga  1260
agcgaaataa aatttcaagt taatcatcat ttggatttt ttaaaatgca atagaatgat  1320
aaataatgaa atgaatttca tctcatttca tccaacccta ctcataaaat tatagtatat  1380
attactttt acttgtattc aatcgcaatt ctattcttt taaattaaaa actcagacat  1440
aattatcatt tctacgttgc attttttaca aacacgtcta cctacttaat tactcttgca  1500
gctagcttgt tacttttaac ttataagagt atcaacggaa catgattgct taaatgga   1558
```

<210> SEQ ID NO 79
<211> LENGTH: 1545
<212> TYPE: DNA
<213> ORGANISM: Glycine max

<400> SEQUENCE: 79

```
acacgtaaag tggacctaat tttaattaag actaaggata tacttataat aattttttta    60
taatttatat ttgttttcta tcacatcact ggctttatct atttatttt cttttttatt   120
ctcatctta tctaaattaa aatgtaaaat tttatgtatg agtaccatta tcaaattttg   180
aaagcaaact aaaattattt ttttatcggc aaaataaaat tattttttta tcggcaaaat   240
aaaatttatt aaacttgggt ataggggtat cgcaacctat acacatagta taatgtcagt   300
gccttcagtc ctactaccaa attttattct attctataaa catatttca ttgtcgattc   360
aatctcttta atttatcaa atttcaatt gagtttatc ttcctctcat ccacattttt   420
ttgctggggt taaagagact aaattaatgt tattaattt aagtataaaa attaactaat   480
tcgttaaatt aattcataag aggaaagtgg gattgcattg gagggtagca agaaagccat   540
```

```
tgaaagaaaa cgcagcagcg atcatttgta taaagtataa actacttcct acgtactata      600
tgtatgaagt gccattctaa cattttttt tcttctaaat tttatattgt gttatagtat       660
gaaaataaaa attactcact agatttggcc tagtgatggg atttgaatag tttgtacaag      720
atgaaggttt aaactttgtt gttgacatta tacatagaaa aatacaagaa aaaaattatt     780
atcatcttaa actctgttct ttaaaaaaaa aacagtagtg ttaaataact gtttttaaga     840
gatgaatagt aattacaaat aattataaga aaattatttt actaatcatt actttgagaa     900
caatgattaa gaaatcaata ataaaaaat ataagaaat aactatttaa cttgcgtttc       960
aatttttttt aagattacaa tattatagtc cgtgaataca catttccctt ttgtgaataa    1020
aggaagtaaa cattggtagg gaaccaagaa gtctaaagca gtttgcttgt ttgccttaaa   1080 ttttttcttta gctcgaaggc atgtgaaatg aatatttcat tgtgagtaat tatgagattt   1140
tcttccaatt aaggcaccaa agatgtaaaa aaatgaaata gtttattttt gtttaatcag    1200
tattagagtt gcttttaatt tgattttttcc tgactgaatg ctaacaactt ttgctaataa  1260
tagttttcat atgaattggc gttgaaagtt aaatcttcag atttaattca cgcattatta   1320
ttattattat tataagaatt ggattagata aagaatggt taaatttatt attattttgt   1380
taggcttata ccttttacata taatattatt attaatttgc agtaggaaac aatattctat 1440
aataagaatg attattaaaa tatgaaataa gaacttttca aaatctgaaa ttatgcagcc  1500
acgctgggcg agtagtatct cgctgagcaa gcagtgcgca ttaca                   1545

<210> SEQ ID NO 80
<211> LENGTH: 2001
<212> TYPE: DNA
<213> ORGANISM: Glycine max

<400> SEQUENCE: 80
ttaaatttaa attgacgtgc tgaactgaca tttcgatttc aaattgacca caagaaaaag    60
agaacgcgta aacattattc atttatttta tttgttcttt atttatttct tctaaagtac   120
ttagactaac taataacgag ttaaatattc ctaaaaaaaa ctaacgagtt aaatagctat   180
atggttgaag tgatgttaag attttagttg tgggatgatt tgttcttgaa taaaaaatac   240
ttaatgttca ttaagtatct tccataaaaa tatcttttc tcctcttgat ttagttatt     300 attaatatta ttgtgtaagt gtttataagt ttgtgattta tcgtaacttt agaatgaatc    360
aaagttctat gatcctaaaa atgtttacac ctagacctag ttgttaaaaa ataaactttc    420
attaagattc cttgtttact tttaaaaatc gacttttaaa ttttttacac atattttat    480 gtcatttatt ttaatatcat gtaatacaca ttattaatcc caaattatac tctgtaatta    540
attgtaaaaa atatacaata ttatacatct acaattttgt tcgtagggta ttatatgttt    600
atttataaga atttaagttt tatataatat aaaaatgaca aaattacatt ttttttgtct    660
cccagcttat ttccattttt tctaattttt gtctctcggt aatttaattc agtcctctta    720
ttttataaaa tcctataatg ttagttccca agccacaata cgttgatcgt tcatgtgtca    780
tatctttatt ggatgatgac cgacacatat tatgttttta ttggtcaata aaaataacaa    840
tgtatttcat cttttatgca gttgacattc aatcacaaca taacatatga cagaatcatc    900
atctaataag aatgtgacat ctaacagtca acatcatttg ttaacggtca atatctaaat    960
gtgacattag aagactaata ttgcacgatt ttacaagata ggaggattaa attcgtgaat   1020
taaattaatg ggggaccaaa tttataatt tccctataaa aatatttata atatcaatca   1080
```

| | |
|---|---|
| attttttaaaa aatgtttcaa atatatctcc taaattactt attattataa aaattaaaat | 1140 |
| tctcaccata taataatcta taactacatg agaatataaa attttatatt aaatccaaaa | 1200 |
| atatcggaaa gaataggggt agttgggtaa atgcatcatg taacatacga gctacctacg | 1260 |
| actatgaggg ttcacctcgt ttaaggttag ttcctgaatc cgaaacagtg agctgaaaat | 1320 |
| caagcccgct ccccacttca cctttcgaca cgtggcactg ttgtgacata ttctctccaa | 1380 |
| tcatcgttag tcatcaggga ccctatttag ggcttctccc attttcttg gaaatttcca | 1440 |
| ttaccaaccc ctccctcctc aatctcctta tgttccttaa tttggtcctt ctttctccac | 1500 |
| cgtctgattc ttcctacttt tcaatcaacc gcgttccac cacagtagta tccacattac | 1560 |
| cctgaatttt aatttgagca gtgtttactt ggcccggtaa tcaaagcaca ggacacaggt | 1620 |
| gatttatgaa gcaaattaag ctaagagaaa aagacagcta gagagagaga aagagatatt | 1680 |
| tgattttgga gttagcatcc attaccattc ccatttgacc tgataaggat gcttttaatt | 1740 |
| tgctgggatt cttaataaca aggtagaata caattaataa tactcgtaca tacctcttag | 1800 |
| tatcacactt tagactttac accatataaa atacatacat gttacagtat atgttatata | 1860 |
| caaggcctac atatatatta tagagattat atatatatat atatatatat atatattcta | 1920 |
| aattttgtga gtggatatta ttactttgag cgtgagaagg ggaagagtag agagagagag | 1980 |
| agagagatgg gaaggggaag a | 2001 |

<210> SEQ ID NO 81
<211> LENGTH: 2001
<212> TYPE: DNA
<213> ORGANISM: Glycine max

<400> SEQUENCE: 81

| | |
|---|---|
| gagataaatg tggttttgta cctagtcaac ttccgcgtat gatatgagac acgattacat | 60 |
| taagcgtgac atgtacgtat tggaaatgta tgtgtccaag aaaataagga aatataaccct | 120 |
| caaaaatttg taagagaatg gatttcccat atttgttcaa aagctaagct tacagctttg | 180 |
| ccgtgctatt ctgctattgc acagctatgt atatctatat ccaaatgcga tatatagcaa | 240 |
| aatgaaataa aatttagcaa gattaactta agtataataa catgtttttt tacttttata | 300 |
| taattagaaa ttattttgta cattgattaa taattactta taagtacaga taaaatatac | 360 |
| aaaaatatag atttgaaaag tattttaagt aagtactagt ttatttaata aaaatatgtg | 420 |
| agaagatcca taattacatg agaagagtat ttttcactct caagaaaatg aagagacgga | 480 |
| cttattaaat agataaataa ttttttaatat atctatgttg aatgaacgaa tttagaaaca | 540 |
| cttcttgaat ttattttttt ttaaaaaaga tgcgaatttt ccaaattatt tttccctatt | 600 |
| agaagctatt ttctaaacaa tcttttttac aaacaatttt ttctaataat ctcttgtagt | 660 |
| taagaaaata gttccacatc ctagcgtagg gaaaaggtag ctaagtaggt aggtgctaga | 720 |
| aattgtaacc ttcaagatca catcttattt ttcattgtac tgatgagtga tgacaacgtg | 780 |
| agtttcaatt ccaaagataa caactaatat tagggatgtt gacaattata tataaatata | 840 |
| tatagattca attcatatct acgaaaatta cttatgatat atagcaaggt aattattatt | 900 |
| attaataata tcaagagtat gaagccggat aaatatgctt ttttttaaaac cggaggatac | 960 |
| tatagtaacc ttcatatata gatctacccc attgccaccc taattaataa tgtgctggaa | 1020 |
| aatatcttac tagtcacttt caatttcaa ccaaaaatgt aaatatacat tatttctcct | 1080 |
| attgattgtt ttcacatcaa gtactaccag ctttccattt aattaccact tactggcaat | 1140 |
| gaaaaaaatc tcatctgtta cttttccaat aattctgcta ttttaacaag tgaagaacaa | 1200 |

```
tgcttcaagg tgtggcttca ctaatgaagt tatttatact atagtgaata taagccagtg    1260
ataaagtgac acgtgtggaa tccattttaa ggtatgtgac gacgttatga tactcttgct    1320
gtgcctctct gtagacagta gaaaatgaca cagattttca ctgcaaacag aaaattatag    1380
gtaacggaga gataggttga aaaaacaagg tcacaagaat aaaaaagttt aacgtaggaa    1440
aaataatatc attttgtaa gtaatagtat ctatctatat gacagctgtc actacgcgcc    1500
agttttctcc cactggagca acgagtgttg agtgtctcac acgcgcctat gttgcgtgtg    1560
ggggaggtga ttgtcttcca aaaatacgtt aacatggaaa atcatgggaa agagaaagtt    1620
acatgaaact agaagaact ccaaccctaa gctgcactcc attttttct ggtggagatg    1680 gaaaatcctg aggataaaaa ggaaacttag aaaagagagt acatatacaa tacaagacaa    1740
cttcacacac acaacacttt cctctctctc tctctctctc tctagggttc cgagtttgaa    1800
gttgaaagtg ttgaactatc tctagctagc ttttcacaaa tttggttgca cttgcaactg    1860
aggcaggaaa gagggggcacg agaggaggaa gaggaaagag aagaaaaacc aagaaaagtg    1920
gagaaaggga taggtgttgt acagaaatag aaattaaaat tgagtgaaaa ttaaagagaa    1980
gaaggagtga tagggagata t                                              2001

<210> SEQ ID NO 82
<211> LENGTH: 1643
<212> TYPE: DNA
<213> ORGANISM: Glycine max

<400> SEQUENCE: 82
taaaaatata tataacatgg ttttaaataa taaaacatta aaataaaata ataacgtatc      60
aaataaaatc ataaaaatat actaataaat aagtcaactt aatattattt attatatatt     120
taaatatata tatatatata tatatatata tatatatata atttttttat ttaaaataaa     180
aataaaaccg taaacaattt aaattaaaaa aacacaggtt aacaaacaa aaacaagttt      240 tccaaatgaa aaaaagcaaa aaaatatttt acgactttaa agtcataaaa taaattttt      300 ttttaatgaa atcgtaaata attttataac tttgatttaa agtaaaaaaa aattacgact     360
ttaaaatctt aaaaaaaata aaatttaaac tgaagttgta aataatttta cgacttcaat     420
taaaaaaaaa taaaaagtca tatcagatgt tacgactttt gagttagaag tcataacatc     480
tgttataact tatcccatt tggataattt ttcaaaatat acaccttatt ggaaaattgg      540
gtaaaatttt acccctaatt gataaaaag tcaacgatat aatttcccat ttagattcca      600
accattaaca gattttaat tgatgaatag tataaatttt tatagttgct ccttataaat      660
taataacttg aaaaaataat gatatttaat ggaatctgat taaaatttg aaaaacaaaa      720 tataagaact ctgtcaacag cttttaaatt agagattat cttaaaactc aataaaatta     780
taatatatgg atcgatctaa attagtaaat tctgaatagt actaatgtaa ccttaatact     840
attattatcc atgcctatct gaaagactaa attcccgttt tgcatgctag aaaatgaaag     900
ccagtgataa agtgacacgt gggggtccag tttaaggtat ctgacgacgt tcttgcagtg     960
ctctactaac gtgaacacag tggaaaaaaa tgacagaatt ttcttaatat catccacagt    1020
taaagacagc tgtctccacg cgcccgtgta ttagaggcg cccacaagcc aataggttat     1080
aatgagcgtg tttcatacgc gctataagtg agaacgggaa aatattttt gccaaaaata    1140 ccttaaccca gtaaagcatg ataaaaagaa acttgtatga aacaggaaac tcggaccaac    1200
cctagcaaga tgcactccat ttaatggtgg agattggaac aaagagaaaa atagaaaaag    1260
```

-continued

```
aaaaaaagtg aacatctgag gataaaaaag ccaagtttga tagacacaac tgtgttgttg      1320
ttgttgttga tgatgtttgc tttgttctct ttctctctcc tcaaatttt tcctctctct      1380 ctagggttcc aagagtgtct tgaactactc cagaaccctc tcttgttttt cacaaatttg     1440
ggtttagtag agtactgacc cagaaaagaa ggttcaacag gtacctaaga gagggataq      1500 aaagaaaaaa atagaaactg tacgtataaa agaagaaaga aacaaagata taaggaaaaa     1560
gggaaaatat tttgaataag gaagatataa ggcaatatat aaaaatatta gtatttgata    1620
ataattaggt gtagaaatat tat                                             1643
```

<210> SEQ ID NO 83
<211> LENGTH: 2001
<212> TYPE: DNA
<213> ORGANISM: Glycine max

<400> SEQUENCE: 83

```
agctgtttca cacaaactat taattactgg ccaggttaat tactcaagaa gtagtaatac      60
tatcagtatt gatattaggt tatatttcc tattacaagt ttatattgtc ctgtacaact      120
ttgtagtttt actaagtttc taaactaagt aaataattac aatataaaaa aatctttaca      180
ttactccgtc tatcctataa caattattgt cttagaccat ttttatacaa ataaaaaaa      240 ataaaaaagt ttaattactt atttacttct tatacttttt aaatttatct ttttttagttt     300 ctataattag taagtatatt ttttaatcca caaaatatat attttaattt ctaaaatgtt     360
cctgcagtta acttttttt aactaacaaa gttaaaaaaa ttaacgagat aaataccttt      420
taggaattaa aatataaatt tgaaggatta aaaaattat ttattaaatt ttagagacta      480
aaaaattcat ttattaatta taagaactaa aaggaataag tttaaaaatt ataagaatta     540
aatgggtaat taaccaaaaa aataataaat agataaaata aaataatatt tttataaat      600 taatattata taattattaa tttatttta gattttgtag ttgatcgtta atatagccaa      660
cgttcctgct gcaagaagct acccggata ttccgtcccc atctaccaaa acaatcggaa      720
atgtttcaga ttttatagtt gatctcttaa tatataagag atataggtgg aaaattcatt      780
aatgttatat taaaactaa aattacaatt atattaggat aaaaatattt tcttataacg      840
gatgaagtat tgattaatta gaaattttt atgtatgatg attttgttaa ttttatgat      900 aattatttta aaatcattta taacagattt ttaattaatc cgtagtataa attttttatg     960
ctatttgtgt atcgaaatta aactatgtta aattactcct tataatttaa taacttgata     1020
gaaaaataat gatatttaat gaacagggat ctgattaatt ttttttaaaa aaatataaga    1080
actctgtcaa ctgcttttaa attagatatt tatcttaaaa ctcaataaaa ttatatgtaa    1140
tggatagatc taaattctaa atattaatgt aaccttaata ctattattat ccatgcctat    1200
ctgaaagact aaatttccgt tttgcatgct agaaaatgga agccagtgat aatctgacac    1260
gtggggtcca gtttaaggta tctgacgacg ttcttgcagt gctctactta cgtgaacaca    1320
gtaaaaaaaa tgacagattt tttcttaaaa gcatccacag ttaaagacag ctgtctccac    1380
gcgcccgtgt aaaacacgcg accccgcatc aaagagggtt acactccgag tgtgtttctc    1440
acgctctata agtgcgattg ggtaaatatt tgtttgccaa aaatacctta accgagtaaa    1500
gcatgataaa aaaaaacttg tatgaaacag gaaactcaga ccaaccctag taagatgcac    1560
aacattttat ggtggagatt ggaacaaaga gataaaaaga aagagaaaaa aagtgaacat    1620
ctgaggataa aaaagccaag ttagataaca ggagagatga cacaactgt gttgtagttg    1680 ttgttgttga tgtttgcttt gttctctttc tctctctctc tagggtttca agagtgtttt    1740
```

| gaactactcc agaaccctct cttgtttttc acaaatttgg gttcagtaga gtactgaccc | 1800 |
| agaaagaag attcaacagg tacctaagag aaggaaagag ggggatagaa agaaagaaaa | 1860 |
| agaaatagaa actgcacgta taaaagaaga aagaaagaat caaagaaaat aggaaaaaag | 1920 |
| ggcaaatatt ttgtttgaat aagatataag gcaatagtaa tattagtatt gttgataata | 1980 |
| attaggtaga aaaaatatta t | 2001 |

<210> SEQ ID NO 84
<211> LENGTH: 2001
<212> TYPE: DNA
<213> ORGANISM: Solanum lycopersicum

<400> SEQUENCE: 84

| aataagatga aagttatttt tacgctaaat aagatgaaag aatcttattt ttatgttaaa | 60 |
| taagatgaat attttatttt aaagctaaat aagatgaaag tttaagttaa atgagatgaa | 120 |
| catttaaatt ttaatatata cgacataatc atggcaatac acacaaaaaa aatatttaag | 180 |
| ctaaataaga ggtaattttt atttgtaaga atgaataact aaatcttgta caaaaaaaaa | 240 |
| aaactaaata aggtgagggt atttttgtaa acaaccaaca acttattctc aaaaaaaata | 300 |
| aataataaat attaatttaa atatgacaaa ccaaacaaac aactaatccc tatacaacat | 360 |
| attccagcat aactagtatt caaatcaaac aaccctctca tgaaatccat aagcaagaa | 420 |
| ataaaacaaa attgcaaaac aatcaataga ttaaggtcta ataagacata agtagataag | 480 |
| tgaatcgttg aagaagacat tgaattttga tatagtacaa ctccatacct ttttatggtt | 540 |
| attcatgtta atcttagggt attcgatata actttacaag taaaatctgt aaaagatata | 600 |
| cattattctt atctttattt agaaagatta ttttgattg actctcaaat caaaaatagt | 660 |
| gtaatcgagt atgattttc aaaaaaacaa aaaaacatca atataacaat atgagcgaaa | 720 |
| taaactaagt aataggcatt gtaaaaaagg aagaaaaaga tgcttatgac ttatctccgt | 780 |
| tactgaattg gttttcctct tctccctaat aagcaaagag ccaaagacta atattgaaat | 840 |
| gagttatttc ctcatatgat attcgacatt aatcctttca tcatcaatta gtttttcga | 900 |
| atgaagttag actcaaaatc ccttgtgaaa ctttcaaaaa attaggttta tgagttgagt | 960 |
| tggtttcaga atgctaaaaa taaaatgcat aatacatata ttgtatccta aatttggctt | 1020 |
| caaattttaa ctttgacctc taactttcat aatgcacaaa caaacacttt gactatctaa | 1080 |
| ctttcaaata aataaacaca tgagtcttac atgacaaaaa tatacatacg acaccacgta | 1140 |
| ggacgaaaaa tgacatgtaa gacatgtgtg tctatttgtt caattttata caagtttaac | 1200 |
| tgtttaagtg tctacttgtg cacacccaaa gtggaagggc ataaatgtta tttgaagtca | 1260 |
| agttaaagcc atacaaaata aaattgaat tatgtcttat ttaagatgga taagtagttt | 1320 |
| agctaaataa attttgtta gtaagttttc catttctata aatttacagt gaagaagtga | 1380 |
| gttatttgct tacgcatgat atgtacgtaa tatccactaa tacaccgacg cgtgtccagc | 1440 |
| caatttagta cacgcctttg ttctttcact gatggaccgc acaaatgaga agcaaaagct | 1500 |
| ccaacaaact aaccaagcgc gtgtatccca gacaacgaat agttgttgtg cgtgtactcc | 1560 |
| acgcgcatca acagaagcgt aagactagtc cctataatgc attggctaaa tacatgaaac | 1620 |
| ttgaaaagt agtggaaata agaaccaacc ctaaagctct aaggtatcta aatttggagt | 1680 |
| acctaagcaa atcctaaagt taaaacaatg aatccctaaa gaagatagga agaaatgcca | 1740 |
| tagataaaaa caacccatgt tcacttttc tctctctaaa cattgaaatt caaccaaaac | 1800 |

| | |
|---|---|
| aaaaaacaaa agttgataag aatcctttct ttctttctttt gtgtgtgtgt gtgtctagct | 1860 |
| agggtttgca tttcttttcac aattttggtt gtttcagtag gagagaaaag aggatctaag | 1920 |
| agttagccaa gagaagaaat tagtgagaaa ataaagtaga aaagatcat cagaggaagg | 1980 |
| agggatgggt agaggaagag t | 2001 |

<210> SEQ ID NO 85
<211> LENGTH: 1817
<212> TYPE: DNA
<213> ORGANISM: Solanum lycopersicum

<400> SEQUENCE: 85

| | |
|---|---|
| ttacaccccc actaaaaaac ccaaaagtta aaacaaagag catctaacta ttaatatcac | 60 |
| gttagaaacg tgcgatcatg tcatttaaaa gtttatatcg atagagatag tacattttg | 120 |
| ttatttaatt ataggggaa aaaacaaat atatctttga attatcatta ataatatgca | 180 |
| gatatcttcc gtcatacttt tgggacgata ttggtgtccc caccgtccaa aaactagagc | 240 |
| atatatatcc tttactctaa taagactgaa cagagacacg tgacacaatc atattcattg | 300 |
| atcatatatt caatatgaaa atgacaagtc ggtggataag attatgacaa ttgtatgtct | 360 |
| gttagtttaa agggtatata tgttctattt ctgggtggca gggcaccaat atgtcaaaag | 420 |
| tatgacgaaa agtatttgct tacgacaaaa acgatacttg ggggttatat ttgtcttttt | 480 |
| tcccttaatg gtatcctcaa caattgtcaa gctaataaag cgctacttct aattattcaa | 540 |
| atgatcgagt tattttatgt atgttaatat tgcaagcgac ttaatatctc caaacattgt | 600 |
| tcgaactcag cacgtacaat tatcaaacca aagagcaaag taggtctcga caaaacgaag | 660 |
| agtatcataa tacctcgttc gttattcttt cctaaaatat aatttttatg ttgaaagtaa | 720 |
| aaaaaattag cataaaaatt aatctattac gactgacgcg ttgttcaaag tcgagagaat | 780 |
| aatttaaagt ggtaggaaat caaaattgat ttgggtattt atttaactca tattataata | 840 |
| ggctttttt gttttaataa ttcactagga atatattctc tttttcaaga taaattaggt | 900 |
| tttgcaatgc tattatatat aaatagaaac attactagca aattttttga gtgttagaag | 960 |
| tagtagaaaa ttatttattt aagtaaatgt atagaatttt gaatgatgga gaaatgttga | 1020 |
| aagattatta aactgtgaaa taaaaggatt gtgttggctt attggacggt ttttaattaa | 1080 |
| tgaaggaata ttggacggtt gctgattgat gaagacagaa ataaatttga acgaaaatga | 1140 |
| tgaatattgt gaaaatatct aattatgtca ttttaaggga aaaattaatt tcacttcaaa | 1200 |
| tataattaga gtattattag aattttcttt ttctttctaa ataacacaac aatttccttt | 1260 |
| tgtcaaatca accaagttat tagcatccta tggatcacac ctaacaaatg tacataactt | 1320 |
| cttctattct gatttttatg tctcattttt cttttttagtt attaaaaaaa atatattcag | 1380 |
| ttttattta ttttaaaat tctcatttca cactttgtaa ttattaatta tttatttaa | 1440 |
| ttcattatca aattatatcc tataaagtag aactagtgta aaaacaaatt atctttattt | 1500 |
| ttaatcgagt caactcgtcc ttcatacca aaatgtatcc cacactcact ctattaacat | 1560 |
| acagtgagta gtacatgata agtttgttaa ataaatttta taccatcagt acatgcaatt | 1620 |
| ttatgtcaat aaattacaaa tatagatatt tgtgtagtgc acccttcttt tatagtaata | 1680 |
| gattttaga gttagctagt aagtgtataa tatcccttga tttaataaca attattcact | 1740 |
| atattatatt gagatgttta tcaatatttt tttactttat aaaattaata ataatttta | 1800 |
| tattaagttt ttaattt | 1817 |

<210> SEQ ID NO 86
<211> LENGTH: 2001
<212> TYPE: DNA
<213> ORGANISM: Solanum lycopersicum

<400> SEQUENCE: 86

| | | | | | |
|---|---|---|---|---|---|
| ttcaagaatt | tatgttctta | catatttatc | tatctatcta | tctatctatc | tatctatcta | 60 |
| tctatctatc | tatatatata | tatatatata | tatatgaagt | ctcccactta | tcggtaagtg | 120 |
| taatttcttt | tattttttt | aatctattaa | caaatttta | aatttttccc | tgagccataa | 180 |
| caattgtata | atttaaatat | gttctttttc | ttacgaaatg | tcataacaat | tattctcttc | 240 |
| tttattttta | ttttaatatt | gattaaagaa | ataataattt | attattttct | caataattca | 300 |
| tttattagaa | attcgtgagt | tatgtgataa | tgatgaataa | tgaaatttat | gtcaaaatat | 360 |
| tattaatatt | ttgtataatt | attttttcta | taatttttag | tgtatgaata | ttaaaatatt | 420 |
| aataaaggat | tatttgcaag | ttaataagaa | aaagacagct | cgtaagggaa | gcatcgacac | 480 |
| gttggtaatt | aaacactggc | gattgtacta | ttacgttgat | gttcgtgtcc | aaaaggtaat | 540 |
| acgatgtatc | aatgtgaaac | attaatttac | ccaaaaccac | aaaaaggacc | tacacttatt | 600 |
| acatataggg | taactccatg | tacacctata | tatatacata | taataataaa | ataataata | 660 |
| tacattcata | aataattgca | tatatatgta | gagacacact | ttttaaggtg | tataaaaata | 720 |
| taacttttta | gagttcagtt | ctcaggtgaa | atttattagt | atctgctcta | tcattattaa | 780 |
| taggtctatg | tttgagaact | atcaccaagt | tgattgggct | attttagaag | ggtagaggtt | 840 |
| tgacacaaaa | gttaatttag | ataatatttc | taattgatga | atataagaaa | tatgttttta | 900 |
| ttaatcgtac | agatacttat | agttttactt | aattttgcta | ttagattgat | ttgtacaatt | 960 |
| cgtcttataa | gtataaaatt | taaaatttgt | ataattttat | ttttgattat | ataaatcaag | 1020 |
| aattttatgt | atgtttgtcc | taactatttg | tatataattt | ataaaaaaat | tgataataaa | 1080 |
| ttgtcttgtt | tgtatactga | gaaacgaaat | atacaaacaa | atttctgaaa | aaattctgac | 1140 |
| cgtataaaata | cagaatttat | atatatttaa | cgtatttata | tattcgcaag | tgaaacttat | 1200 |
| aagcagacat | aaatatgcat | accaacataa | atatacaaac | ctcaatctta | atagcaaata | 1260 |
| aatataaata | taaaacacaa | ttatcgaaac | tataagtcta | aaatcttaat | atatctatttt | 1320 |
| tatttgctat | tagtaagatc | atgagggga | ggcagatgtg | agttatgagg | attcactagc | 1380 |
| tttgactaaa | ttgttaaata | gttaataagt | atacgtaaca | aatttgtgta | cttagtaggc | 1440 |
| gtttaattat | agaacatttt | tttaagaaaa | taaaaatttc | tttatttaag | tttttcaaaa | 1500 |
| aaaaaatcat | ctcttaaaat | ttgtaaaaga | attcatattt | gacgtgaaaa | gattattacg | 1560 |
| tcatatcagg | gaattaaaga | ataaccagtt | taaattatat | tattgtttat | ttattgacta | 1620 |
| gcggatattt | atttaattat | attctcagta | ttattttata | tgacatcatt | tttttagttg | 1680 |
| atctcaaaaa | aatgttacct | tacttcacac | aaatattcaa | gatttatatt | aaactacaag | 1740 |
| tttccaaaaa | ataaaaataa | ttcttaaaaa | taaaaaatgt | gtcacataaa | atgaaacata | 1800 |
| tatatttaaa | catttatatg | tgacttatca | atttgagttg | ggttatatga | aagtgacaaa | 1860 |
| cgattagata | gggcataaca | gtgcttctct | ctctttccat | taaatttggt | agtccacata | 1920 |
| cagagagagt | agaaaaagtg | tgttaaccta | gagtggaata | atagtgtttt | tcttgttaga | 1980 |
| gacaagaaaa | gagagaaaaa | t | | | | 2001 |

<210> SEQ ID NO 87
<211> LENGTH: 1882
<212> TYPE: DNA

<213> ORGANISM: Solanum lycopersicum

<400> SEQUENCE: 87

| | | | | | |
|---|---|---|---|---|---|
| gttatggttt | tggttctttt | ttctgtcctt | ttgttcttag | ggtaataaat | aaatagcttt | 60 |
| gttgggccat | ggggtttcct | aatattacaa | cattgtatct | attttttctta | tatctgacgt | 120 |
| ataaggtata | ataatttcag | gataaatttt | atcgtgtgtt | tagttgaaag | cttaggtagt | 180 |
| tattcttaga | ttatttctcc | tacccccattt | atatttaat | aacggaatat | gttatctcat | 240 |
| atgtatagca | aataaaataa | taacttatt | tgaagtaatt | aattaattct | gaaataattt | 300 |
| attcacgatc | aaatgatcct | tattaatatt | actttagacc | cttttaaata | ttgcatttt | 360 |
| ggtaattctg | caaactgctt | ttgttatttc | ttctgcctgt | gtcccttgtc | tctctataat | 420 |
| taatatataa | gtaaaatgtg | ttttgatgtt | tagggccaaa | aaagaagac | aagtcaatac | 480 |
| tattaaccat | tattattttt | ggtttctcac | caactaaacct | tttaatatca | agttttgcc | 540 |
| cctattttgg | ggtggtattt | aatttgtatc | aaattacaaa | ataaataaaa | ggagacataa | 600 |
| gtttagaatt | ttttttaggt | ataagttgtg | tagtacctaa | tttggaagac | ataagttaaa | 660 |
| agaattttga | agttagattg | atttggaatc | aaaattaaaa | ttttatttaa | ataggtaatt | 720 |
| agattataaa | aaataaatat | tttattggaa | acaacataa | tttgttgaaa | actattaaat | 780 |
| attatgaaaa | ttttaattat | atattttttat | acaatttttt | aaatgagtaa | atcacgattc | 840 |
| gtaaataaag | tatcagaaac | gtttgtaatt | acatttat | aaaaagtttc | caattctcat | 900 |
| tattttataa | actactaaaa | ataaagtttt | ttcccacatt | tccattttaa | tggaaattgt | 960 |
| aagacataat | attaaaggtt | gtaggtatt | gtatcccta | ctgggattgg | ggagtgtttg | 1020 |
| aaaagacctt | tatatggaga | tacattatta | gcccctata | ttggaaatat | catatctata | 1080 |
| aaattcaaaa | gttaattcat | gacgaaaaaa | aatatctaaa | ttatattaaa | gagatcacat | 1140 |
| atttttttcta | gctatgactg | gacatatagt | gcgtggataa | ttttagtatg | aagatctaac | 1200 |
| atcaaaaagc | aagaatggga | tgaatcgtgt | attaatatca | tgtaaggagc | gaactcataa | 1260 |
| gaaaaaaatt | gttcagatca | tattaaaata | tataccaatt | cttaaaccat | cgagacggag | 1320 |
| acttttcaca | aattacatac | atactagaca | ttataaaatat | ctttttacat | catcaatata | 1380 |
| tagtataggt | aagtatatct | tactacacta | tcaatttaaa | ttcatcaata | attactgaac | 1440 |
| aaataattcg | atcgtgaata | tcttttacac | tgtcaacaca | tataattgca | agtcgaaaag | 1500 |
| tatttagcaa | tcaagggttt | tacaagaatt | tttggtgcta | ataaaatgta | taacaacctt | 1560 |
| aaatgttgtt | tgttttttcct | taaacaagac | atagcacact | ccccccttgat | gtatctttt | 1620 |
| gggacatacc | acatgtttct | gttacataag | ttggatattt | tgatattaga | tacctaagaa | 1680 |
| tgtgtcatca | tgttactcca | tacatatcaa | acaatatttc | acttcaattt | gaaatatta | 1740 |
| aaatcaagat | ttgtaatcac | ataaactaaa | atacgttaac | gtaattaatc | aatcttgatt | 1800 |
| caacacaaat | attaatgaga | gaaaatattg | attcaaaaga | taaaagcaca | tagtgtatgg | 1860 |
| gaattgatat | tcaaatacct | aa | | | | 1882 |

<210> SEQ ID NO 88
<211> LENGTH: 1574
<212> TYPE: DNA
<213> ORGANISM: Solanum lycopersicum

<400> SEQUENCE: 88

| | | | | | |
|---|---|---|---|---|---|
| aatgaaaaag | aaaaaataaa | gcaatagatc | ccatcttatt | taaaaaggga | aatagtacaa | 60 |
| cccacttttt | tttttttgtat | ttatatttttt | gattttgttt | ctctctattt | cattcgtttt | 120 |

```
aatttatgtg gggttagtgc gatgtatttta tttcaaaaat aataatgtgg gtgaaatagt      180
gatctttcta ttaaattaga tattttatgt atacattttt tgtcgaatta atataatatt      240
ttctcattaa acttacatgt tccaaaagga tcgaatgatg tacttggttg aattgcgaag      300
taatttttt tagagaaaca acgatcaatt ctcacttaat ttttttttta tattcacgtt       360
ctaaaaatcc taaatctaag aaaaaaatgg gagtaatttg gaacttaaat ctaagacaag      420
tcttaattat gtcttgttta gctaattaaa ctatcaaaat aaaaatattt tttatttaaa      480
atagtatcca aaaagaatt acttttggag agtcaatttt tgaataccttt gttaatttga     540
taaatatttg tatttatatt ataacaataa tttatacttg aacaaagttt tgaaaatact      600
ttccattttg ccctactata cgtactactc aaaatattaa aacccatttt tttcttaaaa      660
gtttggccaa acacttcaa tttcctttaa aagttggcca tactaactac atttaatttg      720
tacaaatcaa aattatttta taactcatat cattggcgga acttgacgtg agttgtctaa      780
aataaacaaa gtttaataaa agtgtataaa ttaaaattac tgttaacttt agaaaaatac      840
caatgagttt gacctttttt acaagttgaa caatacaaac tttaatcaat attattaaaa      900
tatattttca ttttattgat ataagaaatt actacaattt ataatacttt tcctataatt      960
tcaatttttt aaatttctg aaatattaaa ccaatctaat ctaattcaat ttaatcaaat     1020
taattcatat aaagcaaaat taaataggaa aatattccat atcaaagtga gtagtttctc     1080
tattctatt ttatatttca aataggaaaa attcactttt ctataattaa gaataattca     1140
attttaattc ttttcccttt aactcttatg aaataattta taatcacaca actattcaag     1200
tattattta caccataaat ttcaaatctt ttcattttt cttcttaaat attatactaa      1260
atcaaataat atcatataaa ataaaacata aaaaaatata tattttgaga aattaaaaag     1320
aaaataatgt caataatttg tttcttttt tttctcttaa atagagtaca tgaataggat     1380
agaataggtg tggaaaaagg tgtaaataat aaataaacaa tttaacaagt actatgaaaa     1440
atggtattat aattatttaa aatgaaaacc agatggtatt taagaatgtg ttgtcgagtt     1500
ttgattggtt gaaaggacaa catagtatgg tactcatttt tgtatggtgg atatataatg     1560
tctatcacag attt                                                       1574
```

<210> SEQ ID NO 89
<211> LENGTH: 2001
<212> TYPE: DNA
<213> ORGANISM: Zea mays

<400> SEQUENCE: 89

```
agtctcttgt tgggctggac gcctccatca aggcgcgagg tcaagggcac agttaaccgt       60
tgtgctaact ggtggagatc aattccaaca cactggacta gtgctgggac taacttaaaa      120
ataggagcct aaagcacggt ccaacaagaa ataaatagg tcgggctacc acgactcgaa       180
ggtgggtcta gacctgacct caagttacgg cctgttgggc ccagcacggc ccacacatat      240
gggtcggttt gggcctacac ggccccaatg aagcctatat tatttaatttt ctttagtttc     300
gtaaatttat aaactttata ttgttgtgat atttggactt tatgcggtca aatgatgcta      360
gcattgttta atattgtggt tgcaatattt ggattttacg aggtttgaat atataggacg      420
agcttggacc ggcacgattc aacaaaagca cggcttgctt tagagtagaa ctgaccattg      480
tttctacttt tcaggcccta aaagttttt tttatcttct tagcccgatc ccagcactag       540
actggactgg actgagacct tgtactttga agtaagatgc atgagttcgt tatgcggatt      600
```

```
cgcaaggcgc gcgtacagta cagctcggca cccaacagct agtagtacgc acgttccgtt      660
aatccgctgg atggatggat cgatcggaga cggacagggg cggacgcgcg caaacgtac       720 ggtgcagtta ttgtcgtccg ccggatcgat caatcgaccg gcgcggcgga cggatcgaac      780
agtgcccgaa catgcacgtc cgtcccctac gcctgcggcg tgcagcatgc gcgcggatcg      840
tagtccccgg tcgatcggat gcgcgggccg gaccccggcg ctgccgaccg ggaggcggga      900
gacttggttc gtttcgcacc tgctgccttg tctcgcgctc gcgcggcgcg tcaggggtgg      960
ttggtcgcgt acttgcgttg gctgctgcct gggtggctct ccgcctctcc tggccacggc     1020
gagactgatg cgcgcgctgg cccagctttg gtcgctgttg cgagctggtc tggacagcga     1080
cccggcccgg ccggccggcc ggccgccgag accgaaagga agcaacgtac aaccagcagg     1140
aagcaagggg tgagagagag cgagagagga ggggcgtgca gccgtccggt ccagcaggcg     1200
acggaatgga ggacacgccg ggcaggtcgc tgtgcgcctg tgcctgcgtg cgcgatcgcg     1260
agtggccagt caccagcagg ccggccatta aggagagca cgtgacgcg cgccagtcgc       1320 ttccttcgct tcgcttgctc gggcgccggc ggggaccacc agggtaaaag ccgagcgcgc     1380
aggacgcgac ggcgacggcg acggcgacgg acgggacggg tcccatgagc ccatcaccac     1440
gagcggcgtg gacgtggagg tggatggaat gaccgatcga ccgatcgatc gcgagtgatg     1500
actgatgagt gtggcgtgac tccgatccct gatccctccc catccctagc tttccggcaa     1560
cgcgctaccg ggccggggc ctagggtttc ccccctacg gatgctttgc cggaaacggc       1620
aacctgacgc cgaggcgcgc gcaccacccc tgcgcccacc ggctccttcc ctgcgccgcg     1680
ctgatgataa ctcagtccct gcacaggccc cggcccggc cccagcccca ccaccgctac      1740
tccactaggc cctggttgct agccagctcg cttgcttgct tcgattccta tcctagcccc     1800
cgtgccatcg ctttcctctc gttatttagc cctccgttcc cgaccctcat cctccgctcc    1860
agacttccag catctccgct ccggctgcgc tctgccttgc tttcctgcta cctgctctag     1920
cgcgagcgag agaggtacgg cggccgatct ggcggcgcag gcggagggct cggccggggc    1980
cggcaagtcg gcgccgaaca t                                              2001

<210> SEQ ID NO 90
<211> LENGTH: 1032
<212> TYPE: DNA
<213> ORGANISM: Zea mays

<400> SEQUENCE: 90
acatgaggag tgggttgatt ccactaaaat tgatggaatg aacttattat gcatcaactc       60
ataaagcata gagtgattcc acaaaccaaa cacaccatta gtttattgac caacctcagt      120
tctttgatat ataaaagttg tttgatccgt gtgcaacaaa tagttttca ggaatttggg       180 acgtaccca tctcttaaat gtctagactg attggacata ttaatctaat tttagtagct       240
aagtattagc tctcaaacac ctcctgggaa tgctgcccta aaatggaat atcggtacgt       300 cggatcggag aaaggttggg gtatcgtggt ccaaagcatg cgaaagcaac ggcgcagggc      360
tggaaacctg agaccaggtg aggtgcacga cgacatgcat atggtttggg ttaggcctag     420
gagctggttc tctctccatg catggtcagc tcgccgcttt tgccgccttc gtgtatggct     480
tgccccatgc catgcatcgc gccgtgtaca cttgtggcgt aggggcgggg ccgccgcatc     540
ggagcgcccc cgtttcggca cggtcctccc agttttaggg taaacccagc tagggtagtg     600
ggggtaactg gccagcgcca ctccaaatct accctccttc aatttaaagc tgagaaatac     660
tgtagtatat actagagtag agcgagagaa gggagatgtg gatagatggg tggatgggga    720
```

```
cgcgtgaaaa agatgcgaga gagaagagac gaccggacag gcagccacac acagtaacag    780
tagtgaaccc tgcccctttt cccggtctct ccactgatat tccgctcctg tccctgtcct    840
ccccggacgg agctaataga gccggctctg ctcatcatta tatcgtcgcg cacaaatgcg    900
aagcctagca gcacttgtgt ccggcggcct tgtgttcgtg ggggatgtgt ggcatattag    960
ctagctgata agcggccggc cgaagagcaa gcgcagtgag aagaagaagc tcggatcgga   1020
ggaggtcggc at                                                       1032
```

<210> SEQ ID NO 91
<211> LENGTH: 2000
<212> TYPE: DNA
<213> ORGANISM: Zea mays

<400> SEQUENCE: 91

```
tgtctcgatc tctcctctcc tctcctctcc tcccgttggt gtgactgtag tagatccttt     60
gcccgtgtca gaacaagctg ctcctcggac cgggtaatgt taaacatcgg aggagccttt    120
gcctaggatc cgtaacgggg aggaaagaga aaaaaaacta aggatgatta tggataccgt    180
gtaataactg ctaactacag ttagcccatc tcagcggact ctctgcccta tattgtatgt    240
cactttctat tataaactac actatacaac ctatgatgta aaataatgtt ttgcacgttc    300
atatataaat cagtcgaaga aagggtgcct cactacaggg aatggtttct attggacacc    360
ttagcattca atcagtcatg tccccccccc cccaaaaaa aaaatgcacc catccagtcg     420 attttttgtca tatttgaatt cggtggtgct ccatgcacgc gtacctgctt tgaccaattt    480
atacgatcaa tatataactt acgttcttac ggttcttaga ctttatgaga ctttgcaagt    540
atgtttggat acaaatcaca ctaatgtgca tctttgtaaa ctaaattctt ttgattaaat    600
ttgtaatttt aaggtttaac ctgttttgt tgtgtagacg acgttaggca ccgatcgtcg     660
cttcgctata tatctttgtt gtagacgacg ttagactcct agattaaata gcgaaaacc     720 gatcgtcgct tcgctatctt tgtttatttg tttgtggctg ctctacgctg aagagcccac    780
aggccacagc cccacacgac acgttaggca cccccaccca ccatccgcgc ataatataag    840
ctactgcaaa atatatgccg gcggagcccg agcgagcttt gtacttgctc cgccgtggcc    900
tggctccagg atgctttgga tttcgtgcgg cgccgtacgt ccaggcaaac agacaagtgg    960
agctgcatgt cctaaaagcc cggcaatcaa acacgctcta gcagcagcat ggatcacaga   1020
tatcagtcat ggggtggcgc tggcgcgggt gggtggccag gtggaggtgg gtgcatgtcg   1080
tcgtcgtcgt cccatacaga aattggctca cgtatgtata cgctgcgtac aggcagtagt   1140
acacaattac tagcaccaat gcaatccaac ggatggatct tcgcacaccc gccacccggt   1200
taaattaagc tactcctacc tctcccagtc tcccttggcc tgcctctata ttttttggca   1260
gcctccacca gccgggcgga tgggggttgga tcgtcgtatc tgaggcggcg tggtcgtcca   1320
aggcgaaagc aacggcgcag gctgggaccc ctagtaggtg catgaggtcg tgcatggcgc   1380
gcgagatgca tggtttgggt taggcctagg aggttctctc tccatggcat gggtagctcg   1440
cgccgcttgg ctgccgttct cgtgtatgcg catgcaccag gcatttgcac cgcgccgtgt   1500
atatttctgg cgtgggggcc ggcgccgcat tggagctgca gccccgtttc ggcacggaca   1560
cgggacacct cccgttaggg taagcccggg gcagtgggta actgcccagc gccactactc   1620
cgaatttacc ctccttttat ttttaaagct tgggagaggg gagaatggat ggatggatgg   1680
atgtagacgc gtgaaaaaga tgcgcgagac cggcagcgtg tgctacaggg gcagccaggc   1740
```

```
acacacacac acagtgaccc tgcccctttt cccggccgtc tcgctctcca ccgatattcc    1800
gctcctcctg tccagtcctc ctcccccgag ccggctcatt atatcgtccg tcgcgcagca    1860
caacgcaagt ttgctagcgg ccggatcagc agccacaaaa cgaggagagc aaccacgctg    1920
cacacagaga cgcccgtgtg tgagatatag agcaagctcg atcgaaggaa ggagggaagc    1980
tagagatcgt acgtcgccat                                                2000

<210> SEQ ID NO 92
<211> LENGTH: 2001
<212> TYPE: DNA
<213> ORGANISM: Zea mays

<400> SEQUENCE: 92
gtcgaaacgc cgacaatttg ttacacggtt accactgcac agcgagtacg acaacaagcc      60
taagatagtc cacttcttcg cattcctata cttctcactg tgatctacgg cactacgaca     120
ctatttcgag gcaaaaacag agggaagatg cctaaccaaa attctaatga agaattacac     180
cgtgaatgat ggcggcggtg gacgacggtg gcaatggcaa aaccctaacc ctgcatcatt     240
ttcccttcac cttctatttt tttccacgtg catagcatgg cagtccctcg acaatagaaa     300
cacatgtaag gtttcagtgg atatatccca atcgttgtac ttaagcagca ttcataaggt     360
gatttagttt ttttccctaa atcttgcaac gtgcataact tcgcgattga aactttaatt     420
aatacatgta atcagtcgaa tggaatgcac tggtttttag gcatgtatat gacctcaaat     480
catccacgca aggaatggat aaaatgacaa atcttcattg tcttcttaaa ttcaggcgat     540
cttcgtaaaa acagttgatt catataaaaa tagaaaatat atttggagaa attttctgca     600
tgtccttgta attttgctta gtaccatatt tatcatcgta aatgttataa tcccttctat     660
ataccactct gatacaattt cgtacctttt taattatgcc aacgcaagtg ggcgagtgat     720
atagtaggga ctagaatatc tgtgatgata aataatgtac tagacaaaat tacagtagca     780
tacatgaaat tgtcccttat atttgccatg cattttttgc tattacatct tagcataata     840
atcttggaag cacatcgcat gagttatcga ttcaagttag atatatagat gcatagtaga     900
caacatttag ttacgcaacg gcatctggtt ccaagaggag ctttgcaaga gatcaattga     960
atttagggcc tggaatcgtt accaaatcag tgatgattgc cggttgggtt cacatgagca    1020
gataaaaaaa tggagatgat catcgtcctt tcagaatcgc taacagatat ggaagtgatg    1080
aagtccagga ctccacatga tcttactaca cacatgccag aagtctggaa caagaacatg    1140
ccggatccct aagcagaaaa cggatcgtat agcggtctcc tttctggaaa aagcgacgca    1200
aaacggatcg atgacctctc tcaccatgtc aacccgtgct gaggagctcc gtcctgtctg    1260
cacgcactat ggcaatggcg accggcctct tccgagctgc gaatcataac ggcatgtctg    1320
caagctcgat cgctgcaagc atgccttccc gttggaagga tcgagctgct cgatggagga    1380
aagaggaaag cagcgcgccg cgcatggcta tagcagttgg caggtgaggg cctctagcgg    1440 caacggggc ctttgcccaa aatcacggca agccgaggtt ccacctggaa aaatccactc    1500
cgttgctctc tccctttttct ctctctctag catcgacctg tcgaatcctc actggtctat    1560
tcagttcggc aacagaggaga gagatagaca gagagacgga cggaggctg acacatggcc    1620 ggatattggg gtgcggaatt gaatttggtt aatgcaaaag gtggcgtgtg aggacggacc    1680
gacggaggca atcacgagac gggaggggtt ggccttttgc ctctagggtt ccgggtcgcc    1740
caccacctta ccggaaatgg caatgcggga cgcgccccaa tcactcacca caccacccct    1800
ttcttctcgc ccttttaacc caatcgtctc tccaccaccc aactcctcct gcctgtgctc    1860
```

```
tcctcctttt tctccactcc gcttttgctt ggttccatcg ggccggagag gagaagctag    1920
ctaactagca gcagctctgt tggtgtgtgt gtgtgtggag ggtagctgca gctggggcta    1980
gctggaaagg tcgggagcca t                                              2001
```

<210> SEQ ID NO 93
<211> LENGTH: 668
<212> TYPE: DNA
<213> ORGANISM: Zea mays

<400> SEQUENCE: 93

```
atcgaagata gggttgctcg aaacaaaaaa aaatctgca gccgcagact gtatgcccta      60
cgctattttg ccgtaggaga gttggaacct ttgatgtagc gtttgtacta ctcggggtac    120
gctatccact atttggttga ggtatggtgg gaaagaaatg ataaaatata tggttgttgg    180
tgtagagttg atatatgaaa taaatatgac tgcagatgat tattgtgata tatggtaaat    240
acttttgatg ataaaaataa aatatttttt tagagtagta cggatagcct tatcgaccta    300
tgtacctggc agcgctgtga tccatcagct agcgaccaat cactcgccca ccacggcatc    360
gccaggagct gttgcttttt gcgagctgca tggtggggc ctccatcgaa ggcgagggga    420
cggggcagag cgccctgatc gacgcgtgat aaccgattga tgtgccccca gttcgcccgt    480
accagcgcgc gcccctcgg cctcgtcctg cgtccgcctg cgtgctggtg cggcgcgctc    540
gcgctggcgg acgtccagac cgcaataatc tcgcggcctc gcgcgaggag gaccgaggac    600
aggaggtgcg atgcgatgca ataaaggttg ccgtacgcga gtgagtcgga cagagagaga    660
gagagaga                                                             668
```

<210> SEQ ID NO 94
<211> LENGTH: 718
<212> TYPE: DNA
<213> ORGANISM: Zea mays

<400> SEQUENCE: 94

```
ttatttggtg cttcaccgcc ggagccaggc tagctataca ctttgtagtt gtttgtaggg     60
gtatatagga gcagtatcta cagtagcagc actcttcacc ggtccagcta gtaaatgcgg    120
tatctgtcgt ctgtcgagct aacctatcat atcagcgcca tgcgccccgg ccggtcgtaa    180
cctagctagg agtagctagc taggactagc tagctaggag cctaagcgcc cagcccagtg    240
ggtggtagcc taccaagggt gaggaagagg agctgagcta ggaccgcgag gcgagcgaga    300
tccaatctgc accccacgaa cgaaaagatt cttccccgcc ggcgtcgctc tctcatccgt    360
cgacgtctcg ctccttcctt cctctctctc tctctctctc tctctctctc              420
tttctctctc tcagccagca gcaagcatat agcccagcac caccacatgc ccaagggccc    480
tccctctccc tcgtcgtcgg gccaattgag tgtgagagct cgaaaaaacc caggggatcg    540
gccggaccag cagcgagcga gcgcgagctc tgcgtcgtg tgtgtgtctg cgcgctagat    600
tagatcacct ccatcgtcaa taattgcagg cagatccata tagtctgctg gtggcgagac    660
aaagcaacgg atcgtcgtcg atccggagag cggaaagcgc gcagatcgcg gcggccat     718
```

<210> SEQ ID NO 95
<211> LENGTH: 21
<212> TYPE: RNA
<213> ORGANISM: Glycine max

<400> SEQUENCE: 95

-continued agaaucuuga ugaugcugca u                                    21

<210> SEQ ID NO 96
<211> LENGTH: 21
<212> TYPE: RNA
<213> ORGANISM: Glycine max

<400> SEQUENCE: 96
ggaaucuuga ugaugcugca g                                    21

<210> SEQ ID NO 97
<211> LENGTH: 21
<212> TYPE: RNA
<213> ORGANISM: Glycine max

<400> SEQUENCE: 97
ugaaucuuga ugaugcugca u                                    21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
atgcagcatc atcaagattc t                                    21

<210> SEQ ID NO 99
<211> LENGTH: 21
<212> TYPE: RNA
<213> ORGANISM: Glycine max

<400> SEQUENCE: 99
augcagcauc aucaagauuc u                                    21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ctgcagcatc atcaagattc c                                    21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
atgcagcatc atcaagattc a                                    21

<210> SEQ ID NO 102
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 102
ggcagagccg tgcccgtctc atccctgcc cgtgcaagca gctaggtagg acgatttgag      60
cgtggtgtta ggccgaaccg ctgaaggaag attgctccac tgttgactgc atttgggcta    120
ggtgcatcgg gataaatgta ttgcttatat tcagcaatat aatgttcatc ccgatatgcc    180
tagcccaaat atagtcgata gtggaagaac ggtaacatat gtggtttgca gcaggtgagc    240
aggatgggtg tggatgattg aatatctctg ttcagtgttt tcatcatctg actgaacact    300
gaatcagctt gctgacgtta gaggttag                                       328

<210> SEQ ID NO 103
<211> LENGTH: 21
<212> TYPE: RNA
<213> ORGANISM: Glycine max

<400> SEQUENCE: 103
ugacagaaga gagugagcac a                                               21

<210> SEQ ID NO 104
<211> LENGTH: 21
<212> TYPE: RNA
<213> ORGANISM: Glycine max

<400> SEQUENCE: 104
uugacagaag auagagagca c                                               21

<210> SEQ ID NO 105
<211> LENGTH: 21
<212> TYPE: RNA
<213> ORGANISM: Glycine max

<400> SEQUENCE: 105
ugacagaaga gagugagcac u                                               21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gtgctcactc tcttctgtca a                                               21

<210> SEQ ID NO 107
<211> LENGTH: 21
<212> TYPE: RNA
<213> ORGANISM: Glycine max

<400> SEQUENCE: 107
gugcucacuc ucuucuguca a                                               21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
```

```
tgtgctcact ctcttctgtc a                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gtgctctctc tcttctgtca a                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
agtgctcact ctcttctgtc a                                              21
```